(12) United States Patent
Chen et al.

(10) Patent No.: US 11,840,685 B2
(45) Date of Patent: Dec. 12, 2023

(54) INHIBITION OF UNINTENDED MUTATIONS IN GENE EDITING

(71) Applicant: ShanghaiTech University, Shanghai (CN)

(72) Inventors: Jia Chen, Shanghai (CN); Bei Yang, Shanghai (CN); Li Yang, Shanghai (CN); Xingxu Huang, Shanghai (CN); Lijie Wang, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 17/862,354

(22) Filed: Jul. 11, 2022

(65) Prior Publication Data

US 2023/0094769 A1   Mar. 30, 2023

Related U.S. Application Data

(63) Continuation of application No. 17/427,040, filed as application No. PCT/CN2020/074218 on Feb. 3, 2020, now Pat. No. 11,384,353.

(30) Foreign Application Priority Data

Feb. 2, 2019   (WO) ................ PCT/CN2019/074577

(51) Int. Cl.
| | |
|---|---|
| *C12N 15/10* | (2006.01) |
| *C12N 9/22* | (2006.01) |
| *C12N 9/50* | (2006.01) |
| *C12N 9/78* | (2006.01) |
| *C12N 15/11* | (2006.01) |

(52) U.S. Cl.
CPC ............. *C12N 15/102* (2013.01); *C12N 9/22* (2013.01); *C12N 9/506* (2013.01); *C12N 9/78* (2013.01); *C12N 15/111* (2013.01); *C07K 2319/50* (2013.01); *C07K 2319/85* (2013.01); *C12N 2310/20* (2017.05); *C12Y 304/22044* (2013.01); *C12Y 305/04004* (2013.01); *C12Y 305/04005* (2013.01)

(58) Field of Classification Search
CPC .................................................... C12N 15/102
See application file for complete search history.

(56) References Cited

PUBLICATIONS

Adikususma et al., "Versatile single-step-assembly CRISPR/Cas9 vectors for dual gRNA expression", PLOS One, 12(12): e0187236. 2017.*
Li, M. et al "First-In-Class Small Molecule Inhibitors of the Single-Strand DNA Cytosine Deaminase APOBEC3G" ACS Chem Biol. Mar. 16, 2012; 7(3): 506-517. doi:10.1021/cb200440y (25 pages).

* cited by examiner

*Primary Examiner* — Suzanne M Noakes
(74) *Attorney, Agent, or Firm* — Sheppard Mullin Richter & Hampton LLP

(57) ABSTRACT

Provided are fusion proteins and related molecules useful for conducting base editing with reduced or no off-target mutations. The fusion protein may include a first fragment comprising a nucleobase deaminase or a catalytic domain thereof, a second fragment comprising a nucleobase deaminase inhibitor, and a protease cleavage site between the first fragment and the second fragment. Also provided are improved prime editing systems, including prime editing guide RNA with improved stability.

13 Claims, 52 Drawing Sheets

Specification includes a Sequence Listing.

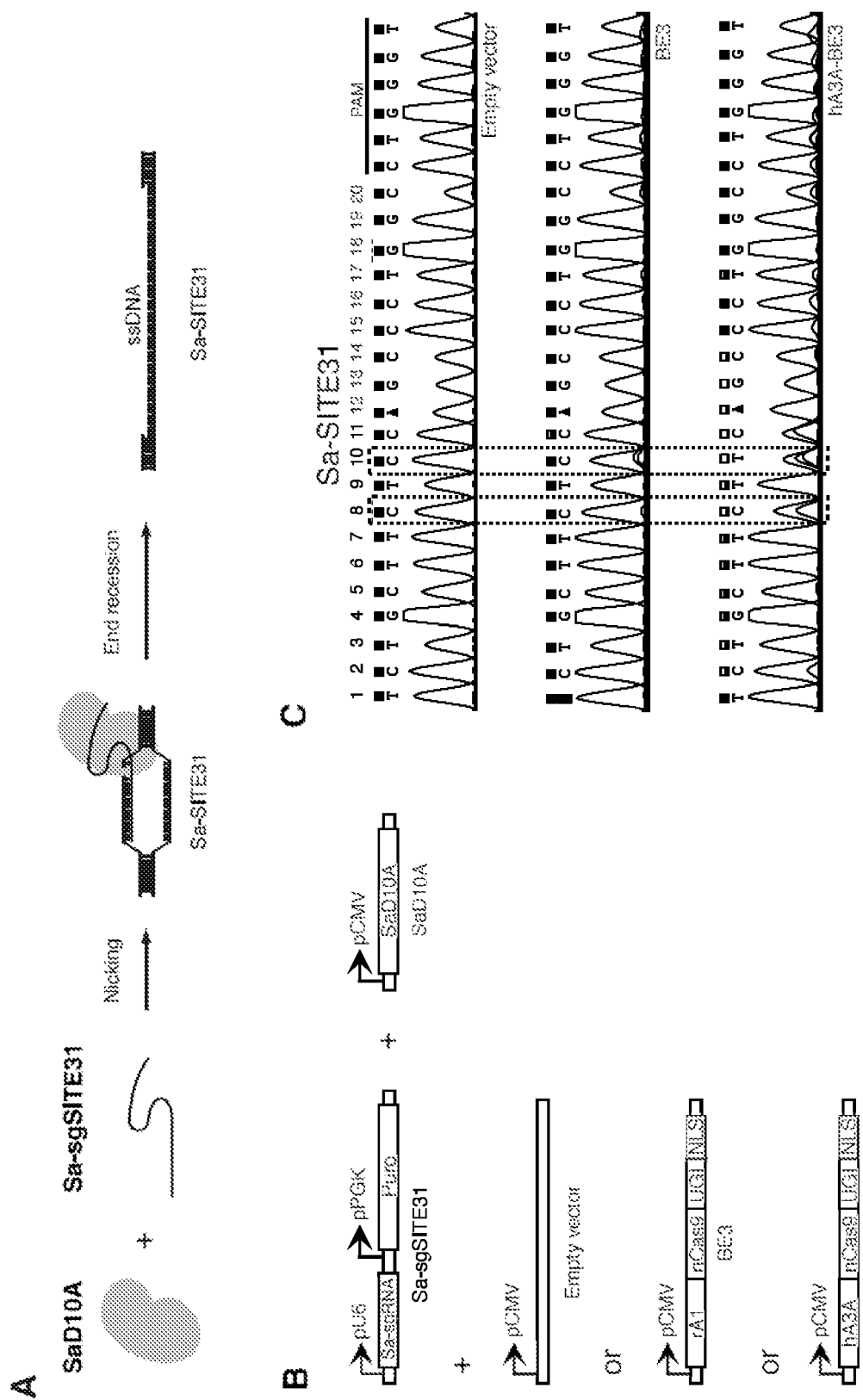
FIG. 1A-C

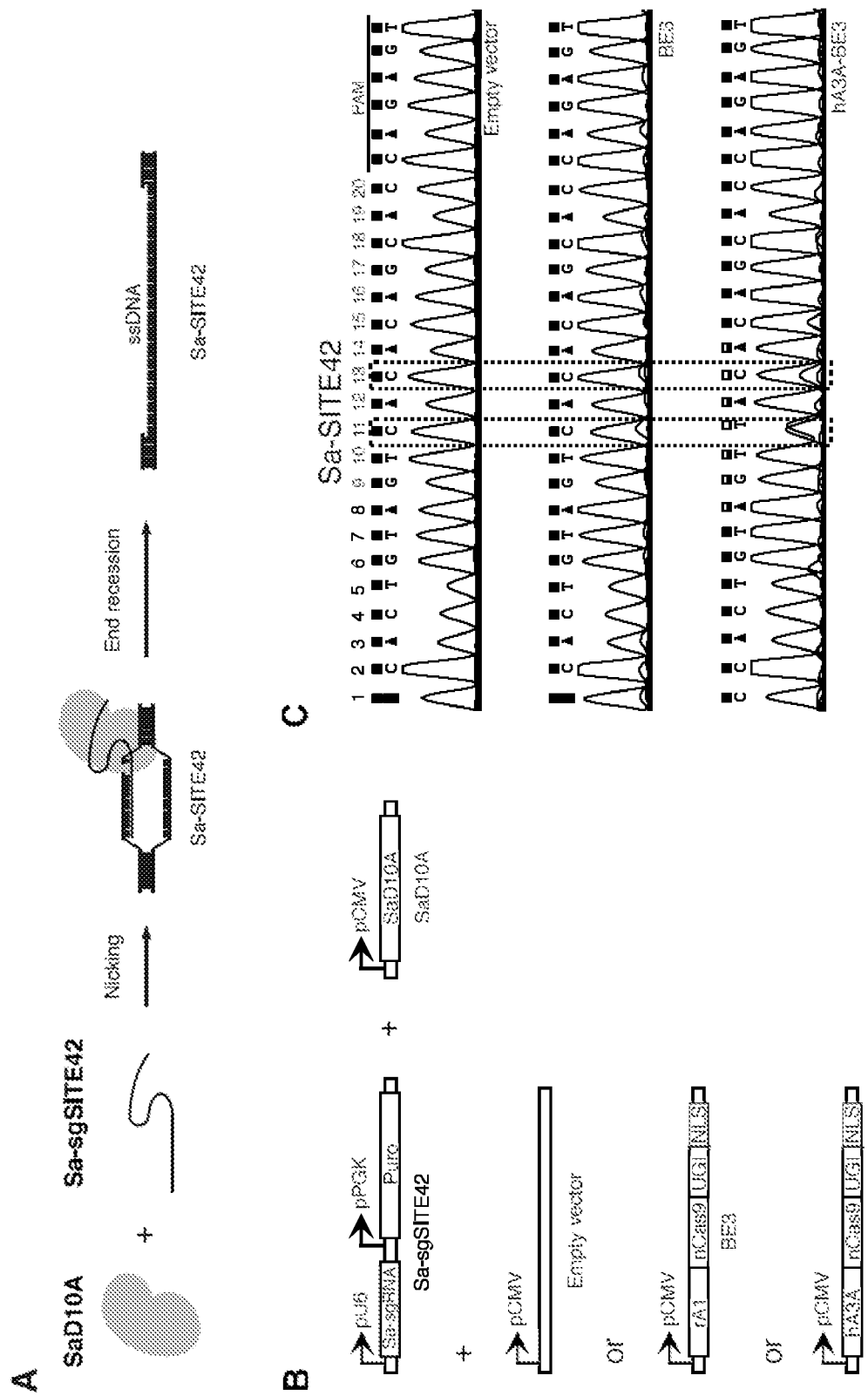
FIG. 2A-C

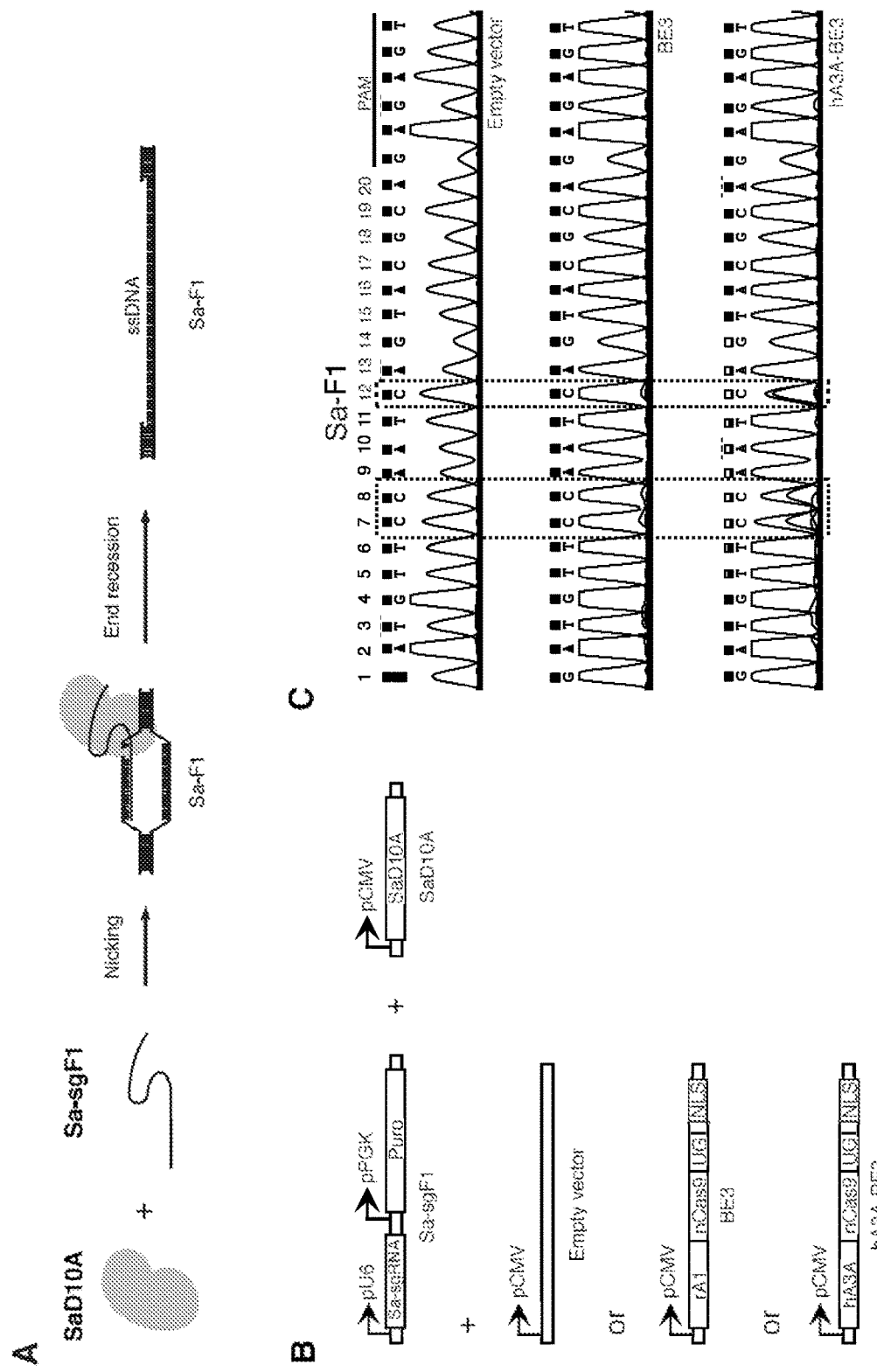
FIG. 3A-C

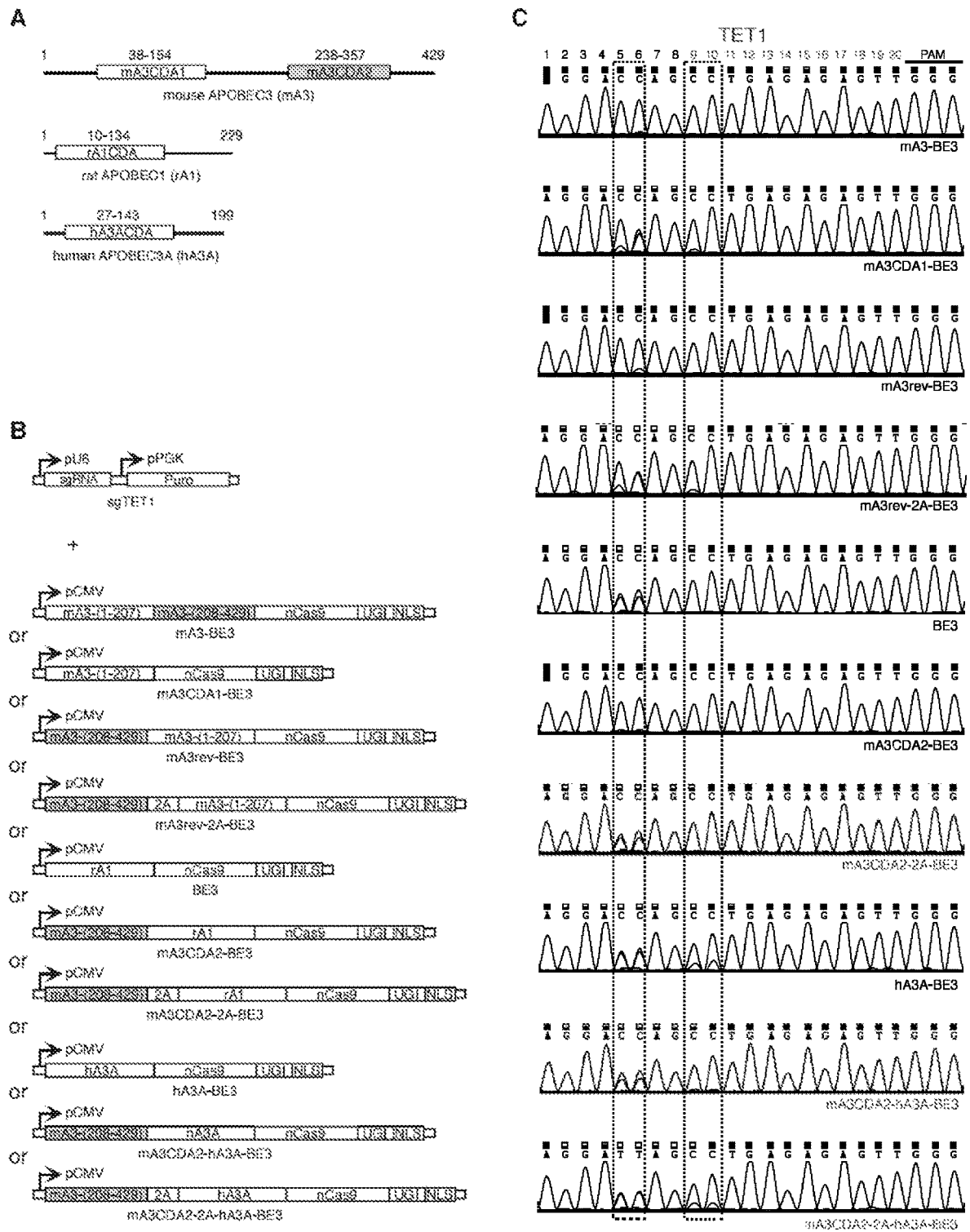
FIG. 4A-C

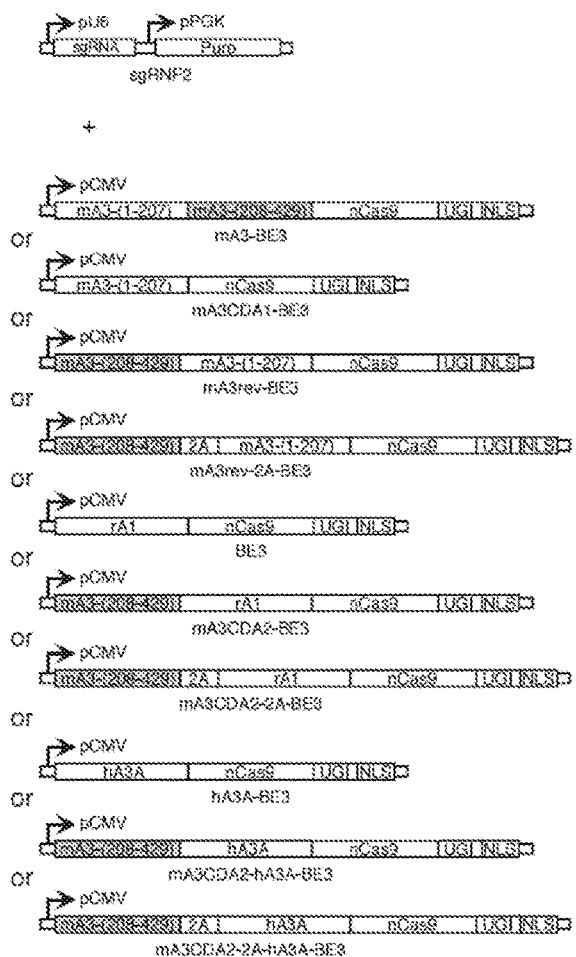
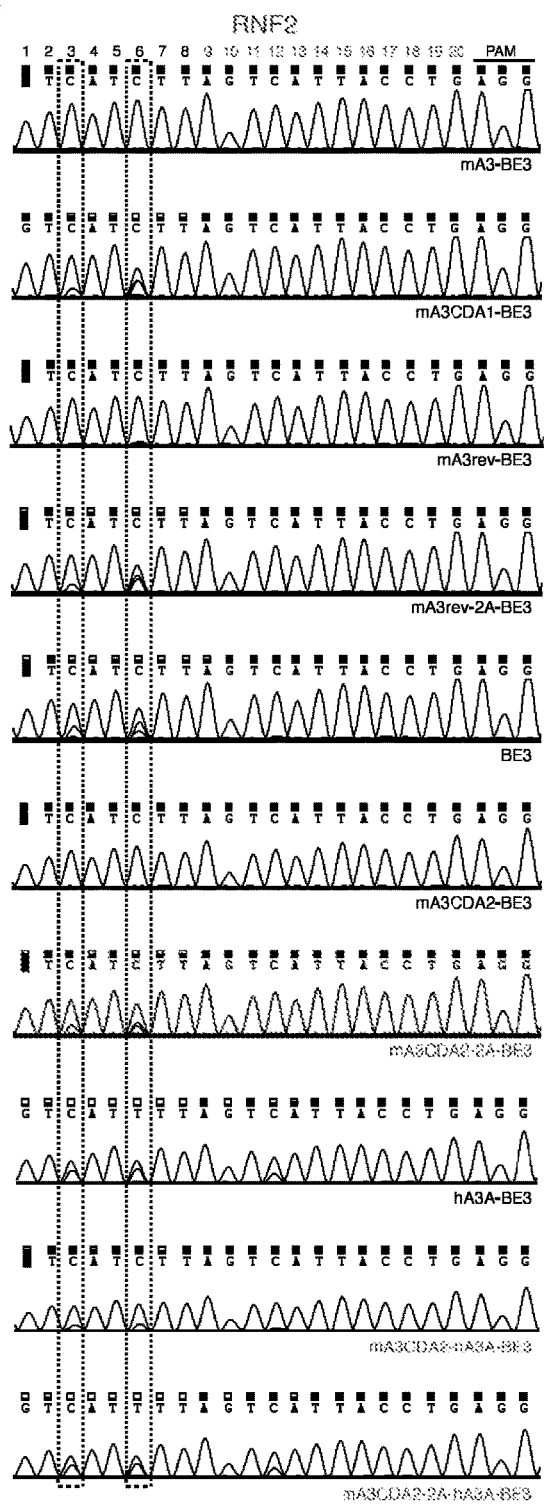
FIG. 5A-C

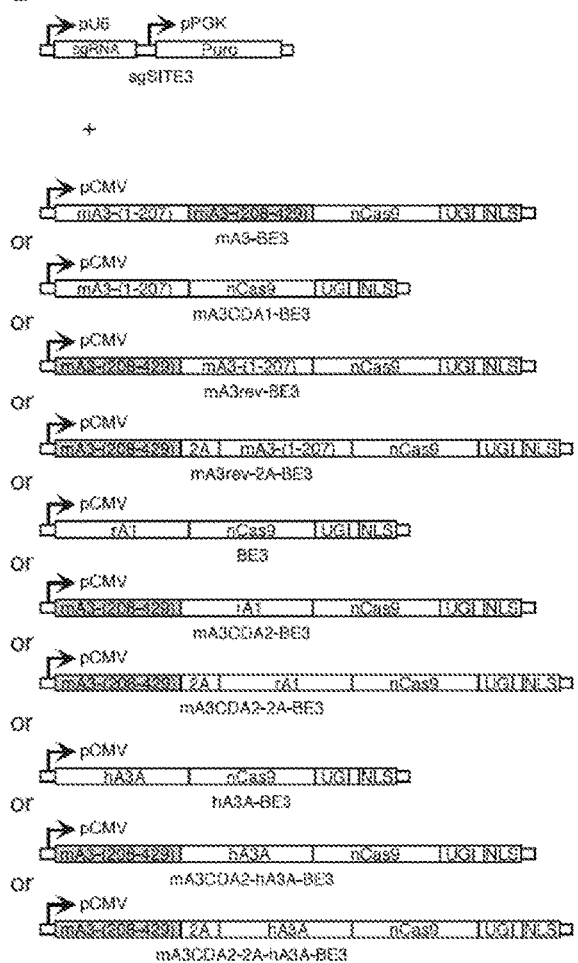
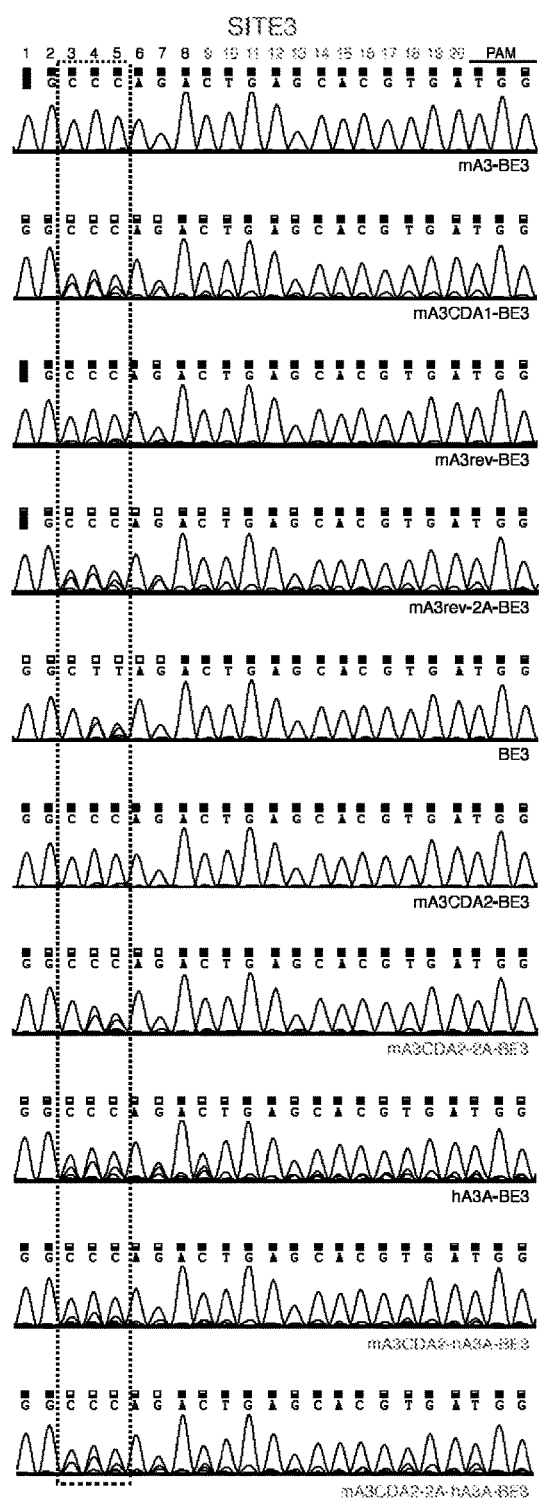
FIG. 6A-C

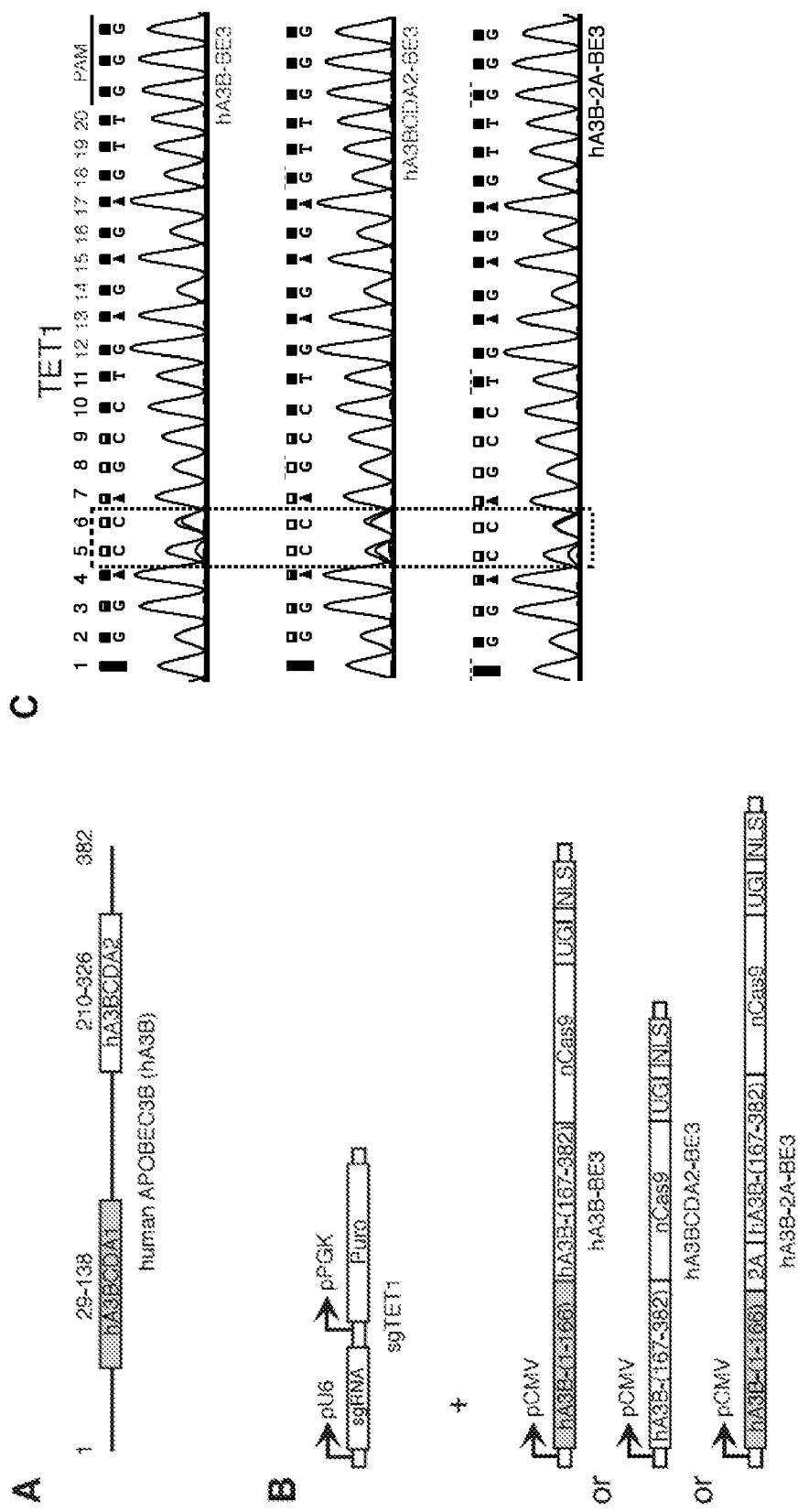
FIG. 7A-C

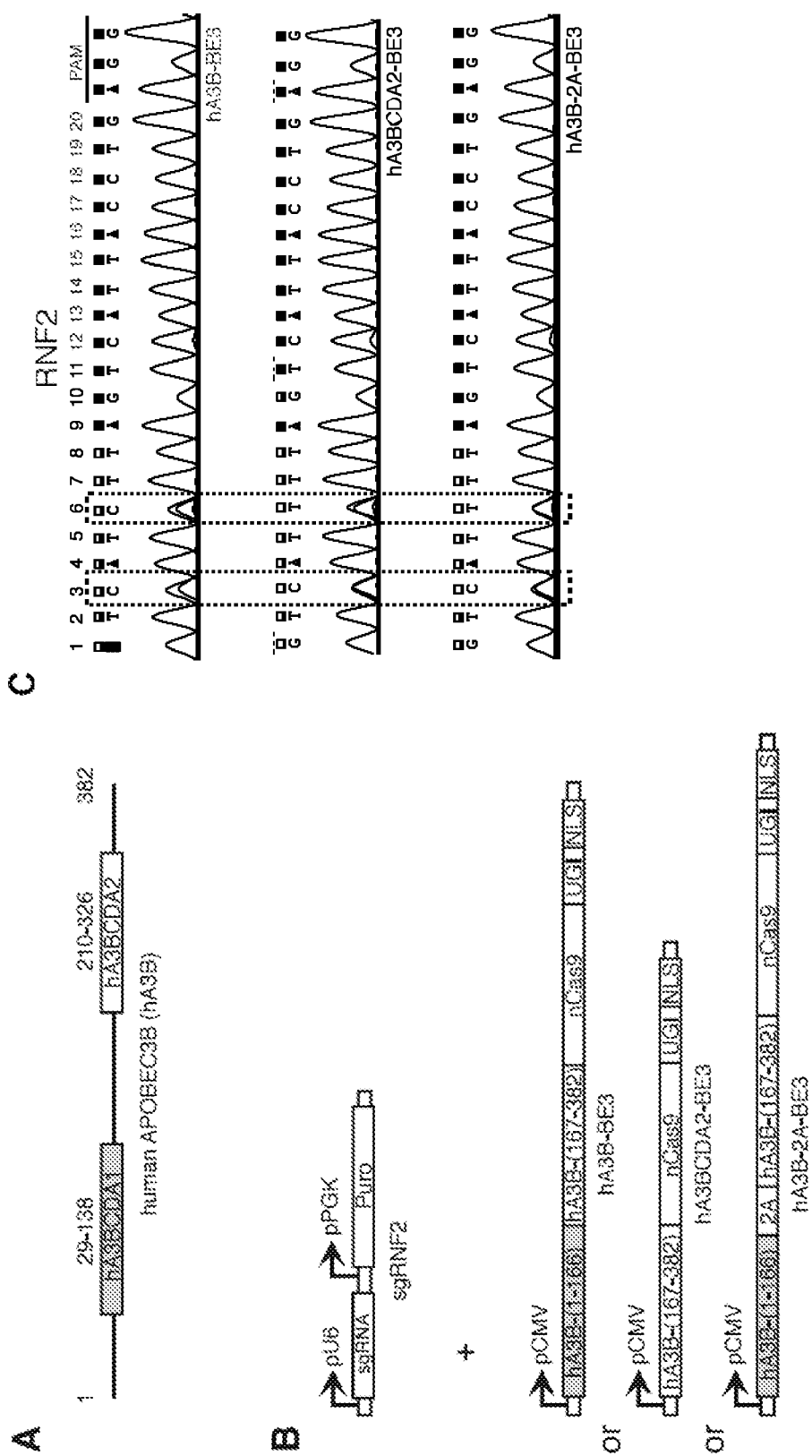
FIG. 8A-C

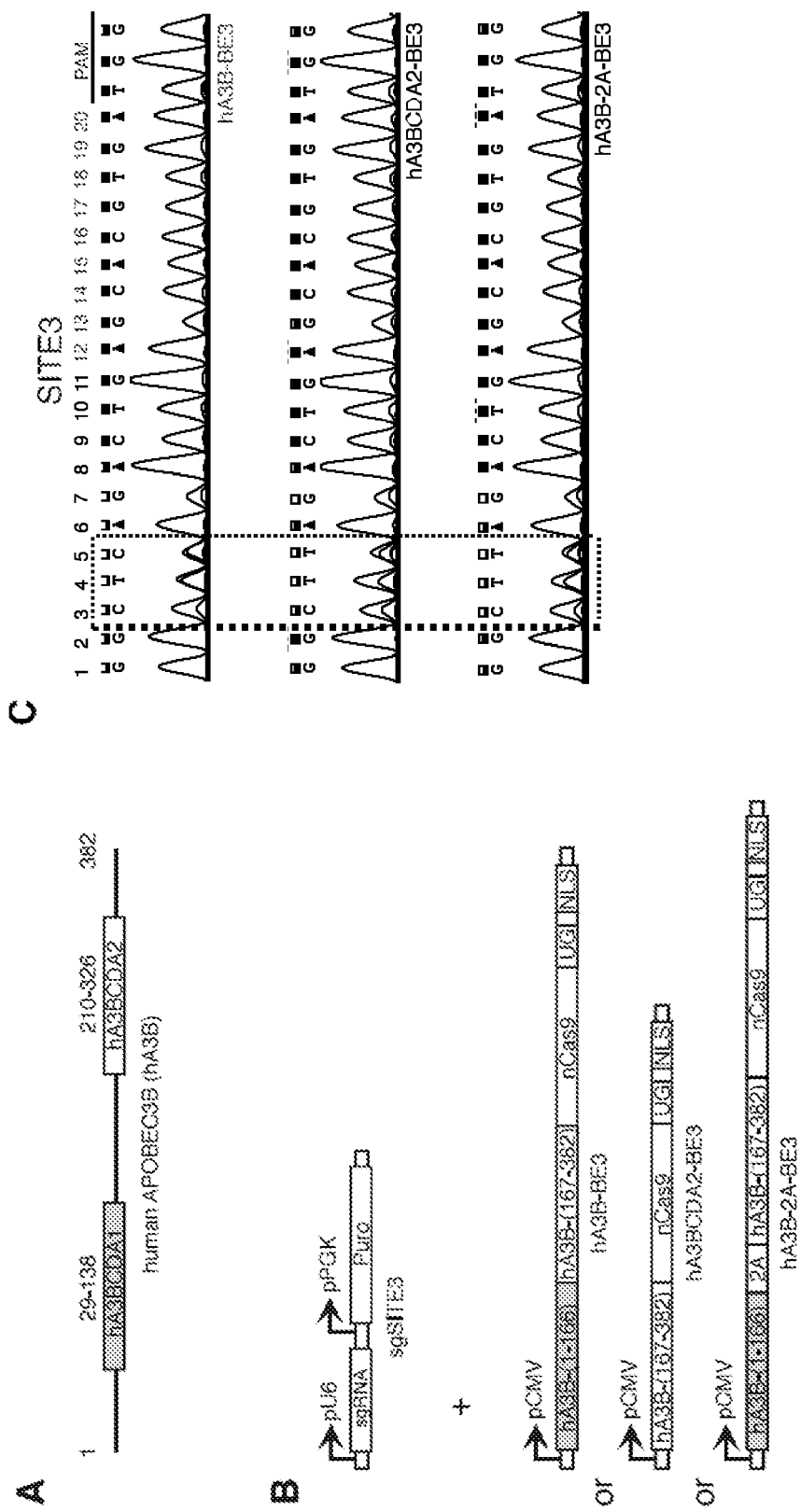
FIG. 9A-C

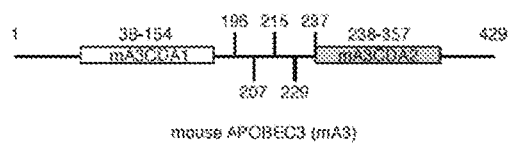
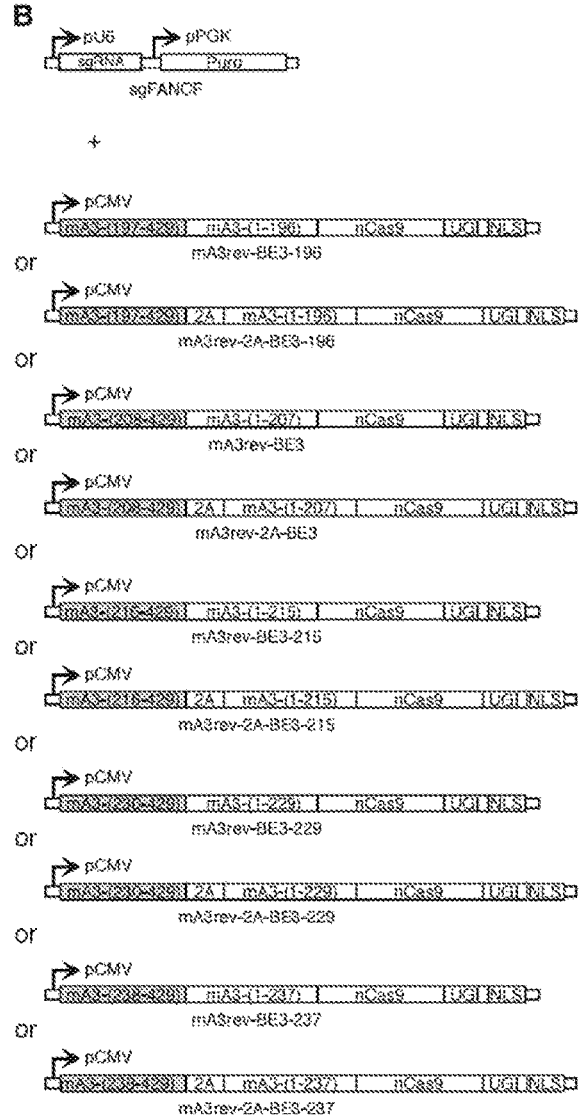
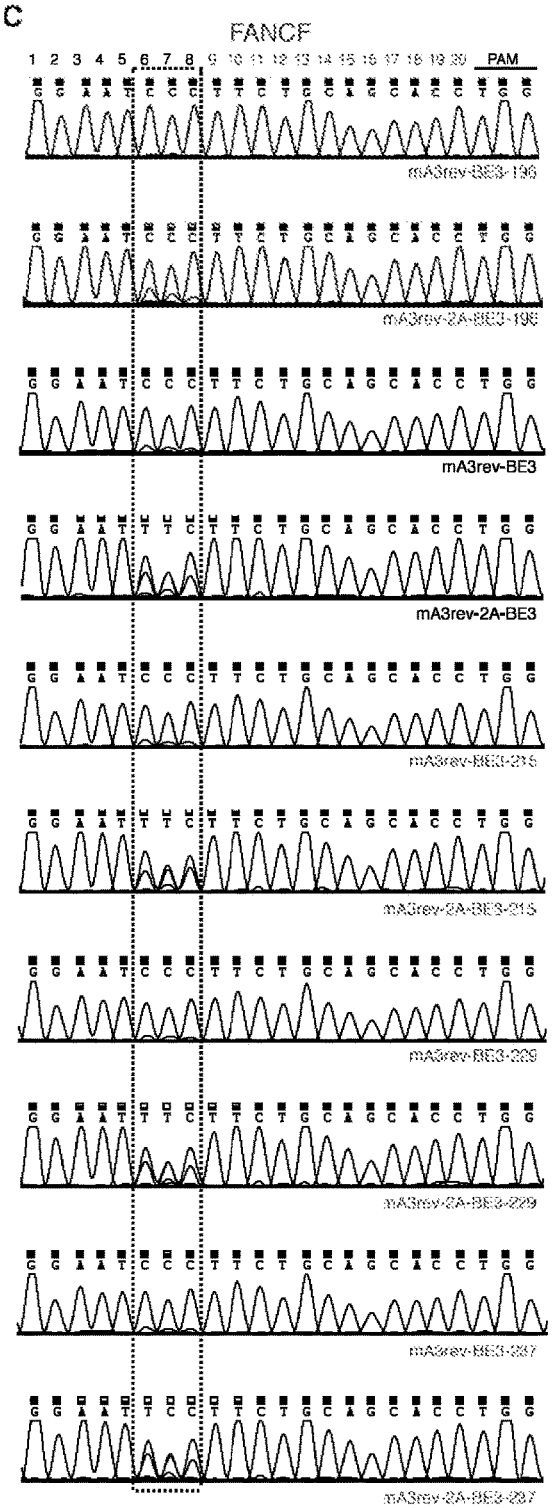
FIG. 10A-C

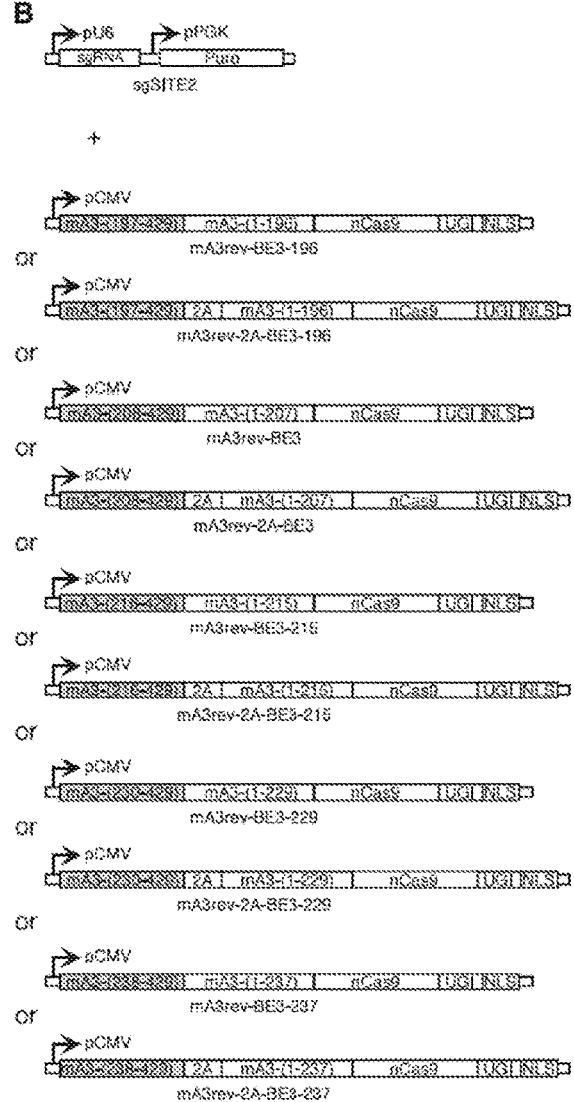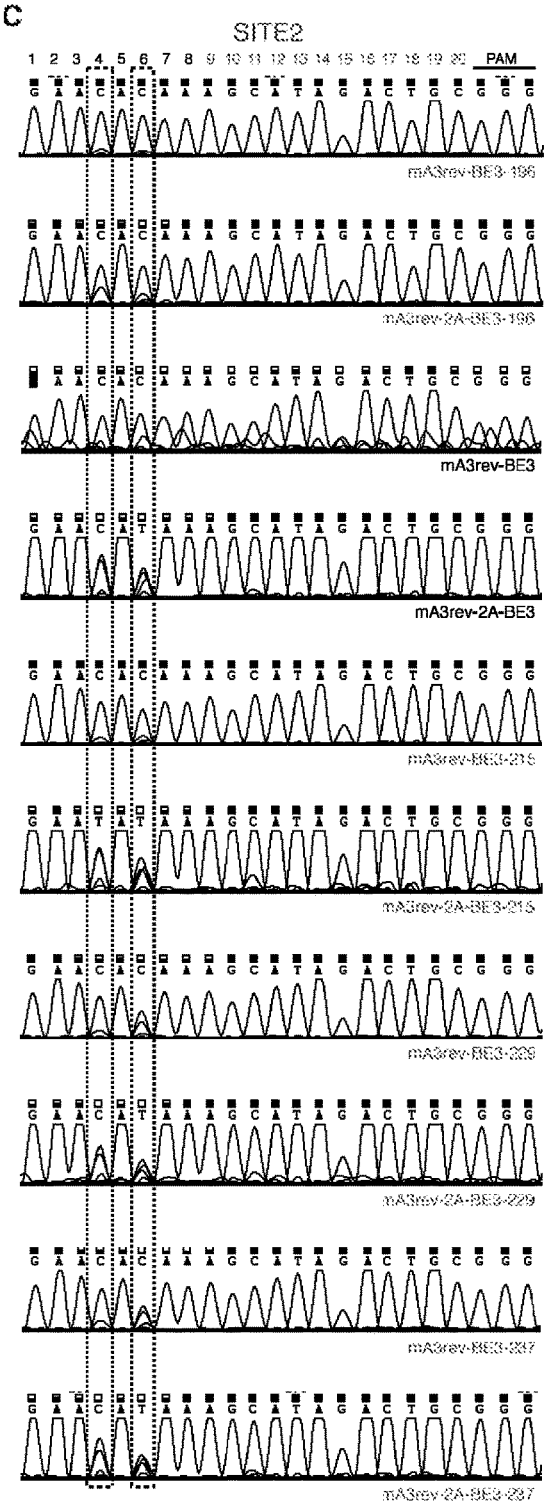
FIG. 11A-C

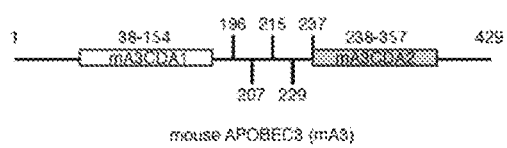
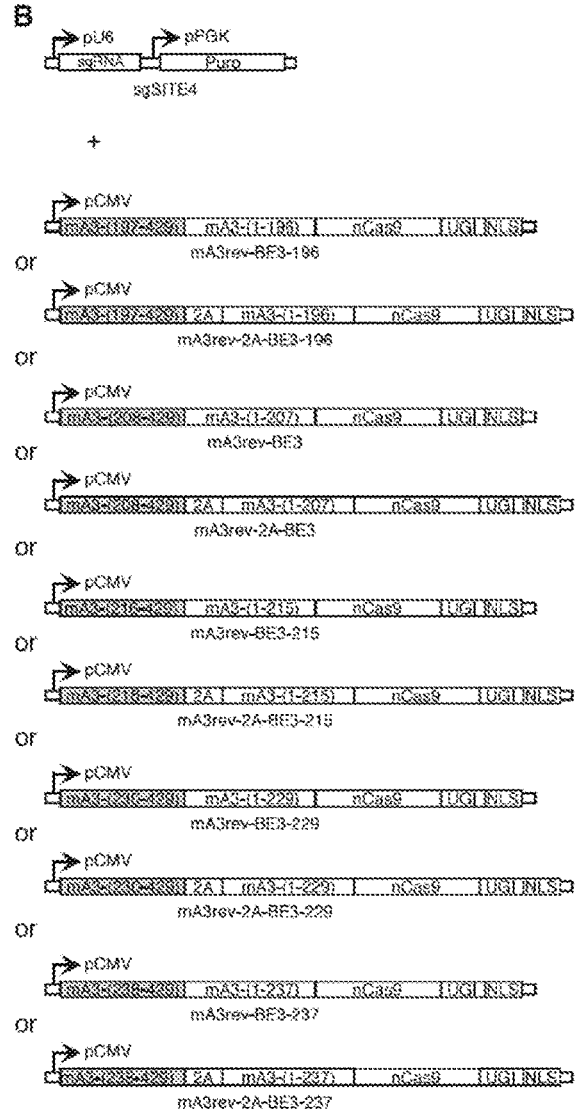
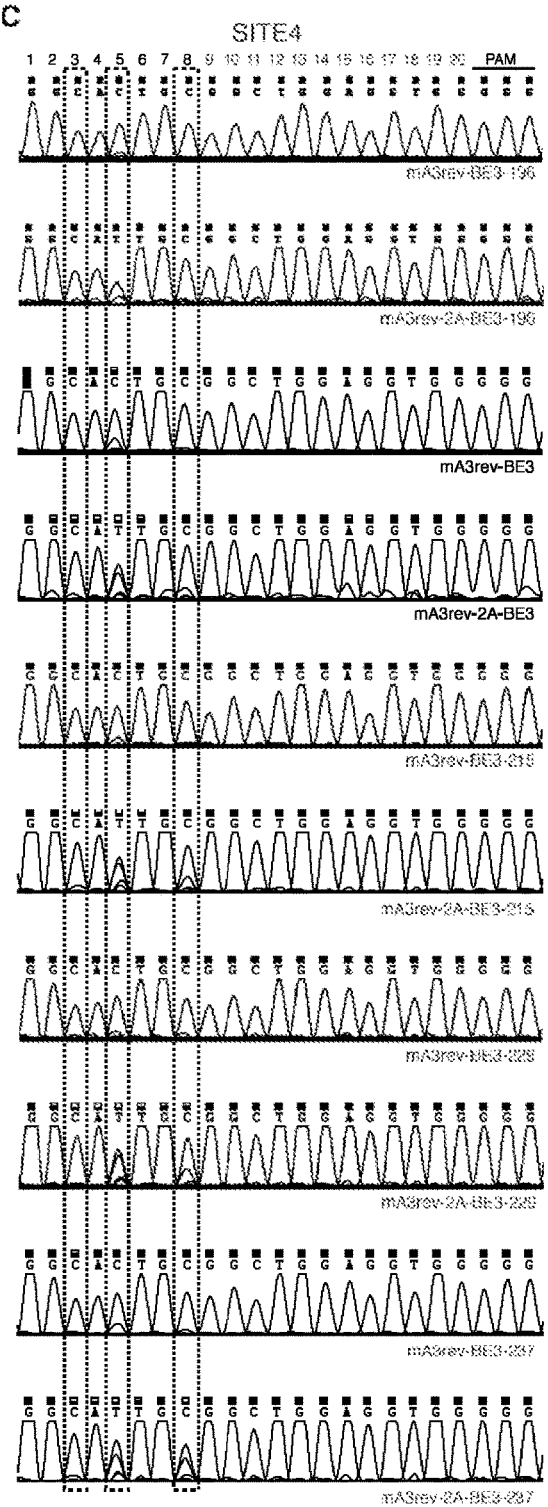
FIG. 12A-C

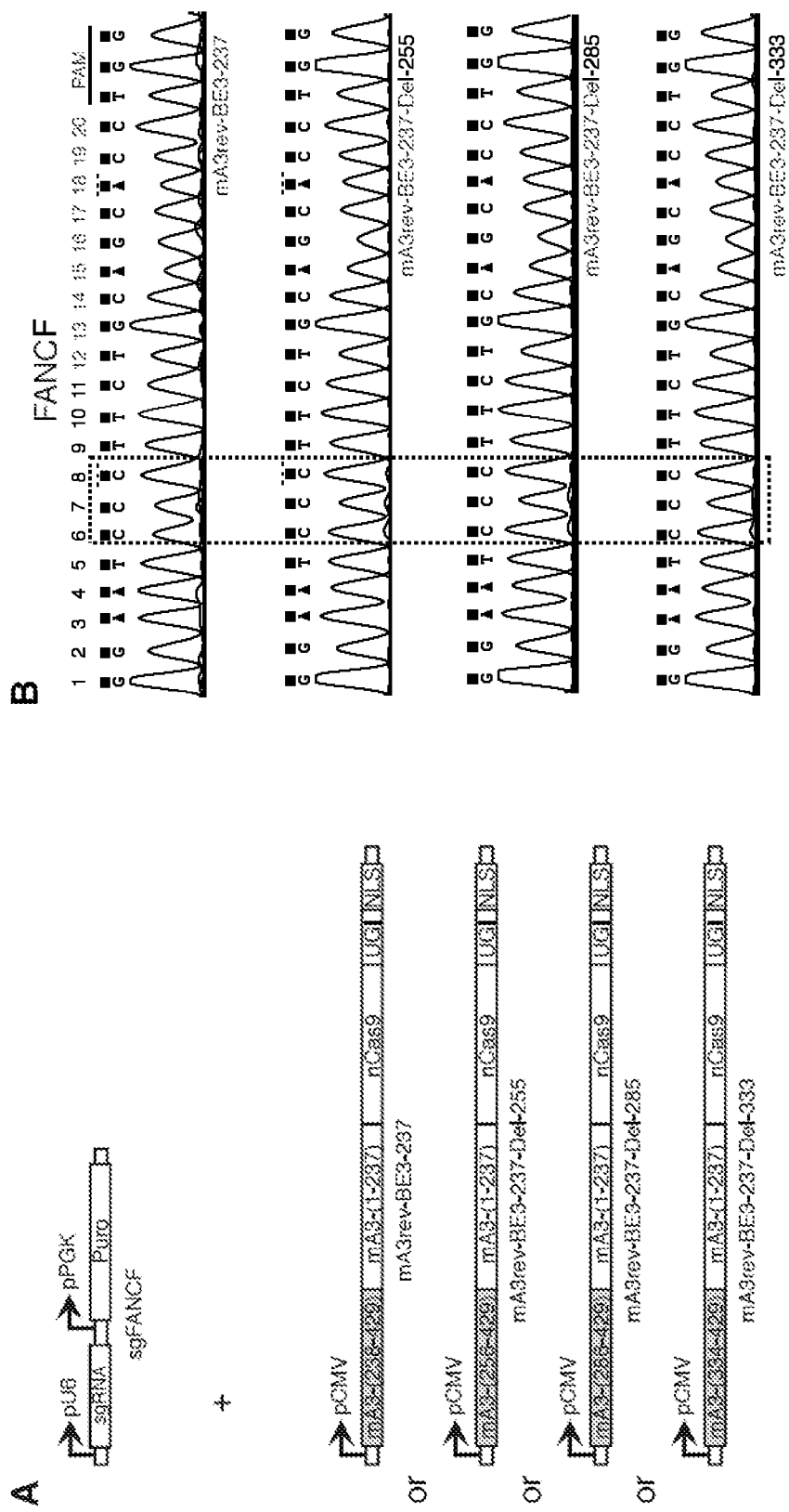
FIG. 13A-B

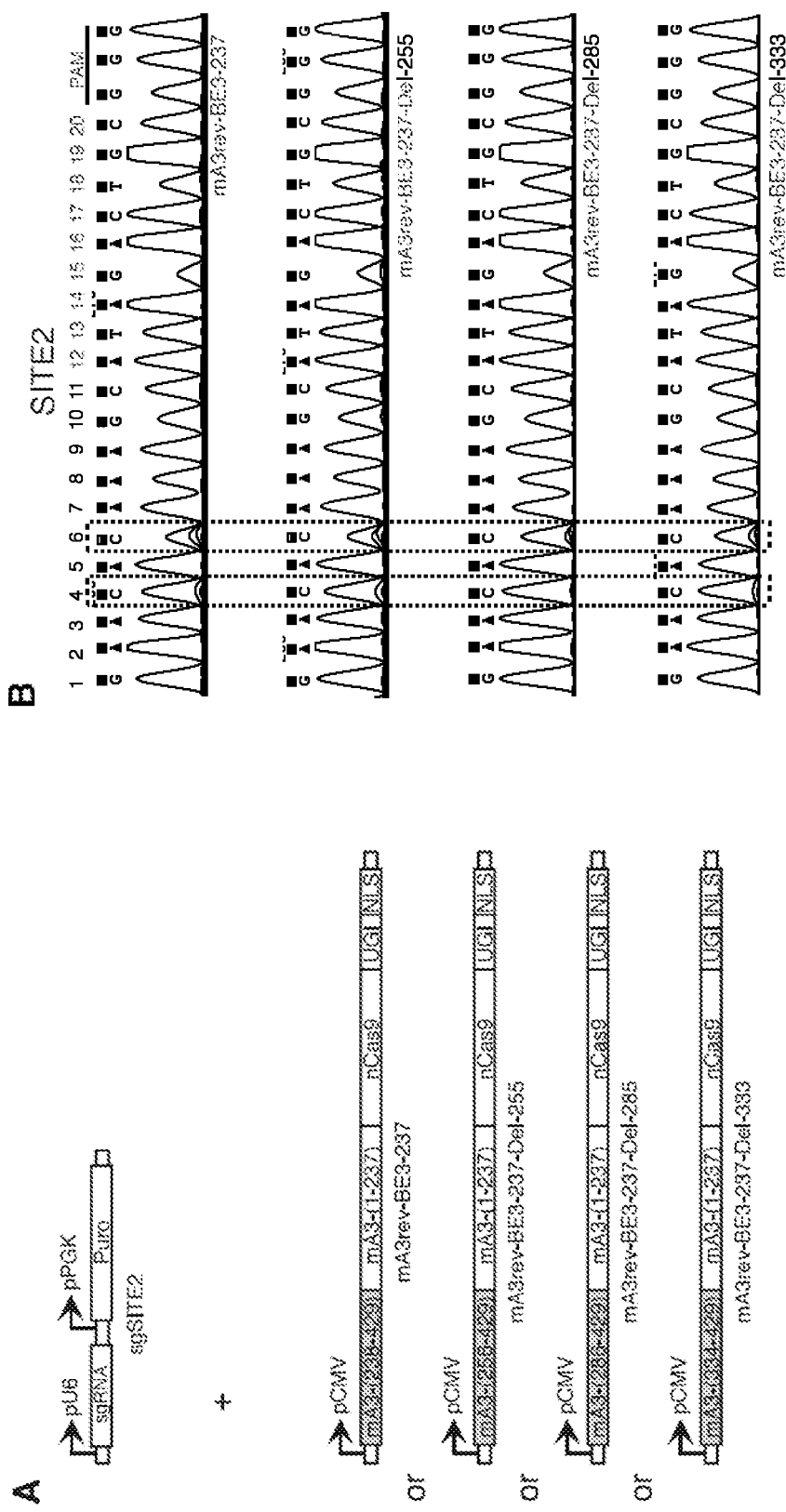
FIG. 14A-B

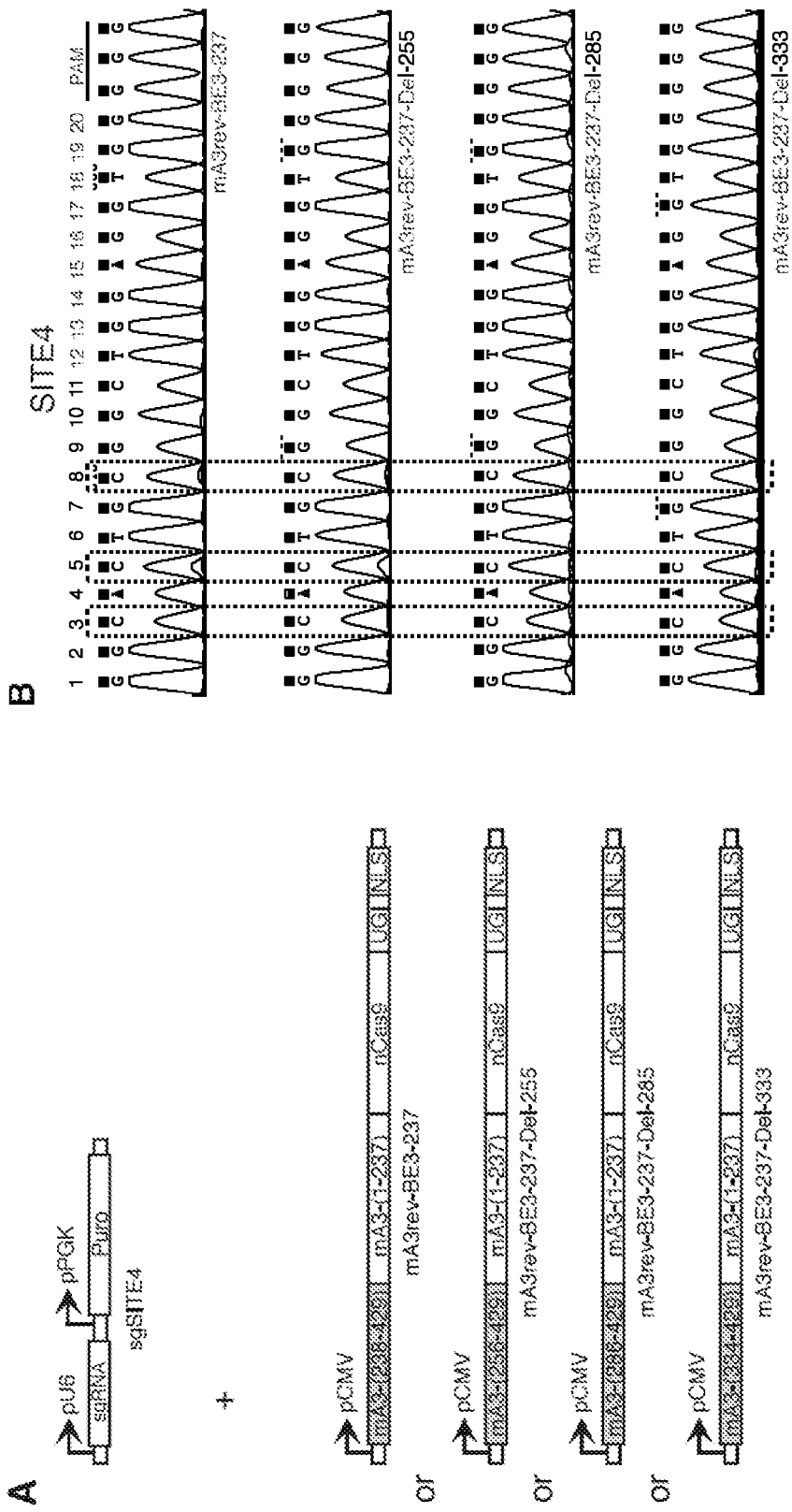
FIG. 15A-B

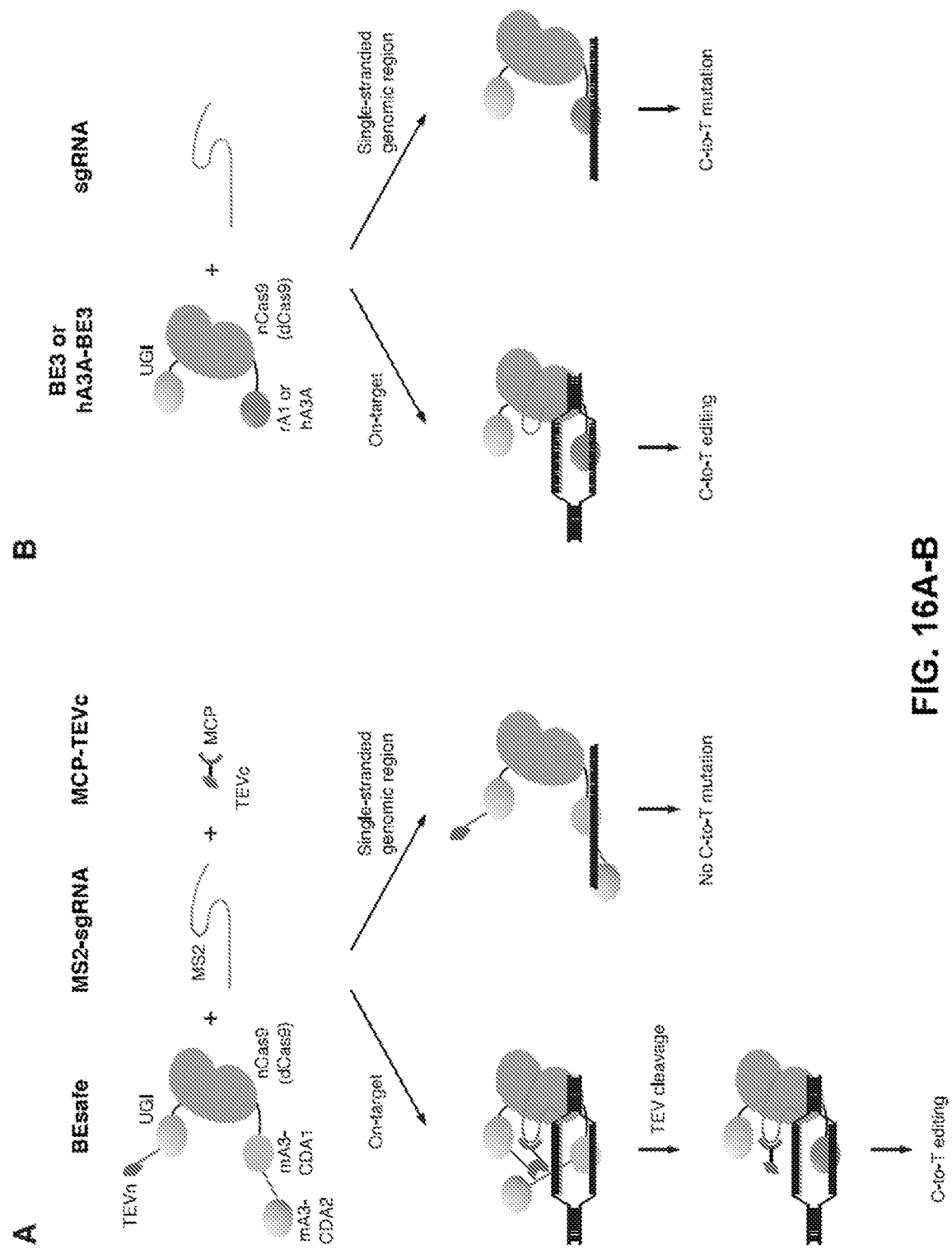
FIG. 16A-B

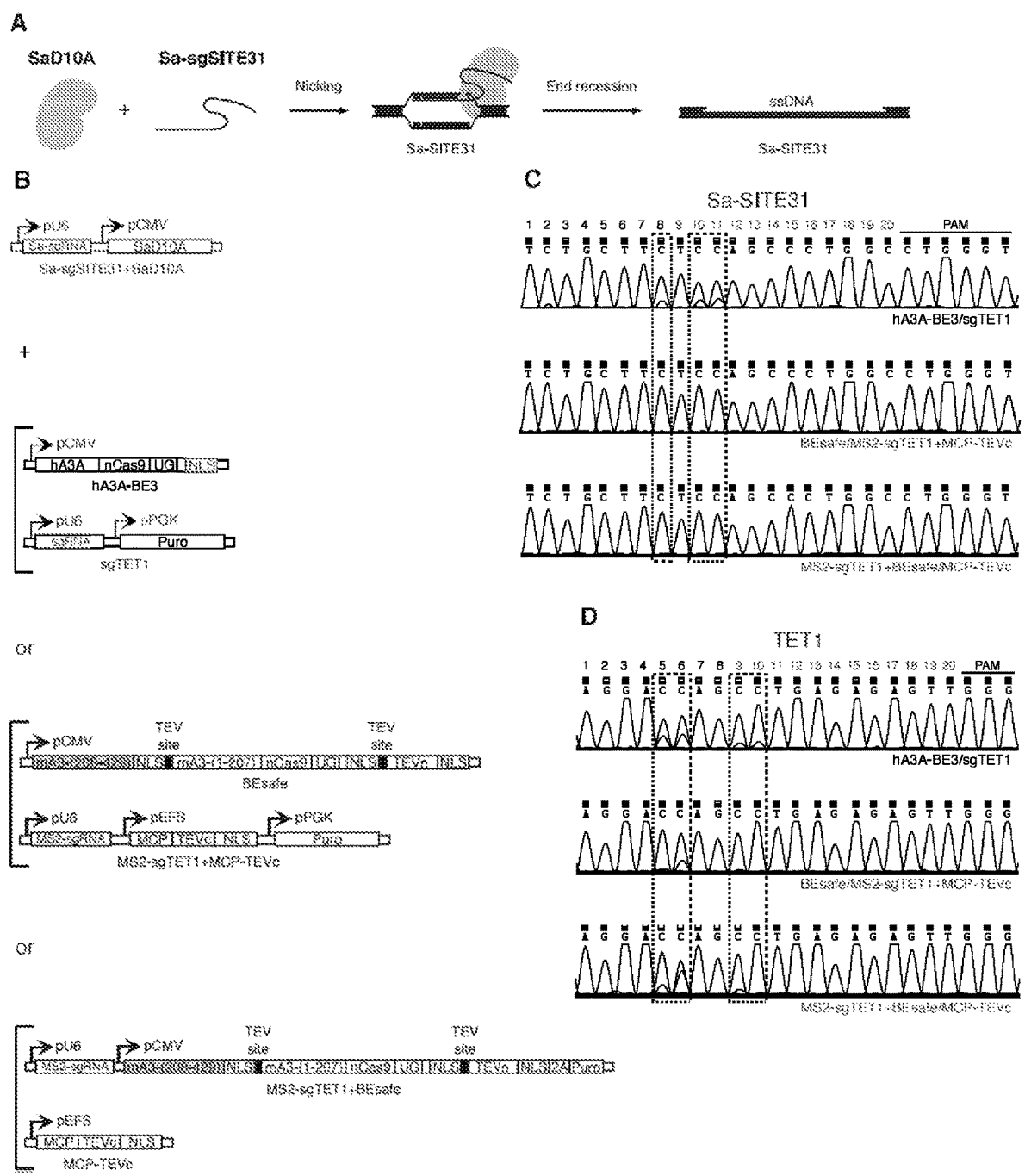
FIG. 17A-D

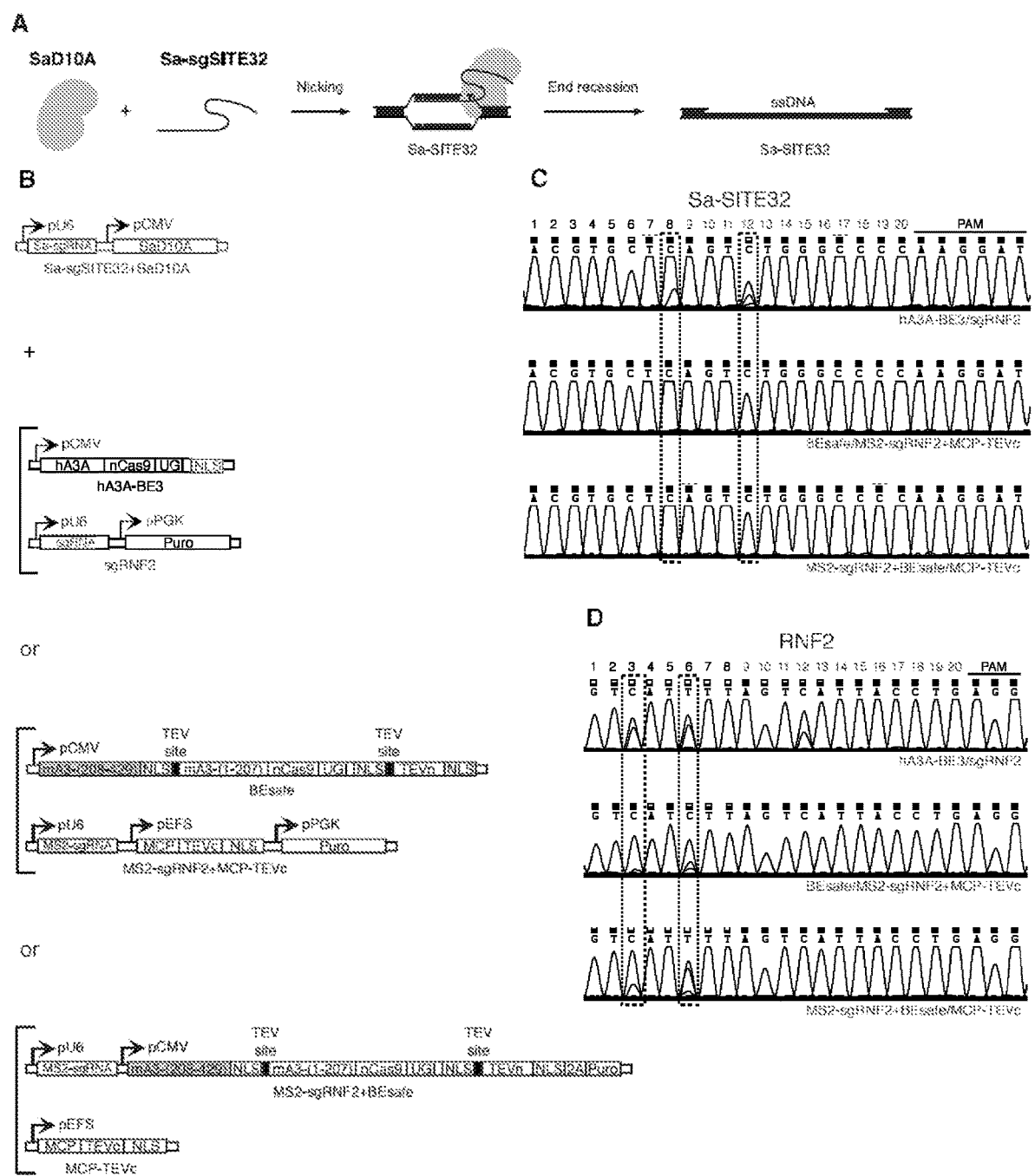
FIG. 18A-D

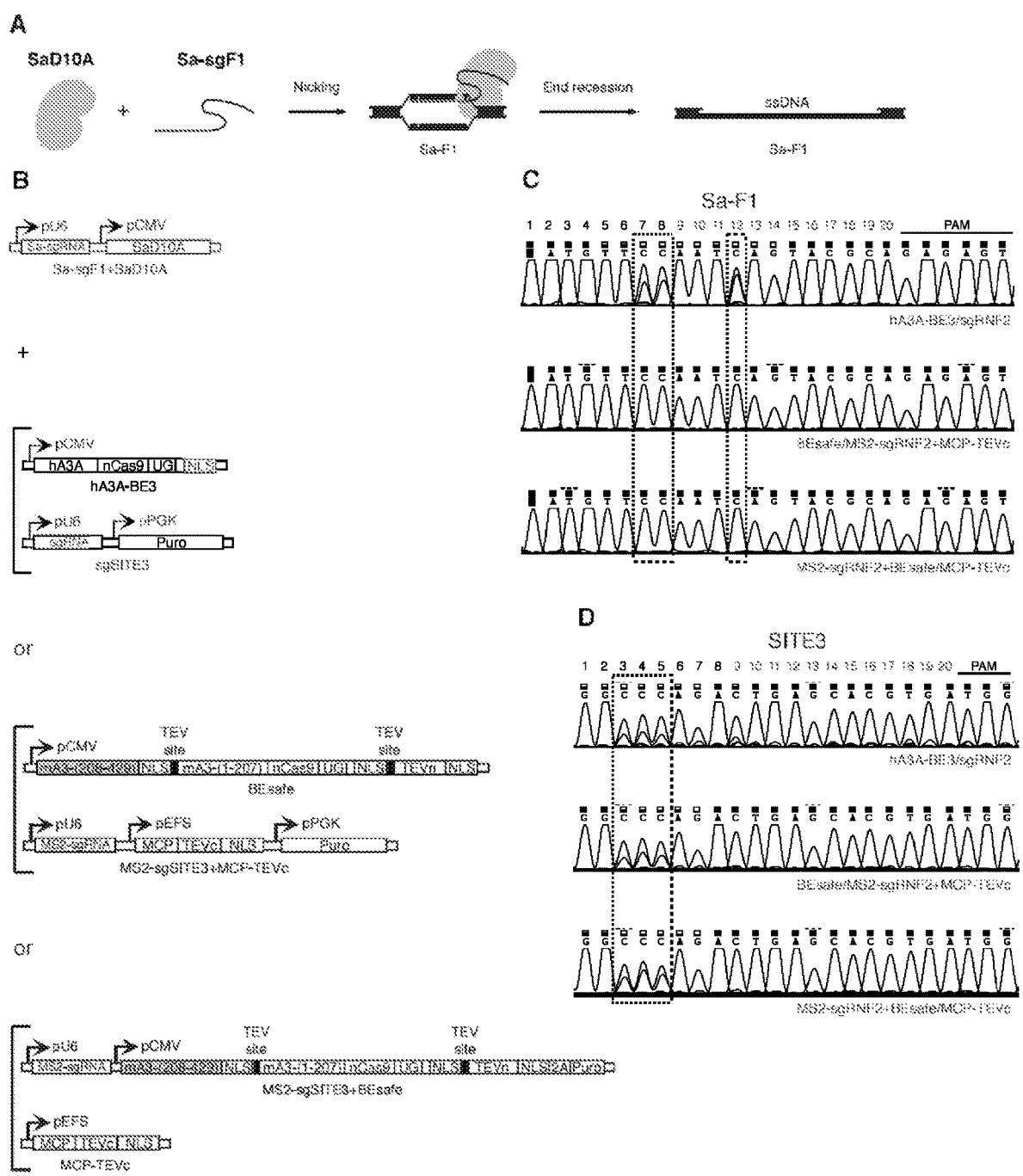
FIG. 19A-D

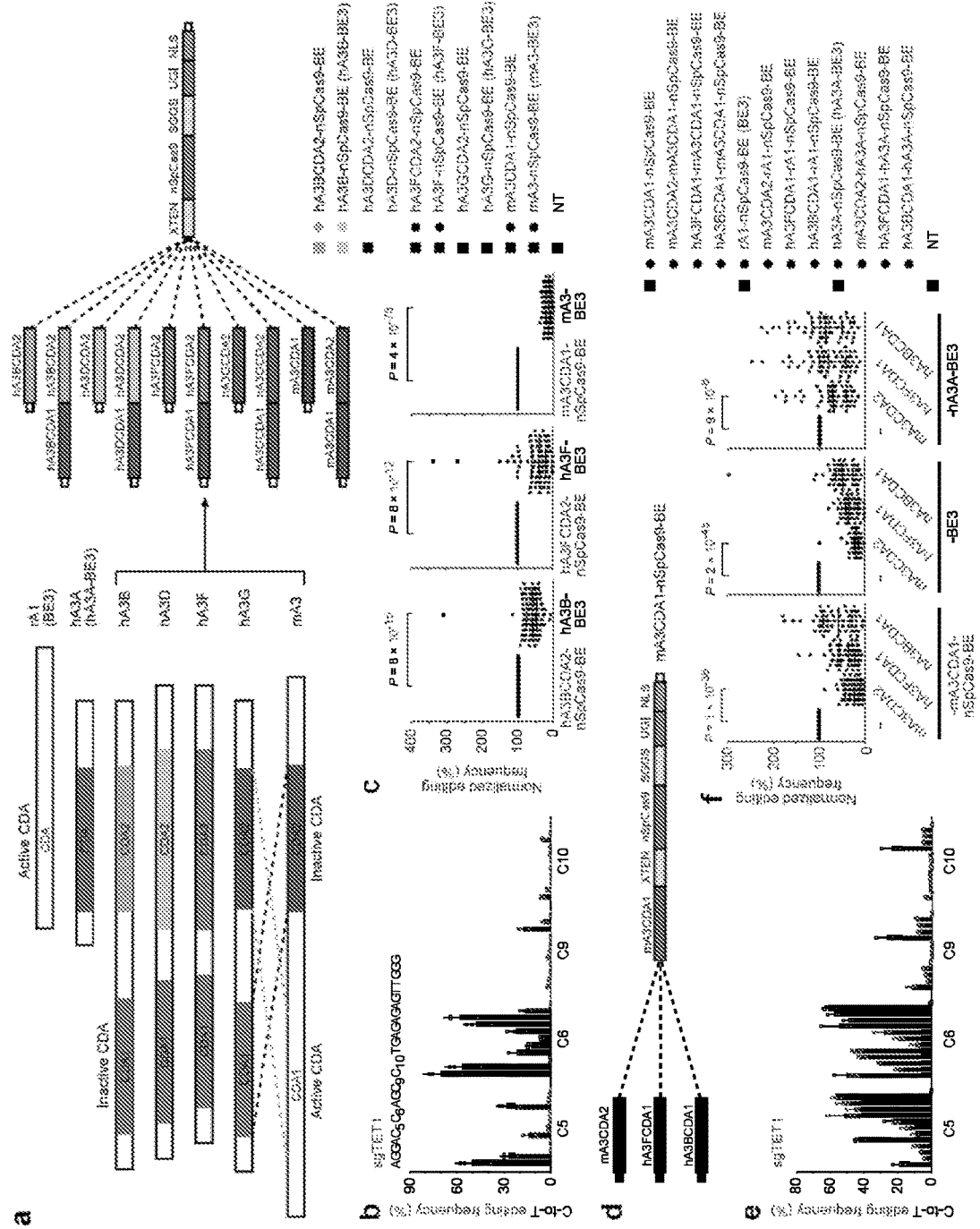
FIG. 20a-f

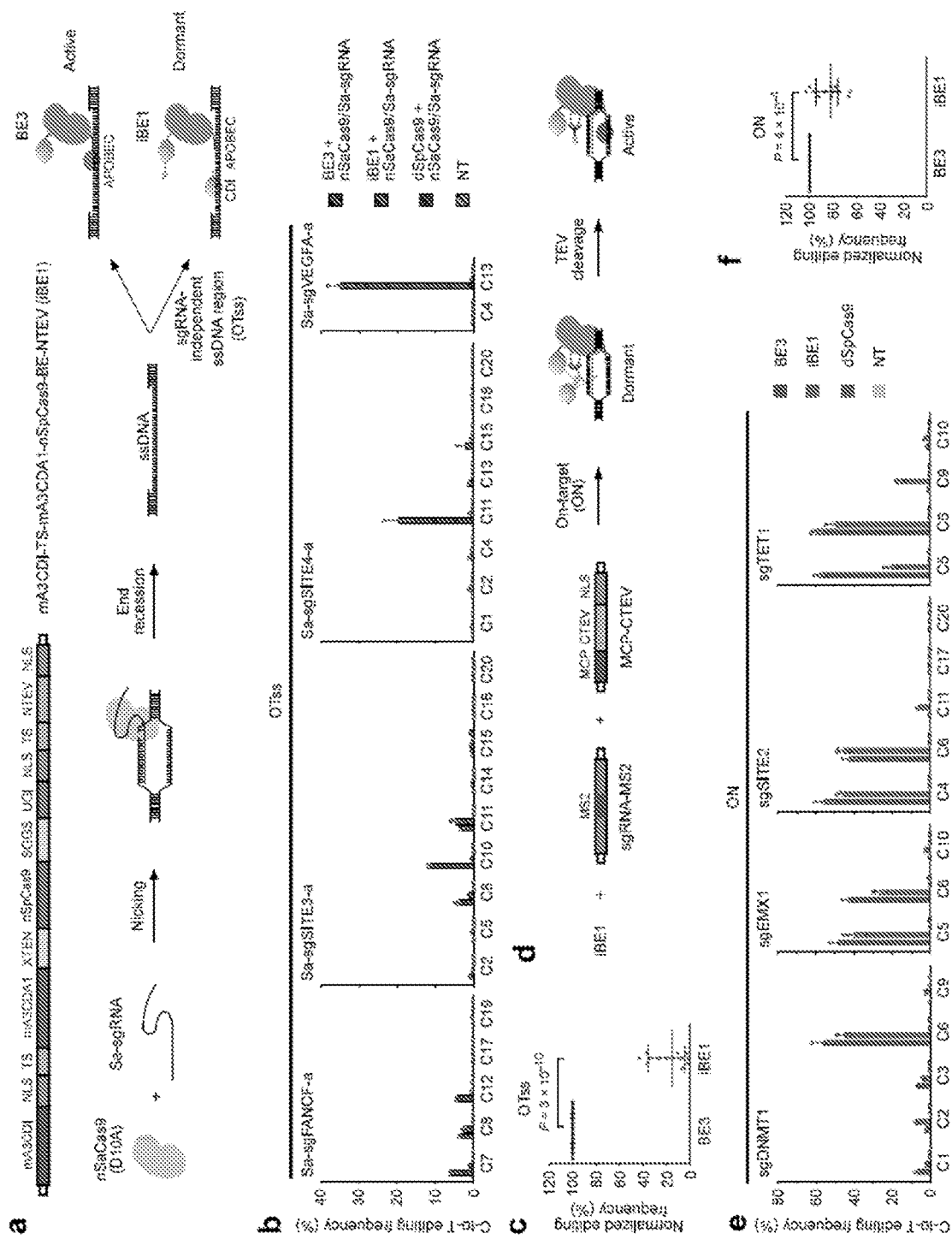
FIG. 21a-f

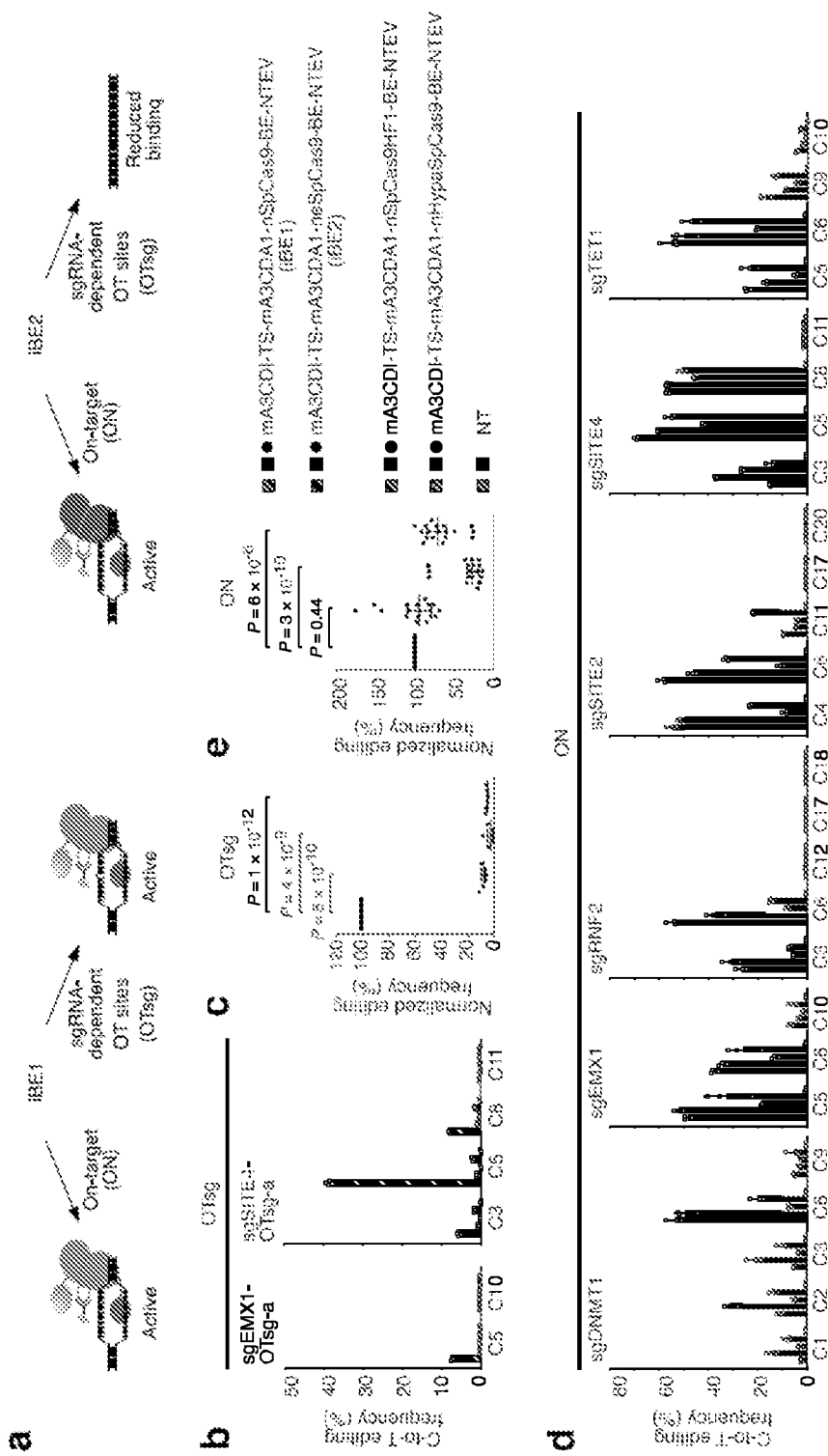
FIG. 22a-e

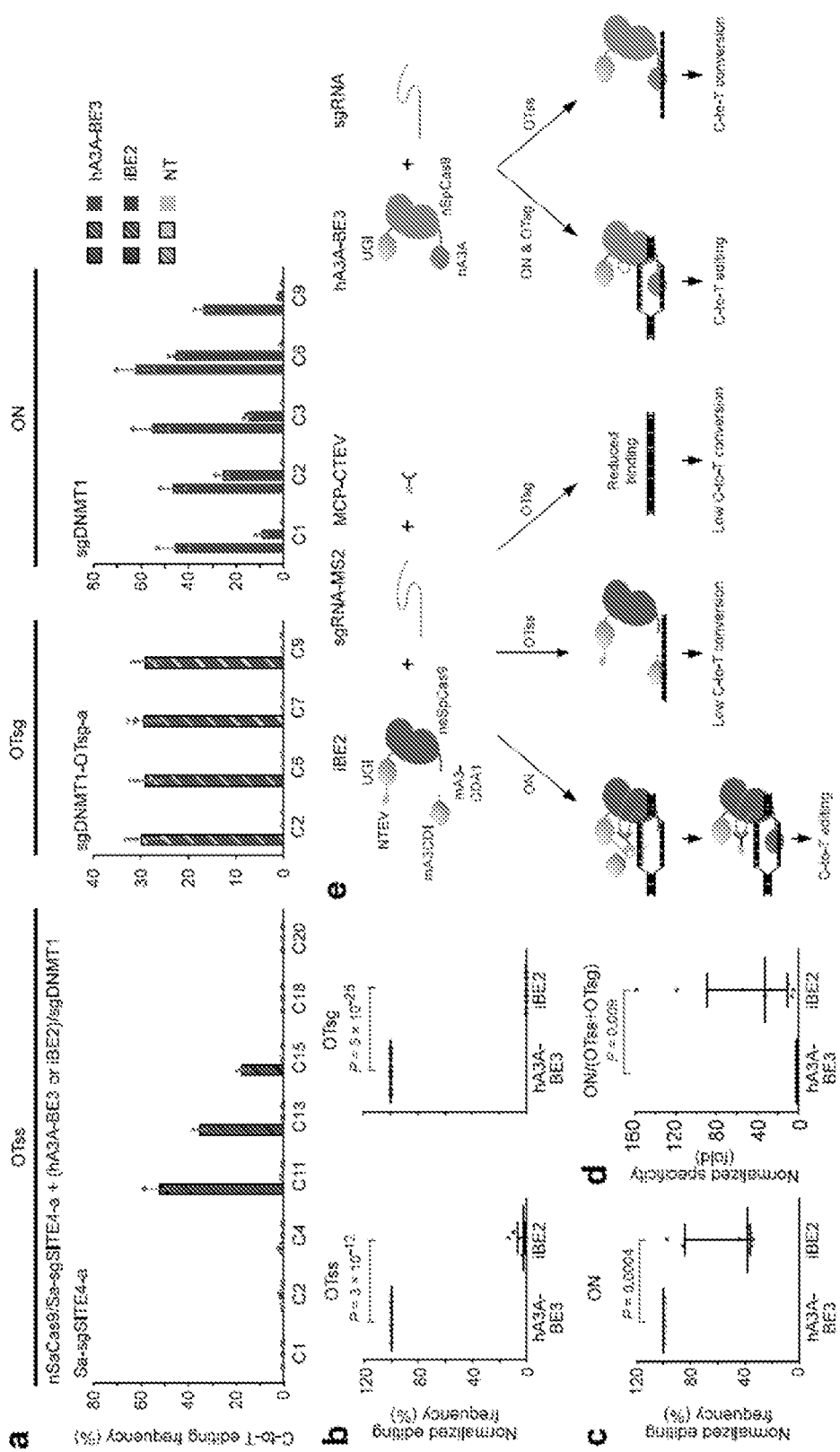
FIG. 23a-e

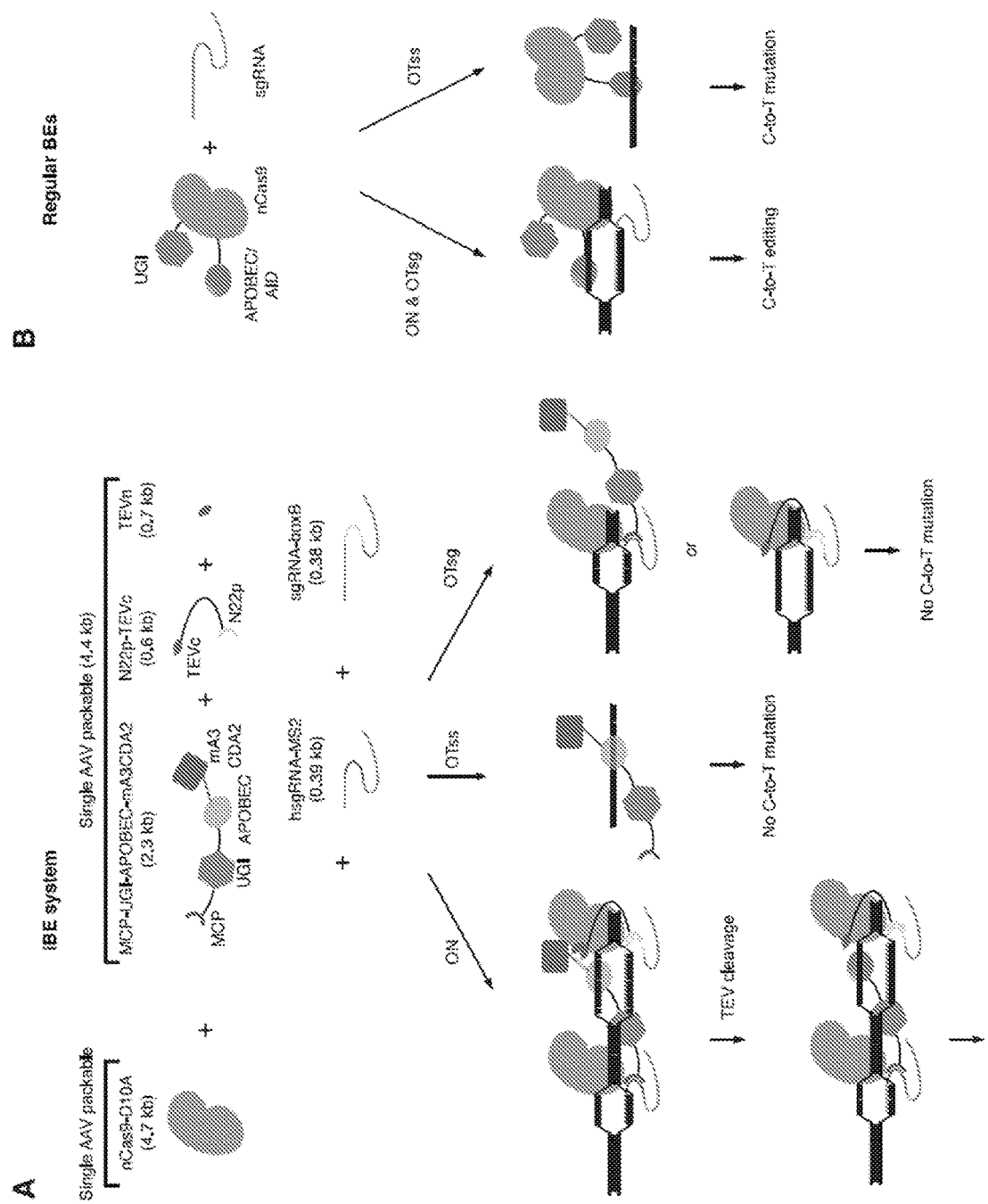
FIG. 24A-B

A
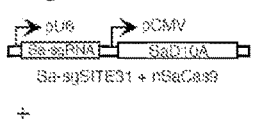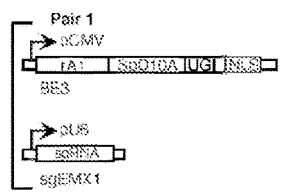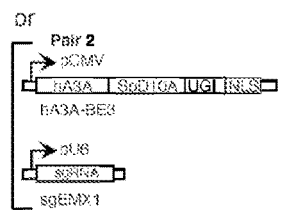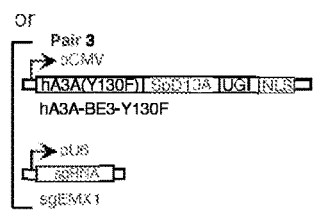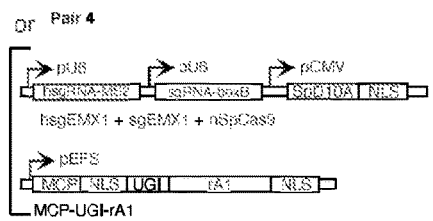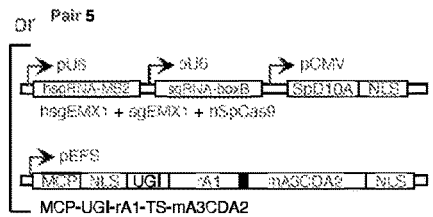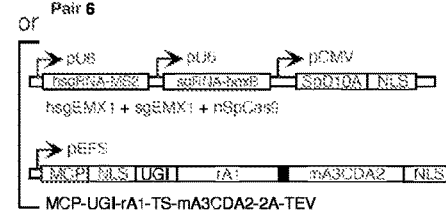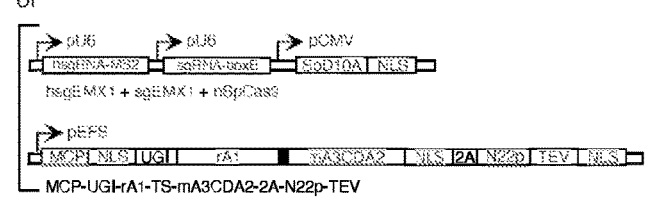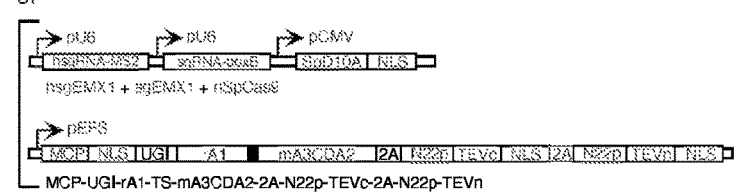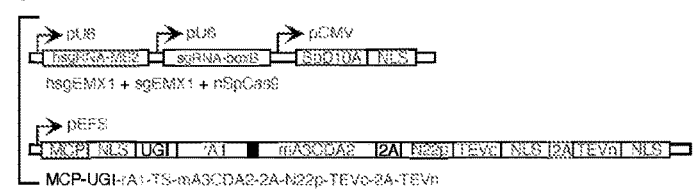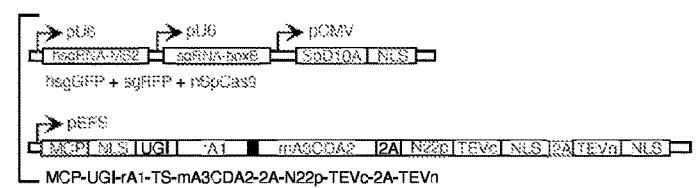
FIG. 26A

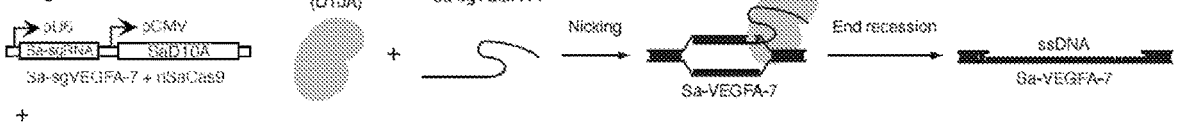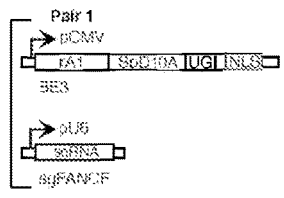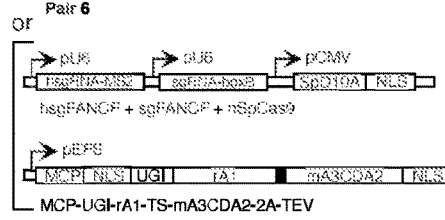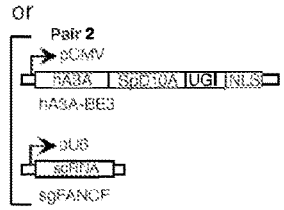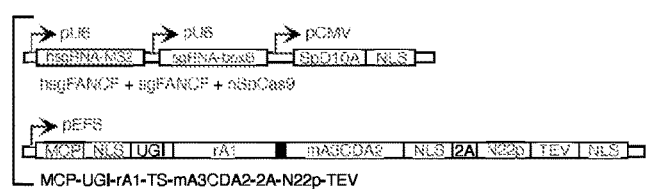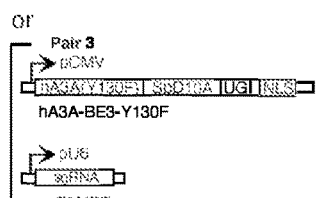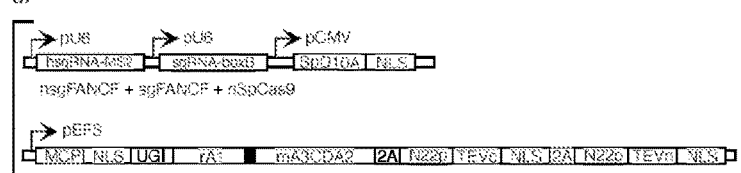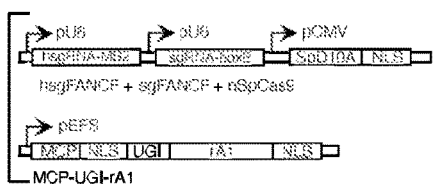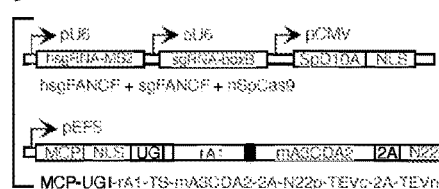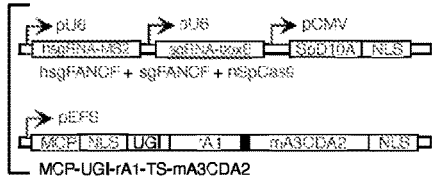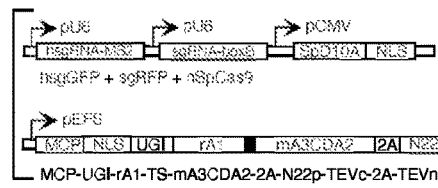
FIG. 27A A
To generate OTss
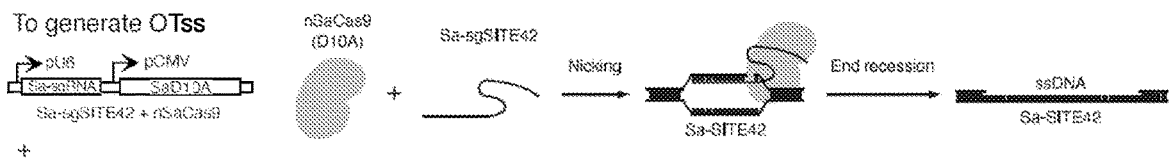
To induce on-target editing
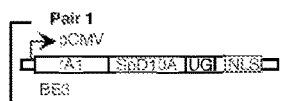
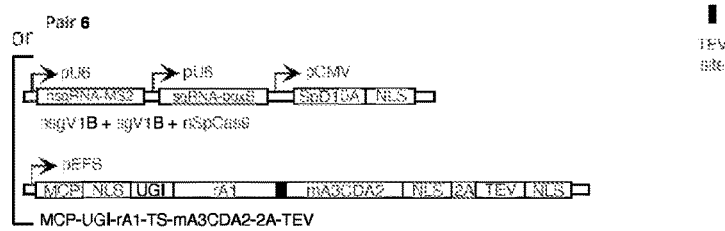
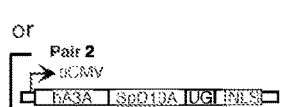
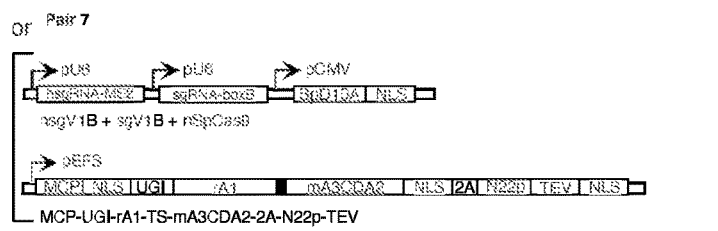
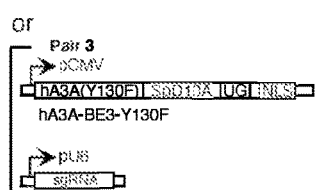
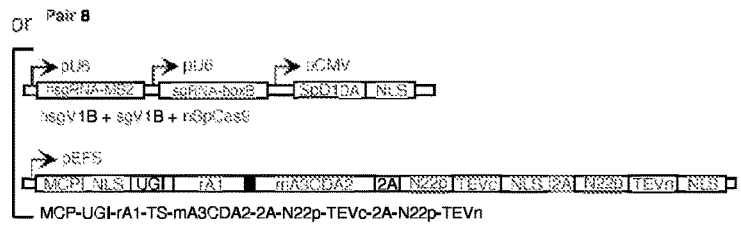
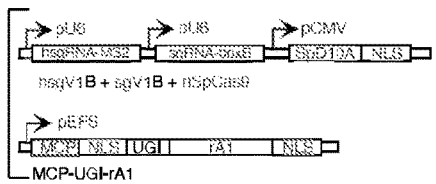
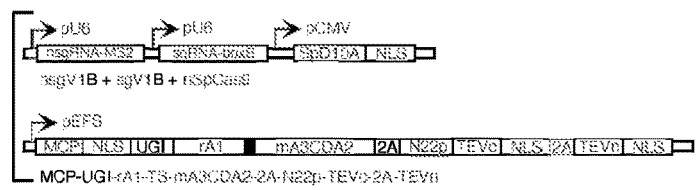
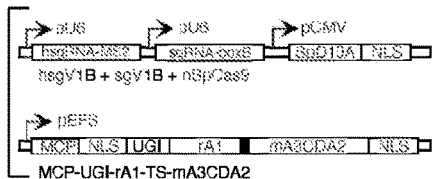
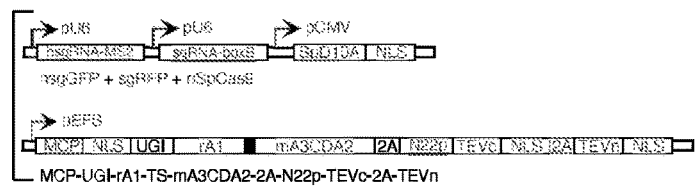
FIG. 28A

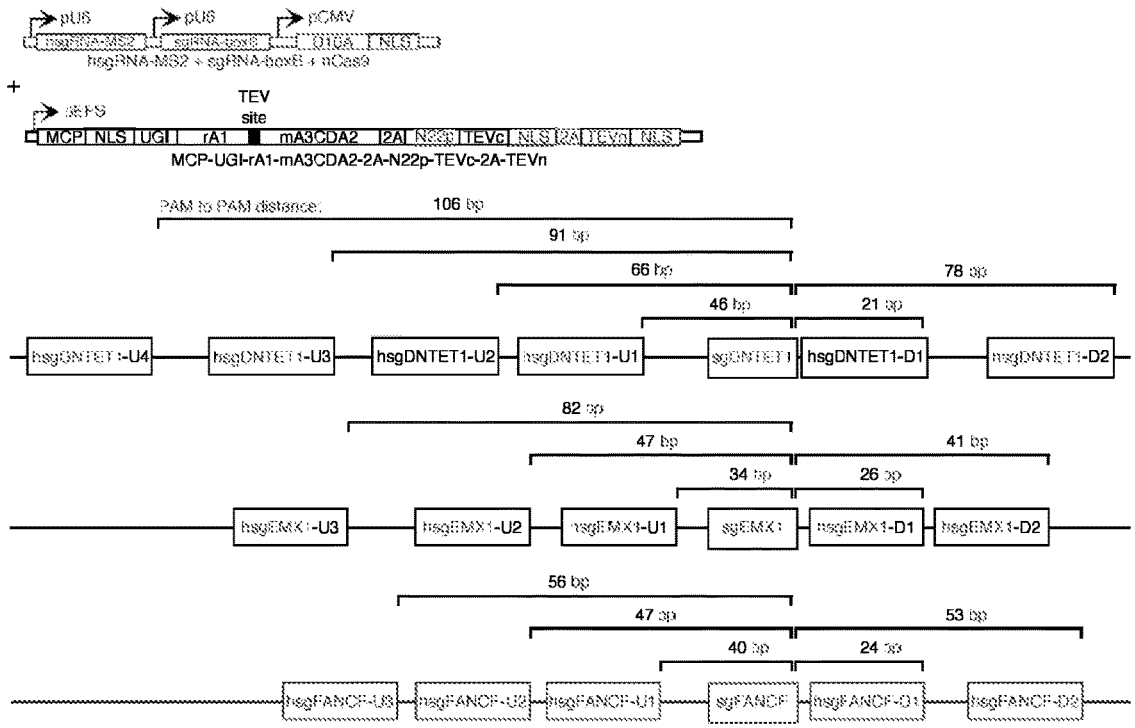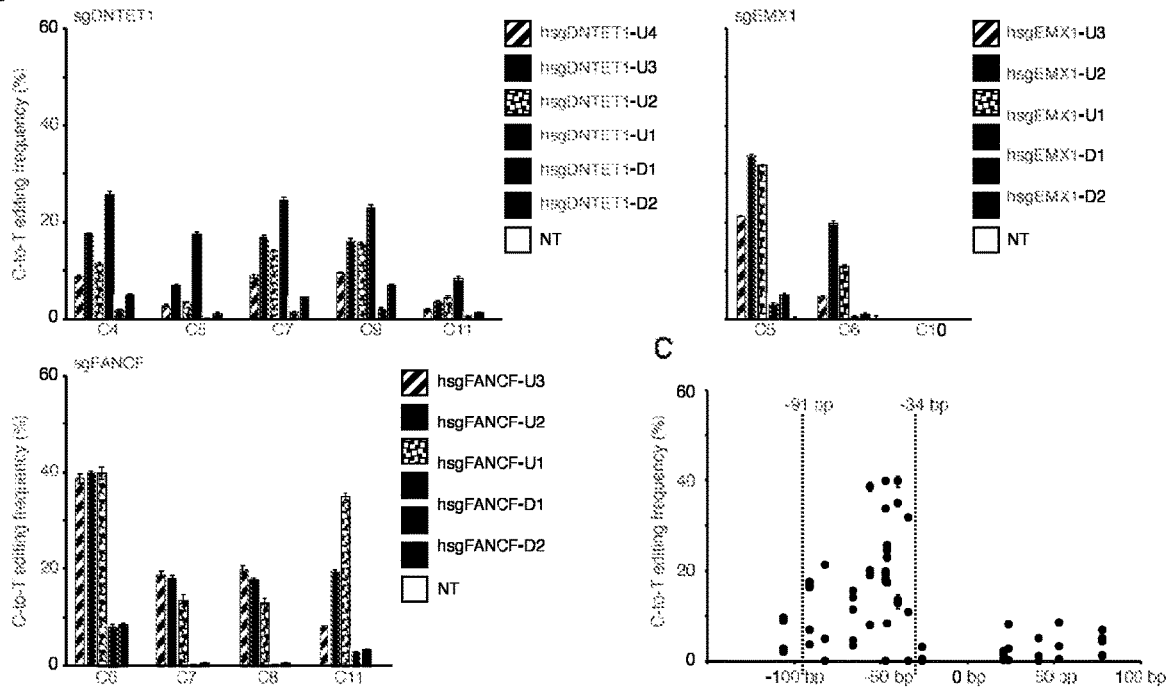
FIG. 29A-C

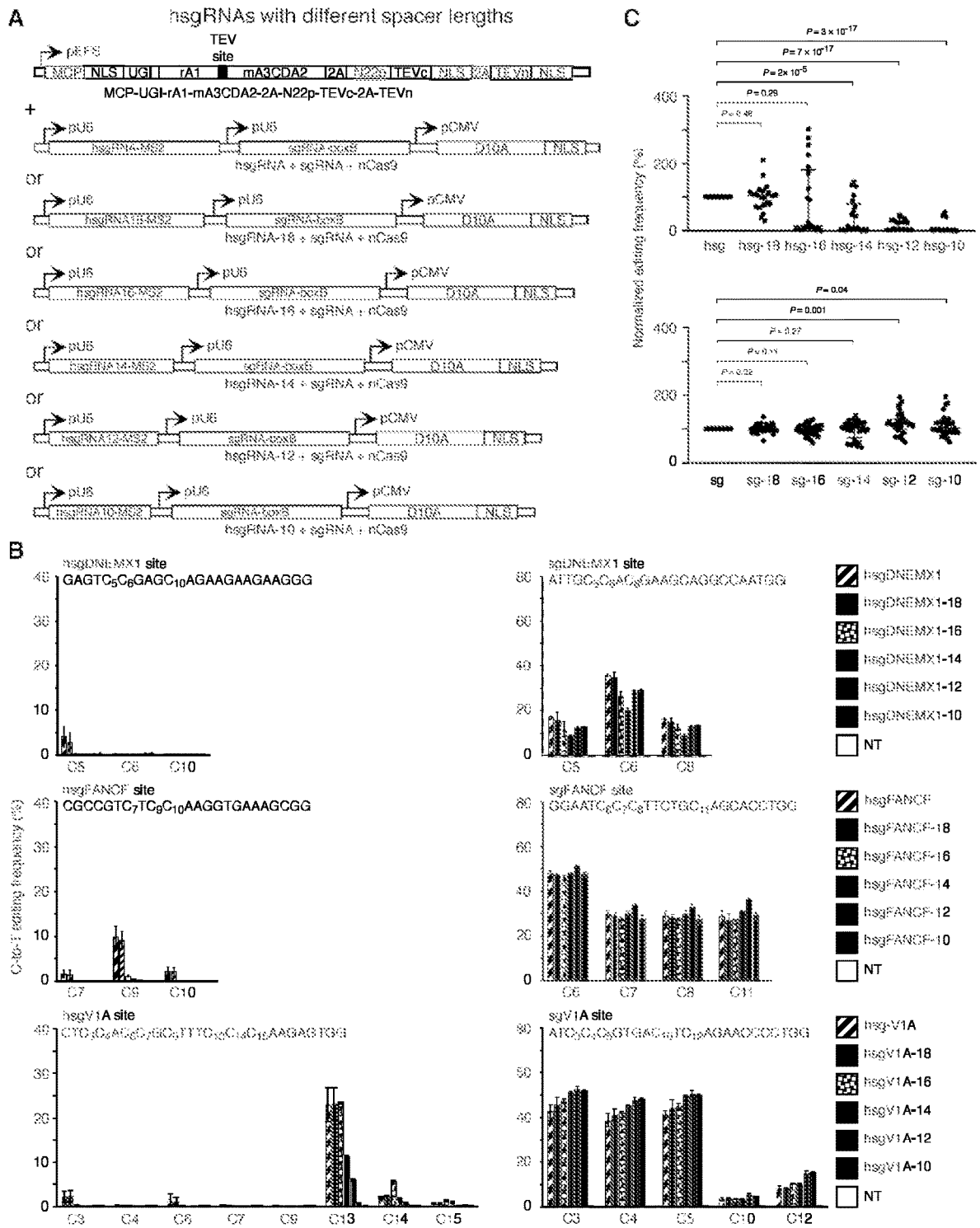
FIG. 30A-C

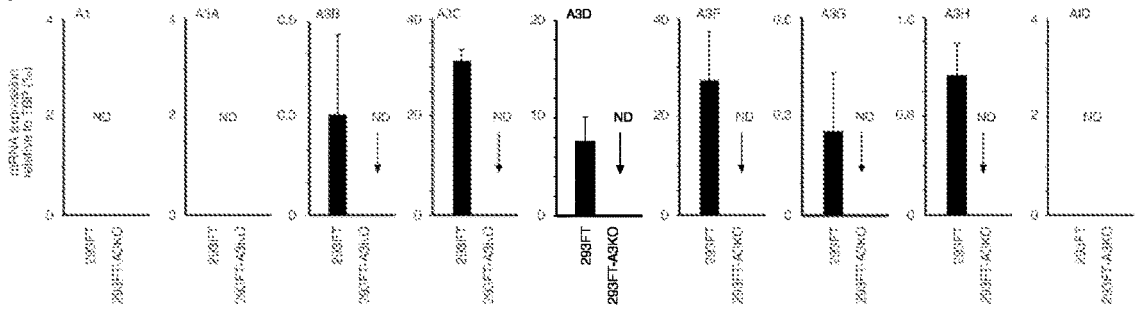
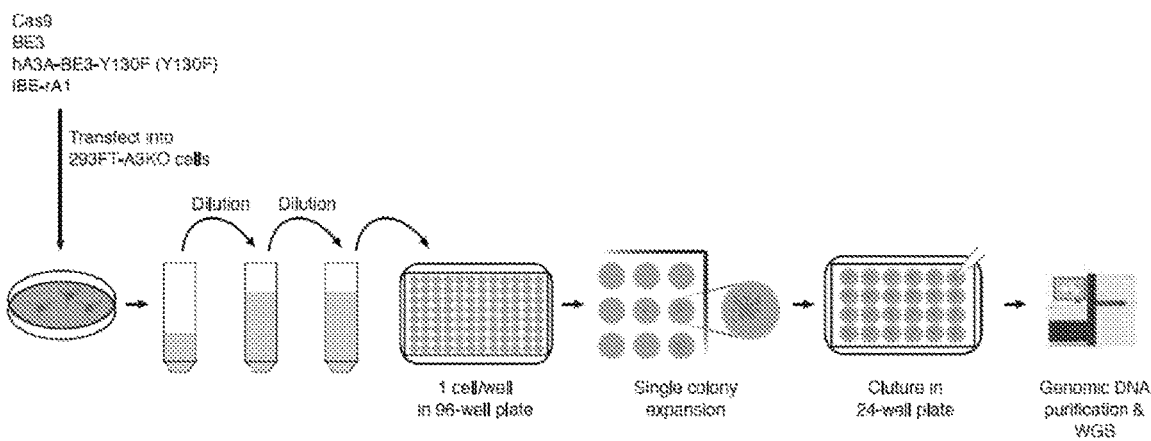
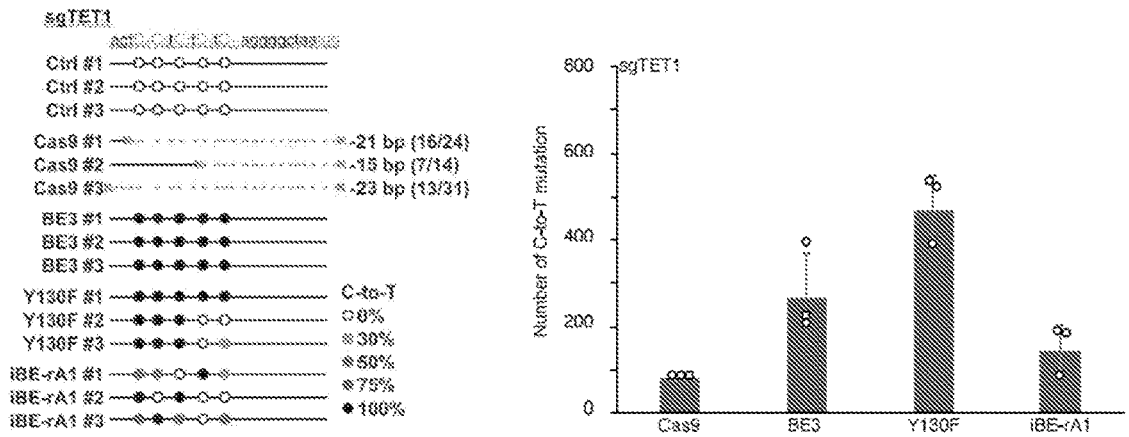
FIG. 32A-C

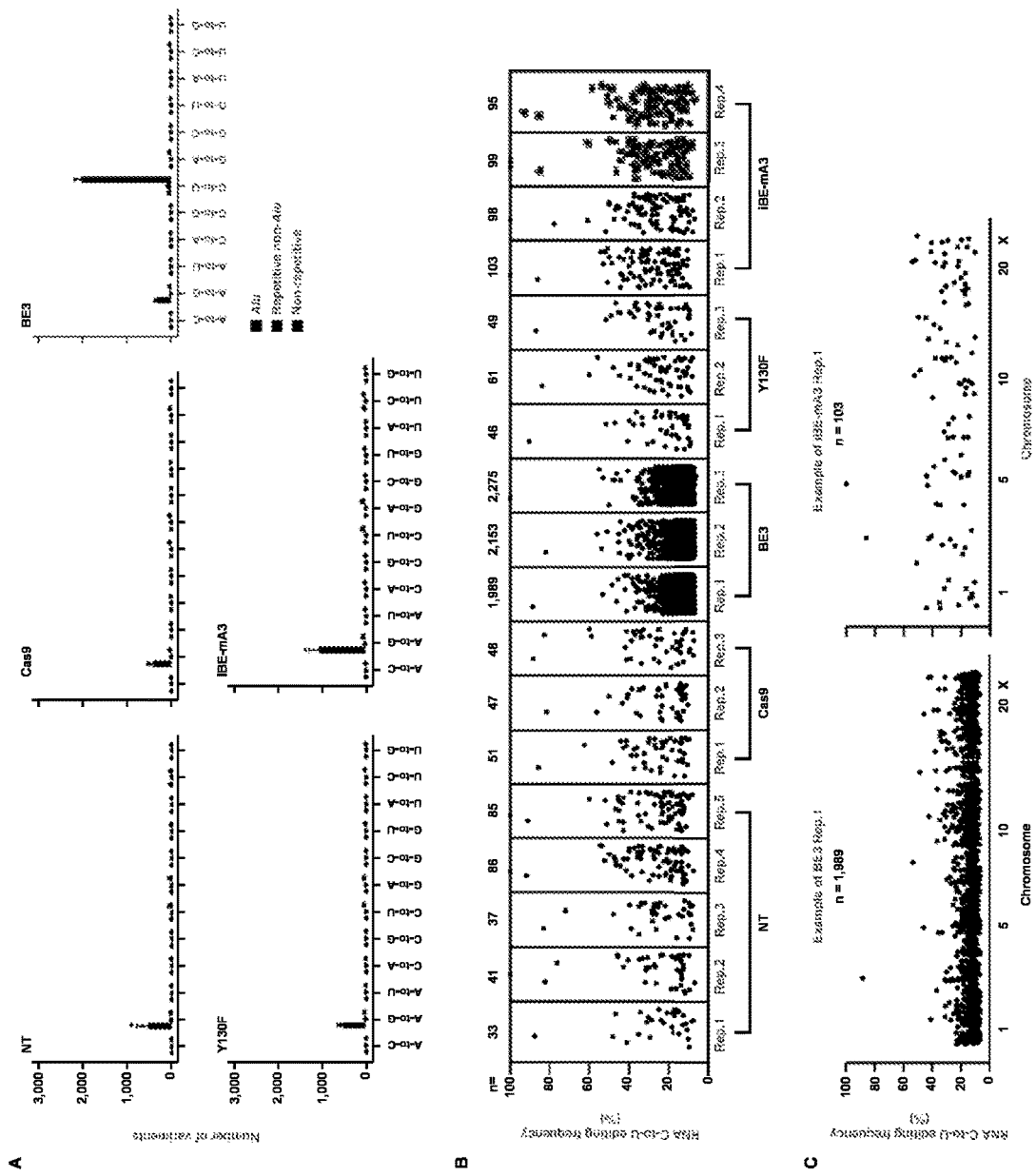
FIG. 33A-C

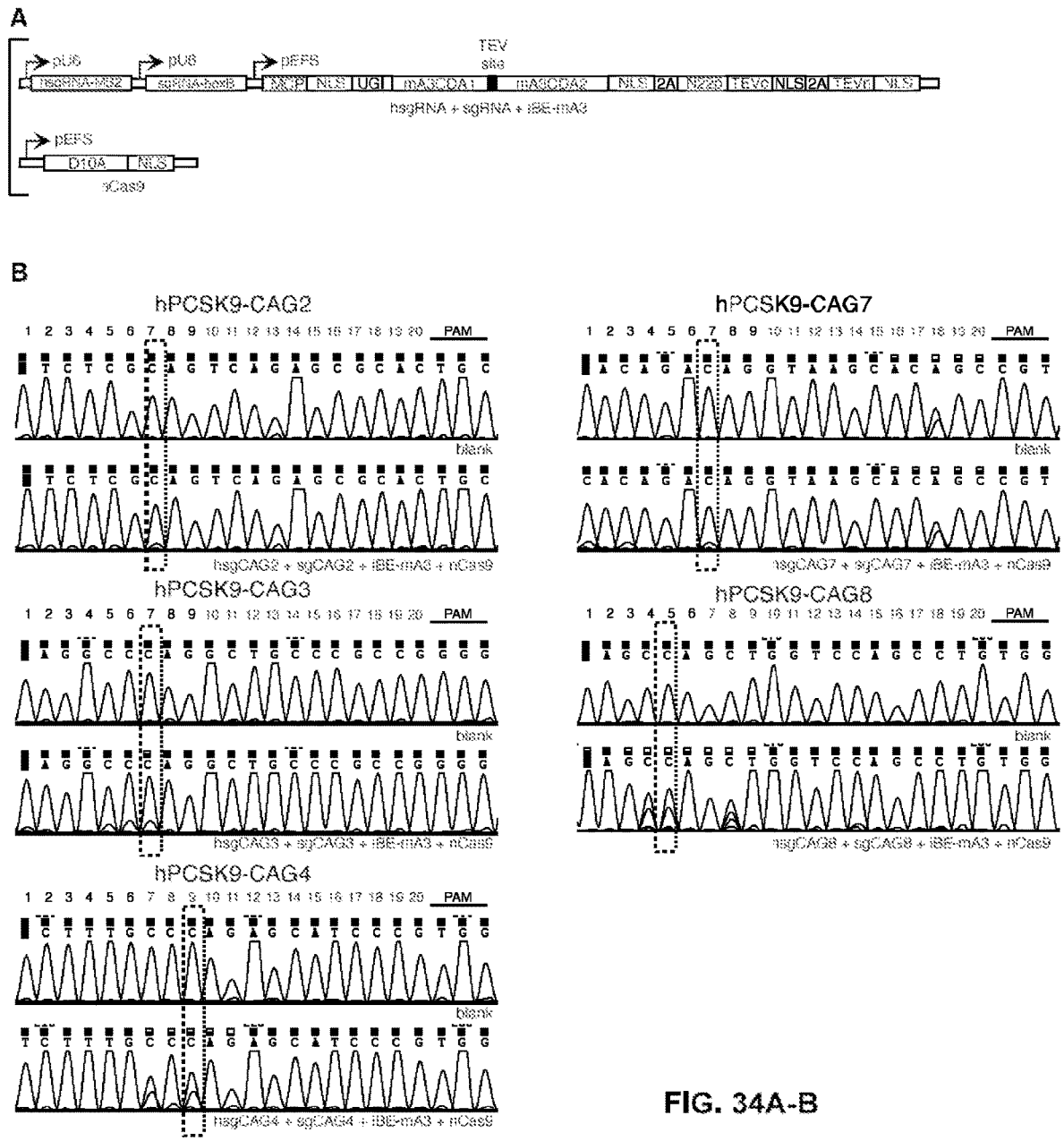
FIG. 34A-B

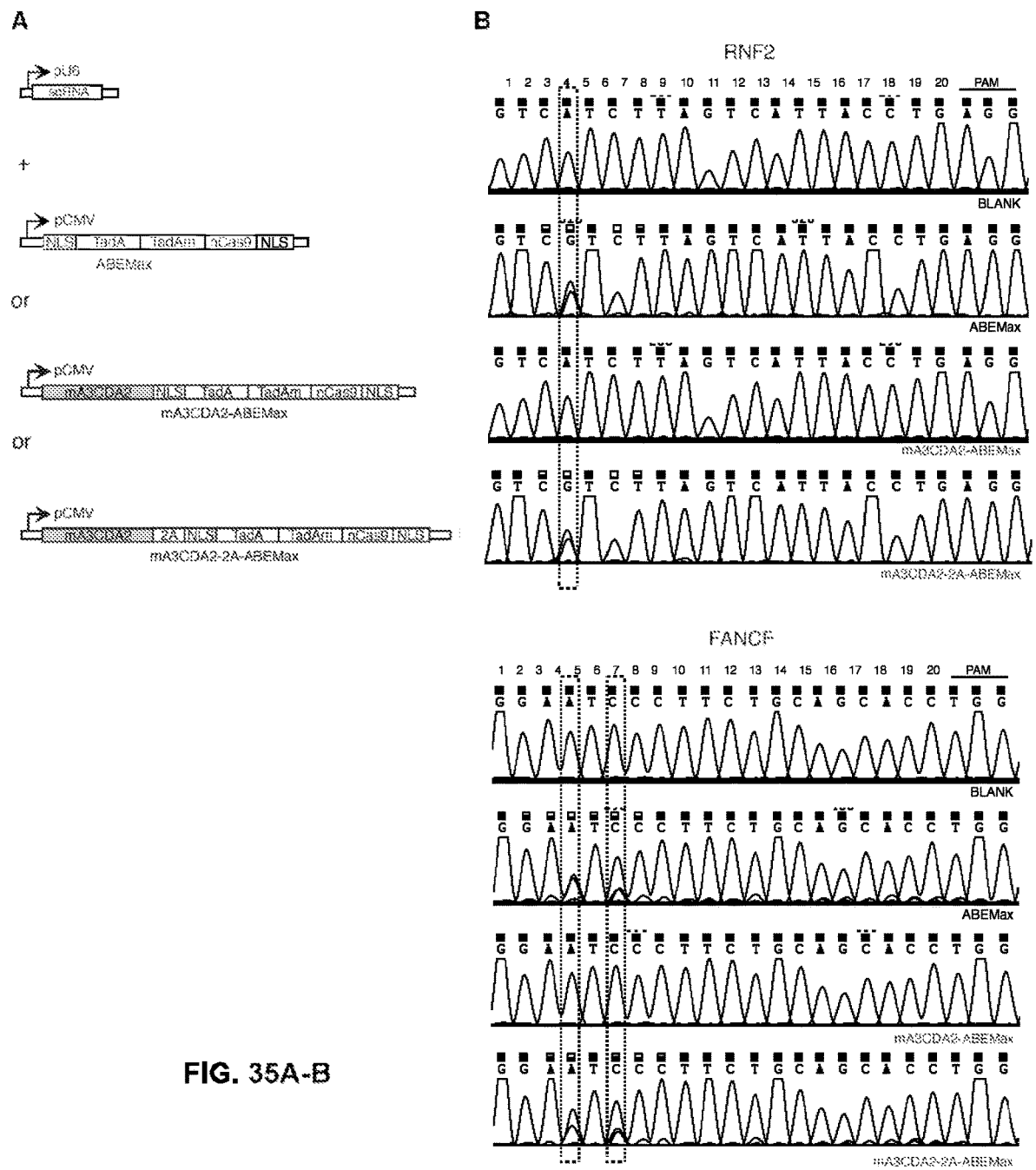
FIG. 35A-B

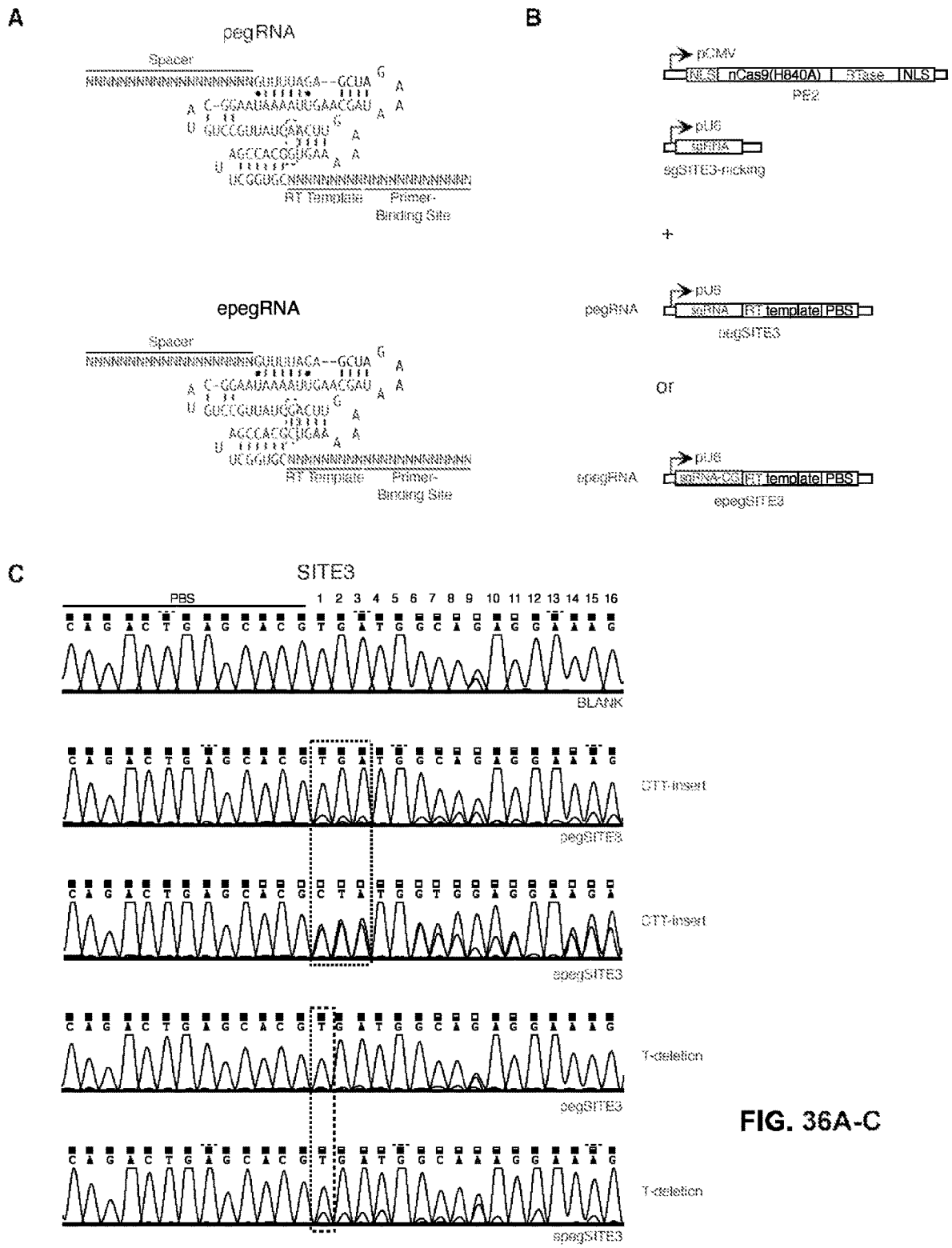
FIG. 36A-C

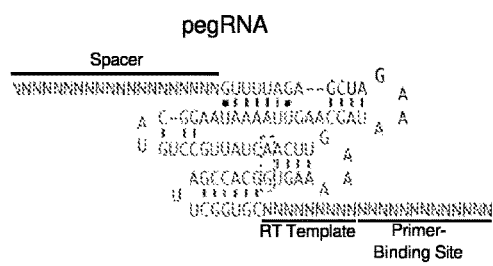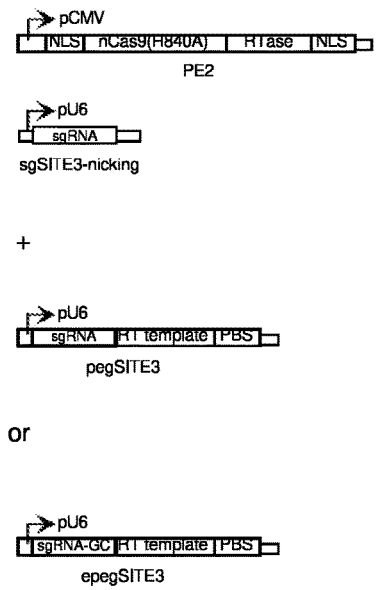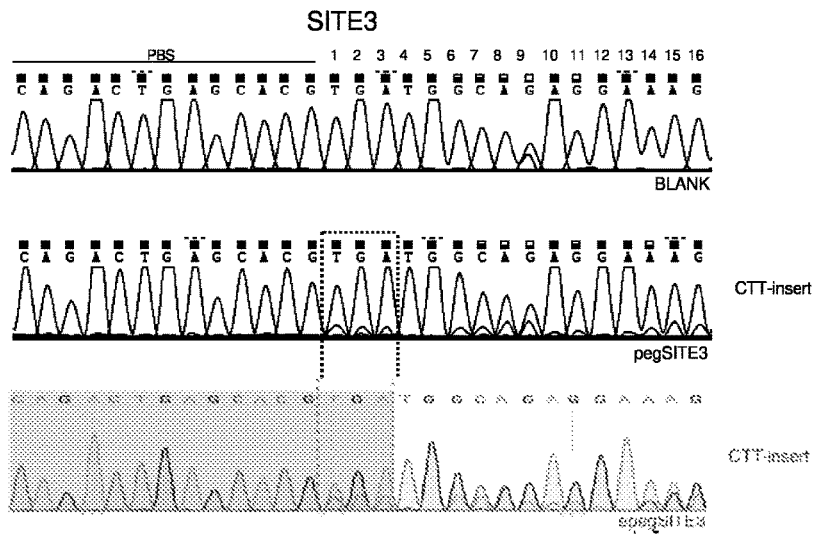
FIG. 36E-G

A
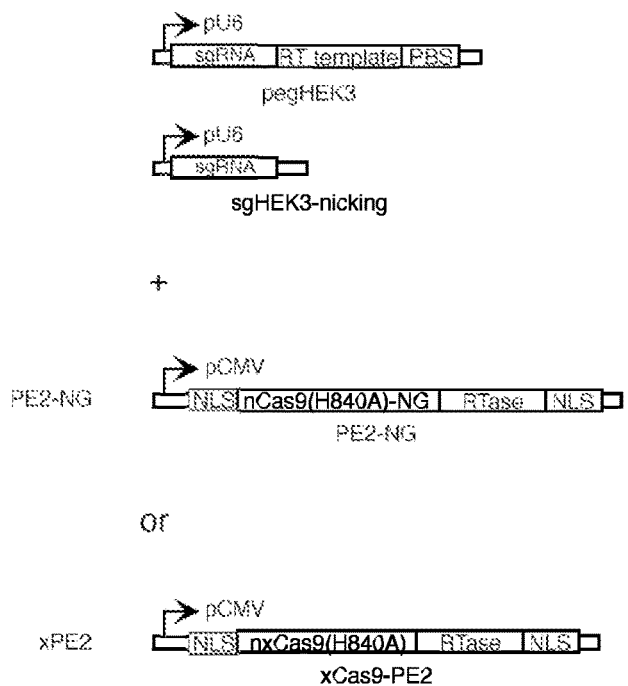
B
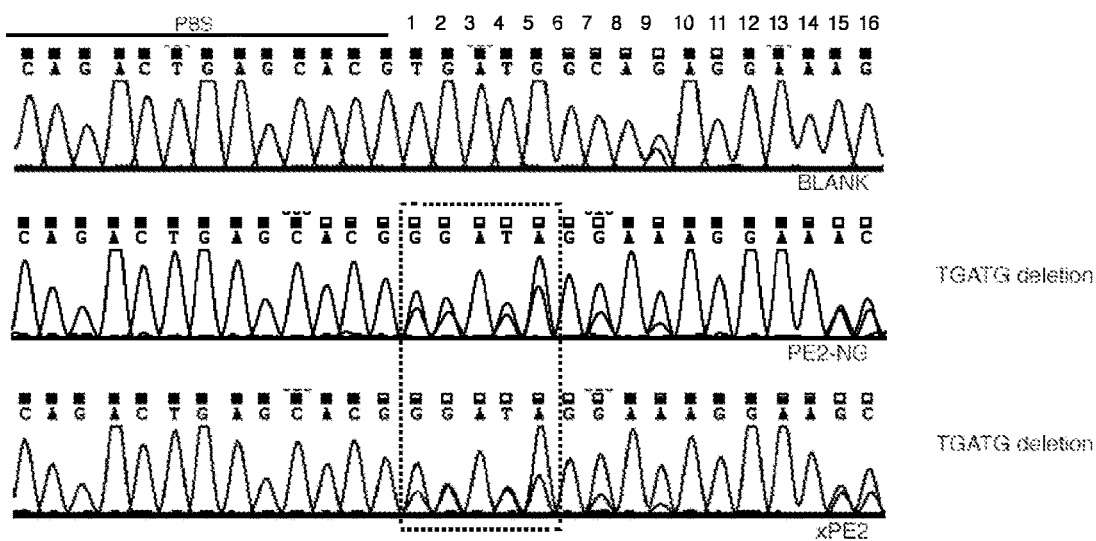
FIG. 37A-B

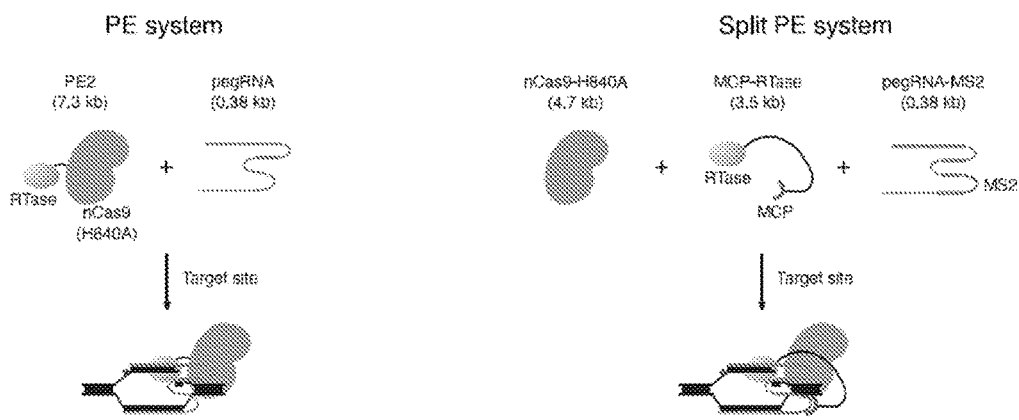
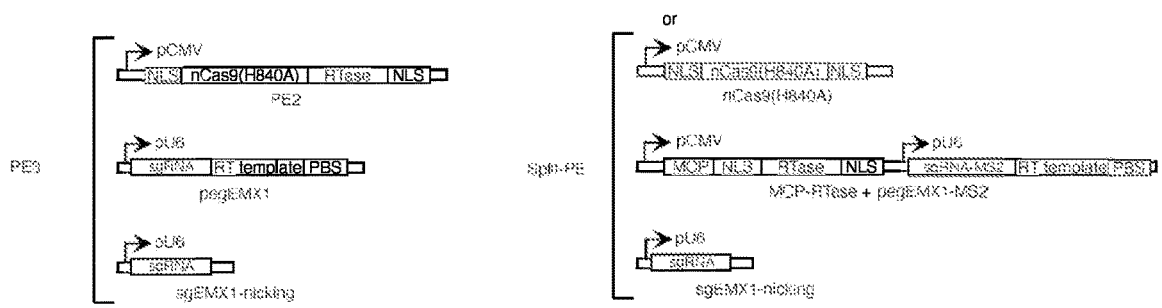
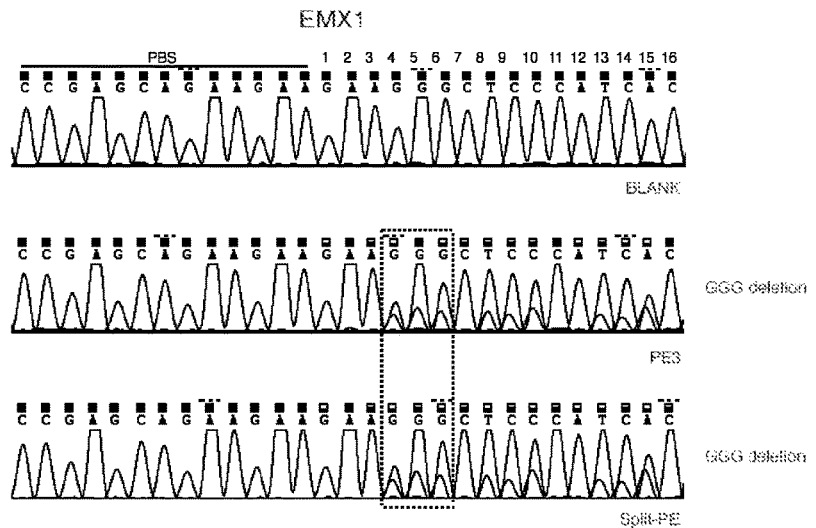
FIG. 38A-C

| | | | SEQ ID NO: |
|---|---|---|---|
| Homo sapiens A3B(29-138) (103) | 124 | 131 | 93 |
| Gorilla A3B(29-138) (103) | | | 94 |
| Pan paniscus A3B(29-138) (103) | | | 95 |
| Pan troglodytes A3B(29-138) (103) | | | 96 |
| Gorilla A3F(30-127) (99) | -------- | | 97 |
| Pan troglodytes A3F(30-137) (101) | | | 98 |
| Homo sapiens A3F(30-137) (101) | | | 99 |
| Macaca leonina A3F(30-137) (101) | | | 100 |
| Macaca nemestrina A3F(30-137) (101) | | | 101 |
| Rhinopithecus roxellana A3F(30-137) (101) | | | 102 |
| Mandrillus leucophaeus A3F(30-130) (101) | -------- | | 103 |
| Macaca mulatta A3F(30-137) (101) | | | 104 |
| Theropithecus gelada A3F(30-137) (101) | | P | 105 |
| Cercocebus atys A3B(29-138) (103) | C | | 106 |
| Macaca fascicularis A3B(29-138) (103) | C | | 107 |
| Macaca mulatta A3B(29-138) (103) | C | | 108 |
| Macaca leonina A3B(29-138) (103) | C | | 109 |
| Mandrillus leucophaeus A3B(29-138) (103) | C | | 110 |
| Macaca nemestrina A3B(29-138) (103) | | | 111 |
| Rhinopithecus bieti A3F(29-138) (103) | | | 112 |
| Rhinopithecus roxellana A3B(29-138) (103) | | | 113 |
| Chlorocebus sabaeus A3B(29-138) (103) | | | 114 |
| Nomascus leucogenys A3B(30-139) (102) | | | 115 |
| Cercocebus atys A3F(29-138) (103) | X | P | 116 |
| Papio anubis A3F(29-138) (103) | | P | 117 |
| Chlorocebus aethiops A3D(29-150) (115) | | | 118 |
| Chlorocebus sabaeus A3D(29-134) (99) | | | 119 |
| Chlorocebus sabaeus A3F(29-150) (115) | | | 120 |
| Erythrocebus patas A3D(29-150) (115) | | | 121 |
| Macaca fascicularis A3D(29-159) (124) | | R | 122 |
| Macaca fascicularis A3F(29-138) (103) | | P | 123 |
| Macaca nemestrina A3D(29-138) (103) | | P | 124 |
| Macaca leonina A3D(29-138) (103) | | P | 125 |
| Macaca mulatta A3D(29-138) (103) | | P | 126 |
| Gorilla A3D(29-150) (115) | V | R | 127 |
| Pan paniscus A3D(29-150) (115) | V | R | 128 |
| Pan troglodytes A3D(29-150) (115) | V | R | 129 |
| Homo sapiens A3D(29-150) (115) | WV | L | 130 |
| Nomascus leucogenys A3D(29-150) (115) | | P | 131 |
| Saimiri boliviensis A3G(29-138) (103) | | P | 132 |
| Saimiri boliviensis A3F(29-138) (103) | | R | 133 |
| Piliocolobus tephrosceles A3F(36-145) (103) | | R | 134 |
| Colobus angolensis palliatus A3F(29-138) (103) | | | 135 |
| Pongo abelii A3F(30-150) (114) | G | R | |
| Consensus (124) | WDRALCRL | | |

FIG. 40D

INHIBITION OF UNINTENDED MUTATIONS IN GENE EDITING

CROSS-REFERENCE TO RELATED PATENT APPLICATIONS

This application is a continuation of U.S. application Ser. No. 17/427,040, filed Jul. 29, 2021, now U.S. Pat. No. 11,384,353, which is a U.S. National Stage Application under 35 U.S.C. § 371 of International Application No. PCT/CN2020/074218, filed Feb. 3, 2020, which claims the priority to PCT/CN2019/074577, filed on Feb. 2, 2019, the contents of each of which are hereby incorporated by reference in their entirety into the present disclosure.

REFERENCE TO AN ELECTRONIC SEQUENCE LISTING

The contents of the electronic sequence listing (292057.xml; Size: 388,026 bytes; and Date of Creation: Dec. 15, 2022) is herein incorporated by reference in its entirety.

BACKGROUND

Genome editing is a type of genetic engineering in which DNA is inserted, deleted or replaced in the genome of a living organism using engineered nucleases (molecular scissors). Utilizing genome editing tools to genetically manipulate the genome of cells and living organism has broad applications in life sciences researches, biotechnology/agricultural technology development and most importantly pharmaceutical/clinical innovations. For example, genome editing can be used to correct the driver mutations underlying genetic diseases and leading to complete cure of these diseases in living organisms. Genome editing can also be used to engineer the genome of crops, increasing the yield of crops and conferring crops resistance to environmental contamination or pathogen infection. In addition, microbial genome transformation through accurate genome editing is of great significance in the development of renewable bioenergy.

CRISPR/Cas (Clustered regularly interspaced short palindromic repeats/CRISPR-associated protein) system has been the most powerful genomic editing tool since its conception for its unparalleled editing efficiency, convenience and the potential applications in living organisms. Directed by a guide RNA (gRNA), the Cas nuclease can generate DNA double strand breaks (DSBs) at the targeted genomic sites in various cells (both cell lines and cells from living organisms). These DSBs are then repaired by the endogenous DNA repair system, which could be utilized to perform desired genome editing.

In general, two major DNA repair pathways can be activated by DSBs, non-homologous end joining (NHEJ) and homology-directed repair (HDR). NHEJ can introduce random insertions/deletions (indels) in the genomic DNA region around the DSBs, leading to open reading frame (ORF) shift and ultimately gene inactivation. In contrast, when HDR is triggered, the genomic DNA sequence at the target site can be replaced by the sequence of the exogenous donor DNA template through a homologous recombination mechanism, which can result in the correction of genetic mutation. However, the practical efficiency of HDR-mediated gene correction is low (normally <5%) because the occurrence of homologous recombination is both cell type-specific and cell cycle-dependent and NHEJ is triggered more frequently than HDR is. The relatively low efficiency of HDR therefore limited the translation of CRISPR/Cas genome editing tools in the field of precision gene therapy (diseases-driven gene correction).

Base editors (BE), which integrate the CRISPR/Cas system with the APOBEC (apolipoprotein B mRNA editing enzyme, catalytic polypeptide-like) AID (activation-induced cytidine deaminase) family, was recently developed that greatly enhanced the efficiency of CRISPR/Cas-meditated gene correction. Through the fusion with the Cas9 nickase (nCas9) or a catalytically dead Cpf1 (dCpf1 also known as dCas12a), the cytosine (C) deamination activity of APOBEC/AID family members can be purposely directed to the target bases in the genome and to catalyze C to Thymine (T) substitutions at these bases.

However, as APOBEC/AID family members can induce C-to-T base substitution mutations in single-stranded DNA (ssDNA) regions, the specificity of the current base editing system is compromised, thereby limiting the applications, for instance, using BEs to restore the T-to-C mutation that result in human diseases for therapeutic purposes. Hence, creating novel BEs that can specifically edit cytosines in target region but not cause C-to-T mutations in other ssDNA regions is desirable. Such novel BEs will enable us to perform more specific base editing in various living organisms. Importantly, the high specificity of such BEs will promote the potential clinical translation, particularly in the gene therapies that involve restoring disease-related T-to-C mutations.

SUMMARY

The present disclosure, in some embodiments, provides base editors useful for genome editing that cause reduced or even no off-target mutations common to current base editors. In certain embodiments, a nucleobase deaminase inhibitor is cleavably fused to a nucleobase deaminase involved for genome editing. In the presence of the nucleobase deaminase inhibitor, the nucleobase deaminase is unable to (is less able to) react with a nucleotide molecule. At a target editing location, the nucleobase deaminase inhibitor can be cleaved releasing a fully active nucleobase deaminase that can then carry out the editing as desired.

Accordingly, in one embodiment, provided is a fusion protein comprising: a first fragment comprising a nucleobase deaminase or a catalytic domain thereof, a second fragment comprising a nucleobase deaminase inhibitor, and a protease cleavage site between the first fragment and the second fragment.

In some embodiments, the nucleobase deaminase is an adenosine deaminase. In some embodiments, the adenosine deaminase is selected from the group consisting of tRNA-specific adenosine deaminase (TadA), adenosine deaminase tRNA specific 1 (ADAT1), adenosine deaminase tRNA specific 2 (ADAT2), adenosine deaminase tRNA specific 3 (ADAT3), adenosine deaminase RNA specific B1 (ADARB1), adenosine deaminase RNA specific B2 (ADARB2), adenosine monophosphate deaminase 1 (AMPD1), adenosine monophosphate deaminase 2 (AMPD2), adenosine monophosphate deaminase 3 (AMPD3), adenosine deaminase (ADA), adenosine deaminase 2 (ADA2), adenosine deaminase like (ADAL), adenosine deaminase domain containing 1 (ADAD1), adenosine deaminase domain containing 2 (ADAD2), adenosine deaminase RNA specific (ADAR) and adenosine deaminase RNA specific B1 (ADARB1).

In some embodiments, the nucleobase deaminase is a cytidine deaminase. In some embodiments, the cytidine deaminase is selected from the group consisting of APOBEC3B (A3B), APOBEC3C (A3C), APOBEC3D (A3D), APOBEC3F (A3F), APOBEC3G (A3G), APOBEC3H (A3H), APOBEC1 (A1), APOBEC3 (A3), APOBEC2 (A2), APOBEC4 (A4) and AICDA (AID). In some embodiments, the cytidine deaminase is a human or mouse cytidine deaminase. In some embodiments, the catalytic domain is mouse A3 cytidine deaminase domain 1 (CDA1) or human A3B cytidine deaminase domain 2 (CDA2).

In some embodiments, the nucleobase deaminase inhibitor is an inhibitory domain of a nucleobase deaminase. In some embodiments, the nucleobase deaminase inhibitor is an inhibitory domain of a is a cytidine deaminase. In some embodiments, the nucleobase deaminase inhibitor is an inhibitory domain of an adenosine deaminase. In some embodiments, the nucleobase deaminase inhibitor comprises an amino acid sequence selected from SEQ ID NO: 1-2 and Tables 1 and 2 (SEQ ID NO: 48-135), or an amino acid sequence having at least 85% sequence identity to any of the amino acid sequence selected from SEQ ID NO: 1-2 and Tables 1 and 2. In some embodiments, the nucleobase deaminase inhibitor comprises the amino acid sequence of SEQ ID NO:1, amino acids residues AA76-AA149 of SEQ ID NO:1 or the amino acid sequence of SEQ ID NO:2.

In some embodiments, the first fragment further comprises a clustered regularly interspaced short palindromic repeats (CRISPR)-associated (Cas) protein. In some embodiments, the Cas protein is selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, xSpCas9, SpCas9-NG, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, and RanCas13b.

In some embodiments, the protease cleavage site is a protease cleavage site a protease selected from the group consisting of TuMV protease, PPV protease, PVY protease, ZIKV protease and WNV protease.

In some embodiments, the protease cleavage site is a self-cleavage site. In some embodiments, the protease cleavage site is a TEV protease cleavage site. In some embodiments, the fusion protein further comprises a third fragment comprising a TEV protease or a fragment thereof. In some embodiments, the third fragment comprises a TEV protease fragment which alone is not able to cleave the TEV protease cleavage site.

Also provided, in another embodiment, is a fusion protein comprising: a first fragment comprising a cytidine deaminase or a catalytic domain thereof, a clustered regularly interspaced short palindromic repeats (CRISPR)-associated (Cas) protein, and a first TEV protease fragment, a second fragment comprising a cytidine deaminase inhibitor, and a TEV protease cleavage site between the first fragment and the second fragment, wherein the first TEV protease fragment alone is not able to cleave the TEV protease cleavage site.

In some embodiments, the fusion protein further comprises a uracil glycosylase inhibitor (UGI). In some embodiments, the cytidine deaminase inhibitor, the TEV protease cleavage site, the cytidine deaminase or a catalytic domain thereof, the Cas protein, and the first TEV protease fragment are arranged from the N-terminus to the C-terminus. In some embodiments, the first TEV protease fragment is the N-terminal domain (SEQ ID NO:3) or the C-terminal domain (SEQ ID NO:4) of the TEV protease. In some embodiments, the TEV protease cleavage site has the amino acid sequence of SEQ ID NO:5.

Further provided, in one embodiment, is a method for conducting genomic editing in a cell at a target site, comprising introducing to the cell: (a) a fusion protein of the present disclosure, (b) a guide RNA that targets the target site or a crRNA that targets the target site and a tracrRNA, and further comprises a tag sequence, and (c) a second TEV protease fragment coupled to an RNA recognition peptide that is able to bind the tag sequence.

In some embodiments, one or more of the molecules is introduced to the cell by a polynucleotide encoding the molecule. In some embodiments, the first TEV protease fragment and the second TEV protease fragment, when in interaction, are able to cleave the TEV protease cleavage site. In some embodiments, the second TEV protease fragment is fused to the RNA recognition peptide.

In some embodiments, the tag sequence comprises a MS2 sequence (SEQ ID NO:16). In some embodiments, the RNA recognition peptide comprises a MS2 coat protein (MCP, SEQ ID NO:22). In some embodiments, the tag sequence comprises a PP7 sequence (SEQ ID NO:18) and the RNA recognition peptide comprises a PP7 coat protein (PCP, SEQ ID NO: 23), or the tag sequence comprises a boxB sequence (SEQ ID NO:20) and the RNA recognition peptide comprises a boxB coat protein (N22p, SEQ ID NO:24).

Also provided, in one embodiment, is a kit or package for conducting gene editing, comprising: (a) a fusion protein of the present disclosure, and (b) a second TEV protease fragment coupled to an RNA recognition peptide that is able to bind an RNA sequence.

Yet another embodiment provides a fusion protein comprising: a first fragment comprising first cytidine deaminase or a catalytic domain thereof, and a second fragment comprising an inhibitory domain of a second cytidine deaminase, wherein the first cytidine deaminase is same as or different from the second cytidine deaminase.

In another embodiment, a fusion protein is provided comprising a first fragment comprising: a nucleobase deaminase or a catalytic domain thereof, a nucleobase deaminase inhibitor, a first RNA recognition peptide, and a TEV protease cleavage site between the nucleobase deaminase or a catalytic domain thereof and the nucleobase deaminase inhibitor.

In some embodiments, the fusion protein further comprises a second fragment comprising: a TEV protease fragment which alone is not able to cleave the TEV protease cleavage site, and a second RNA recognition peptide. In some embodiments, the fusion protein further comprises a self-cleavage site between the first fragment and the second fragment.

In some embodiments, the fusion protein further comprises a third fragment comprising a second TEV protease fragment, wherein the first TEV protease fragment is able to cleave the TEV protease site in the presence of the second TEV protease fragment. In some embodiments, the fusion protein further comprises a second self-cleavage site between the second fragment and the third fragment, ad upon cleavage of the second self-cleavage site, the fusion protein releases the second TEV protease fragment which is not fused to any RNA recognition peptide.

Also provided, in one embodiment, is a dual guide RNA system, comprising: a target single guide RNA comprising a first spacer having sequence complementarity to a target nucleic acid sequence proximate to a first PAM site, a helper single guide RNA comprising a second spacer having sequence complementarity to a second nucleic acid sequence proximate to a second PAM site, a clustered regularly interspaced short palindromic repeats (CRISPR)-associated (Cas) protein, and a nucleobase deaminase, wherein the second PAM site is from 34 to 91 bases from the first PAM site. In some embodiments, the second spacer is 8-15 bases in length. In some embodiments, the second spacer is 9-12 bases in length.

In one embodiment, provided is guide RNA comprising a scaffold which comprises, from the 5' to 3' direction, a first stem loop portion, a second stem loop portion, a third stem loop portion, and a fourth stem loop portion, wherein the third stem loop comprises five base pairings within. In another embodiment, the present disclosure provides a guide RNA comprising a scaffold derived from SEQ ID NO:31 by introducing a base pairing between the bases at positions 45 and 55. In some embodiments, the scaffold comprises a sequence selected from the group consisting of SEQ ID NO:32-43. In some embodiments, the guide RNA is at least 100, or 120 nucleotides in length.

Another embodiment provides a method for conducting genetic editing in a cell at a target site, comprising introducing to the cell: a first viral particle enclosing a first construct encoding a clustered regularly interspaced short palindromic repeats (CRISPR)-associated (Cas) protein, and a second viral particle enclosing a second construct encoding a reverse-transcriptase fused to an RNA recognition peptide.

In some embodiments, the second construct further encodes a guide RNA comprising an RNA recognition site that the RNA recognition peptide binds to. In some embodiments, the Cas protein is SpCas9-NG (SEQ ID NO:46) or xSpCas9 (SEQ ID NO:47).

Polynucleotides encoding the fusion proteins of the present disclosure, constructs containing the polynucleotides, cells containing the polynucleotides or the constructs, and compositions comprising any of the above are also provided, without limitation.

BRIEF DESCRIPTION OF THE DRAWINGS

FIG. 1A-C: Unintended base substitutions caused by current BEs in Sa-SITE31 ssDNA region. 1A: Schematic diagram illustrating the co-expression of SaD10A nickase and Sa-sgSITE31 to trigger the formation of ssDNA region at Sa-sgSITE31 on-target site. 1B: Schematic diagram illustrating the co-transfection of the plasmid expressing Sa-sgSITE31 and the plasmid expressing SaD10A nickase with the plasmid expressing BE3, the plasmid expressing hA3A-BE3 or an empty vector. 1C: The untended base substitutions caused by BE3 and hA3A-BE3. Dashed boxes represent the locations of untended base substitutions at Sa-sgSITE31 target site. The sequences shown in FIG. 1C, from top to bottom, have the sequences of SEQ ID NO: 204, 204 and 205, respectively.

FIG. 2A-C: Unintended base substitutions caused by current BEs in Sa-SITE42 ssDNA region. 2A: Schematic diagram illustrating the co-expression of SaD10A nickase and Sa-sgSITE42 to trigger the formation of ssDNA region at Sa-sgSITE42 on-target site. 2B: Schematic diagram illustrating the co-transfection of the plasmid expressing Sa-sgSITE42 and the plasmid expressing SaD10A nickase with the plasmid expressing BE3, the plasmid expressing hA3A-BE3 or an empty vector. 2C: The untended base substitutions caused by BE3 and hA3A-BE3. Dashed boxes represent the locations of untended base substitutions at Sa-sgSITE42 target site. The sequences shown in FIG. 2C, from top to bottom, have the sequences of SEQ ID NO: 206, 206 and 207, respectively.

FIG. 3A-C: Unintended base substitutions caused by current BEs in Sa-F1 ssDNA region. 3A: Schematic diagram illustrating the co-expression of SaD10A nickase and Sa-sgF1 to trigger the formation of ssDNA region at Sa-sgF1 on-target site. 3B: Schematic diagram illustrating the co-transfection of the plasmid expressing Sa-sgF1 and the plasmid expressing SaD10A nickase with the plasmid expressing BE3, the plasmid expressing hA3A-BE3 or an empty vector. 3C: The untended base substitutions caused by BE3 and hA3A-BE3. Dashed boxes represent the locations of untended base substitutions at Sa-sgF1 target site. The sequences shown in FIG. 3C have the sequence of SEQ ID NO: 208.

FIG. 4A-C: mA3CDA2 inhibits C-to-T base editing activity in TET1 region. 4A: Schematic diagram illustrating the regions of CDA domains in mA3, rA1 and hA3A. 4B: Schematic diagram illustrating the co-transfection of the plasmid expressing sgTET1 with the plasmid expressing mA3-BE3, the plasmid expressing mA3CDA1-BE3, the plasmid expressing mA3rev-BE3, the plasmid expressing mA3rev-2A-BE3, the plasmid expressing BE3, the plasmid expressing mA3CDA2-BE3, the plasmid expressing mA3CDA2-2A-BE3, the plasmid expressing hA3A-BE3, the plasmid expressing mA3CDA2-hA3A-BE3 or the plasmid expressing mA3CDA2-2A-hA3A-BE3. 4C: mA3CDA2 inhibits C-to-T editing activity of mA3CDA1-BE3, BE3 and hA3A-BE3. Dashed boxes represent the locations of C-to-T base editing at sgTET1 target site. The sequences shown in FIG. 4C, from top to bottom, have the sequences of SEQ ID NO: 209, 209, 209, 209, 209, 209, 209, 209, 209, and 210, respectively.

FIG. 5A-C: mA3CDA2 inhibits C-to-T base editing activity in RNF2 region. 5A: Schematic diagram illustrating the regions of CDA domains in mA3, rA1 and hA3A. 5B: Schematic diagram illustrating the co-transfection of the plasmid expressing sgRNF2 with the plasmid expressing mA3-BE3, the plasmid expressing mA3CDA1-BE3, the plasmid expressing mA3rev-BE3, the plasmid expressing mA3rev-2A-BE3, the plasmid expressing BE3, the plasmid expressing mA3CDA2-BE3, the plasmid expressing mA3CDA2-2A-BE3, the plasmid expressing hA3A-BE3, the plasmid expressing mA3CDA2-hA3A-BE3 or the plasmid expressing mA3CDA2-2A-hA3A-BE3. 5C: mA3CDA2 inhibits C-to-T editing activity of mA3CDA1-BE3, BE3 and hA3A-BE3. Dashed boxes represent the locations of C-to-T base editing at sgRNF2 target site. The sequences shown in FIG. 5C, from top to bottom, have the sequences of SEQ ID NO: 211, 211, 211, 211, 211, 211, 211, 212, 211, and 212, respectively.

FIG. 6A-C: mA3CDA2 inhibits C-to-T base editing activity in SITE3 region. 6A: Schematic diagram illustrating the regions of CDA domains in mA3, rA1 and hA3A. 6B: Schematic diagram illustrating the co-transfection of the plasmid expressing sgSITE3 with the plasmid expressing mA3-BE3, the plasmid expressing mA3CDA1-BE3, the plasmid expressing mA3rev-BE3, the plasmid expressing mA3rev-2A-BE3, the plasmid expressing BE3, the plasmid expressing mA3CDA2-BE3, the plasmid expressing mA3CDA2-2A-BE3, the plasmid expressing hA3A-BE3, the plasmid expressing mA3CDA2-hA3A-BE3 or the plasmid expressing mA3CDA2-2A-hA3A-BE3. 6C: mA3CDA2 inhibits C-to-T editing activity of mA3CDA1-BE3, BE3 and hA3A-BE3. Dashed boxes represent the locations of C-to-T base editing at sgSITE3 target site. The sequences shown in FIG. 6C, from top to bottom, have the sequences of SEQ ID NO: 213, 213, 213, 213, 214, 213, 213, 213, 213, and 213, respectively.

FIG. 7A-C: hA3BCDA1 inhibits C-to-T base editing activity in TET1 region. 7A: Schematic diagram illustrating the regions of CDA domains in hA3B. 7B: Schematic diagram illustrating the co-transfection of the plasmid expressing sgTET1 with the plasmid expressing hA3B-BE3, the plasmid expressing hA3BCDA2-BE3 or the plasmid expressing hA3B-2A-BE 3. 7C: hA3BCDA1 inhibits C-to-T editing activity of hA3BCDA2-BE3. Dashed boxes represent the locations of C-to-T base editing at sgTET1 target site. The sequences shown in FIG. 7C have the sequence of SEQ ID NO: 215.

FIG. 8A-C: hA3BCDA1 inhibits C-to-T base editing activity in RNF2 region. 8A: Schematic diagram illustrating the regions of CDA domains in hA3B. 8B: Schematic diagram illustrating the co-transfection of the plasmid expressing sgRNF2 with the plasmid expressing hA3B-BE3, the plasmid expressing hA3BCDA2-BE3 or the plasmid expressing hA3B-2A-BE 3. 8C: hA3BCDA1 inhibits C-to-T editing activity of hA3BCDA2-BE3. Dashed boxes represent the locations of C-to-T base editing at sgRNF2 target site. The sequences shown in FIG. 8C, from top to bottom, have the sequences of SEQ ID NO: 216, 217 and 217, respectively.

FIG. 9A-C: hA3BCDA1 inhibits C-to-T base editing activity in SITE3 region. 9A: Schematic diagram illustrating the regions of CDA domains in hA3B. 9B: Schematic diagram illustrating the co-transfection of the plasmid expressing sgSITE3 with the plasmid expressing hA3B-BE3, the plasmid expressing hA3BCDA2-BE3 or the plasmid expressing hA3B-2A-BE3. 9C: hA3BCDA1 inhibits C-to-T editing activity of hA3BCDA2-BE3. Dashed boxes represent the locations of C-to-T base editing at sgSITE3 target site. The sequences shown in FIG. 9C, from top to bottom, have the sequences of SEQ ID NO: 218, 219 and 219, respectively.

FIG. 10A-C: Mapping the split site of mA3 by examining base editing efficiency in FANCF region. 10A: Schematic diagram illustrating the regions of two CDA domains in mA3 and the sites (AA196/AA197, AA207/AA208, AA215/AA216, AA229/AA230, AA237/AA238) used to split mA3. 10B: Schematic diagram illustrating the co-transfection of the plasmid expressing sgFANCF with the plasmid expressing mA3rev-BE3-196, the plasmid expressing mA3rev-2A-BE3-196, the plasmid expressing mA3rev-BE3, the plasmid expressing mA3rev-2A-BE3, the plasmid expressing mA3rev-BE3-215, the plasmid expressing mA3rev-2A-BE3-215, the plasmid expressing mA3rev-BE3-229, the plasmid expressing mA3rev-2A-BE3-229, the plasmid expressing mA3rev-BE3-237 or the plasmid expressing mA3rev-2A-BE3-237. 10C: The splitting sites spanning from AA196/AA197 to AA237/AA238 generally keep C-to-T editing efficiencies. Dashed boxes represent the locations of C-to-T base editing at sgFANCF target site. The sequences shown in FIG. 10C, from top to bottom, have the sequences of SEQ ID NO: 220, 220, 220, 221, 220, 221, 220, 221, 220 and 222, respectively.

FIG. 11A-C: Mapping the split site of mA3 by examining base editing efficiency in SITE2 region. 11A: Schematic diagram illustrating the regions of two CDA domains in mA3 and the sites (AA196/AA197, AA207/AA208, AA215/AA216, AA229/AA230, AA237/AA238) used to split mA3. 11B: Schematic diagram illustrating the co-transfection of the plasmid expressing sgSITE2 with the plasmid expressing mA3rev-BE3-196, the plasmid expressing mA3rev-2A-BE3-196, the plasmid expressing mA3rev-BE3, the plasmid expressing mA3rev-2A-BE3, the plasmid expressing mA3rev-BE3-215, the plasmid expressing mA3rev-2A-BE3-215, the plasmid expressing mA3rev-BE3-229, the plasmid expressing mA3rev-2A-BE3-229, the plasmid expressing mA3rev-BE3-237 or the plasmid expressing mA3rev-2A-BE3-237. 11C: The splitting sites spanning from AA196/AA197 to AA237/AA238 generally keep C-to-T editing efficiencies. Dashed boxes represent the locations of C-to-T base editing at sgSITE2 target site. The sequences shown in FIG. 11C, from top to bottom, have the sequences of SEQ ID NO: 223, 223, 223, 224, 223, 225, 223, 224, 223, and 224, respectively.

FIG. 12A-C: Mapping the split site of mA3 by examining base editing efficiency in SITE4 region. 12A: Schematic diagram illustrating the regions of two CDA domains in mA3 and the sites (AA196/AA197, AA207/AA208, AA215/AA216, AA229/AA230, AA237/AA238) used to split mA3. 12B: Schematic diagram illustrating the co-transfection of the plasmid expressing sgSITE4 with the plasmid expressing mA3rev-BE3-196, the plasmid expressing mA3rev-2A-BE3-196, the plasmid expressing mA3rev-BE3, the plasmid expressing mA3rev-2A-BE3, the plasmid expressing mA3rev-BE3-215, the plasmid expressing mA3rev-2A-BE3-215, the plasmid expressing mA3rev-BE3-229, the plasmid expressing mA3rev-2A-BE3-229, the plasmid expressing mA3rev-BE3-237 or the plasmid expressing mA3rev-2A-BE3-237. 12C: The splitting sites spanning from AA196/AA197 to AA237/AA238 generally keep C-to-T editing efficiencies. Dashed boxes represent the locations of C-to-T base editing at sgSITE4 target site. The sequences shown in FIG. 12C, from top to bottom, have the sequences of SEQ ID NO: 226, 227, 226, 227, 226, 227, 226, 227, 226 and 227, respectively.

FIG. 13A-B: Mapping the minimal region of mA3 that contains the base-editing inhibitory effect in FANCF region. 13A: Schematic diagram illustrating the co-transfection of the plasmid expressing sgFANCF with the plasmid expressing mA3rev-BE3-237, the plasmid expressing mA3rev-BE3-237-Del-255, the plasmid expressing mA3rev-BE3-237-Del-285 or the plasmid expressing mA3rev-BE3-237-Del-333. 13B: The region spanning from AA334 to AA429 of mA3 contains the base-editing inhibitory effect. Dashed boxes represent the locations of C-to-T base editing at sgFANCF target site. The sequences shown in FIG. 13C have the sequence of SEQ ID NO: 228.

FIG. 14A-B: Mapping the minimal region of mA3 that contains the base-editing inhibitory effect in SITE2 region. 14A: Schematic diagram illustrating the co-transfection of the plasmid expressing sgSITE2 with the plasmid expressing mA3rev-BE3-237, the plasmid expressing mA3rev-BE3-237-Del-255, the plasmid expressing mA3rev-BE3 Del-285 or the plasmid expressing mA3rev-BE3-237-Del-333. 14B: The region spanning from AA334 to AA429 of mA3 contains the base-editing inhibitory effect. Dashed boxes represent the locations of C-to-T base editing at sgSITE2 target site. The sequences shown in FIG. 14B have the sequence of SEQ ID NO: 229.

FIG. 15A-B: Mapping the minimal region of mA3 that contains the base-editing inhibitory effect in SITE4 region. 15A: Schematic diagram illustrating the co-transfection of the plasmid expressing sgSITE4 with the plasmid expressing mA3rev-BE3-237, the plasmid expressing mA3rev-BE3-237-Del-255, the plasmid expressing mA3rev-BE3-237-Del-285 or the plasmid expressing mA3rev-BE3-237-Del-333. 15B: The region spanning from AA334 to AA429 of mA3 contains the base-editing inhibitory effect. Dashed boxes represent the locations of C-to-T base editing at sgSITE4 target site. The sequences shown in FIG. 15B have the sequence of SEQ ID NO: 230.

FIG. 16A-B: Schematic diagram illustrating the working process of BEsafe and BE3 or hA3A-BE3. 16A: BEsafe induces C-to-T base editing at on-target site and avoids causing mutations in non-relevant ssDNA regions. 16B: BE3 or hA3A-BE3 induces C-to-T base editing at on-target site but causes C-to-T mutations in non-relevant ssDNA regions.

FIG. 17A-D: Comparison of hA3A-BE3 and BEsafe in non-relevant Sa-SITE31 ssDNA region and at TET1 on-target site. 17A: Schematic diagram illustrating the co-expression of SaD10A nickase and Sa-sgSITE31 to trigger the formation of ssDNA region at Sa-sgSITE31 on-target site. 17B: Schematic diagram illustrating the co-transfection of the plasmid expressing Sa-sgSITE31 and the plasmid expressing SaD10A nickase with the plasmid expressing hA3A-BE3 and the plasmid expressing sgTET1, with the plasmid expressing BEsafe and the plasmid expressing MS2-sgTET1 and MCP-TEVc or with the plasmid expressing MCP-TEVc and the plasmid expressing MS2-sgTET1 and BEsafe. 17C: Comparing the untended C-to-T mutation frequencies triggered by hA3A-BE3 and BEsafe in the non-relevant Sa-SITE31 ssDNA region. Dashed boxes represent the locations of untended base substitutions at Sa-sgSITE31 target site. 17D: Comparing the base editing efficiencies of hA3A-BE3 and BEsafe at TET1 site. Dashed boxes represent the locations of C-to-T base editing at sgTET1 target site. The sequences shown in FIG. 17C have the sequence of SEQ ID NO: 231. The sequences shown in FIG. 17D have the sequence of SEQ ID NO: 232.

FIG. 18A-D: Comparison of hA3A-BE3 and BEsafe in non-relevant Sa-SITE32 ssDNA region and at RNF2 on-target site. 18A: Schematic diagram illustrating the co-expression of SaD10A nickase and Sa-sgSITE32 to trigger the formation of ssDNA region at Sa-sgSITE32 on-target site. 18B: Schematic diagram illustrating the co-transfection of the plasmid expressing Sa-sgSITE32 and the plasmid expressing SaD10A nickase with the plasmid expressing hA3A-BE3 and the plasmid expressing sgRNF2, with the plasmid expressing BEsafe and the plasmid expressing MS2-sgRNF2 and MCP-TEVc or with the plasmid expressing MCP-TEVc and the plasmid expressing MS2-sgRNF2 and BEsafe. 18C: Comparing the untended C-to-T mutation frequencies triggered by hA3A-BE3 and BEsafe in the non-relevant Sa-SITE32 ssDNA region. Dashed boxes represent the locations of untended base substitutions at Sa-sgSITE32 target site. 18D: Comparing the base editing efficiencies of hA3A-BE3 and BEsafe at RNF2 site. Dashed boxes represent the locations of C-to-T base editing at sgRNF2 target site. The sequences shown in FIG. 18C have the sequence of SEQ ID NO: 233. The sequences shown in FIG. 18D, from top to bottom, have the sequences of SEQ ID NO: 234, 235 and 234, respectively.

FIG. 19A-D: Comparison of hA3A-BE3 and BEsafe in non-relevant Sa-F1 ssDNA region and at SITE3 on-target site. 19A: Schematic diagram illustrating the co-expression of SaD10A nickase and Sa-sgF1 to trigger the formation of ssDNA region at Sa-sgF1 on-target site. 19B: Schematic diagram illustrating the co-transfection of the plasmid expressing Sa-sgF1 and the plasmid expressing SaD10A nickase with the plasmid expressing hA3A-BE3 and the plasmid expressing sgSITE3, with the plasmid expressing BEsafe and the plasmid expressing MS2-sgSITE3 and MCP-TEVc or with the plasmid expressing MCP-TEVc and the plasmid expressing MS2-sgSITE3 and BEsafe. 19C: Comparing the untended C-to-T mutation frequencies triggered by hA3A-BE3 and BEsafe in the non-relevant Sa-F1 ssDNA region. Dashed boxes represent the locations of untended base substitutions at Sa-sgF1 target site. 19D: Comparing the base editing efficiencies of hA3A-BE3 and BEsafe at SITE3 site. Dashed boxes represent the locations of C-to-T base editing at sgSITE3 target site. The sequences shown in FIG. 19C have the sequence of SEQ ID NO: 236. The sequences shown in FIG. 19D have the sequence of SEQ ID NO: 237.

FIG. 20a-f: Identification of cytidine deaminase inhibitors. 20a: Schematic diagrams illustrate the APOBEC family members that have single- or dual-CDA domains (left) and paired base editors that were constructed with one or two CDAs of dual-domain APOBECs (right). 20b: Editing frequencies induced by the indicated BEs at one representative genomic locus. 20c: Statistical analysis of normalized editing frequencies, setting the ones induced by the single-CDA-containing BEs as 100%. n=78 from three independent experiments at 26 editable cytosine sites shown in (b). 20d: Schematic diagrams illustrate the conjugation of different cytidine deaminase inhibitors (CDIs) to the N-terminus of mA3CDA1-nSpCas9-BE. 20e: Editing frequencies induced by the indicated BEs at one representative genomic locus. 20f: Statistical analysis of normalized editing frequencies, setting the ones induced by the BEs without CDI as 100%. n=57 from three independent experiments at 19 editable cytosine sites shown in (e). (b), (e) Means±s.d. were from three independent experiments. NT, non-transfected control. (c), (f) P value, one-tailed Student's t test. The median and interquartile range (IQR) are shown.

FIG. 21a-f: Conjugation of mA3CDI reduced unintended base editing at sgRNA-independent OTss sites. 21a: Schematic diagrams illustrate that BE3 induces C-to-T mutations but CDI-conjugated iBE1 remains dormant at sgRNA-independent OTss sites. 21b: Comparison of C-to-T editing frequencies induced by BE3 and iBE1 in the ssDNA regions triggered by the nSaCas9-generated SSBs. 21c: Statistical analysis of normalized accumulative editing frequencies at four ssDNA sites shown in (b), setting the ones induced by BE3 as 100%. n=12 from three independent experiments. 21d: Schematic diagrams illustrate that the sgRNA-mediated cleavage of CDI restores the editing activity of iBE at on-target sites. 21e: Comparison of C-to-T editing frequencies induced by BE3 and iBE1 at on-target sites. 21f: Statistical analysis of normalized accumulative editing frequencies at four on-target sites shown in (e), setting the ones induced by BE3 as 100%. n=12 from three independent experiments. (c), (0 Means±s.d. were from three independent experiments. (d), (g) P value, one-tailed Student's t test. The median and interquartile range (IQR) are shown.

FIG. 22a-e: neSpCas9 reduced the unintended editing of iBE1 at OTsg sites. 22a: Schematic diagrams illustrate that iBE1 but not iBE2 induces C-to-T editing at the OTsg sites that are partially complementary to sgRNAs. 22b: Comparison of C-to-T editing frequencies induced by iBE1 and the targeting-specificity-improved iBEs at indicated OTsg sites. 22c: Statistical analysis of normalized accumulative editing frequencies at OTsg sites for two sgRNAs used in (b), setting the ones induced by iBE1 as 100%. n=6 from three independent experiments. 22d: Comparison of C-to-T editing frequencies induced by iBE1 and the targeting-specificity-improved iBEs at on-target sites. 22e: Statistical analysis of normalized accumulative editing frequencies at the six on-target sites shown in (d), setting the ones induced by iBE1 as 100%. n=18 from three independent experiments. (b), (d)

Means±s.d. were from three independent experiments. (c), (e) P value, one-tailed Student's t test. The median and interquartile range (IQR) are shown.

FIG. 23a-e: Comparison of the base editing induced by hA3A-BE3 and iBE2. 23a: Comparison of C-to-T editing frequencies induced by hA3A-BE3 and iBE2 at representative OTss, OTsg and on-target sites. 23b-c: Statistical analysis of normalized accumulative editing frequencies at the OTss, OTsg (b) and on-target (c) sites for three sgRNAs used in (a), setting the ones induced by hA3A-BE3 as 100%. n=9 from three independent experiments. 23d: Statistical analysis of the normalized ratios of on-target editing frequencies to the total editing frequencies at OTss and OTsg sites for three sgRNAs used in (a), setting the ones induced by the hA3A-BE3 as 1. n=9 from three independent experiments. 23e: Schematic diagrams illustrate that iBE2 induces specific base editing at on-target sites but not at OTss or OTsg sites, whereas hA3A-BE3 induces base editing at on-target sites and both OTss and OTsg sites. (a) Means±s.d. were from three independent experiments. (b-d) P value, one-tailed Student's t test. The median and IQR are shown.

FIG. 24A-B. Schematic diagram illustrating the working process of isplitBE and regular base editors. 24A: isplitBE induces C-to-T base editing only at on-target site and avoids to cause mutations in non-relevant off-target ssDNA regions (OTss) or at the off-target sites with sequence similarity to the spacer region of sgRNA (OTsg). 24B: BE3 or hA3A-BE3 induces C-to-T base editing at on-target site but causes C-to-T mutations in OTss and OTsg regions.

Figure 25:
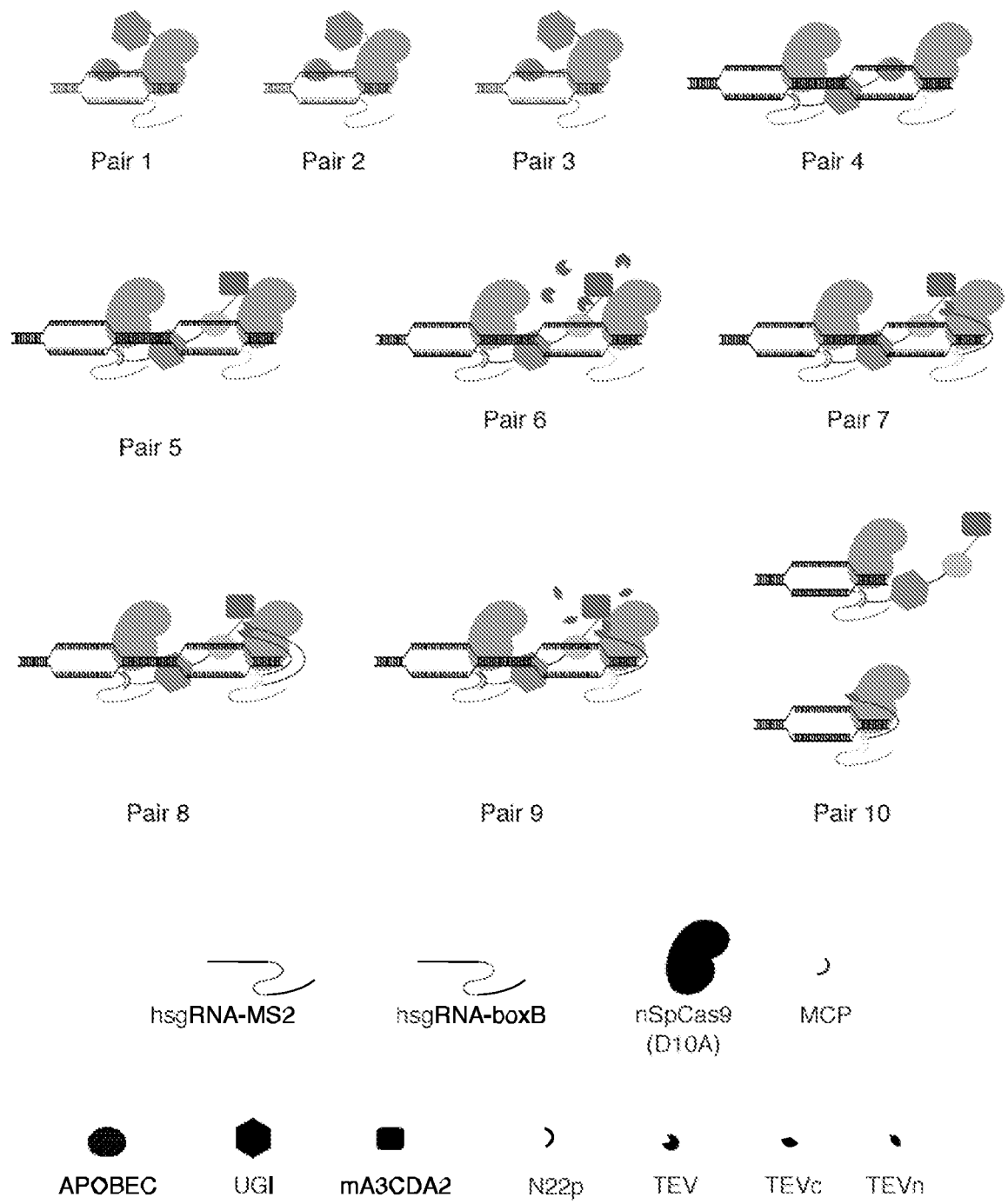

FIG. 25. Schematic diagram illustrating different strategies to remove cytidine deaminase inhibitor (mA3CDA2) at on-target site.

Figure 26B:
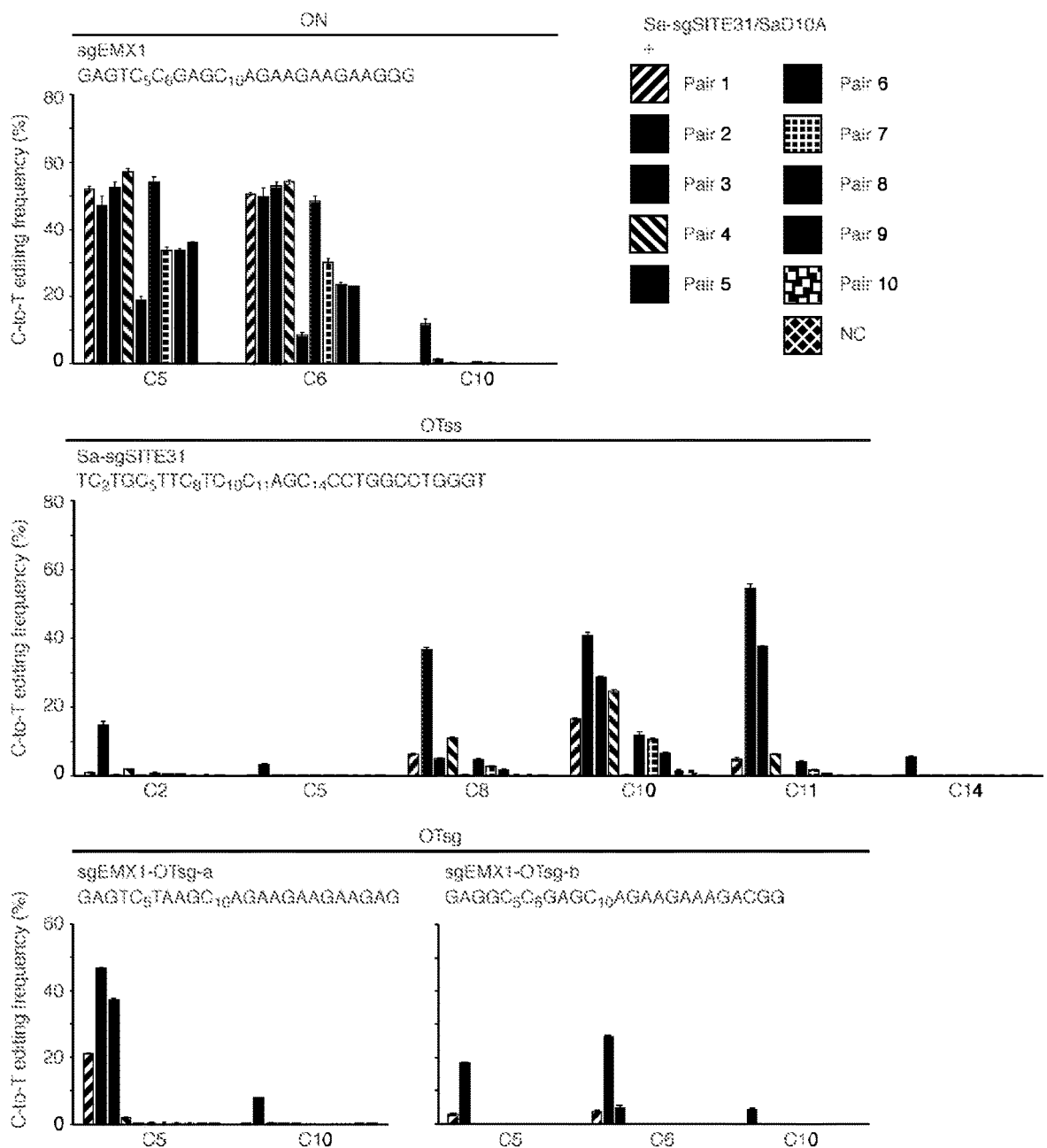

FIG. 26A-B. C-to-T editing at EMX1-ON, Sa-SITE31-OTss and EMX1-OTsg sites induced by different combinations of nCas9 (D10A), APOBEC cytidine deaminase, cytidine deaminase inhibitor (CDI), uracil DNA glycosylase inhibitor (UGI) and TEV protease. 26A: Schematic diagram illustrating the co-transfection of the plasmid expressing Sa-sgSITE31 and the plasmid expressing SaD10A nickase with the indicated ten pairs of plasmid expressing various base editors. 26B: Comparison of editing efficiencies at EMX1-ON, Sa-SITE31-OTss and EMX1-OTsg sites. isplitBE-rA1 (Pair 9) induced substantial editing at ON site but no editing at OTss or OTsg sites. The sequences shown in FIG. 26B, from top to bottom (and left to right), have the sequences of SEQ ID NO: 238-241, respectively.

Figure 27B:
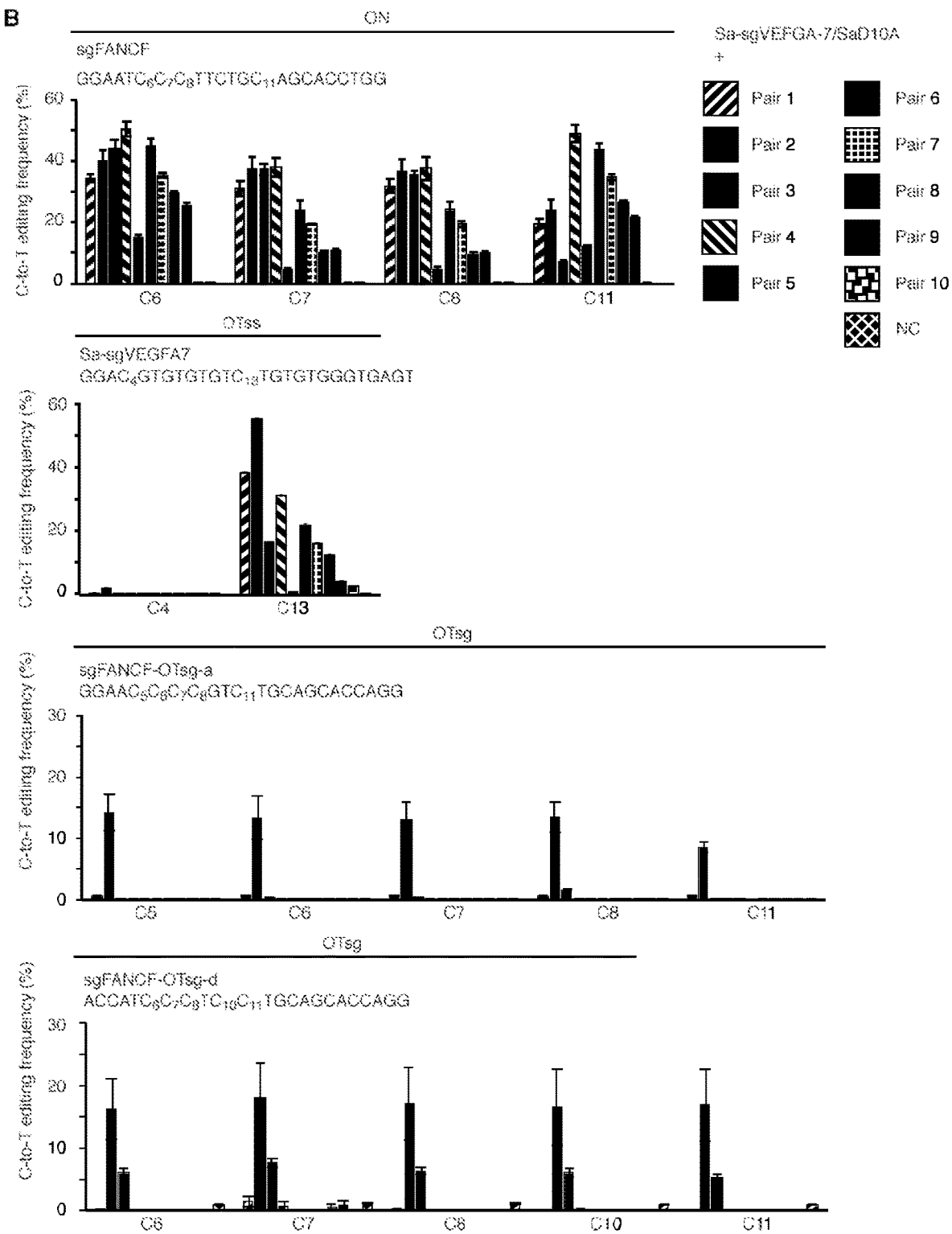

FIG. 27A-B. C-to-T editing at FANCF-ON, Sa-VEGFA-7-OTss and FANCF-OTsg sites induced by different combinations of nCas9 (D10A), APOBEC cytidine deaminase, cytidine deaminase inhibitor (CDI), uracil DNA glycosylase inhibitor (UGI) and TEV protease. 27A: Schematic diagram illustrating the co-transfection of the plasmid expressing Sa-sgVEGFA-7 and the plasmid expressing SaD10A nickase with the indicated ten pairs of plasmid expressing various base editors. 27B: Comparison of editing efficiencies at FANCF-ON, Sa-VEGFA-7-OTss and FANCF-OTsg sites. isplitBE-rA1 (Pair 9) induced substantial editing at ON site but no editing at OTss or OTsg sites. The sequences shown in FIG. 27B, from top to bottom, have the sequences of SEQ ID NO: 242-245, respectively.

Figure 28B:
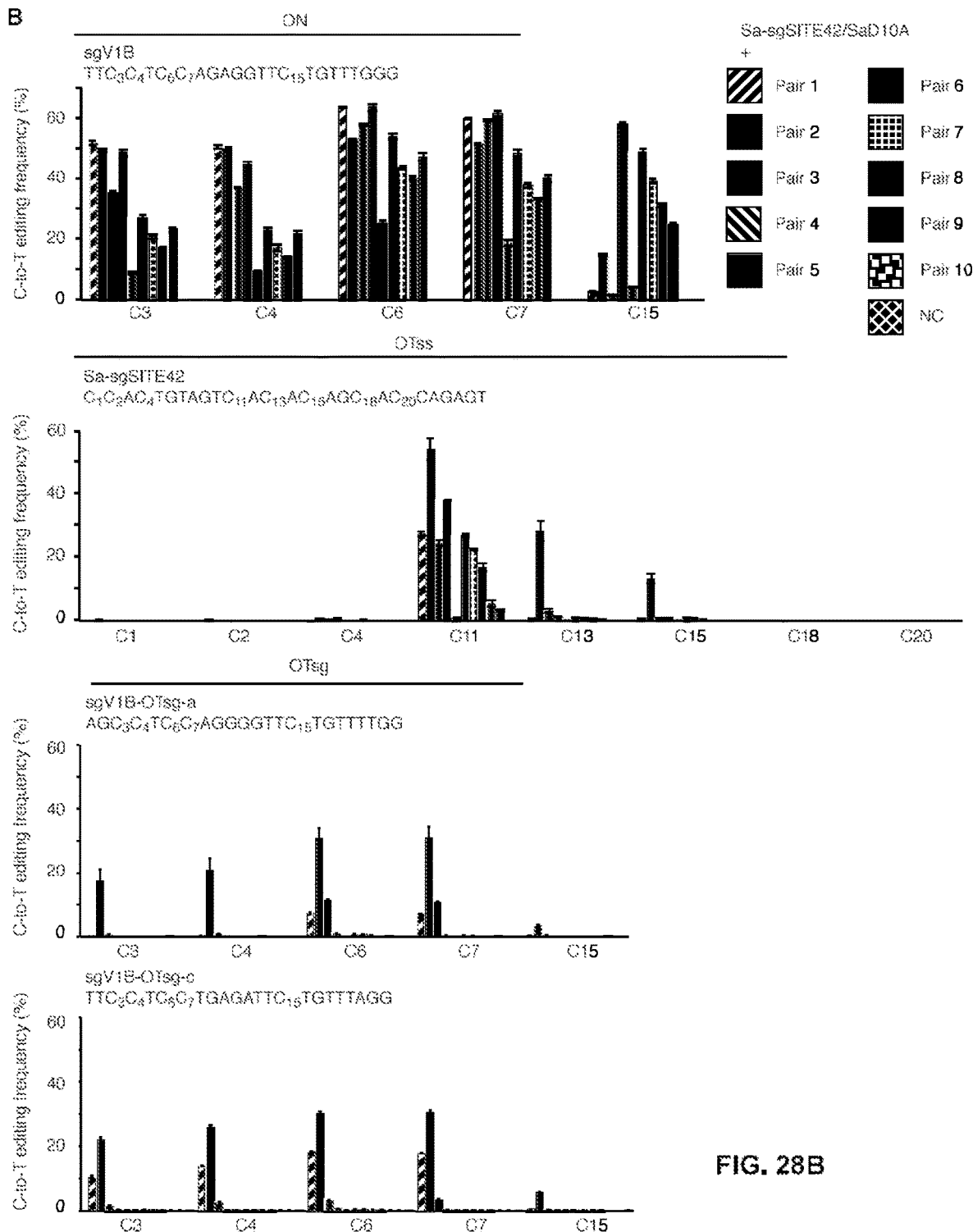

FIG. 28A-B. C-to-T editing at V1B-ON, Sa-SITE42-OTss and V1B-OTsg sites induced by different combinations of nCas9 (D10A), APOBEC cytidine deaminase, cytidine deaminase inhibitor (CDI), uracil DNA glycosylase inhibitor (UGI) and TEV protease. 28A: Schematic diagram illustrating the co-transfection of the plasmid expressing Sa-sgSITE42 and the plasmid expressing SaD10A nickase with the indicated ten pairs of plasmid expressing various base editors. 28B: Comparison of editing efficiencies at V1B-ON, Sa-SITE42-OTss and V1B-OTsg sites. isplitBE-rA1 (Pair 9) induced substantial editing at ON site but no editing at OTss or OTsg sites. The sequences shown in FIG. 28B, from top to bottom, have the sequences of SEQ ID NO: 246-249, respectively.

FIG. 29A-C. Effect of the distance between helper sgRNA (hsgRNA) and sgRNA on base editing efficiency. 29A: Schematic diagram illustrating the distance between hsgRNA and sgRNA at DNTET1, EMX1 and FANCF sites. 29B: Base editing frequencies induced by the indicated sgRNAs and hsgRNAs. 29C: Summary of the effect of distance between hsgRNA and sgRNA. The range of distance for best base editing efficiency is −91 to −34 bp from the PAM of hsgRNA to the PAM of sgRNA.

FIG. 30A-C. Effect of hsgRNA spacer length on base editing efficiency. 30A: Schematic diagram illustrating the co-transfection of sgRNA and the hsgRNAs with different spacer lengths at DNEMX1, FANCF and V1A sites. 30B: Base editing frequencies induced by the indicated sgRNAs and hsgRNAs at the target sties of hsgRNA and sgRNA. 30C: Statistic analysis of the effects of hsgRNA spacer length. The use of hsgRNA with 10-bp spacer greatly reduce the editing efficiency at hsgRNA target sites but maintain the editing efficiency at sgRNA target sites. The sequences shown in FIG. 30B, from top to bottom (from left to right in each row), have the sequences of SEQ ID NO: 250-255, respectively.

Figure 31:
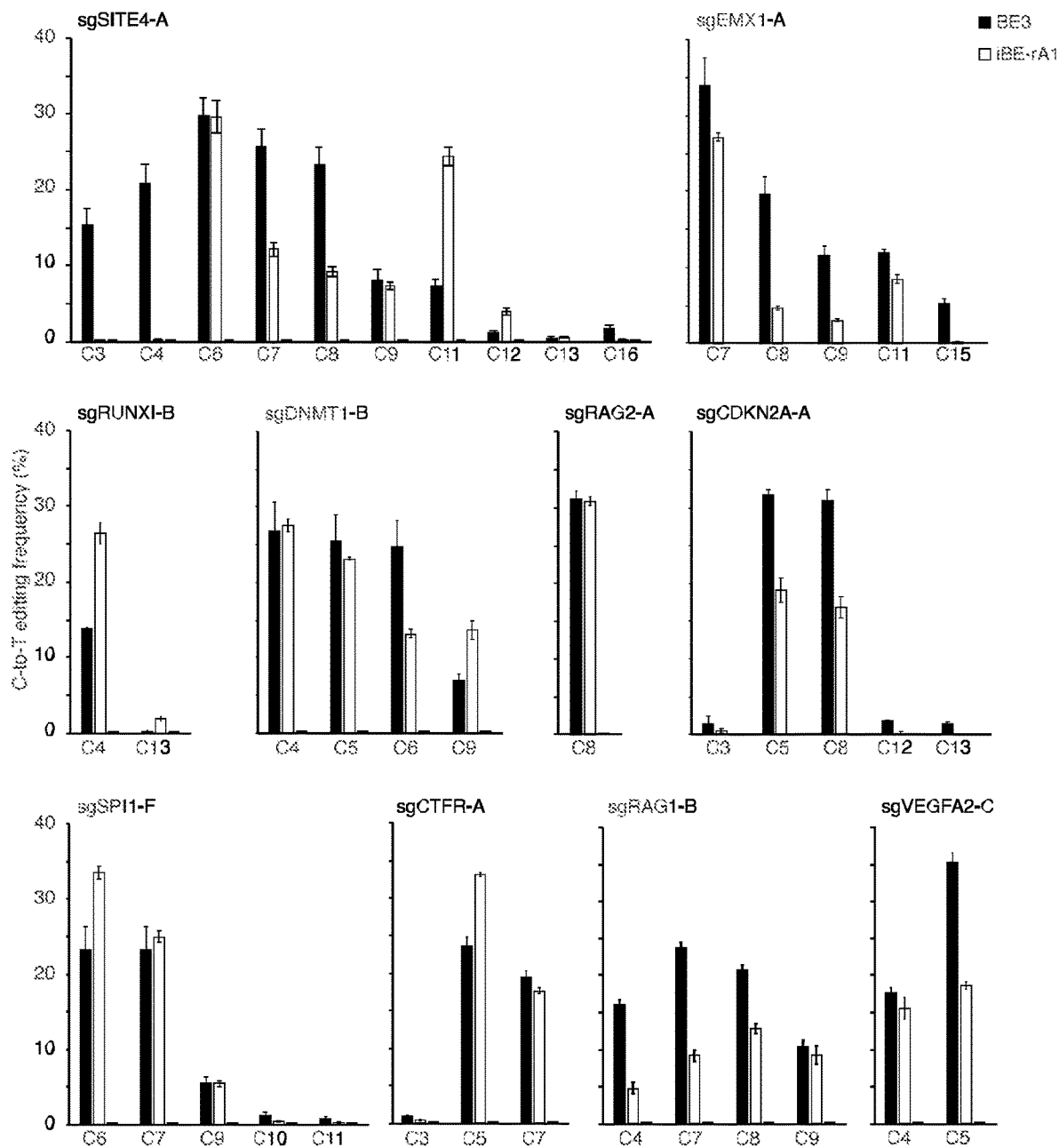

FIG. 31. Comparison of editing efficiency of isplitBE-rA1 and BE3. Editing frequencies induced by indicated base editors at different target sties.

FIG. 32A-C. Comparison of genome-wide C-to-T mutations induced by isplitBE-rA1 and BE3. 32A: mRNA expression levels in wild-type 293FT cells and the APOBEC3 knockout 293FT cells (293FT-A3KO). 32B: Schematic diagram illustrating the procedures to determine genome-wide C-to-T mutations induced by base editors. 32C: On-target editing efficiencies (left) and the number of genome-wide C-to-T mutations induced by Cas9, BE3, hA3A-BE3-Y130F (Y130F) and isplitBE-rA1.

FIG. 33A-C. Comparison of transcriptome-wide C-to-U mutations induced by isplitBE-mA3, BE3 and hA3A-BE3-Y130F (Y130F). 33A: The number of transcriptome-wide C-to-U mutations induced by Cas9, BE3, hA3A-BE3-Y130F (Y130F) and isplitBE-mA 3. 33B: RNA C-to-U editing frequencies induced by Cas9, BE3, hA3A-BE3-Y130F (Y130F) and isplitBE-mA3. 33C: Distribution of RNA C-to-U editing induced by BE3 replicate 1 and isplitBE-mA3 replicate 1.

FIG. 34A-D. Stop codon induced by isplitBE-mA3 in human PCSK9 gene. 34A: Schematic diagram illustrating the co-transfection of sgRNA and the hsgRNAs with isplitBE-mA3 and nCas9. 34B-34D: Editing efficiency induced by isplitBE-mA3 at indicated sites. The sequences shown in FIG. 34B, from top to bottom (from left to right in each row), have the sequences of SEQ ID NO: 256-260, respectively. The paired (up and down) sequences shown in FIG. 34C, from top to bottom (from left to right in each row), have the sequences of SEQ ID NO: 261-265, respectively. The paired (up and down) sequences shown in FIG. 34D, from top to bottom (from left to right in each row), have the sequences of SEQ ID NO: 266-270, respectively.

FIG. 35A-B. Inhibiting effect of mA3CDA2 on the editing efficiency of adenine base editor (ABE). 35A: Schematic diagram illustrating the co-transfection of sgRNA and ABE fused with mA3CDA2 or not. 35B: Editing efficiency induced by indicated ABEs at RNF2 and FANCF sites. The sequences shown in FIG. 35B, from top to bottom, have the sequences of SEQ ID NO: 271, 272, 271, 272, 273, 273, 273 and 273, respectively.

FIG. 36A-G. Enhanced prime editing by manipulating prime editing guide RNA (pegRNA). 36A: Schematic diagram illustrating the change of RNA base pairs to increase stem stability of enhanced pegRNA (epegRNA). 36B: Schematic diagram illustrating the co-transfection of PE2, nicking sgRNA with pegRNA or epegRNA-GC. 36C-36D: Comparison of prime editing efficiencies induced with pegRNA and epegRNA-GC. 36E: Schematic diagram illustrating the change of RNA base pairs to increase stem stability of enhanced pegRNA (epegRNA). 36F: Schematic diagram illustrating the co-transfection of PE2, nicking sgRNA with pegRNA or epegRNA-CG. 36G: Comparison of prime editing efficiencies induced with pegRNA and epegRNA-CG. The sequences shown in FIG. 36A, from top to bottom, have the sequences of SEQ ID NO: 274-275, respectively. The sequences shown in FIG. 36C, from top to bottom, have the sequences of SEQ ID NO: 276, 276, 277, 276 and 276, respectively. The sequences shown in FIG. 36D, from top to bottom, have the sequences of SEQ ID NO: 276, 276, 276, 276 and 278, respectively. The sequences shown in FIG. 36E, from top to bottom, have the sequences of SEQ ID NO: 279-280, respectively. The sequences shown in FIG. 36G have the sequence of SEQ ID NO: 276.

FIG. 37A-B. Prime editing system by using PEs containing different Cas9 proteins. 37A: Schematic diagram illustrating the co-transfection of pegRNA, nicking sgRNA with PE2-NG or xPE2. 37B: Prime editing efficiencies induced by PE2-NG and xPE2. The sequences shown in FIG. 37B, from top to bottom, have the sequences of SEQ ID NO: 276, 281 and 282, respectively.

FIG. 38A-C. Split prime editing (split-PE) system. 38A: Schematic diagram illustrating the working process of PE and split-PE systems. 38B: Schematic diagram illustrating the co-transfection of PE and split-PE systems. 38C: Editing efficiency induced by PE and split-PE systems at EMX1 site. The sequences shown in FIG. 38C have the sequence of SEQ ID NO: 283.

Figure 39A:
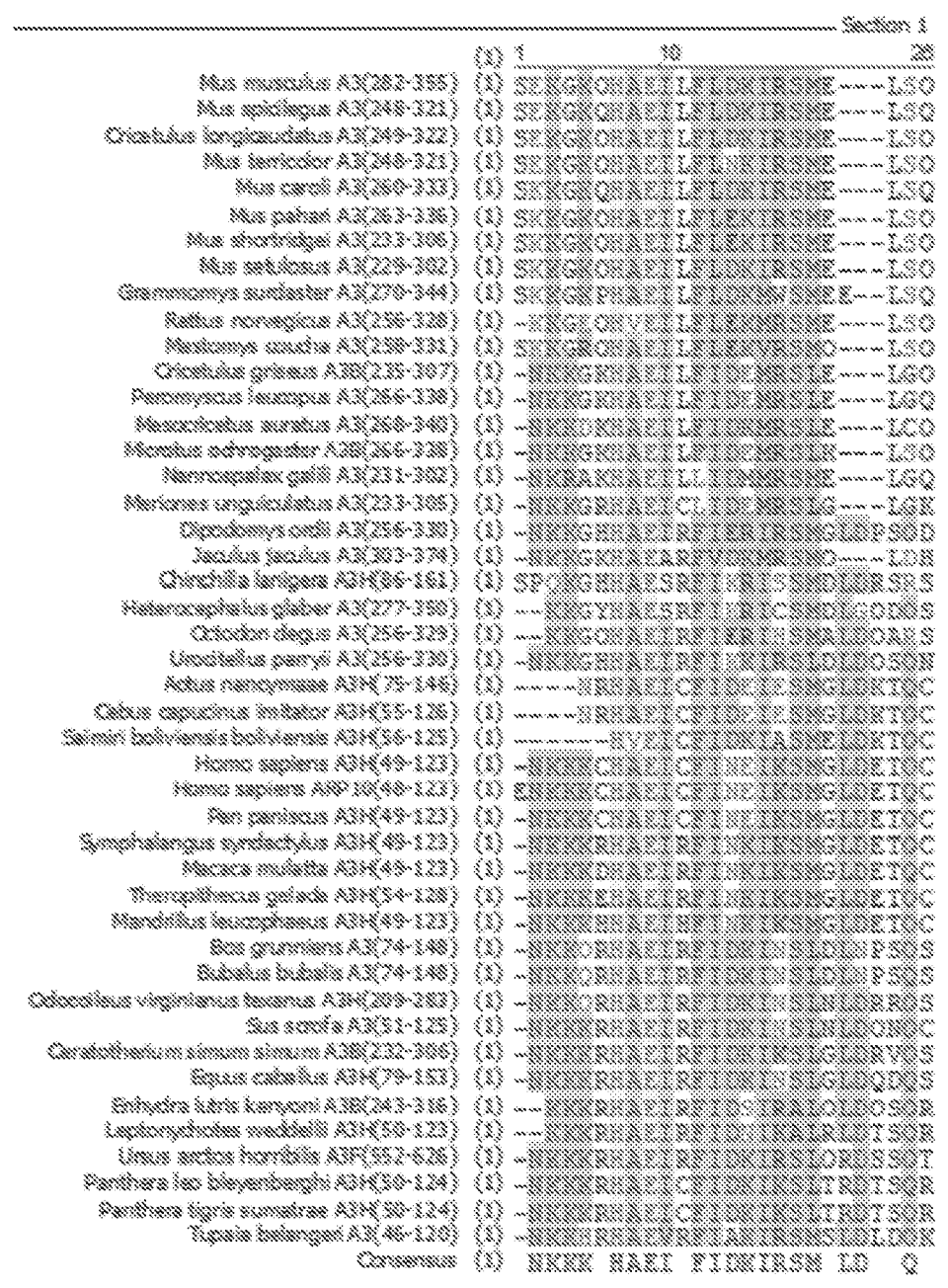
Figure 39B:
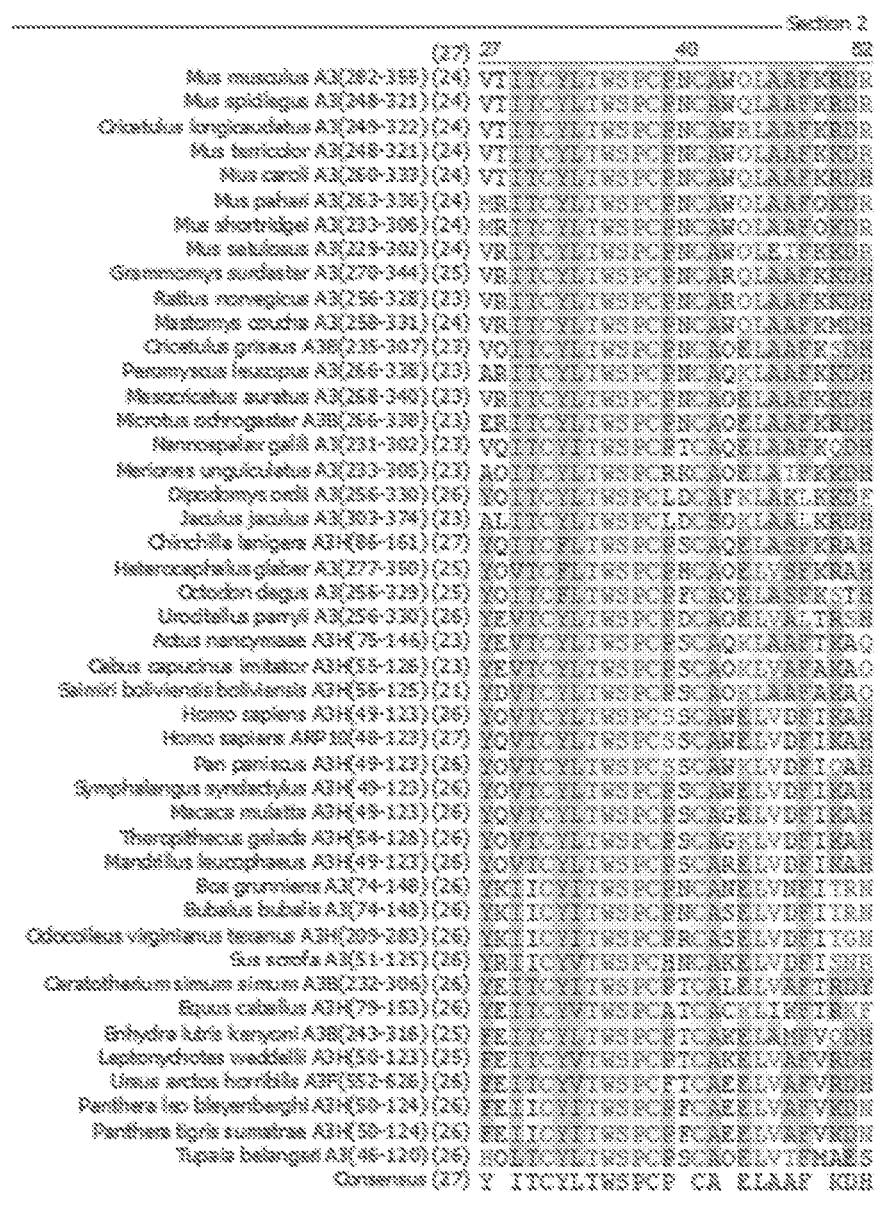
Figure 39C:
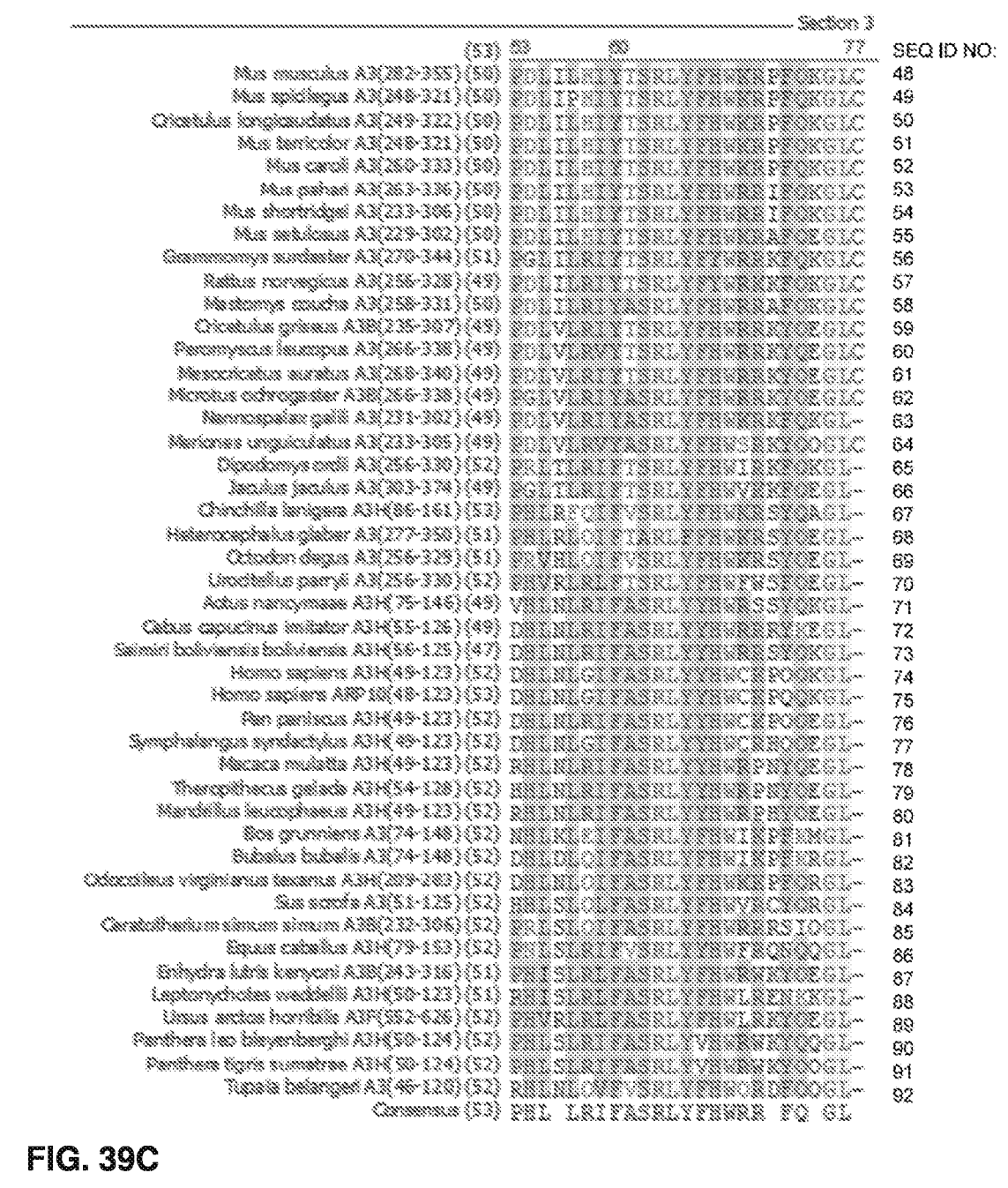

FIG. 39A-C. Alignment of mA3CDA2 core region with other cytidine deaminase domains. The sequences shown in FIG. 39A-C, from top to bottom have the sequences of SEQ ID NO: 48-92, respectively.

Figure 40A:
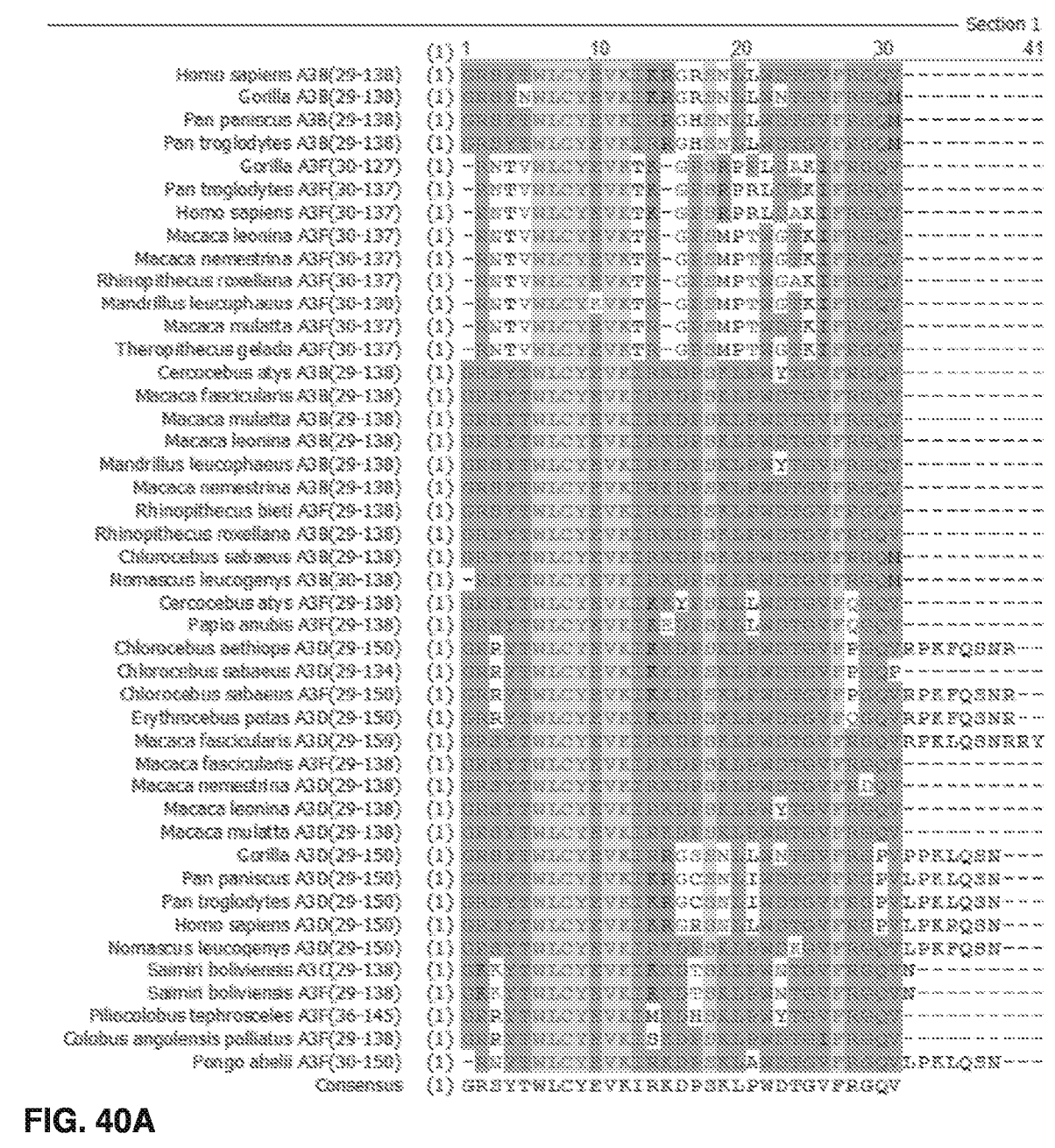
Figure 40B:
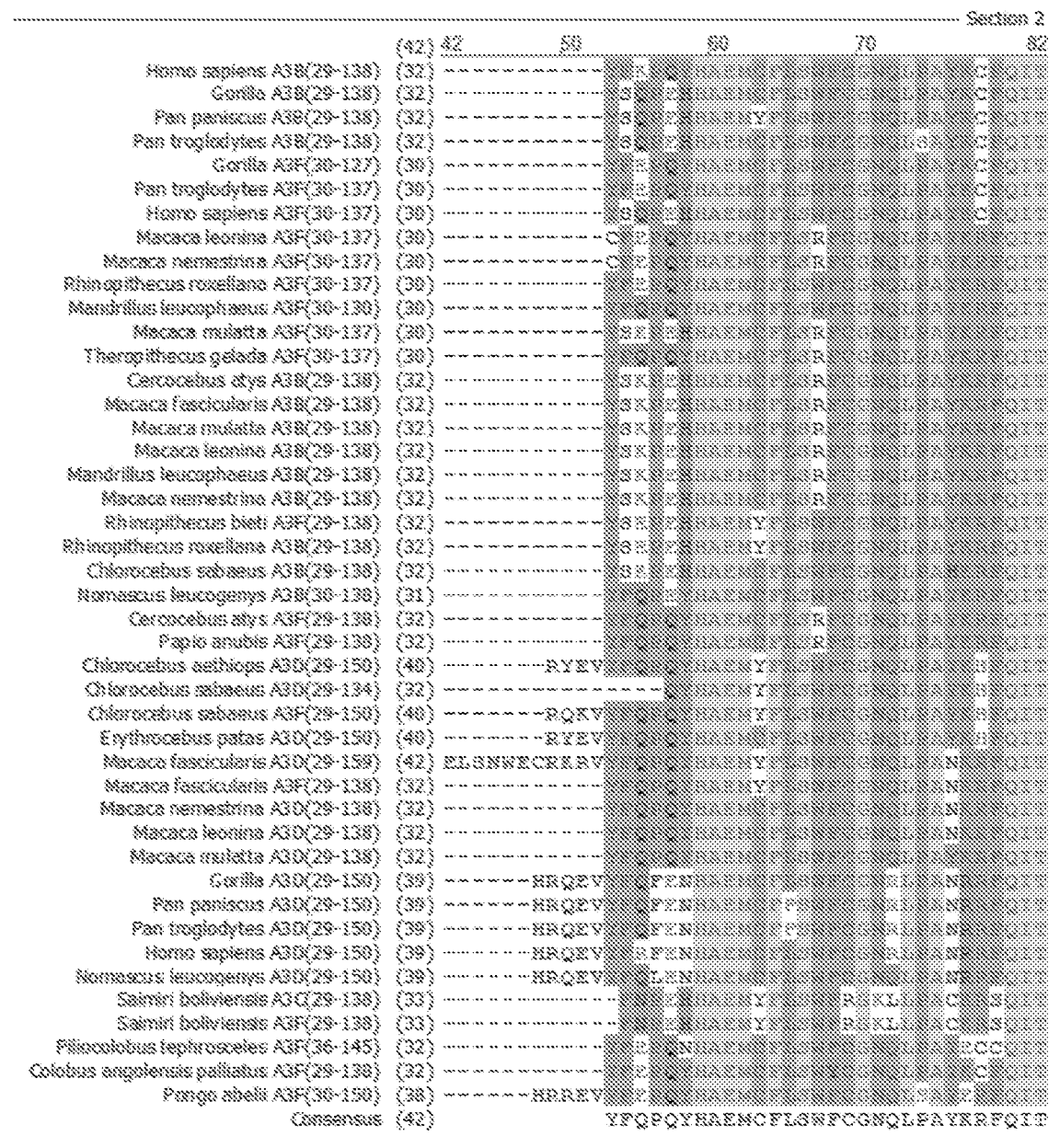
Figure 40C:
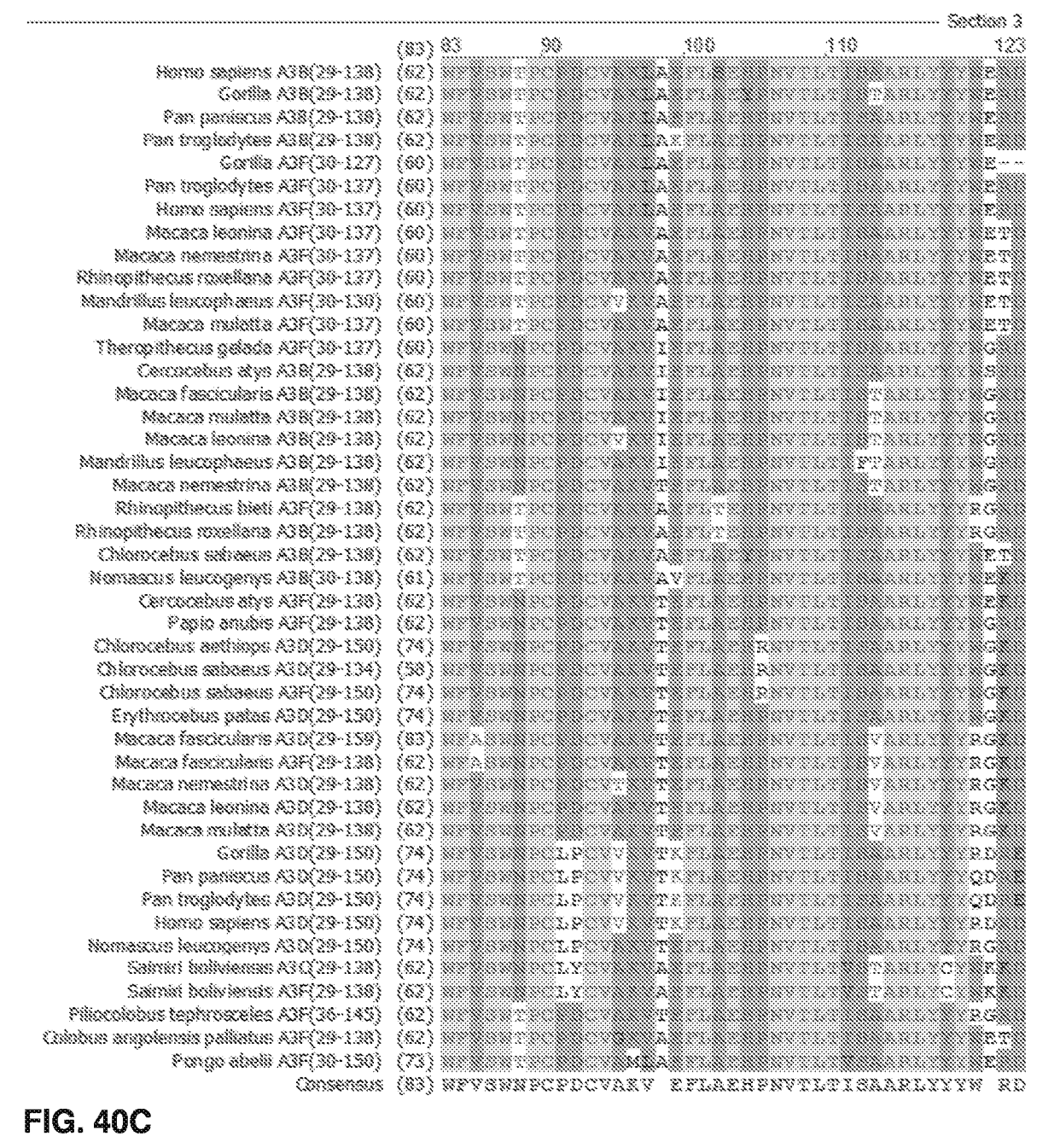

FIG. 40A-D. Alignment of hA3BCDA1 with other cytidine deaminase domains. The sequences shown in FIG. 39A-C, from top to bottom have the sequences of SEQ ID NO: 93-135, respectively.

DETAILED DESCRIPTION

Definitions

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein", "amino acid chain" or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

Use of Nucleobase Deaminase Inhibitor to Reduce Random Insertions and Deletions

As shown in the experimental examples and FIG. 1-3, the currently commonly used base editors BE3 and hA3A-BE3 induced C-to-T mutations in off-target single-stranded DNA regions.

It was discovered surprisingly, however, that the use of the mouse APOBEC3 (mA3) in mA3-BE3 (FIG. 4B, 5B, 6B) generally did not induce C-to-T editing at the tested target sites (FIG. 4C, 5C, 6C). mA3 has two cytidine deaminase (CDA) domains, CDA1 and CDA2 (FIG. 4A, 5A, 6A). When the CDA2 domain was removed from the full-length mA3, the resulting base editor mA3CDA1-BE3 (FIG. 4B, 5B, 6B) induced substantial C-to-T editing (FIG. 4C, 5C, 6C). These results indicate that the mA3-CDA2 domain is an inhibitor of base editing.

Also surprisingly, the mA3-CDA2 domain not only can inhibit the base editing activity of mA3-CDA1, it can also inhibit other nucleobase deaminases. For instance, when mA3-CDA2 was fused to the N-terminus of each of three active BEs, mA3CDA1-BE3, BE3 and hA3A-BE3, the fusion proteins mA3rev-BE3, mA3-CDA2-BE3 and mA3-CDA2-hA3A-BE3 (FIG. 4B, 5B, 6B) had clearly reduced base editing efficiencies (FIG. 4C, 5C, 6C).

Moreover, cleavage of mA3-CDA2 from the fusion proteins restored the base editing efficiency (FIG. 4C, 5C, 6C), suggesting that the inhibition of mA3-CDA2 is associated with its covalent connection to the BEs.

Like mA3, the human APOBEC3B (hA3B) also has two cytidine deaminase (CDA) domains, CDA1 and CDA2 (FIG. 7A, 8A, 9A). Incorporation of the full-length hA3B in hA3B-BE3 (FIG. 7B, 8B, 9B) only induced relatively low levels of C-to-T editing at three tested target sites (FIG. 7C, 8C, 9C). However, hA3B-CDA2-BE3, which was generated by deleting the hA3B-CDA1 domain (FIG. 7B, 8B, 9B) induced higher C-to-T editing (FIG. 7C, 8C, 9C). These results indicate that hA3B-CDA1 is another inhibitor of base editing and the inhibition of hA3B-CDA1 is associated with its covalent connection to the BEs.

Using the sequences of mA3-CDA2 and hA3B-CDA1, the instant inventors were able to identify additional nucleobase deaminase inhibitors/domains in the protein database. Table 1 shows 44 proteins/domains that have significant sequence homology to mA3-CDA2 core sequence (FIG. 39) and Table 2 shows 43 proteins/domains that have significant sequence homology to hA3B-CDA1 (FIG. 40). All of these proteins and domains, as well as their variants and equivalents, are contemplated to have nucleobase deaminase inhibition activities.

Fusion Proteins

Based on these surprising and expected findings, a fusion protein is designed that can be used to generate a base editor with improved base editing specificity and efficiency. In one embodiment, the present disclosure provides a fusion protein that includes a first fragment comprising a nucleobase deaminase or a catalytic domain thereof, a second fragment comprising a nucleobase deaminase inhibitor, and a protease cleavage site between the first fragment and the second fragment.

A base editor that incorporates such a fusion protein has reduced or even no editing capability and accordingly will generate reduced or no off-target mutations. Upon cleavage of the protease cleavage site and release of the nucleobase deaminase inhibitor from the fusion protein at a target site, the base editor that is at the target site will then be able to edit the target site efficiently.

The term "nucleobase deaminase" as used herein, refers to a group of enzymes that catalyze the hydrolytic deamination of nucleobases such as cytidine, deoxycytidine, adenosine and deoxyadenosine. Non-limiting examples of nucleobase deaminases include cytidine deaminases and adenosine deaminases.

"Cytidine deaminase" refers to enzymes that catalyze the irreversible hydrolytic deamination of cytidine and deoxycytidine to uridine and deoxyuridine, respectively. Cytidine deaminases maintain the cellular pyrimidine pool. A family of cytidine deaminases is APOBEC ("apolipoprotein B mRNA editing enzyme, catalytic polypeptide-like"). Members of this family are C-to-U editing enzymes. Some APOBEC family members have two domains, one domain of APOBEC like proteins is the catalytic domain, while the other domain is a pseudocatalytic domain. More specifically, the catalytic domain is a zinc dependent cytidine deaminase domain and is important for cytidine deamination. RNA editing by APOBEC-1 requires homodimerisation and this complex interacts with RNA binding proteins to form the editosome.

Non-limiting examples of APOBEC proteins include APOBEC1, APOBEC2, APOBEC3A, APOBEC3B, APOBEC3C, APOBEC3D, APOBEC3F, APOBEC3G, APOBEC3H, APOBEC4, and activation-induced (cytidine) deaminase (AID).

Various mutants of the APOBEC proteins are also known that have bring about different editing characteristics for base editors. For instance, for human APOBEC3A, certain mutants (e.g., W98Y, Y130F, Y132D, W104A, D131Y and P134Y) even outperform the wildtype human APOBEC3A in terms of editing efficiency or editing window. Accordingly, the term APOBEC and each of its family member also encompasses variants and mutants that have certain level (e.g., 70%, 75%, 80%, 85%, 90%, 95%, 98%, 99%) of sequence identity to the corresponding wildtype APOBEC protein or the catalytic domain and retain the cytidine deaminating activity. The variants and mutants can be derived with amino acid additions, deletions and/or substitutions. Such substitutions, in some embodiments, are conservative substitutions.

"Adenosine deaminase", also known as adenosine aminohydrolase, or ADA, is an enzyme (EC 3.5.4.4) involved in purine metabolism. It is needed for the breakdown of adenosine from food and for the turnover of nucleic acids in tissues.

Non-limiting examples of adenosine deaminases include tRNA-specific adenosine deaminase (TadA), adenosine deaminase tRNA specific 1 (ADAT1), adenosine deaminase tRNA specific 2 (ADAT2), adenosine deaminase tRNA specific 3 (ADAT3), adenosine deaminase RNA specific B1 (ADARB1), adenosine deaminase RNA specific B2 (ADARB2), adenosine monophosphate deaminase 1 (AMPD1), adenosine monophosphate deaminase 2 (AMPD2), adenosine monophosphate deaminase 3 (AMPD3), adenosine deaminase (ADA), adenosine deaminase 2 (ADA2), adenosine deaminase like (ADAL), adenosine deaminase domain containing 1 (ADAD1), adenosine deaminase domain containing 2 (ADAD2), adenosine deaminase RNA specific (ADAR) and adenosine deaminase RNA specific B1 (ADARB1).

Some of the nucleobase deaminases have a single, catalytic domain, while others also have other domains, such as an inhibitory domain as currently discovered by the instant inventors. In some embodiments, therefore, the first fragment only includes the catalytic domain, such as mA3-CDA1 and hA3B-CDA2. In some embodiments, the first fragment includes at least a catalytic core of the catalytic domain. For instance, as demonstrated in the experimental examples, when mA3-CDA1 was truncated at residues 196/197 the CDA1 domain still retained substantial editing efficiencies (FIG. 10C, 11C, 12C).

The present disclosure tested two nucleobase deaminase inhibitors, mA3-CDA2 and hA3B-CDA1, which are the inhibitory domains of the corresponding nucleobase deaminase. Additional nucleobase deaminase inhibitors and inhibitory domains were also identified in the protein databases (see Tables 1 and 2). Their biological equivalents (e.g., having at least about 80%, 85%, 90%, 95%, 97%, 98%, 99%, 99.5% sequence identity, or having one, two, or three amino acid addition/deletion/substitution, and having nucleobase deaminase inhibitor activity) can also be prepared with known methods in the art, such as conservative amino acid substitutions. A "nucleobase deaminase inhibitor," accordingly, refers to a protein or a protein domain that inhibits the deaminase activity of a nucleobase deaminase. In some embodiments, the second fragment includes at least an inhibitory core of the inhibitory protein/domain. For instance, as demonstrated in the experimental examples, when mA3-CDA2 retained residues 334-429, the CDA2 still had the inhibitory effect of base editing (FIG. 13B, 14B, 15B).

In some embodiments, the fusion protein further includes a clustered regularly interspaced short palindromic repeats (CRISPR)-associated (Cas) protein, optionally in the first fragment, next to the nucleobase deaminase or the catalytic domain thereof.

The term "Cas protein" or "clustered regularly interspaced short palindromic repeats (CRISPR)-associated (Cas) protein" refers to RNA-guided DNA endonuclease enzymes associated with the CRISPR (Clustered Regularly Interspaced Short Palindromic Repeats) adaptive immunity system in *Streptococcus pyogenes*, as well as other bacteria. Cas proteins include Cas9 proteins, Cas12a (Cpf1) proteins, Cas12b (formerly known as C2c1) proteins, Cas13 proteins and various engineered counterparts. Example Cas proteins include SpCas9, FnCas9, St1Cas9, St3Cas9, NmCas9, SaCas9, AsCpf1, LbCpf1, FnCpf1, VQR SpCas9, EQR SpCas9, VRER SpCas9, SpCas9-NG, xSpCas9, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, RanCas13b and those provided in Table A below.

TABLE A

Example Cas Proteins

| Cas protein types | Cas proteins |
|---|---|
| Cas9 proteins | Cas9 from *Staphylococcus aureus* (SaCas9)<br>Cas9 from *Neisseria meningitidis* (NmeCas9)<br>Cas9 from *Streptococcus thermophilus* (StCas9)<br>Cas9 from *Campylobacter jejuni* (CjCas9) |
| Cas 12a (Cpf1) proteins | Cas12a (Cpf1) from *Acidaminococcus* sp BV3L6 (AsCpf1)<br>Cas12a (Cpf1) from *Francisella novicida* sp BV3L6 (FnCpf1)<br>Cas12a (Cpf1) from *Smithella* sp SC K08D17 (SsCpf1)<br>Cas12a (Cpf1) from *Porphyromonas crevioricanis* (PcCpf1)<br>Cas12a (Cpf1) from *Butyrivibrio proteoclasticus* (BpCpf1)<br>Cas12a (Cpf1) from Candidatus *Methanoplasma termitum* (CmtCpf1)<br>Cas12a (Cpf1) from *Leptospira inadai* (LiCpf1)<br>Cas12a (Cpf1) from *Porphyromonas macacae* (PmCpf1)<br>Cas12a (Cpf1) from *Peregrinibacteria bacterium* GW2011 WA2 33 70 (Pb3310Cpf1)<br>Casl2a (Cpf1) from *Parcubacteria bacterium* GW2011 GWC2 44 17 (Pb4417Cpf1)<br>Cas12a (Cpf1) from *Butyrivibrio* sp. NC3005 (BsCpf1)<br>Cas12a (Cpf1) from *Eubacterium eligens* (EeCpf1) |
| Cas12b (C2c1) proteins | Cas12b (C2c1) *Bacillus hisashii* (BhCas12b)<br>Cas12b (C2c1) *Bacillus hisashii* with a gain-of-function mutation (see, e.g., Strecker et al., Nature Communications 10 (article 212) (2019)<br>Cas12b (C2c1) *Alicyclobacillus kakegawensis* (AkCas12b)<br>Cas12b (C2c1) *Elusimicrobia bacterium* (EbCas12b)<br>Cas12b (C2c1) *Laceyella sediminis* (Ls) (LsCas12b) |
| Cas13 proteins | Cas13d from *Ruminococcus flavefaciens* XPD3002 (RfCas13d)<br>Cas13a from *Leptotrichia wadei* (LwaCas13a)<br>Cas13b from *Prevotella* sp. P5-125 (PspCas13b)<br>Cas13b from *Porphyromonas gulae* (PguCas13b)<br>Cas13b from *Riemerella anatipestifer* (RanCas13b) |
| Engineered Cas proteins | Nickases (mutation in one nuclease domain)<br>Catalytically inactive mutant (dCas9; mutations in both of the nuclease domains)<br>Enhanced variants with improved specificity (see, e.g., Chen et al., Nature, 550, 407-410 (2017) |

The protease cleavage site between the first fragment and the second fragment can be any known protease cleavage site (peptide) for any proteases. Non-limiting examples of proteases include TEV protease, TuMV protease, PPV protease, PVY protease, ZIKV protease and WNV protease. The protein sequences of example proteases and their corresponding cleavage sites are provided in Table B.

TABLE B

Example Sequences

| Name | Sequence | SEQ ID NO: |
|---|---|---|
| Mouse APOBEC 3 cytidine deaminase domain 2 | MSSSTLSNICLTKGLPETRFWVEGRRMDPLSEEEFYSQFYNQRVKHLCY YHRMKPYLCYQLEQFNGQAPLKGCLLSEKGKQHAEILFLDKIRSMELSQ VTITCYLTWSPCPNCAWQLAAFKRDRPDLILHIYTSRLYFHWKRPFQKG LCSLWQSGILVDVMDLPQFTDCWTNFVNPKRPFWPWKGLEIISRRTQRR LRRIKESWGLQDLVNDFGNLQLGPPMS | 1 |
| Human APOBEC3B cytidine deaminase domain 1 | MNPQIRNPMERMYRDTFYDNFENEPILYGRSYTWLCYEVKIKRGRSNLL WDTGVFRGQVYFKPQYHAEMCFLSWFCGNQLPAYKCFQITWFVSWTPCP DCVAKLAEFLSEHPNVTLTISAARLYYWERDYRRALCRLSQAGARVKI MDYEE FAYCWENFVYNEGQ | 2 |

TABLE B-continued

Example Sequences

| Name | Sequence | SEQ ID NO: |
|---|---|---|
| TEV protease N-terminal domain | MGESLFKGPRDYNPISSTICHLTNESDGHTTSLYGIGFGPFIITNKHLF RRNNGTLLVQSLHGVFKVKNTTTLQQHLIDGRDMIIRMPKDFPPFPQK LKFREPQREERICLVTTNFQT | 3 |
| TEV protease C-terminal domain | MKSMSSMVSDTSCTFPSSDGIFWKHWIQTKDGQCGSPLVSTRDGFIVGI HSASNFTNTNNYFTSVPKNFMELLTNQEAQQWVSGWRLNADSVLWGGHK VFMVKPEEPFQPVKEATQ | 4 |
| TEV protease cleavage site | ENLYFQS | 5 |
| TuMV protease | MASSNSMFRGLRDYNPISNNICHLTNVSDGASNSLYGVGFGPLILTNRH LFERNNGELVIKSRHGEFVIKNTTQLHLLPIPDRDLLLIRLPKDVPPFP QKLGFRQPEKGERICMVGSNFQTKSITSIVSETSTIMPVENSQFWKHWI STKDGQCGSPMVSTKDGKILGLHSLANFQNSINYFAAFPDDFAEKYLHT IEAHEWVKHWKYNTSAISWGSLNIQASQPSGLFKVSKLISDLDSTAVYA Q | 6 |
| TuMV protease cleavage site | GGCSHQS | 7 |
| PPV protease | MASSKSLFRGLRDYNPIASSICQLNNSSGARQSEMFGLGFGGLIVTNQH LFKRNDGELTIRSHHGEFWKDTKTLKLLPCKGRDIVIIRLPKDFPPPFP RRLQFRTPTTEDRVCLIGSNFQTKSISSTMSETSATYPVDNSHFWKHWI STKDGHCGLPIVSTRDGSILGLHSLANSTNTQNFYAAFPDNFETTYLSN QDNDNWIKQWRYNPDEVCWGSLQLKRDIPQSPFTICKLLTDLDGEFVYT Q | 8 |
| PPV protease cleavage site | QVWHQSK | 9 |
| PVY protease | MASAKSLMRGLRDFNPIAQTVCRLKVSVEYGASEMYGFGFGAYIVANHH LFRSYNGSMEVQSMHGTFRVKNLHSLSVLPIKGRDIILIKMPKDFPVFP QKLHFRAPTQNERICLVGTNFQEKYASSIITETSTTYNIPGSTFWKHWI ETDNGHCGLPWSTADGCIVGIHSLANNAHTTNYYSAFDEDFESKYLRT NEHNEWVKSWVYNPDTVLWGPLKLKDSTPKGLFKTTKLVQDLIDHDVW EQ | 10 |
| PVY protease cleavage site | YDVRHQSR | 11 |
| ZIKV protease | MASDMYIERAGDITWEKDAEVTGNSPRLDVALDESGDFSLVEEDGPPMR EGGGGSGGGGSGALWDVPAPKEVKKGETTDGVYRVMTRRLLGSTQVGVG VMQEGVFHTMWHVTKGAALRSGEGRLDPYWGDVKQDLVSYCGPWKLDAA WDGLSEVQLLAVPPGERARNIQTLPGIFKTKDGDIGAVALDYPAGTSGS PILDKCGRVIGLYGNGVVIKNGSYVSAITQGKREEETPVECFE | 12 |
| ZIKV protease cleavage site | KERKRRGA | 13 |
| WNV protease | MASSTDMWIERTADISWESDAEITGSSERVDVRLDDDGNFQLMNDPGAP WKGGGGSGGGGVLWDTPSPKEYKKGDTTTGVYRIMTRGLLGSYQAGAG VMVEGVFHTLWHTTKGAALMSGEGRLDPYWGSVKEDRLCYGGPWKLQHK WNGQDEVOMIVVEPGKNVKNVQTKPGVFKTPEGEIGAVTLDFPTGTSGS PIVDKNGDVIGLYGNGVIMPNGSYISAIVQGERMDEPIPAGFEPEML | 14 |
| WNV protease cleavage site | KQKKRGGK | 15 |
| MS2 | ACAUGAGGAUCACCCAUGU | 16 |
| sgRNA scaffold with 2 × MS2 | GUUUGAGAGCUAGGCCAACAUGAGGAUCACCCAUGUCUGCAGGGCCUAG CAAGUUCAAAUAAGGCUAGUCCGUUAUCAACUUGGCCAACAUGAGGAUC ACCCAUGUCUGCAGGGCCAAGUGGCACCGAGUCGGUGC | 17 |
| PP7 | GGAGCAGACGAUAUGGCGUCGCUCC | 18 |
| sgRNA scaffold with 2 × PP7 | GUUUGAGAGCUACCGGAGCAGACGAUAUGGCGUCGCUCCGGUAGCAAGU UCAAAUAAGGCUAGUCCGUUAUCAACUUGGAGCAGACGAUAUGGCGUCG CUCCAAGUGGCACCGAGUCGGUGC | 19 |
| boxB | GCCCUGAAGAAGGGC | 20 |

TABLE B-continued

Example Sequences

| Name | Sequence | SEQ ID NO: |
|---|---|---|
| sgRNA scaffold with 2 × boxB | GUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 21 |
| MS2 coat protein (MCP) | MASNFTQFVLVDNGGTGDVTVAPSNFANGIAEWISSNSRSQAYKVTCSVRQSSAQNRKYTIKVEVPKGAWRSYLNMELTIPIFATNSDCELIVKAMQGLLKDGNPIPSAIAANSGIY | 22 |
| PP7 coat protein (PCP) | MGSKTIVLSVGEATRTLTEIQSTADRQIFEEKVGPLVGRLRLTASLRQNGAKTAYRVNLKLDQADWDSGLPKVRYTQVWSHDVTIVANSTEASRKSLYDLTKSLVATSQVEDLVVNLVPLGR | 23 |
| boxB coat protein (N22p) | MGNARTRRRERRAEKQAQWKAAN | 24 |
| UGI | TNLSDIIEKETGKQLVIQESILMLPEEVEEVIGNKPESDILVHTAYDESTDENVMLLTSDAPEYKPWALVIQDSNGENKIKML | 25 |
| P2A | GSGATNFSLLKQAGDVEENPGP | 26 |
| T2A | GSGEGRGSLLTCGDVEENPGP | 27 |
| E2A | GSGQCTNYALLKLAGDVESNPGP | 28 |

In some embodiments, the protease cleavage site is a self-cleaving peptide, such as the 2A peptides. "2A peptides" are 18-22 amino-acid-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified. A few non-limiting examples of 2A peptides are provided in SEQ ID NO:26-28.

In some embodiments, the protease cleavage site is a cleavage site (e.g., SEQ ID NO:5) for the TEV protease. In some embodiments, the fusion protein further includes a third fragment that includes the TEV protease or a fragment thereof. In some embodiments, the TEV protease fragment in the fusion protein in not active, that, is, not able to cleave the TEV cleavage site on its own. However, in the presence of the remaining portion of the TEV protease, this fragment will be able to execute the cleavage. As further described below, such an arrangement provides additional control and flexible of the base editing capabilities. The TEV fragment may be the TEV N-terminal domain (e.g., SEQ ID NO:3) or the TEV C-terminal domain (e.g., SEQ ID NO:4).

Various arrangement of the fragments can be made. Non-limiting examples include, from N-terminal side to C-terminal side:

(1) first fragment (e.g., catalytic domain)—protease cleavage site—second fragment (e.g., inhibitory domain);
(2) first fragment (e.g., catalytic domain and Cas protein)—protease cleavage site—second fragment (e.g., inhibitory domain);
(3) first fragment (e.g., catalytic domain, Cas protein and TEV N-terminal domain)—protease cleavage site (e.g., TEV cleavage site)—second fragment (e.g., inhibitory domain);
(4) second fragment (e.g., inhibitory domain)—protease cleavage site (e.g., TEV cleavage site)—first fragment (e.g., catalytic domain, Cas protein and TEV N-terminal domain); and
(5) second fragment (e.g., inhibitory domain)—protease cleavage site (e.g., TEV cleavage site)—first fragment (e.g., Cas protein, catalytic domain, and TEV C-terminal domain).

In some embodiments, provided are fusion proteins comprising a first fragment comprising first nucleobase deaminase (e.g., cytidine deaminase) or a catalytic domain thereof, and a second fragment comprising an inhibitory domain of a second nucleobase deaminase, wherein the first nucleobase deaminase is different from the second nucleobase deaminase. In some embodiments, each of the first and second nucleobase deaminases is independently selected from the group of human and mouse APOBEC3B (A3B), APOBEC3C (A3C), APOBEC3D (A3D), APOBEC3F (A3F), APOBEC3G (A3G), APOBEC3H (A3H), APOBEC1 (A1), APOBEC3 (A3), APOBEC2 (A2), APOBEC4 (A4) and AICDA (AID).

The fusion proteins may include other fragments, such as uracil DNA glycosylase inhibitor (UGI) and nuclear localization sequences (NLS).

The "Uracil Glycosylase Inhibitor" (UGI), which can be prepared from Bacillus subtilis bacteriophage PBS1, is a small protein (9.5 kDa) which inhibits E. coli uracil-DNA glycosylase (UDG) as well as UDG from other species. Inhibition of UDG occurs by reversible protein binding with a 1:1 UDG:UGI stoichiometry. UGI is capable of dissociating UDG-DNA complexes. A non-limiting example of UGI is found in Bacillus phage AR9 (YP_009283008.1). In some embodiments, the UGI comprises the amino acid sequence of SEQ ID NO:25 or has at least at least 70%, 75%, 80%, 85%, 90% or 95% sequence identity to SEQ ID NO:25 and retains the uracil glycosylase inhibition activity.

The fusion protein, in some embodiments, may include one or more nuclear localization sequences (NLS).

A "nuclear localization signal or sequence" (NLS) is an amino acid sequence that tags a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal (NES), which targets proteins out of the nucleus. A non-limiting example of NLS is the internal SV40 nuclear localization sequence (iNLS).

Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE C

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

In some embodiments, a peptide linker is optionally provided between each of the fragments in the fusion protein. In some embodiments, the peptide linker has from 1 to 100 amino acid residues (or 3-20, 4-15, without limitation). In some embodiments, at least 10%, 20%, 30%, 40%, 50%, 60%, 70%, 80% or 90% of the amino acid residues of peptide linker are amino acid residues selected from the group consisting of alanine, glycine, cysteine, and serine.

For any fusion protein of the present disclosure, biological equivalents thereof are also provided. In some embodiments, the biological equivalents have at least about 70%, 75%, 80%, 85%, 90%, 95%, 98%, or 99% sequence identity with the reference fusion protein. Preferably, the biological equivalents retained the desired activity of the reference fusion protein. In some embodiments, the biological equivalents are derived by including one, two, three, four, five or more amino acid additions, deletions, substitutions, of the combinations thereof. In some embodiments, the substitution is a conservative amino acid substitution.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

TABLE D

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gin, D-Gln |
| Glycine | Ala, D-Ala, Pro, D-Pro, Aib, B-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

On-Target Activation of Fusion Proteins

The present disclosure also provides compositions and methods in which a fusion protein of the present disclosure, which includes both a nucleobase deaminase or the catalytic domain thereof and an inhibitor, is activated where its activity is desired. The technology is illustrated in FIG. 16.

In an illustrative configuration, the fusion protein (A) includes (a) a first fragment comprising a nucleobase deaminase (e.g., cytidine deaminase) or a catalytic domain thereof, optionally with a clustered regularly interspaced short palindromic repeats (CRISPR)-associated (Cas) protein, and a first TEV protease fragment, (b) a second fragment comprising a nucleobase deaminase inhibitor, and (c) a TEV protease cleavage site between the first fragment and the second fragment. In some embodiments, wherein the first TEV protease fragment alone is not able to cleave the TEV protease cleavage site.

When the fusion protein is used, in vitro or in vivo, to conduct gene editing in a cell, two additional molecules can be introduced. In one example, one molecule (B) is a single guide RNA (sgRNA) that further incorporates a tag sequence that can be recognized by an RNA recognition peptide. The sgRNA, alternatively, can be replaced by a crRNA that targets the target site and a CRISPR RNA (crRNA) alone, or in combination with a trans-activating CRISPR RNA (tracrRNA). Examples of tag sequences and corresponding RNA recognition peptides include MS2/MS2 coat protein (MCP), PP7/PP7 coat protein (PCP), and boxB/boxB coat protein (N22p), the sequences of which are provided in Table B. The molecule (B) may be provided as a DNA sequence encoding the RNA molecule.

The other additional molecule (C), in some embodiments, includes a second TEV protease fragment coupled to the RNA recognition peptide (e.g., MCP, PCP, N22p). The first TEV fragment and the second TEV fragment, in some embodiments, when present together, are able to cleave a TEV protease site.

Such co-presence can be triggered by the molecule (C) binding to the molecule (B) by virtue of the tag sequence-RNA recognition protein interaction. Meanwhile, the fusion protein (A) and the molecule (B) will be both present at the target genome locus for gene editing. Therefore, the molecule (B) brings both of the TEV protease fragments from the fusion protein (A) and molecule (C) together, which will activate the TEV protease, leading to removal of the nucleobase deaminase inhibitor from the fusion protein and activation of the base editor. It can be readily appreciated that such activation only occurs at the target genome site, not at off-target single-stranded DNA regions. As such, base editing does not occur at the single-stranded DNA regions that sgRNA does not bind to (as demonstrated in FIG. 17-19).

"Guide RNAs" are non coding short RNA sequences which bind to the complementary target DNA sequences. A guide RNA first binds to the Cas enzyme and the gRNA sequence guides the complex via pairing to a specific location on the DNA, where Cas performs its endonuclease activity by cutting the target DNA strand. A "single guide RNA," frequently simply referred to as "guide RNA", refers to synthetic or expressed single guide RNA (sgRNA) that consists of both the crRNA and tracrRNA as a single construct. The tracrRNA portion is responsible for Cas endonuclease activity and the crRNA portion binds to the target specific DNA region. Therefore, the trans activating RNA (tracrRNA, or scaffold region) and crRNA are two key components and are joined by tetraloop which results in formation of sgRNA.

The scaffold of the guide RNA has a stem-loop structure in itself and attaches to the endonuclease enzyme. A typical scaffold has a structure as illustrated in FIG. 36A (upper), which includes, from the 5' to the 3' end, (a) a repeat region, (b) a tetraloop, (c) an anti-repeat that is at least partially complementary to the repeat region, (d) stem loop 1, (e) a linker, (0 stem loop 2, and (g) stem loop 3. The scaffold sequence is generally conserved, but the loops in stem loop 1 and stem loop 3 can have different sequences. More importantly, the loops of tetraloop and stem loop 2 can be entirely replaced with even much longer sequences. Sequences such as RNA tags (e.g., MS2, PP7, boxB) can be inserted here, enabling recognition by the corresponding recognition peptides. Example scaffold sequences are shown below.

TABLE E

Example sgRNA Scaffold Sequences

| SEQ ID NO: | Sequence |
| --- | --- |
| 29 | GUUUUAGAGCUAGAAAUAGCAAG<br>UU<u>AAAAUAAGGCUA</u>GUCCGUUAU<br>CAACUUGAAAAAGUGGCACCGAG<br>UCGGUGC |
| 30 | GUUUUAGAGCUAGAAAUAGCAAG<br>UU<u>AAAAUAAGGCAU</u>GUCCGUUAU<br>CAACUUGAAAAAGUGGCACCGAU<br>UCGGUGC |
| 196 | GUUUGAGAGCUAGAAAUAGCAAG<br>UU<u>CAAAUAAGGCUA</u>GUCCGUUAU<br>CAACUUGAAAAAGUGGCACCGAG<br>UCGGUGC |

With reference to these example scaffold sequences, the fragment of positions 1-12 (e.g., GUUUUAGAGCUA, SEQ ID NO:197; GUUUGAGAGCUA, SEQ ID NO:198) represents the repeat region, which forms about 8-12 base pairings with the anti-repeat, which includes positions 17-30 (e.g., UAGCAAGUUAAAAU, SEQ ID NO:199). The GAAA loop (SEQ ID NO:200) between them is the tetraloop. As shown in SEQ ID NO:17, this entire loop can be replaced with a MS2 sequence. Stem loop 1 roughly includes positions 31-39 and includes a small loop (e.g., UA, AU, AA, or UU, without limitation). Stem loop 1 generally has 3-4 base parings in the stem. Stem loop 2, including positions 48-61 (e.g., AACUUGAAAAAGUG, SEQ ID NO:201), generally includes 4 base parings in the stem, and a GAAA (SEQ ID NO:200) loop which can be totally replaced. The remaining, positions 62-76 (e.g., GCACCGA-GUCGGUGC, SEQ ID NO:202; GCACCGAUUCGGUGC; SEQ ID NO:203) constitute stem loop 3, which generally includes 4 base pairings in the stem. The small loop (U and G here in the example) can be any nucleotide.

Accordingly, the sequence of the scaffold can be expressed as: GUUUNAGAGCUAX$_1$UAGCAA-GUUNAAAUAAGGCNNGUCCGUUAUCAACUUX$_2$A AGUGGCACCGANUCGGUGC (SEQ ID NO:31), where N represents any base, and X1 and X2 denotes any nucleotide sequence of a length of 2-50 bases. The terms "guide RNA" and "single guide RNA" encompasses those that include additional sequences, such as MS2, PP7 and boxB, inserted into one or more loops in the RNA.

Various embodiments and examples of nucleobase deaminases, catalytic domains, nucleobase deaminase inhibitors, and Cas proteins are provided in the disclosures. For instance, a nucleobase deaminase can be a cytidine deaminases and adenosine deaminases. Non-limiting examples of cytidine deaminases include APOBEC1, APOBEC2, APOBEC3A, APOBEC3B, APOBEC3C, APOBEC3D, APOBEC3F, APOBEC3G, APOBEC3H, APOBEC4, and activation-induced (cytidine) deaminase.

Non-limiting examples of adenosine deaminases include tRNA-specific adenosine deaminase (TadA), adenosine deaminase tRNA specific 1 (ADAT1), adenosine deaminase tRNA specific 2 (ADAT2), adenosine deaminase tRNA specific 3 (ADAT3), adenosine deaminase RNA specific B1 (ADARB1), adenosine deaminase RNA specific B2 (ADARB2), adenosine monophosphate deaminase 1 (AMPD1), adenosine monophosphate deaminase 2 (AMPD2), adenosine monophosphate deaminase 3 (AMPD3), adenosine deaminase (ADA), adenosine deaminase 2 (ADA2), adenosine deaminase like (ADAL), adenosine deaminase domain containing 1 (ADAD1), adenosine deaminase domain containing 2 (ADAD2), adenosine deaminase RNA specific (ADAR) and adenosine deaminase RNA specific B1 (ADARB1).

Example Cas proteins include SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, and KKH SaCas9 and those provided in Table A.

The fusion proteins may include other fragments, such as uracil DNA glycosylase inhibitor (UGI) and nuclear localization sequences (NLS), each of which is discussed herein.

The base editors and base editing methods described in this disclosure can be applied to perform high-specificity and high-efficiency base editing in the genome of various eukaryotes.

The present disclosure provides compositions and methods. Such compositions comprise an effective amount of a fusion protein, and an acceptable carrier. In some embodiments, the composition further includes a guide RNA that has a desired complementarity to a target DNA. Such a composition can be used for base editing in a sample.

The fusion proteins and the compositions can be used for base editing. In one embodiment, a method for editing a target polynucleotide is provided, comprising contacting to the target polynucleotide a fusion protein of the present disclosure and a guide RNA having at least partial sequence complementarity to the target polynucleotide, wherein the editing comprises deamination of a cytosine (C) in the target polynucleotide.

In one embodiment, provided is a method of editing a cytosine on a nucleic acid sequence in a sample. In some embodiments, the method entails contacting the sample a fusion protein of the present disclosure, or a polynucleotide encoding the fusion protein. In some embodiments, further added is a suitable guide RNA. Design of the guide RNA is readily available to the skilled artisan.

The contacting between the fusion protein (and the guide RNA) and the target polynucleotide can be in vitro, in particular in a cell culture. When the contacting is ex vivo, or in vivo, the fusion proteins can exhibit clinical/therapeutic significance. The in vivo contacting may be administration to a live subject, such as a human, an animal, a yeast, a plant, a bacterium, a virus, without limitation.

Configurations of Induced and Split Base Editors

Various configurations of constructs have been tested to implement the induced and split base editor (isplitBE) design (FIG. 24). Among the configuration tested (FIG. 25), Pair 9 of Example 3 exhibited superior editing efficiency and minimized off-target editing (greatly improved specificity). Pair 9 employs a dual sgRNA system, in which a helper sgRNA (hsgRNA) is used to target a site proximate the main target site. Such dual targeting improves specificity (FIG. 32-33).

In configuration Pair 9 (FIG. 25-28), the nucleobase deaminase inhibitor is only released when both sgRNA are bound to the target sequences, ensuring that the nucleobase deaminase does not edit at off-target sites. Configuration Pair 9 includes 6 different molecules, which can be produced from two separate constructs, for instance (FIGS. 26A and 34A).

The first molecule can include just a Cas protein, which has a suitable size for packaging in a common vehicle, AAV. The second molecule includes, among others, a nucleobase deaminase (e.g., APOBEC), a nucleobase deaminase inhibitor (e.g., mA3-CDA2), and an RNA recognition peptide (e.g., MCP). A protease cleavage site (e.g., TEV site) is inserted between the nucleobase deaminase and the nucleobase deaminase inhibitor, which enables removal of the nucleobase deaminase inhibitor at proper timing/location. Optionally, the second molecule further includes a UGI.

The third molecule is a fusion between an inactive portion of the protease (e.g., TEVc) fused to different RNA recognition peptide (e.g., N22p). The fourth molecule is a standalone TEVn which, in combination with the first portion, can carry out the protease activity to remove the nucleobase deaminase inhibitor from the second molecule.

The fifth molecule is a helper sgRNA containing an RNA recognition site (e.g., MS2) recognizable by the RNA recognition peptide in the $2^{nd}$ molecule. The sixth molecule is a regular sgRNA that contains an RNA recognition site (e.g., boxB) recognizable by the RNA recognition peptide in the $3^{rd}$ molecule.

At the correct target site in the genome (or RNA), both the hsgRNA and the sgRNA will bind, and each recruits a Cas protein to the binding site. The hsgRNA will also recruit the $2^{nd}$ molecule by virtue of the MS2-MCP binding, and the sgRNA will recruit the $3^{rd}$ molecule by virtue of the boxB-N22p binding. Therefore, the TEVc of the 3rd molecule is in contact with the TEV site. Since the standalone TEVn is present in the entire cell, it can also be present here, which ensures that the TEVc is active and cleaves the nucleobase deaminase inhibitor from the nucleobase deaminase in molecule 2, thereby activating the nucleobase deaminase.

It is further discovered that an optimal distance between the hsgRNA binding site and the regular sgRNA binding site is from 34-91 bp (from PAM to PAM), with the hsgRNA on the upstream.

Moreover, even though the proper binding of both hsgRNA and regular sgRNA is required for the intended editing in the target site for regular sgRNA, the editing in the target site for hsgRNA is not desirable. It is discovered herein that when the spacer length of the hsgRNA (spacer is the target complementary region) is from 8-15 bases, such a hsgRNA is still sufficient to provide dual recognition to ensure binding specificity, but greatly reduce the editing in the hsgRNA target site.

In accordance with one embodiment of the disclosure, therefore, provided is a fusion protein comprising a first fragment comprising: a nucleobase deaminase or a catalytic domain thereof, a nucleobase deaminase inhibitor, a first RNA recognition peptide, and a TEV protease cleavage site between the nucleobase deaminase or a catalytic domain thereof and the nucleobase deaminase inhibitor.

In some embodiments, the fusion protein further comprises a second fragment comprising: a TEV protease fragment which alone is not able to cleave the TEV protease cleavage site, and a second RNA recognition peptide. In some embodiments, the fusion protein further comprises a self-cleavage site between the first fragment and the second fragment.

In some embodiments, the fusion protein further comprises a third fragment comprising a second TEV protease fragment, wherein the first TEV protease fragment is able to cleave the TEV protease site in the presence of the second TEV protease fragment. In some embodiments, the fusion protein further comprises a second self-cleavage site between the second fragment and the third fragment, ad upon cleavage of the second self-cleavage site, the fusion protein releases the second TEV protease fragment which is not fused to any RNA recognition peptide.

Also provided, in one embodiment, is a dual guide RNA system, comprising: a target single guide RNA comprising a first spacer having sequence complementarity to a target nucleic acid sequence proximate to a first PAM site, a helper single guide RNA comprising a second spacer having sequence complementarity to a second nucleic acid sequence proximate to a second PAM site, a clustered regularly interspaced short palindromic repeats (CRISPR)-associated (Cas) protein, and a nucleobase deaminase.

In some embodiments, the second PAM site is located within 150 bases, or alternatively within 140, 130, 120, 110, 100, 95, 94, 93, 92, 91, 90, 89, 88, 87, 86, 85, 84, 83, 82, 81, 80, 75 or 70 bases from the second PAM site. In some embodiments, the second PAM site is located at least 10 bases, or alternatively at least 15, 20, 25, 30, 31, 32, 33, 34, 35, 36, 37, 38, 39, 40, 45, 50, 55, or 60 bases from the first PAM. In some embodiments, the second PAM site is upstream from the first PAM site. In some embodiments, the second PAM site is downstream from the first PAM site. In some embodiments, the distance is from 20-100, 25-95, 30-95, 34-95, 34-90, 35-90, 40-90, 40-84, 45-85, or 50-80 bases, without limitation.

In some embodiments, the second (helper) spacer is 8-15 bases in length. In some embodiments, the second spacer is 8-14, 8-13, 8-12, 8-11, 8-10, 9-15, 9-14, 9-13, 9-12, 9-11, 9-10, 10-15, 10-14, 10-13, 10-12, 10-11, 11-15, 11-14, 11-13, 11-12, 12-15, 12-14, 12-13, or 13-15 bases in length. The first spacer, by contrast, is at least 16, 17, 18, or 19 bases in length.

Various "split" base editing systems are also described here, which allow the Cas protein and the nucleobase deaminase to be packaged into separate delivery vehicles (e.g., AAV).

In some embodiments, pairs of regular sgRNA and hsgRNA are provided that can mediate efficient editing to generate early stop codons in PCSK9 genes, which can have clinic benefits. Based on the discoveries here, suitable target sites for sgRNA and hsgRNA have been selected for converting a non-stop codon to a stop codon. Take C-to-T/U editing as an example, a non-stop codon can be CAG, CAA or CGA.

Examples of such target sites are illustrated in Table 4. It is readily understood that the sequences in Table 4 are used to show the location of the target. The actual sgRNA and hsgRNA, however, does not need to bind to the entire sequence. In fact, for hsgRNA for instance, a binding of 8-15 nucleotides could well be enough as explained above. Accordingly, the spacer sequence on the hsgRNA can be complementary to a sub-sequence of any shown in Table 4, or even overlap with any of them. The same is true for sgRNA as well, with a preferred spacer length of 18-24 nucleotides, without limitation.

In one embodiment, provided is a pair of helper guide RNA/guide RNA for editing a human PCSK9 nucleic acid sequence, wherein the guide RNA specifically targets a first site on the PCSK9 nucleic acid to enable base editing to convert a non-stop codon to a stop codon, and wherein the helper guide RNA specifically targets a second site on the PCSK9 nucleic acid that is 20 to 100 bases from the first site. In some embodiments, the second site is about 20-100, 25-95, 30-95, 34-95, 34-91, 34-90, 35-90, 40-90, 40-84, 45-85, or 50-80 bases away from the first site.

In some embodiments, the hsgRNA has a spacer that is 8-15 bases in length. In some embodiments, the spacer is 8-14, 8-13, 8-12, 8-11, 8-10, 9-15, 9-14, 9-13, 9-12, 9-11, 9-10, 10-15, 10-14, 10-13, 10-12, 10-11, 11-15, 11-14, 11-13, 11-12, 12-15, 12-14, 12-13, or 13-15 bases in length. In some embodiments, the sgRNA has a spacer that is at least 16, 17, 18, or 19 bases in length.

Spacer sequences for the sgRNA/hsgRNA can be readily designed. For instance, for each target site shown in Table 4, a spacer may be the complementary sequence of the desired length (i.e., complementary to a sub-sequence of any of SEQ ID NO:166-180 or 181-195). Specific examples of pairs of binding sites include, without limitation, SEQ ID NO:166 and 181; SEQ ID NO:167 and 182; SEQ ID NO:168 and 183; SEQ ID NO:169 and 184; SEQ ID NO:170 and 185; SEQ ID NO:171 and 186; SEQ ID NO:172 and 187; SEQ ID NO:173 and 188; SEQ ID NO:174 and 189; SEQ ID NO:175 and 190; SEQ ID NO:176 and 191; SEQ ID NO:177 and 192; SEQ ID NO:178 and 193; SEQ ID NO:179 and 194; and SEQ ID NO:180 and 195.

Example sgRNA/hsgRNA sequences have also been designed and tested. See Table 3. Moreover, polynucleotide sequences encoding the helper guide RNA and guide RNA are also provided.

With such pairs of sgRNA/hsgRNA sequences, methods of inactivating a PSCK9 gene in a cell can be carried out. In some embodiments, the method entails contacting the cell with a pair of helper guide RNA and guide RNA of the present disclosure, a clustered regularly interspaced short palindromic repeats (CRISPR)-associated (Cas) protein, and a nucleobase deaminase. Each of these elements have been further described in the instant disclosure.

Enhanced Prime Editing

Improved prime editing systems are also provided, in some embodiments. In particular, certain prime editing guide RNA (pegRNA) molecules provided herein have improved stability. These pegRNA contain a scaffold that, compared to the conventional guide RNA, has one additional base pairing (see, FIGS. 36A and 36E). Using the standard scaffold (SEQ ID NO:31) at a template, the improved scaffold may have a sequence of any of SEQ ID NO:32-43.

As discussed above, a typical guide RNA scaffold has a structure which includes, from the 5' to the 3' end, (a) a repeat region, (b) a tetraloop, (c) an anti-repeat that is at least partially complementary to the repeat region, (d) stem loop 1, (e) a linker, (0 stem loop 2, and (g) stem loop 3. In other words, the scaffold includes 4 stem loops. The third stem loop (counted from 5' to 3'), also referred to as "Stem loop 2", includes 4 base pairings in the conventional design. In the new design, this stem loop has 5 base pairing.

In one embodiment, provided is a guide RNA comprising a scaffold which comprises, from the 5' to 3' direction, a first stem loop portion, a second stem loop portion, a third stem loop portion, and a fourth stem loop portion, wherein the third stem loop comprises five base pairings within.

The sequence of the scaffold can be expressed as: GUUUNAGAGCUAX$_1$UAGCAAGUUNAAAUAAGGC-NNGUCCGUUAUCAACUUX$_2$A AGUGGCACCGA-NUCGGUGC (SEQ ID NO:31), where N represents any base, and X1 and X2 denotes any nucleotide sequence of a length of 2-50 bases (or 2-40, 3-40, 4-40, 4-30, 2-30, 4-20 bases). Accordingly, in some embodiments, the base pairings comprise one between positions 45 and 55, according to the positions in SEQ ID NO:31. In some embodiments, the scaffold has at least 75%, 80%, 85%, 90%, 95%, 96%, 97%, 98%, or 99% sequence identity to SEQ ID NO:31 and includes give base pairings in the third stem loop.

In one embodiment, therefore, provided is a guide RNA comprising a scaffold derived from SEQ ID NO:31 by introducing a base pairing between the bases at position 45 and position 55, and optionally allowing one, two, three, four, or five base additions, deletions, substitutions, or the combination thereof, as long as it maintains the stem loops structure or the scaffold/guide RNA functionality. In some embodiments, the scaffold comprises a sequence selected from the group consisting of SEQ ID NO:32-43. In some embodiments, the guide RNA is at least 100 nucleotides, or 105, 110, 115, 120, 125, 130, 140 or 150 nucleotides in length. In some embodiments, the guide RNA further includes a spacer (e.g., 8-25 nucleotides), a reverse-transcriptase template, and/or a primer-binding site.

Improved prime editor proteins are also provided, in some embodiments. In one embodiment, the prime editor includes a Cas protein and a reverse-transcriptase linked through a linker tested to optimized for the performance of the prime editor. In one embodiment, the prime editor comprises the amino acid sequence of SEQ ID NO:44. In one embodiment, the prime editor comprises the amino acid sequence of SEQ ID NO:45. Both these prime editors have been tested and shown to exhibit superior editing efficiency and specificity.

Various "split" prime editing systems are also described here, which allow the Cas protein and the reverse transcriptase to be packaged into separate delivery vehicles (e.g., AAV).

With the split prime editing systems, methods for conducting genetic editing in a cell at a target site are also provided. In some embodiments, the method entails introducing to the cell a first viral particle enclosing a first construct encoding a clustered regularly interspaced short palindromic repeats (CRISPR)-associated (Cas) protein, and a second viral particle enclosing a second construct encoding a reverse-transcriptase fused to an RNA recognition peptide. In some embodiments, the second construct further encodes a guide RNA comprising an RNA recognition site that the RNA recognition peptide binds to.

In some embodiments, the second construct further encodes a guide RNA comprising an RNA recognition site that the RNA recognition peptide binds to. In some embodiments, the Cas protein is selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, SpCas9-NG, xSpCas9, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, and RanCas13b. In some embodiments, the Cas protein is SpCas9-NG or xSpCas9.

Non-limiting examples of reverse-transcriptases include human immunodeficiency virus (HIV) reverse-transcriptase, moloney murine leukemia virus (MMLV) reverse-transcriptase and avian myeloblastosis virus (AMV) reverse-transcriptase

EXAMPLES

Example 1. Fusion Base Editors with Reduced Off-Target Editing Activity

Single-guide RNAs (sgRNAs) and base editors (BEs) mentioned in the examples are for SpCas9, unless specifically pointed out, e.g., the sgRNA for SaCas9 (Sa-sgRNAs). To test whether the current base editing system can induce C-to-T mutations in ssDNA regions, we used SaD10A nickase and Sa-sgRNA to make a DNA single-stranded break (SSB), which can trigger end recession to generate a ssDNA region. (FIGS. 1A, 2A and 3A). We co-transfected SaD10A, Sa-sgRNA (Sa-sgSITE31, Sa-sgSITE42 and Sa-sgF1) with two published BEs, i.e., BE3 and hA3A-BE3 or an empty vector (FIGS. 1B, 2B and 3B) and determine the mutagenesis around the ssDNA regions triggered by SaD10A. At three tested sites (Sa-SITE31, Sa-SITE42 and Sa-F1) the expression of BE3 or hA3A-BE3 induced C-to-T mutations, whereas the expression of an empty vector did not (FIGS. 1C, 2C and 3C). These results indicated that the current base editors, which contain catalytically active cytidine deaminases, indeed cause unintended mutations in non-relevant ssDNA regions (FIGS. 1, 2 and 3).

To inhibit the activity of cytidine deaminase at non-relevant sites, e.g., ssDNA regions, we proposed to fuse base editors with a base editing inhibitor. Mouse APOBEC3 (mA3) comprises two cytidine deaminase (CDA) domains (CDA1 and CDA2, FIG. 4A, 5A, 6A) and the use of full-length mA3 in mA3-BE3 (FIG. 4B, 5B, 6B) did not induce C-to-T editing at three tested target sites (FIG. 4C, 5C, 6C). However, mA3CDA1-BE3, which is generated by deleting mA3CDA2 from mA3-BE3 (FIG. 4B, 5B, 6B), induced substantial C-to-T editing (FIG. 4C, 5C, 6C). These results suggest that mA3CDA2 is a natural inhibitor of base editing. Thus, we added mA3CDA2 to the N-terminus of three active BEs, i.e., mA3CDA1-BE3, BE3 and hA3A-BE3, to generate mA3rev-BE3, mA3CDA2-BE3 and mA3CDA2-hA3A-BE3 (FIG. 4B, 5B, 6B). As we expected, the adding of mA3CDA2 to the N-terminus clearly reduced the base editing efficiencies (FIG. 4C, 5C, 6C).

Next, we considered whether the cleavage of mA3CDA2 can restore the base editing efficiency. 2A self-cleavage peptides were inserted between mA3CDA2 and the rest part of BE in mA3rev-BE3, mA3CDA2-BE3 and mA3CDA2-hA3A-BE3 to generate mA3rev-2A-BE3, mA3CDA2-2A-BE3 and mA3CDA2-2A-hA3A-BE3 (FIG. 4B, 5B, 6B). Correspondingly, the base editing efficiencies restored in mA3rev-2A-BE3, mA3CDA2-2A-BE3 and mA3CDA2-2A-hA3A-BE3 (FIG. 4C, 5C, 6C), indicating that the inhibition of mA3CDA2 depends on its covalent connection to BEs. We also searched protein database for the domains similar to mA3CDA2 core sequence and found at least 44 proteins have the similar domains (Table 1).

Human APOBEC3B (hA3B) also comprises two cytidine deaminase (CDA) domains (CDA1 and CDA2, FIG. 7A, 8A, 9A) and the use of full-length hA3B in hA3B-BE3 (FIG. 7B, 8B, 9B) only induced relatively low levels of C-to-T editing at three tested target sites (FIG. 7C, 8C, 9C). However, hA3BCDA2-BE3, which is generated by deleting hA3BCDA1 from hA3B-BE3 (FIG. 7B, 8B, 9B), induced higher C-to-T editing (FIG. 7C, 8C, 9C). In addition, 2A self-cleavage peptides were inserted between hA3BCDA1 and hA3BCDA2 to generate hA3B-2A-BE3 (FIG. 7B, 8B, 9B), which induces higher C-to-T editing efficiencies than hA3B-BE3 (FIG. 7C, 8C, 9C). These results indicate that hA3BCDA1 is another inhibitor of base editing and the inhibition of hA3BCDA1 depends on its covalent connection to BEs. We also searched protein database for the domains similar to hA3BCDA1 and found at least 43 proteins have the similar domains (Table 2).

Next, we planned to use mA3 to develop novel BEs. The two BEs, mA3rev-BE3 and mA3rev-2A-BE3, were made by splitting mA3 between amino acid (AA)207 and AA208 and then we determined where to split mA3CDA2 can keep the highest editing efficiency (FIG. 10A, 11A, 12A). As mA3CDA1 ends at amino acid (AA)154 and mA3CDA2 starts from AA238, we split mA3CDA2 at AA196/AA197, AA215/AA216, AA229/AA230 and AA237/AA238 to generate mA3rev-BE3-196, mA3rev-2A-BE3-196, mA3rev-BE3-215, mA3rev-2A-BE3-215, mA3rev-BE3-229, mA3rev-2A-BE3-229, mA3rev-BE3-237, and mA3rev-2A-BE3-237 (FIG. 10B, 11B, 12B). Although the splitting of mA3 at AA207/AA208 and AA215/AA216 keeps the highest editing efficiencies, the results also showed that the splitting sites spanning from AA196/AA197 to AA237/AA238 generally keep substantial editing efficiencies (FIG. 10C, 11C, 12C).

Furthermore, we tried to determine the minimal region of mA3 that has a base editing inhibitory effect. We deleted various N-terminal parts of mA3CDA2 in mA3rev-BE-237 to develop mA3rev-BE-237-Del-255, mA3rev-BE-237-Del-285 and mA3rev-BE-237-Del-333, which contains the AA256-AA429, AA286-AA429 and AA334-AA429 parts of mA3 as the base editing inhibitor respectively (FIG. 13A, 14A, 15A). By comparing with mA3rev-BE-237, which contains the AA238-AA429 part of mA3, mA3rev-BE-237-Del-255, mA3rev-BE-237-Del-285 and mA3rev-BE-237-Del-333 showed similar editing efficiencies (FIG. 13B, 14B, 15B). These results indicated that the AA334-AA429 part of mA3 still has the inhibitory effect of base editing.

In order to develop base editors that do not cause C-to-T mutation in non-relevant ssDNA regions, we replaced the 2A self-cleavage site with a cleavage site of TEV protease in mA3rev-2A-BE3 and then fused the N-terminal part of TEV protease (TEVn) [Gray et al., 2010, Cell, doi: 10.1016/j.cell.2010.07.014] to the C-terminus of mA3rev-2A-BE3 with another TEV cleavage site. The newly developed BE is named BEsafe. In addition, we put one MS2 loop into the sgRNA to generate MS2-sgRNA [Ma et al., 2016, Nature Biotechnology, doi: 10.1038/nbt.3526] and then fused the C-terminal part of TEV protease (TEVc) with MS2 coat protein (MCP), which can bind to MS2 loop (FIG. 16A). When BEsafe, MS2-sgRNA and MCP-TEVc were co-expressed, the TEVn fused in BEsafe and the TEVc of MCP-TEVc that can be recruited by MS2-sgRNA would associate and restore the protease activity at on-target site. The subsequent cleavages at TEV sites would remove mA3CDA2 and TEVn from the N- and C-terminus of BEsafe and the resulted mA3CDA1-BE3 can induce efficient base editing at on-target site (FIG. 16A). On contrary, the BEsafe would not induce C-to-T mutations in non-relevant ssDNA regions because the cytidine deaminase activity of mA3CDA1 is inhibited by mA3CDA2 (FIG. 16B).

We then compared the performance of BEsafe and hA3A-BE3 at on-target sites and non-relevant ssDNA regions (FIG. 17, 18, 19). We co-transfected the plasmid expressing Sa-sgRNA and SaD10A, which can trigger ssDNA formation at Sa-sgRNA target sites (FIG. 17A, 18A, 19A), with the hA3A-BE3 expression plasmid and the sgRNA expression plasmid, with the BEsafe expression plasmid and the plasmid expressing MS2-sgRNA and MCP-TEVc or with the MCP-TEVc expression plasmid and the plasmid expressing MS2-sgRNA and BEsafe (FIG. 17B, 18B, 19B). We examined the C-to-T mutation frequencies in non-relevant ssDNA regions (Sa-sgRNA on-target sites, orthogonal to those of SpCas9) (FIG. 17C, 18C, 19C) and the base editing efficiencies at sgRNA on-target sites of hA3A-BE3 and BEsafe, both of which are SpCas9-derived (FIG. 17D, 18D, 19D). We found that BEsafe did not cause any C-to-T mutation in the non-relevant ssDNA regions (Sa-sgRNA on-target sites) but hA3A-BE3 caused obvious mutations (FIG. 17C, 18C, 19C). At sgRNA on-target sites, BEsafe induced base editing comparable to hA3A-BE3, while the expression of both MS2-sgRNA and BEsafe from one single plasmid yielded higher base editing efficiencies than the expression of only BEsafe from one plasmid did (FIG. 17D, 18D, 19D).

The base editors and base editing method described in this invention could be applied to perform high-specificity and high-efficiency base editing in the genome of various eukaryotes.

For the first time, a base editing system was established to avoid causing C-to-T mutations in non-relevant ssDNA regions and to induce efficient base editing at on-target sites. The BEsafe base editing system and the accompanying methods disclosed in this invention could be utilized to perform highly specific base editing that cannot be implemented by the currently existing BEs as the cytidine deaminases in current BEs can cause unintended mutations in non-relevant ssDNA regions. Importantly, the high specificity and efficiency of this BEsafe base editing system will promote the potential clinical translation, especially in the gene therapies that involve restoring disease-related mutations.

TABLE 1 mA3CDA2 Core Sequence Related Domains

| Name | Sequence | SEQ ID NO: |
|---|---|---|
| Mouse APOBEC3 cytidine deaminase domain 2 core (AA282-AA355) | SEKGKQHAEILFLDKIRSMELSQVTITCYLTWSPCPNCAWQLAAFKRDRP DLILHIYTSRLYFHWKRPFQKGLC | 48 |
| Mus spicilegus A3 (AA248-AA321) | SEKGKQHAEILFLDKIRSMELSQVTITCYLTWSPCPNCAWQLAAFKRDRP DLIPHIYTSRLYFHWKRPFQKGLC | 49 |
| Cricetulus longicaudatus A3 (AA249-AA322) | SEKGKQHAEILFLDKIRSMELSQVTITCYLTWSPCPNCAWRLAAFKRDRP DLILHIYTSRLYFHWKRPFQKGLC | 50 |
| Mus terricolor A3 (AA248-AA321) | SEKGKQHAEILFLNKIRSMELSQVTITCYLTWSPCPNCAWQLAAFKKDRP DLILHIYTSRLYFHWKRPFQKGLC | 51 |
| Mus caroli A3 (AA260-AA333) | SKKGKQHAEILFLDKIRSMELSQVTITCYLTWSPCPNCAWQLAAFKRDHP DLILHIYTSRLYFHWKRPFQKGLC | 52 |
| Mus pahari A3 (AA263-AA336) | SKKGKQHAEILFLEKIRSMELSQMRITCYLTWSPCPNCAWQLAAFQKDRP DLILHIYTSRLYFHWRRIFQKGLC | 53 |

TABLE 1-continued mA3CDA2 Core Sequence Related Domains

| Name | Sequence | SEQ ID NO: |
|---|---|---|
| *Mus shortridgei* A3 (AA233-AA306) | SKKGKQHAEILFLEKIRSMELSQMRITCYLTWSPCPNCAWQLAAFQKDRP DLILHIYTSRLYFHWRRIFQKGLC | 54 |
| *Mus setulosus* A3 (AA29-AA302) | SKKGKQHAEILFLDKIRSMELSQVRITCYLTWSPCPNCAWQLETFKKDRP DLILHIYTSRLYFHWKRAFQEGLC | 55 |
| *Grammomys surdaster* A3 (AA270-AA344) | SKKGKPHAEILFLDKMWSMEELSQVRITCYLTWSPCPNCARQLAAFKKDH PGLILRIYTSRLYFYWRRKFQKGLC | 56 |
| *Rattus norvegicus* A3 (AA256-AA328) | KKGEQHVEILFLEKMRSMELSQVRITCYLTWSPCPNCARQLAAFKKDHPD LILRIYTSRLYFYWRKKFQKGLC | 57 |
| *Mastomys coucha* A3 (AA258-AA331) | SKKGRQHAEILFLEKVRSMQLSQVRITCYLTWSPCPNCAWQLAAFKMDHP DLILRIYASRLYFHWRRAFQKGLC | 58 |
| *Cricetulus griseus* A3B (AA235-AA307) | NKKGKHAEILFIDEMRSLELGQVQITCYLTWSPCPNCAQELAAFKSDHPD LVLRIYTSRLYFHWRRKYQEGLC | 59 |
| *Peromyscus leucopus* A3 (AA266-AA338) | NKKGKHAEILFIDEMRSLELGQARITCYLTWSPCPNCAQKLAAFKKDHPD LVLRVYTSRLYFHWRRKYQEGLC | 60 |
| *Mesocricetus auratus* A3 (AA268-AA340) | NKKDKHAEILFIDKMRSLELCQVRITCYLTWSPCPNCAQELAAFKKDHPD LVLRIYTSRLYFHWRRKYQEGLC | 61 |
| *Microtus ochrogaster* A3B (AA266-AA338) | NKKGKHAEILFIDEMRSLKLSQERITCYLTWSPCPNCAQELAAFKRDHPG LVL RIYAS RLYFHWRRKYQE GLC | 62 |
| *Nannospalax galili* A3 (AA231-AA302) | NKRAKHAEILLIDMMRSMELGQVQITCYITWSPCPTCAQELAAFKQDHPD LVLRIYASRLYFHWKRKFQKGL | 63 |
| *Meriones unguiculatus* A3 (AA233-AA305) | NKKGRHAEICLIDEMRSLGLGKAQITCYLTWSPCRKCAQELATFKKDHPD LVLRVYASRLYFHWSRKYQQGLC | 64 |
| *Dipodomys ordii* A3 (AA256-AA330) | NKKGHHAEIRFIERIRSMGLDPSQDYQITCYLTWSPCLDCAFKLAKLKKD FPRLTLRIFTSRLYFHWIRKFQKGL | 65 |
| *Jaculus jaculus* A3 (AA303-AA374) | NKKGKHAEARFVDKMRSMQLDHALITCYLTWSPCLDCSQKLAALKRDHPG LTLRIFTSRLYFHWVKKFQEGL | 66 |
| *Chinchilla lanigera* A3H (AA86-AA161) | SPQKGHHAESRFIKRISSMDLDRSRSYQITCFLTWSPCPSCAQELASFKR AHPHLRFQIFVSRLYFHWKRSYQAGL | 67 |
| *Heterocephalus glaber* A3 (AA277-AA350) | KKGYHAESRFIKRICSMDLGQDQSYQVTCFLTWSPCPHCAQELVSFKRAH PHLRLQIFTARLFFHWKRSYQEGL | 68 |
| *Octodon degus* A3 (AA256-AA329) | KKGQHAEIRFIERIHSMALDQARSYQITCFLTWSPCPFCAQELASFKSTH PRVHLQIFVSRLYFHWKRSYQEGL | 69 |
| *Urocitellus parryii* A3 (AA256-AA330) | NKKGHHAEIRFIKKIRSLDLDQSQNYEVTCYLTWSPCPDCAQELVALTRS HPHVRLRLFTSRLYFHWFWSFQEGL | 70 |
| *Aotus nancymaae* A3H (AA75-AA146) | NRHAEICFIDEIESMGLDKTQCYEVTCYLTWSPCPSCAQKLAAFTKAQVH LNLRIFASRLYYHWRSSYQKGL | 71 |
| *Cebus capucinus imitator* A3H (AA55-AA126) | NRHAEICFIDEIESMGLDKTQCYEVTCYLTWSPCPSCAQKLVAFAKAQDH LNLRIFASRLYYHWRRRYKEGL | 72 |
| *Saimiri boliviensis boliviensis* A3H (AA56-AA125) | HVEICFIDKIASMELDKTQCYDVTCYLTWSPCPSCAQKLAAFAKAQDHLN LRIFASRLYYHWRRSYQKGL | 73 |
| *Homo sapiens* A3H (AA49-AA123) | NKKKCHAEICFINEIKSMGLDETQCYQVTCYLTWSPCSSCAWELVDFIKA HDHLNLGIFASRLYYHWCKPQQKGL | 74 |
| *Homo sapiens* ARP 10 (AA48-AA123) | ENKKKCHAEICFINEIKSMGLDETQCYQVTCYLTWSPCSSCAWELVDFIK AHDHLNLGIFASRLYYHWCKPQQKGL | 75 |
| *Pan paniscus* A3H (AA49-AA123) | NKKKCHAEICFINEIKSMGLDETQCYQVTCYLTWSPCSSCAWKLVDFIQA HDHLNLRIFASRLYYHWCKPQQEGL | 76 |

TABLE 1-continued mA3CDA2 Core Sequence Related Domains

| Name | Sequence | SEQ ID NO: |
|---|---|---|
| *Symphalangus syndactylus* A3H (AA49-AA123) | NKKKRHAEIRFINKIKSMGLDETQCYQVTCYLTWSPCPSCAWELVDFIKA HDHLNLGIFASRLYYHWCRHQQEGL | 77 |
| *Macaca mulatta* A3H (AA49-AA123) | NKKKDHAEIRFINKIKSMGLDETQCYQVTCYLTWSPCPSCAGELVDFIKA HRHLNLRIFASRLYYHWRPNYQEGL | 78 |
| *Theropithecus gelada* A3H (AA54-AA128) | NKKKEHAEIRFINKIKSMGLDETQCYQVTCYLTWSPCPSCAGKLVDFIKA HHHLNLRIFASRLYYHWRPNYQEGL | 79 |
| *Mandrillus leucophaeus* A3H (AA49-AA123) | NKKKHHAEIHFINKIKSMGLDETQCYQVTCYLTWSPCPSCARELVDFIKA HRHLNLRIFASRLYYHWRPHYQEGL | 80 |
| *Bos grunniens* A3 (AA74-AA148) | NKKQRHAEIRFIDKINSLDLNPSQSYKIICYITWSPCPNCANELVNFITR NNHLKLEIFASRLYFHWIKPFKMGL | 81 |
| *Bubalus bubalis* A3 (AA74-AA148) | NKKQRHAEIRFIDKINSLDLNPSQSYKIICYITWSPCPNCASELVDFITR NDHLDLQIFASRLYFHWIKPFKRGL | 82 |
| *Odocoileus virginianus texanus* A3H (AA209-AA283) | NKKQRHAEIRFIDKINSLNLDRRQSYKIICYITWSPCPRCASELVDFITG NDHLNLQIFASRLYFHWKKPFQRGL | 83 |
| *Sus scrofa* A3 (AA51-AA125) | NKKKRHAEIRFIDKINSLNLDQNQCYRIICYVTWSPCHNCAKELVDFISN RHHLSLQLFASRLYFHWVRCYQRGL | 84 |
| *Ceratotherium simum simum* A3B (AA232-AA306) | NKKKRHAEIRFIDKIKSLGLDRVQSYEITCYITWSPCPTCALELVAFTRD YPRLSLQIFASRLYFHWRRRSIQGL | 85 |
| *Equus caballus* A3H (AA79-AA153) | NKKKRHAEIRFIDKINSLGLDQDQSYEITCYVTWSPCATCACKLIKFTRK FPNLSLRIFVSRLYYHWFRQNQQGL | 86 |
| *Enhydra lutris kenyoni* A3B (AA243-AA316) | KKKKRHAEIRFIDSIRALQLDQSQRFEITCYLTWSPCPTCAKELAMFVQDH PHISLRLFASRLYFHWRWKYQEGL | 87 |
| *Leptonychotes weddellii* A3H (AA50-AA123) | KKKKRHAEIRFIDNIKALRLDTSQRFEITCYVTWSPCPTCAKELVAFVRDH RHISLRLFASRLYFHWLRENKKGL | 88 |
| *Ursus arctos horribilis* A3F (AA552-AA626) | NKKKRHAEIRFIDKIRSLQRDSSQTFEITCYVTWSPCFTCAEELVAFVRD HPHVRLRLFASRLYFHWLRKYQEGL | 89 |
| *Panthera leo bleyenberghi* A3H (AA50-AA124) | NKKKRHAEICFIDKIKSLTRDTSQRFEIICYITWSPCPFCAEELVAFVKD NPHLSLRIFASRLYVHWRWKYQQGL | 90 |
| *Panthera tigris sumatrae* A3H (AA50-AA124) | NKKKRHAEICFIDKIKSLTRDTSQRFEIICYITWSPCPFCAEELVAFVKD NPHLSLRIFASRLYVHWRWKYQQGL | 91 |
| *Tupaia belangeri* A3 (AA46-AA120) | NKKHRHAEVRFIAKIRSMSLDLDQKHQLTCYLTWSPCPSCAQELVTFMAE SRHLNLQVFVSRLYFHWQRDFQQGL | 92 |

TABLE 2 hA3BCDA1-Related Domains

| Name | Sequence | SEQ ID NO: |
|---|---|---|
| Gorilla A3B (AA29-AA138) | GRSYNWLCYEVKIKRGRSNLLWNTGVFRGQMYSQPEHHAEMCFLSWFCGN QLPAYKCFQITWFVSWTPCPDCVAKLAEFLAEYPNVTLTISTARLYYYWE RDYRRALCRL | 93 |
| *Pan paniscus* A3B (AA29-AA138) | GRSYTWLCYEVKIRRGHSNLLWDTGVFRGQMYSQPEHHAEMYFLSWFCGN QLPAYKCFQITWFVSWTPCPDCVAKLAEFLAEHPNVTLTISAARLYYYWE RDYRRALCRL | 94 |

TABLE 2-continued hA3BCDA1-Related Domains

| Name | Sequence | SEQ ID NO: |
|---|---|---|
| Pan troglodytes A3B (AA29-AA138) | GRSYTWLCYEVKIRRGHSNLLWDTGVFRGQMYSQPEHHAEMCFLSWFCGN QLSAYKCFQITWFVSWTPCPDCVAKLAKFLAEHPNVTLTISAARLYYYWE RDYRRALCRL | 95 |
| Gorilla A3F (AA30-AA137) | RNTVWLCYEVKTKGPSRPPLDAKIFRGQVYFEPQYHAEMCFLSWFCGNQL PAYKCFQITWFVSWTPCPDCVAKLAEFLAEHPNVTLTISAARLYYYWE | 96 |
| Pan troglodytes A3F (AA30-AA137) | RNTVWLCYEVKTKGPSRPRLDTKIFRGQVYFEPQYHAEMCFLSWFCGNQL PAYKCFQITWFVSWTPCPDCVAKLAEFLAEHPNVTLTISAARLYYYWERD YRRALCRL | 97 |
| Human sapiens A3F (AA30-AA137) | RNTVWLCYEVKTKGPSRPRLDAKIFRGQVYSQPEHHAEMCFLSWFCGNQL PAYKCFQITWFVSWTPCPDCVAKLAEFLAEHPNVTLTISAARLYYYWERD YRRALCRL | 98 |
| Macaca leonine A3F (AA30-AA137) | RNTVWLCYEVKTRGPSMPTWGTKIFRGQVCFEPQYHAEMCFLSRFCGNQL PAYKRFQITWFVSWTPCPDCVAKVAEFLAEHPNVTLTISAARLYYYWETD YRRALCRL | 99 |
| Macaca nemestrina A3F (AA30-AA137) | RNTVWLCYEVKTRGPSMPTWGTKIFRGQVCFEPQYHAEMCFLSRFCGNQL PAYKRFQITWFVSWTPCPDCVAKVAEFLAEHPNVTLTISAARLYYYWETD YRRALCRL | 100 |
| Rhinopithecus roxellana A3F (AA30-AA137) | RNTVWLCYEVKTRGPSMPTWGAKIFRGQVYFEPQYHAEMCFLSWFCGNQL PAYKRFQITWFVSWTPCPDCVAKVAEFLAEHPNVTLTISAARLYYYWETD YRRALCRL | 101 |
| Mandrillus leucophaeus A3F (AA30-AA130) | RNTVWLCYKVKTRGPSMPTWGTKIFRGQVYFQPQYHAEMCFLSWFCGNQL PAYKRFQITWFVSWTPCPDCVVKVAEFLAEHPNVTLTISAARLYYYWETD Y | 102 |
| Macaca mulatta A3F (AA30-AA137) | RNTVWLCYEVKTRGPSMPTWDTKIFRGQVYSKPEHHAEMCFLSRFCGNQL PAYKRFQITWFVSWTPCPDCVAKVAEFLAEHPNVTLTISAARLYYYWETD YRRALCRL | 103 |
| Theropithecus gelada A3F (AA30-AA137) | RNTVWLCYEVKTRGPSMPTWGTKIFRGQVYFQPQYHAEMCFLSRFCGNQL PAYKRFQITWFVSWNPCPDCVAKVIEFLAEHPNVTLTISAARLYYWGRD WRRALRRL | 104 |
| Cercocebus atys A3B (AA29-AA138) | GRSYTWLCYEVKIRKDPSKLPWYTGVFRGQVYSKPEHHAEMCFLSRFCGN QLPAYKRFQITWFVSWNPCPDCVAKVIEFLAEHPNVTLTISAARLYYYWS RDWQRALCRL | 105 |
| Macaca fascicularis A3B (AA29-AA138) | GRSYTWLCYEVKIRKDPSKLPWDTGVFRGQVYSKPEHHAEMCFLSRFCGN QLPAYKRFQITWFVSWNPCPDCVAKVIEFLAEHPNVTLTISTARLYYYWG RDWQRALCRL | 106 |
| Macaca mulatta A3B (AA29-AA138) | GRSYTWLCYEVKIRKDPSKLPWDTGVFRGQVYSKPEHHAEMCFLSRFCGN QLPAYKRFQITWFVSWNPCPDCVAKVIEFLAEHPNVTLTISTARLYYYWG RDWQRALCRL | 107 |
| Macaca leonina A3B (AA29-AA138) | GRSYTWLCYEVKIRKDPSKLPWDTGVFRGQVYSKPEHHAEMCFLSRFCGN QLPAYKRFQITWFVSWNPCPDCVVKVIEFLAEHPNVTLTISTARLYYYWG RDWQRALCRL | 108 |
| Mandrillus leucophaeus A3B (AA29-AA138) | GRSYTWLCYEVKIRKDPSKLPWYTGVFRGQVYSKPEHHAEMCFLSRFCGN QLPAYKRFQITWFVSWNPCPDCVAKVIEFLAEHPNVTLTIFTARLYYYWG RDWQRALCRL | 109 |
| Macaca nemestrina A3B (AA29-AA138) | GRSYTWLCYEVKIRKDPSKLPWDTGVFRGQVYSKPEHHAEMCFLSRFCGN QLPAYKRFQITWFVSWNPCPDCVAKVTEFLAEHPNVTLTISTARLYYYWG RDWQRALCRL | 110 |
| Rhinopithecus bieti A3F (AA29-AA138) | GRSYTWLCYEVKIRKDPSKLPWDTGVFRGQVYSEPEHHAEMYFLSWFCGN QLPAYKRFQITWFVSWTPCPDCVAKVAEFLTEHPNVTLTISAARLYYYRG RDWRRALCRL | 111 |
| Rhinopithecus roxellana A3B (AA29-AA138) | GRSYTWLCYEVKIRKDPSKLPWDTGVFRGQVYSEPEHHAEMYFLSWFCGN QLPAYKRFQITWFVSWTPCPDCVAKVAEFLTEHPNVTLTISAARLYYYRG RDWRRALCRL | 112 |
| Chlorocebus sabaeus A3B (AA29-AA138) | GRSYTWLCYEVKIRKDPSKLPWDTGVFRGQMYSKPEHHAEMCFLSWFCGN QLPAHKRFQITWFVSWTPCPDCVAKVAEFLAEYPNVTLTISAARLYYYWE TDYRRALCRL | 113 |

TABLE 2-continued hA3BCDA1-Related Domains

| Name | Sequence | SEQ ID NO: |
|---|---|---|
| *Nomascus leucogenys* A3B (AA30-AA138) | RSYTWLCYEVKIRKDPSKLPWDTGVFRGQMYFQPEYHAEMCFLSWFCGNQLPAYKRFQITWFVSWTPCPDCVAKVAVFLAEHPNVTLTISAARLYYYWEKDWQRALCRL | 114 |
| *Cercocebus atys* A3F (AA29-AA138) | GRSYTWLCYEVKIKKYPSKLLWDTGVFQGQVYFQPQYHAEMCFLSRFCGNQLPAYKRFQITWFVSWNPCPDCVAKVTEFLAEHPNVTLTISAARLYYYWEKDXRRALRRL | 115 |
| *Papio anubis* A3F (AA29-AA138) | GRSYTWLCYEVKIKEDPSKLLWDTGVFQGQVYFQPQYHAEMCFLSRFCGNQLPAYKRFQITWFVSWNPCPDCVAKVTEFLAEHPNVTLTISAARLYYYWGRDWRRALRRL | 116 |
| *Chlorocebus aethiops* A3D (AA29-AA150) | GRRYTWLCYEVKIKKDPSKLPWDTGVFPGQVRPKFQSNRRYEVYFQPQYHAEMYFLSWFCGNQLPAYKHFQITWFVSWNPCPDCVAKVTEFLAEHRNVTLTISAARLYYYWGKDWRRALCRL | 117 |
| *Chlorocebus sabaeus* A3D (AA29-AA134) | GRRYTWLCYEVKIKKDPSKLPWDTGVFPGQPQYHAEMYFLSWFCGNQLPAYKHFQITWFVSWNPCPDCVAKVTEFLAEHRNVTLTISAARLYYYWGKDWRALCRL | 118 |
| *Chlorocebus sabaeus* A3F (AA29-AA150) | GRRYTWLCYEVKIKKDPSKLPWDTGVFPGQVRPKFQSNRRQKVYFQPQYHAEMYFLSWFCGNQLPAYKHFQITWFVSWNPCPDCVAKVTEFLAEHRNVTLTISAARLYYYWGKDWRRALCRL | 119 |
| *Erythrocebus patas* A3D (AA29-AA150) | GRRYTWLCYEVKIKKDPSKLPWDTGVFQGQVRPKFQSNRRYEVYFQPQYHAEMCFLSWFCGNQLPAYKHFQITWFVSWNPCPDCVAKVTEFLAEHPNVTLTISAARLYYYWGKDWRRALCRL | 120 |
| *Macaca fascicularis* A3D (AA29-AA159) | GRSYTWLCYEVKIRKDPSKLPWDTGVFRGQVRPKLQSNRRYELSNWECRKRVYFQPQYHAEMYFLSWFCGNQLPANKRFQITWFASWNPCPDCVAKVTEFLAEHPNVTLTISVARLYYYRGKDWRRALRRL | 121 |
| *Macaca fascicularis* A3F (AA29-AA138) | GRSYTWLCYEVKIRKDPSKLPWDTGVFRGQVYFQPQYHAEMYFLSWFCGNQLPANKRFQITWFASWNPCPDCVAKVTEFLAEHPNVTLTISVARLYYYRGKDWRRALRRL | 122 |
| *Macaca nemestrina* A3D (AA29-AA138) | GRSYTWLCYEVKIRKDPSKLPWDTGVFRDQVYFQPQYHAEMCFLSWFCGNQLPANKRFQITWFVSWNPCPDCVTKVTEFLAEHPNVTLTISVARLYYYRGKDWRRALRRL | 123 |
| *Macaca leonina* A3D (AA29-AA138) | GRSYTWLCYEVKIRKDPSKLPWYTGVFRGQVYFQPQYHAEMCFLSWFCGNQLPANKRFQITWFVSWNPCPDCVAKVTEFLAEHPNVTLTISVARLYYYRGKDWRRALRRL | 124 |
| *Macaca mulatta* A3D (AA29-AA138) | GRSYTWLCYEVKIRKDPSKLPWDTGVFRGQVYFQPQYHAEMCFLSWFCGNQLPAYKRFQITWFVSWNPCPDCVAKVTEFLAEHPNVTLTISVARLYYYRGKDWRRALCRL | 125 |
| Gorilla A3D (AA29-AA150) | GRSYTWLCYEVKIRRGSSNLLWNTGVFRGPVPPKLQSNHRQEVYFQFENHAEMCFLSWFCGNRLPANRRFQITWFVSWNPCLPCWKVTKFLAEHPNVTLTISAARLYYYRDREWRRVLRRL | 126 |
| *Pan paniscus* A3D (AA29-AA150) | GRSYTWLCYEVKIKRGCSNLIWDTGVFRGPVLPKLQSNHRQEVYFQFENHAEMCFFSWFCGNRLPANRRFQITWFVSWNPCLPCWKVTKFLAEHPNVTLTISAARLYYYQDREWRRVLRRL | 127 |
| *Pan troglodytes* A3D (AA29-AA150) | GRSYTWLCYEVKIKRGCSNLIWDTGVFRGPVLPKLQSNHRQEVYFQFENHAEMCFFSWFCGNRLPANRRFQITWFVSWNPCLPCWKVTKFLAEHPNVTLTISAARLYYYQDREWRRVLRRL | 128 |
| *Homo sapiens* A3D (AA29-AA150) | GRSYTWLCYEVKIKRGRSNLLWDTGVFRGPVLPKRQSNHRQEVYFRFENHAEMCFLSWFCGNRLPANRRFQITWFVSWNPCLPCWKVTKFLAEHPNVTLTISAARLYYYRDRDWRWVLLRL | 129 |
| *Nomascus leucogenys* A3D (AA29-AA150) | GRSYTWLCYEVKIRKDPSKLPWDKGVFRGQVLPKFQSNHRQEVYFQLENHAEMCFLSWFCGNQLPANRRFQITWFVSWNPCLPCVAKVTEFLAEHPNVTLTISAARLYYYRGRDWRRALRRL | 130 |
| *Saimiri boliviensis* A3C (AA29-AA138) | GKKYTWLCYEVKIKKDTSKLPWNTGVFRGQVNFNPEHHAEMYFLSWFRGKLLPACKRSQITWFVSWNPCLYCVAKVAEFLAEHPNVTLTVSTARLYCYWKKDWRRALRKL | 131 |
| *Saimiri boliviensis* A3F (AA29-AA138) | GKKYTWLCYEVKIKKDTSKLPWNTGVFRGQVNFNPEHHAEMYFLSWFRGKLLPACKRSQITWFVSWNPCLYCVAKVAEFLAEHPNVTLTVSTARLYCYWKKDWRRALRKL | 132 |

TABLE 2-continued hA3BCDA1-Related Domains

| Name | Sequence | SEQ ID NO: |
|---|---|---|
| Piliocolobus tephrosceles A3F (AA36-AA145) | GRRYTWLCYEVKIMKDHSKLPWYTGVFRGQVYFEPQNHAEMCFLSWFCGN QLPAYECCQITWFVSWTPCPDCVAKVTEFLAEHPNVTLTISAARLYYYRG RDWRRALRRL | 133 |
| Colobus angolensis palliatus A3F (AA29-AA138) | GRRYTWLCYEVKISKDPSKLPWDTGIFRGQVYFEPQYHAEMCFLSWYCGN QLPAYKCFQITWFVSWTPCPDCVGKVAEFLAEHPNVTLTISAARLYYYWE TDYRRALCRL | 134 |
| Pongo abelii A3F (AA30-AA150) | RNYTWLCYEVKIRKDPSKLAWDTGVFRGQVLPKLQSNHRREVYFEPQYHA EMCFLSWFCGNQLSAYERFQITWFVSWTPCPDCVAMLAEFLAEHPNVTLT VSAARLYYYWERDYRGALRRL | 135 |

Example 2. Further Assessment of Inhibitor-Conjugated Base Editors

This example developed an efficient method to demonstrate that the APOBEC moiety of base editors (BEs) directly induced mutations at off-target single-stranded DNA (OTss) sites in an sgRNA-independent manner. By testing a series of APOBEC proteins with two cytidine deaminase (CDA) domains, we identified that the catalytically-inactive CDA domains of certain dual-domain APOBECs function as cytidine deaminase inhibitors (CDIs). By taking advantage of this finding and the concept of split-TEV protease, an induced base editor (iBE) by sgRNA-guided cleavage of CDI was developed, which links a nSpCas9-BE and a CDI with a TEV cleavage site. At sgRNA-independent OTss sites, iBE1 remained dormant owing to the covalently linked CDI. Whereas, at on-target sites, iBE1 was activated by sgRNA-guided TEV cleavage of CDI, resulting in efficient base editing. By using 'enhanced specificity' SpCas9 nickase, iBE2 was further developed to reduce unintended OTsg mutations. Due to its minimum off-target effects and uncompromised on-target editing efficiency, the editing specificity of iBEs was significantly higher than that of the previously-reported BEs. Thus, the iBE system described in this example provides a new layer of regulation for the specificity of current base editing system and secures its application against off-target mutations.

Methods

Cell Culture and Transfection

HEK293FT cells from ATCC were maintained in DMEM (10566, Gibco/Thermo Fisher Scientific)+10% FBS (16000-044, Gibco/Thermo Fisher Scientific) and regularly tested to exclude *mycoplasma* contamination.

For base editing in genomic DNA, HEK293FT cells were seeded in a 24-well plate at a density of $1.1 \times 10^5$ per well and transfected with 250 µl serum-free Opti-MEM that contained 5.35 µl LIPOFECTAMINE LTX (Life, Invitrogen), 2.14 µl LIPOFECTAMINE plus (Life, Invitrogen), 1 µg pCMV-BE3 (or hA3B-BE3, hA3BCDA2-nSpCas9-BE, hA3D-BE3, hA3DCDA2-nSpCas9-BE, hA3F-BE3, hA3FCDA2-nSpCas9-BE, hA3G-BE3, hA3GCDA2-nSpCas9-BE, mA3-BE3, mA3CDA1-nSpCas9-BE, mA3CDA2-mA3CDA1-nSpCas9-BE, hA3FCDA1-mA3CDA1-nSpCas9-BE, hA3BCDA1-mA3CDA1-nSpCas9-BE, hA3BCDA2-rA1-nSpCas9-BE, hA3FCDA1-rA1-nSpCas9-BE, hA3BCDA1-rA1-nSpCas9-BE, hA3A-BE3, mA3CDA2-hA3A-nSpCas9-BE, hA3FCDA1-hA3A-nSpCas9-BE, hA3BCDA1-hA3A-nSpCas9-BE, mA3CDA2F1-mA3CDA1-nSpCas9-BE, mA3CDA2F2-mA3CDA1-nSp-Cas9-BE, mA3CDA2F3-mA3CDA1-nSpCas9-BE, mA3CDA1-T2A-mA3CDA1-nSpCas9-BE, EGFP-mA3CDA1-nSpCas9-BE, EGFP-T2A-mA3CDA1-nSpCas9-BE, mA3CDA1-T2A-rA1-nSpCas9-BE, EGFP-rA1-nSpCas9-BE, EGFP-T2A-rA1-nSpCas9-BE, mA3CDA1-T2A-hA3A-nSpCas9-BE, EGFP-hA3A-nSpCas9-BE, EGFP-T2A-hA3A-nSpCas9-BE, pCMV-dSpCas9, iBE1, iBE2, mA3CDA1-TS-mA3CDA1-nSpCas9HF1-BE-NTEV or mA3CDA1-TS-mA3CDA1-nHypaSpCas9-BE-NTEV) expression vector, 0.64 µg sgRNA expression vector without or with 0.5 µg Sa-sg-SaD10A expression vector. After 24 hr, puromycin (ant-pr-1, InvivoGen) was added to the medium at the final concentration of 4 µg/ml. After another 48 hr, the genomic DNA was extracted from the cells with QuickExtract™ DNA Extraction Solution (QE09050, Epicentre) for subsequent sequencing analysis.

DNA Library Preparation and Sequencing

Target genomic sequences were PCR amplified by high-fidelity DNA polymerase PrimeSTAR HS (Clonetech) with primer sets flanking examined sgRNA target sites. Indexed DNA libraries were prepared by using the TruSeq ChIP Sample Preparation Kit (Illumina) with minor modifications. Briefly, the PCR products amplified from genomic DNA regions were fragmented by Covaris S220. The fragmented DNAs were then PCR amplified by using the TruSeq ChIP Sample Preparation Kit (Illumina). After quantitated with Qubit High-Sensitivity DNA kit (Invitrogen), PCR products with different tags were pooled together for deep sequencing by using the Illumina Hiseq X10 (2×150) or NextSeq 500 (2×150) at CAS-MPG Partner Institute for Computational Biology Omics Core, Shanghai, China. Raw read qualities were evaluated by FastQC. For paired-end sequencing, only R1 reads were used. Adaptor sequences and read sequences on both ends with Phred quality score lower than 30 were trimmed. Trimmed reads were then mapped with the BWA-MEM algorithm (BWA v0.7.17) to target sequences. After piled up with samtools (v1.9), base substitutions were further calculated.

Base Substitution Calculation

Base substitutions were selected at each position of the examined sgRNA target sites that were mapped with at least 1000 independent reads, and obvious base substitutions were only observed at the targeted base editing sites. Base substitution frequencies were calculated by dividing base substitution reads by total reads. For each sgRNA, the ratio of C-to-T base substitution over indel was calculated by dividing the sum of C-to-T base substitution frequencies at all editing sites by the indel frequency of 50-bp region around sgRNA target site (from upstream eight nucleotides to the target site to downstream 19 nucleotides to PAM sites).

Results

Cytosine or adenine base editors (CBEs/BEs or ABEs) that fuse native cytidine deaminases or in vitro evolved adenosine deaminases with CRISPR-Cas9 have been developed to induce targeted C-to-T or adenine to guanine (A-to-G) conversions with high efficiencies. Because BEs use catalytically dead Cas9 (dCas9) protein or Cas9 nickase (nCas9) to direct their binding to genomic DNA, unintended base substitutions were expected to be induced at OTsg sites that are partially complementary to sgRNA. In this scenario, the use of high-fidelity Cas9 in BEs can reduce these OTsg mutations. Meanwhile, since free APOBECs can induce unexpected C-to-T mutations in single-stranded DNA (ssDNA) regions, the APOBEC moiety of BEs may directly trigger unexpected mutations at OTss sites. In other words, the off-target mutations induced by BEs may also occur at OTss sites independent of the guidance of sgRNA; however, OTss mutations were not revealed due to the lack of a quantitative and reproducible way for detection.

This example set up an efficient method to quantitatively evaluate BE-induced OTss mutations by co-expressing S. aureus and S. pyogenes Cas9 orthologs (CESSCO). In CESSCO, the expression of nSaCas9/Sa-sgRNA pairs generated DNA single-strand breaks (SSBs) at specific genomic loci and led to the formation of a genomic ssDNA region in a programmable way. At the same time, co-expressed BE3 in the absence of sgRNA (sgRNA means Sp-sgRNA hereafter) was used to examine whether sgRNA-independent C-to-T base substitutions can be induced by BE3 alone in the ssDNA regions generated around nSaCas9/Sa-sgRNA-introduced SSBs. After deep-sequencing the genomic regions targeted by nSaCas9/Sa-sgRNA, it was clearly shown that C-to-T mutations at OTss sites were induced by the rat APOBEC1 (rA1)-containing BE3 but not by dSpCas9 in the absence of sgRNA, confirming that OTss mutations are caused by the APOBEC moiety of BEs in an sgRNA-independent manner.

This example then sought to reduce OTss mutations by exploiting members of APOBEC family suitable for highly-specific BE construction. Most of commonly used BEs were constructed with single domain APOBECs, such as rA1 in BE3, but not with dual-domain APOBECs. Usually, in APOBECs with two CDA domains, one is catalytically active, while the other one is catalytically inactive, which plays a regulatory role on the cytidine deamination activity and thus may be suited for constructing highly-specific BEs with reduced OTss effects. To attempt this possibility, we constructed and compared the C-to-T editing efficiencies of ten paired BEs, which have either one catalytically active CDA domain or two CDA domains of five dual-domain APOBECs (FIG. 20a), i.e., human APOBEC3B (hA3B), human APOBEC3D (hA3D), human APOBEC3F (hA3F), human APOBEC3G (hA3G) and mouse APOBEC3 (mA3).

As revealed in FIG. 20b,c, the BEs constructed with certain APOBECs (hA3B, hA3F and mA3) containing two CDA domains induced significantly lower editing efficiencies than their paired BEs having only the active CDA domain. This result shows that the catalytically inactive CDA domains from these dual-domain APOBECs, i.e., hA3B, hA3F and mA3, exhibit an inhibitory function on their corresponding active CDA domains.

To examine whether the inhibitory function is general, we covalently linked the catalytically inactive CDA domains of mA3, hA3F or hA3B individually to the N-terminus of mA3CDA1-nSpCas9-BE (FIG. 20d) and two other commonly used BEs, i.e., BE3 and hA3A-BE3. All these catalytically inactive CDA domains showed broad-spectrum inhibitory effects on all tested BEs, and among them, the CDA2 of mA3 (mA3CDA2) manifested the strongest inhibitory effect (FIG. 20e,f). Detailed mapping analysis further revealed that residues 282-355 of mA3CDA2 exhibited an inhibitory effect similar to that of full-length mA3CDA2. Collectively, these results showed that the catalytically-inactive domains of certain dual-domain APOBECs indeed exhibit general inhibitory effects on cytidine deaminase activity, and we thus defined them as cytidine deaminase inhibitors (CDI).

Next, we sought to test whether the cleavage of mA3CDI (mA3CDA2) from its covalently-linked BEs can restore their base editing capacity. We used self-cleaving peptides (T2A) to link mA3CDI and mA3CDA1-nSpCas9-BE for examination. After self-cleavage of mA3CDI, the editing efficiency of mA3CDI-T2A-mA3CDA1-nSpCas9-BE was regained to the levels similar to EGFP-mA3CDA1-nSpCas9-BE or EGFP-T2A-mA3CDA1-nSpCas9-BE, ~10-fold higher than that of the non-cleavable-mA3CDI fused BE. The self-cleavage of mA3CDI from BE3 and hA3A-BE3 also enhanced their editing efficiencies, albeit to different extents.

These results served as a critical proof-of-concept for developing an iBE system for precise base editing with low OTss mutations. iBE1 was constructed by using TEV protease cleavage site (TS) to link three critical modules, i.e., mA3CDI, mA3CDA1-nSpCas9-BE and the N-terminal half of TEV protease (NTEV) (FIG. 21a). In theory, due to the covalent linkage of a CDI, iBE1 remains dormant when it binds to OTss sites by its APOBEC moiety (FIG. 21a). Notably, NTEV itself is inactive but forms a functional TEV protease only when the C-terminal half (CTEV) is recruited. Thus, iBE1 can be guided by its CRISPR-Cas moiety to perform efficient base editing at on-target sites where the CDI is cleaved by the sgRNA-induced assembly of functional TEV protease (FIG. 21d).

After being expressed in cells, iBE1 remained dormant in the sgRNA-independent OTss regions as expected (FIG. 21b) and induced much lower (~20%) level of C-to-T mutations compared to BE3 (FIG. 21c). At on-target sites, the RNA binding protein (MCP)-fused CTEV can be recruited by the MS2-fused sgRNA (FIG. 21d), which leads to the removal of mA3CDI from iBE1 and therefore enables efficient base editing. The comparison of on-target editing efficiency induced by BE3 and iBE1 across multiple genomic loci (FIG. 21e) demonstrated that iBE1 induced on-target base editing at a similar level as BE3 did (FIG. 21f, ~80% of BE3). Together, this example shows that we have developed an iBE system, which catalyzes efficient base editing at on-target sites with suppressed OTss mutations, through the manipulation of CDI.

As Cas9 has been known to induce unintended editing at OTsg sites that have partial sequence complementarity to the sgRNA, we also aimed to further reduce OTsg mutations by replacing the unmodified nSpCas9 in iBE1 with its engineered versions that have improved targeting specificity (FIG. 22a). We tested three engineered versions of nSpCas9, i.e., neSpCas9, nSpCas9HF1 and nHypaSpCas9, and found that using either of these targeting-specificity-improved Cas9 proteins greatly reduced OTsg mutations (FIG. 22b,c). Meanwhile, the use of neSpCas9 did not compromise the on-target editing efficiencies, whereas the use of the other two decreased the on-target editing efficiencies (FIG. 22d,e). In this scenario, we set to replace nSpCas9 with neSpCas9 to construct iBE2.

As an early developed BE, the editing efficiency of BE3 is restricted under certain conditions and additional BEs with improved editing efficiencies were developed later, e.g., AncBE4max or hA3A-BE3. hA3A-BE3 is a highly active BE in various contexts and we thus compared the performance of iBE2 to that of hA3A-BE3, in terms of editing efficiency and specificity (FIG. 23a). Although the average on-target editing frequency of iBE2 was ~50% of hA3A-BE3 (FIG. 23a,c), the C-to-T mutations induced by iBE2 at OTss and OTsg sites were close to the background level, while hA3A-BE3 induced substantial mutations at these off-target sites (FIG. 23a,b). Taken together, the average editing specificity of iBE2 was ~40-fold higher than that of hA3A-BE3 (FIG. 23d).

In this example, we first developed an efficient method (CESSCO) to quantitatively evaluate sgRNA-independent OTss mutations and confirmed that the BEs with a regular APOBEC-nCas9 backbone indeed induced OTss mutations in an sgRNA-independent manner (FIG. 21a, 21b, 23a, 23b). Consistent with our findings, recent whole genome sequencing studies also showed that BE3 induced substantial off-target mutations in mice and rice plants, assumedly also in an sgRNA-independent manner. Importantly, we took advantage of our discovery of CDIs to develop iBEs, which remain dormant at OTss sites due to the covalent linkage of CDI but can be activated by sgRNA-mediated cleavage of CDI at on-target sites (FIG. 21a,d). iBEs induced a significantly low level of unintended mutations in sgRNA-independent ssDNA regions, while it performed on-target editing efficiently (FIG. 21b,c,e,f).

By substituting nSpCas9 with the specificity-improved enSpCas9, highly-specific iBE2 was developed to further reduce unintended editing at OTsg sites (FIGS. 22 and 23e). The iBE system is compatible with the BEs having different Cas moieties and the engineered BEs with improved performance, and does not change the characteristics of constructed BEs, such as editing window. In addition, since there are abundant members within APOBEC family, other CDIs may be identified in the future, which would further enrich the repertoire of CDI-conjugated iBE system. As both editing precision and efficiency is essential for base editors, especially in their therapeutic applications, the iBE system developed here will bring a new layer of regulation for the specificity of current base editing system and secure its application against off-target mutations.

Example 3. Testing of Different Configurations of Induced and Split Base Editors This example tested a number of different configurations of molecules for implementing the induced and split base editor (isplitBE) system.

The working process of isplitBE is illustrated in FIG. 24A, as comparison to the conventional BEs as shown in FIG. 24B. In the illustrated isplitBE system, a nCas9-D10A construction is packaged in an AAV vehicle. A typical AAV vehicle has a 4.7 kb capacity, and the nCas9 construct is about 4.7 kb in length. Another AVV vehicle can package the nucleic acids (about 4.4 kb in total length) for encoding: (a) a fusion protein that includes MCP, UGI, APOBEC, a TEV recognition site (TEV site), and mA3CDA2; (b) a fusion protein with TEVc and N22p; (c) a standalone TEVn, (d) a helper sgRNA (hsgRNA) with a MS2 tag, and (e) another sgRNA with a boxB tag.

At a target site (ON, left lower branch), each of the hsgRNA and sgRNA binds to two adjacent sites on a target DNA, and the MCP- and N22p-containing fusion proteins bind to the MS2 tag and boxB tag of the hsgRNA and sgRNA, respectively. Due to proximity of TEVc (in the presence of free TEVn) and the TEV site, the TEVc/TEVn cleaves the TEV site, removing the mA3CDA2 from the APOBEC. Without the attached mA3CDA2, the APOBEC can highly efficiently carry out the desired editing.

At off-target sites, which may be a non-specific binding site (OTss, lower middle branch) or a site that only binds one of the guide RNAs, the TEVc/TEVn complex is not recruited to the TEV site-containing fusion protein, and thus the APOBEC cannot be activated. By contrast, in the conventional BE system (FIG. 24B), the APOBEC is already active and can cause C-to-T editing whenever it is recruited to a single-stranded nucleotide sequence.

Ten different configurations (Pairs 1-10), as illustrated in FIG. 25, were prepared and tested. For instance, as shown in FIG. 26A, Pair 1 included two constructs, the first of which contained rA1 fused to nCas9-D10A (spD10A), along with a UGI and an NLS, and the second of which contained a sgRNA targeting EMX1. Pair 2 is similar to Pair 1 but rA1 was replaced by hA3A. Pair 3 is also similar and used a mutant hA3A instead (Y130F).

In Pair 4, the rA1 and the nCas9 proteins were placed on different constructs. rA1 was further fused to an MCP protein which recognizes a MS2 tag on the helper sgRNA. In Pair 5, a mA3CDA2 was further fused to the rA1, via a TEV recognition site (black solid box). In Pair 6, a TEV protein was further fused, through a self-cleavage site 2A, to the rA1-mA3CDA2 fusion. Self cleavage of 2A would release the TEV from the fusion protein.

Pair 7 is different from Pair 6 by fusing the TEV to a N22p protein, which would recognize the boxB tag on the sgRNA. In Pair 8, the TEV protein was divided into TEVn and TEVc, separated by the 2A self cleavage site. In Pair 9, only the TEVc was fused to a N22p while the TEVn was free of any RNA tag-binding proteins. In Pair 10, the helper sgRNA targeted GFP, rather than a nearby site.

The constructs in FIG. 26A were designed for C-to-T editing at target site EMX1-ON, and the off-target editing at Sa-SITE31-OTss and EMX1-OTsg sites is examined as well. The testing results are shown in FIG. 26B. isplitBE-rA1 (Pair 9) induced substantial editing at ON site but no editing at OTss or OTsg sites.

Likewise, all of these configurations were tested with the FANCF-ON, Sa-VEGFA-7-OTss and FANCF-OTsg sites (see schematic diagram in FIG. 27A). FIG. 27B shows the comparison of editing efficiencies for different base editors at FANCF-ON, Sa-VEGFA-7-OTss and FANCF-OTsg sites. Again, isplitBE-rA1 (Pair 9) induced substantial editing at ON site but no editing at OTss or OTsg sites.

A further testing was done with the V1B-ON, Sa-SITE42-OTss and V1B-OTsg sites (see schematic diagram in FIG. 28A). Again, as shown in FIG. 28B, isplitBE-rA1 (Pair 9) induced substantial editing at ON site but no editing at OTss or OTsg sites.

Example 4. Tuning of Parameters in the isplitBE Systems

Out of the 10 tested configurations, Pair 9 exhibited the best performance in terms of editing specificity. Pair 9 employs two sgRNA, a helper sgRNA (hsgRNA) and a regular sgRNA. The dual use of sgRNA further enhances specificity as it requires that both target sites are in proximity from each other.

In a first assay of this example, the optimal distance between the two target sites was assessed. A schematic diagram is presented in FIG. 29A illustrating the distance between hsgRNA and sgRNA at DNTET1, EMX1 and FANCF sites. FIG. 29B shows the base editing frequencies induced by the indicated sgRNAs and hsgRNAs. The summary of FIG. 29C shows the effect of distance between hsgRNA and sgRNA. Based on the summary, the optimal range of distance for best base editing efficiency is −91 to −34 bp from the PAM of hsgRNA to the PAM of sgRNA.

The second assay tested the effect of hsgRNA spacer length on base editing efficiency and precision. FIG. 30A presents a schematic diagram illustrating the co-transfection of sgRNA and the hsgRNAs with different spacer lengths at DNEMX1, FANCF and VIA sites. FIG. 30B shows the base editing frequencies induced by the indicated sgRNAs and hsgRNAs at the target sties of hsgRNA and sgRNA. The statistic analysis in FIG. 30C shows the effects of hsgRNA spacer length. As shown, the use of hsgRNA with 10-nt spacer greatly reduced the editing efficiency at hsgRNA target sites but maintained the editing efficiency at sgRNA target sites. Accordingly, a spacer of 9-15 nt in the helper sgRNA sequence can be a good range to ensure efficient editing at the sgRNA target site, while minimizing the editing at the hsgRNA target site.

Example 5. Genome- and Transcriptome-Wide Evaluation

The overall efficiency of the isplitBE system was compared to the conventional BE3. The results are shown in FIG. 31 (editing frequencies induced by indicated base editors at different target sties). There is no apparent sacrifice of efficiency even when the isplitBE had greatly improved specificity.

Normal cells have a background level of C-to-T mutations attributable to their endogenous APOBEC3 activities. To obtain a more accurate measurement of off-target C-to-T mutations, an APOBEC3 knockout 293FT cell line (293FT-A3KO) was used. FIG. 32A shows the mRNA expression levels in wild-type 293FT cells and the APOBEC3 knockout 293FT cells. FIG. 32B presents a schematic diagram illustrating the procedures to determine genome-wide C-to-T mutations induced by base editors, and the testing results are shown in FIG. 32C (on-target editing efficiencies (left) and the number of genome-wide C-to-T mutations induced by Cas9, BE3, hA3A-BE3-Y130F (Y130F) and isplitBE-rA1). While BE3 and Y130F both had fairly high off-target edits, isplitBE-rA1's off-target editing rate is close to the background (Cas9 only).

This example then compared transcriptome-wide C-to-U mutations induced by isplitBE-mA3, BE3 and hA3A-BE3-Y130F (Y130F). The numbers of transcriptome-wide C-to-T(U) mutations induced by Cas9, BE3, hA3A-BE3-Y130F (Y130F) and isplitBE-mA3 are shown in FIG. 33A. FIG. 33B shows RNA C-to-U editing frequencies induced by Cas9, BE3, hA3A-BE3-Y130F (Y130F) and isplitBE-mA3. FIG. 33C shows distribution of RNA C-to-U editing induced by BE3 replicate 1 and isplitBE-mA3 replicate 1. Again, isplitBE induced much lower C-to-U editing than BE3.

Example 6. PCSK9 Knockouts

Proprotein convertase subtilisin/kexin type 9 (PCSK9) is an enzyme encoded by the PCSK9 gene in humans on chromosome 1. It is the 9th member of the proprotein convertase family of proteins that activate other proteins. PCSK9 is inactive when first synthesized, because a section of peptide chains blocks their activity; proprotein convertases remove that section to activate the enzyme. The PCSK9 gene contains one of 27 loci associated with increased risk of coronary artery disease.

PCSK9 is ubiquitously expressed in many tissues and cell types. PCSK9 binds to the receptor for low-density lipoprotein particles (LDL), which typically transport 3,000 to 6,000 fat molecules (including cholesterol) per particle, within extracellular fluid. The LDL receptor (LDLR), on liver and other cell membranes, binds and initiates ingestion of LDL-particles from extracellular fluid into cells, thus reducing LDL particle concentrations. If PCSK9 is blocked, more LDLRs are recycled and are present on the surface of cells to remove LDL-particles from the extracellular fluid. Therefore, blocking PCSK9 can lower blood LDL-particle concentrations.

This example tested an approach to inactivate PCSK9 by introducing stop codons through base editing using the present technology. The sequences of the sgRNA/hsgRNA used are shown in Table 3, and the target sites on PCSK9 are shown in Table 4.

Figure 34C:
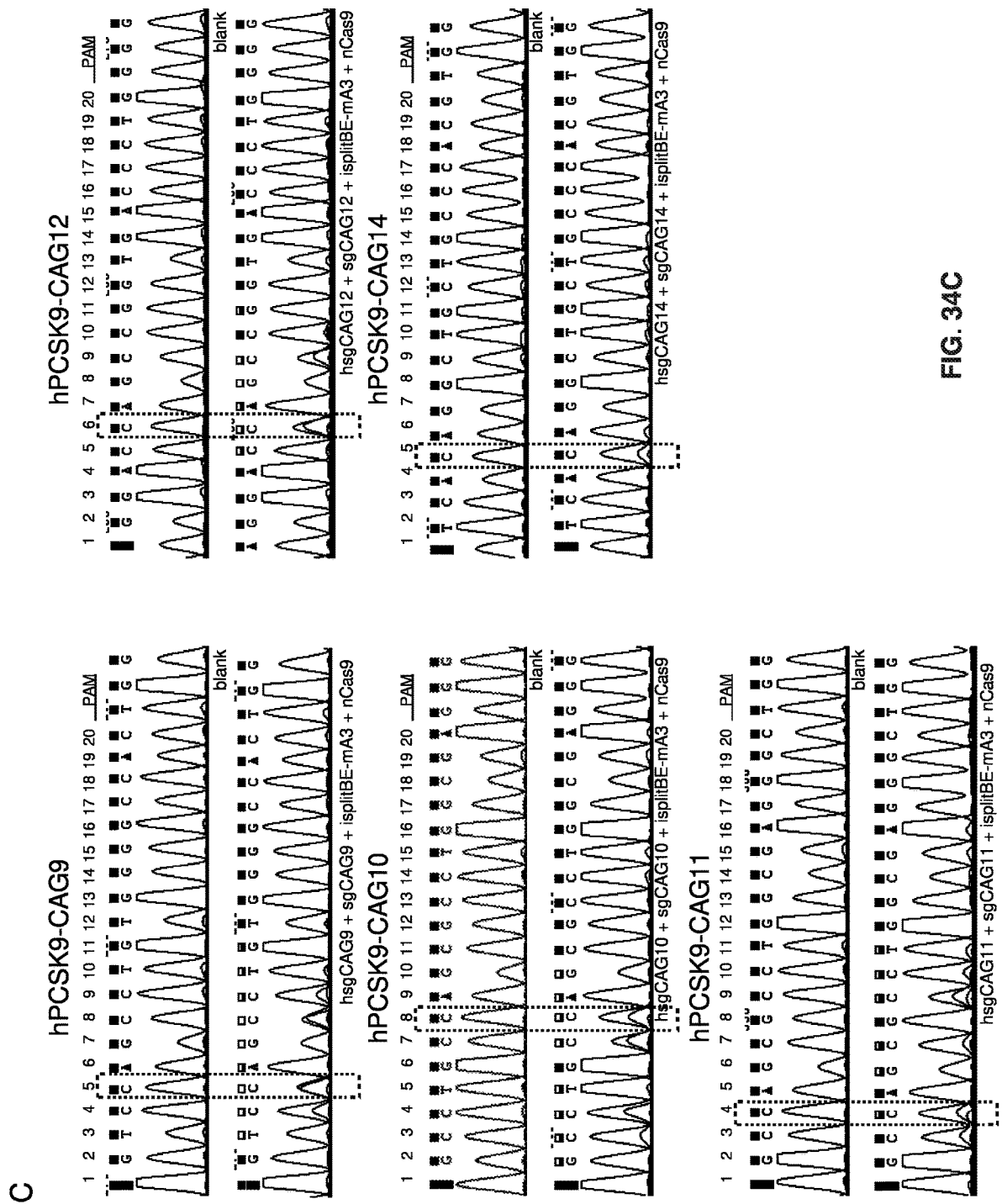
Figure 34D:
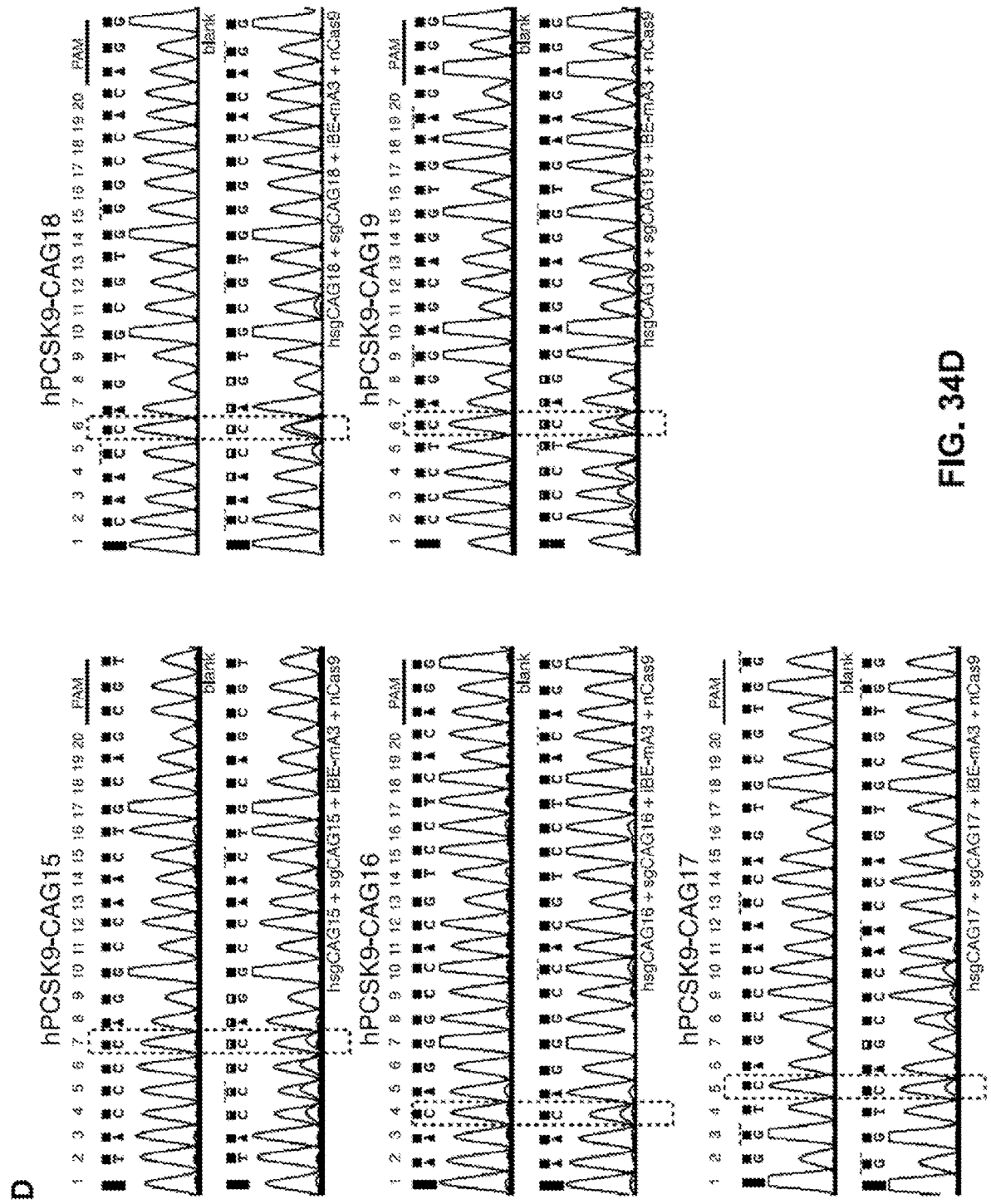

The numbers of stop codons generated by base editing were measured for the human PCSK9 gene. FIG. 34A presents a schematic diagram illustrating the co-transfection of sgRNA and the hsgRNAs with isplitBE-mA3 and nCas9. Editing efficiencies induced by isplitBE-mA3 at indicated sites are shown in FIG. 34B-D. These results demonstrate the high efficiency and specificity of the method.

TABLE 3

Regular sgRNA and hsgRNA scaffolds and target sites in PCSK9 genes

| Name | Sequence | SEQ ID NO: |
|---|---|---|
| hsgCAG2-MS2 | GAGGUUGCCUGGCACCUACGGUUUGAGAGCUAGGCCAACAUGAGGAUCACCCAU GUCUGCAGGGCCUAGCAAGUUCAAAUAAGGCUAGUCCGUUAUCAACUUGAAAAA GUGGCACCGAGUCGGUGC | 136 |
| hsgCAG3-MS2 | GAGACCCACCUCUCGCAGUCGUUUGAGAGCUAGGCCAACAUGAGGAUCACCCAU GUCUGCAGGGCCUAGCAAGUUCAAAUAAGGCUAGUCCGUUAUCAACUUGAAAAA GUGGCACCGAGUCGGUGC | 137 |
| hsgCAG4-MS2 | GCCCCAUGUCGACUACAUCGGUUUGAGAGCUAGGCCAACAUGAGGAUCACCCAU GUCUGCAGGGCCUAGCAAGUUCAAAUAAGGCUAGUCCGUUAUCAACUUGAAAAA GUGGCACCGAGUCGGUGC | 138 |

TABLE 3-continued

Regular sgRNA and hsgRNA scaffolds and target sites in PCSK9 genes

| Name | Sequence | SEQ ID NO: |
|---|---|---|
| hsgCAG7-MS2 | AUGGUCACCGACUUCGAGAAGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 139 |
| hsgCAG8-MS2 | ACCUUGGCUUUGUUCCUCCCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 140 |
| hsgCAG9-MS2 | GGCUUUGUUCCUCCCAGGCCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 141 |
| hsgCAG10-MS2 | GUGGUGCUGCUGCCCCUGGCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 142 |
| hsgCAG11-MS2 | UGCUGCUGCCCCUGGCGGGUGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 143 |
| hsgCAG12-MS2 | ACCCACCUCCUCACCUUUCCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 144 |
| hsgCAG14-MS2 | AGCGACUGCAGCACCUGCUUGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 145 |
| hsgCAG15-MS2 | AACGCUUUUGGGGGUGAGGGGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 146 |
| hsgCAG16-MS2 | CCACACAGCUCCACCAGCUGGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 147 |
| hsgCAG17-MS2 | CACUGGGAGGUGGAGGACCUGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 148 |
| hsgCAG18-MS2 | CCCACAAGCCGCCUGUGCUGGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 149 |
| hsgCAG19-MS2 | AGGUCUGGAAUGCAAAGUCAGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 150 |
| sgCAG2-boxB | CUCUCGCAGUCAGAGCGCACGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 151 |
| sgCAG3-boxB | CAGGCCCAGGCUGCCCGCCGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 152 |
| sgCAG4-boxB | UCUUUGCCCAGAGCAUCCCGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 153 |
| sgCAG7-boxB | CACAGACAGGUAAGCACGGCGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 154 |
| sgCAG8-boxB | AAGCCAGCUGGUCCAGCCUGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 155 |
| sgCAG9-boxB | GGUCCAGCCUGUGGGGCCACGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 156 |
| sgCAG10-boxB | CGCCUGCCAGCGCCUGGCGAGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 157 |

TABLE 3-continued

Regular sgRNA and hsgRNA scaffolds and target sites in PCSK9 genes

| Name | Sequence | SEQ ID NO: |
|---|---|---|
| sgCAG11-boxB | UGCCAGCGCCUGGCGAGGGCGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 158 |
| sgCAG12-boxB | AAGACCAGCCGGUGACCCUGGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 159 |
| sgCAG14-boxB | AUCACAGGCUGCUGCCCACGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 160 |
| sgCAG15-boxB | CUACCCCAGGCCAACUGCAGGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 161 |
| sgCAG16-boxB | CAACAGGGCCACGUCCUCACGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 162 |
| sgCAG17-boxB | AGGUCAGCCCAACCAGUGCGGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 163 |
| sgCAG18-boxB | CCAACCAGUGCGUGGGCCACGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 164 |
| sgCAG19-boxB | CCCCUCAGGAGCAGGUGAAGGUUUGAGAGCUAGGGCCCUGAAGAAGGGCCCUAG CAAGUUCAAAUAAGGCUAGUCCGUUAUCAACUUGGGCCCUGAAGAAGGGCCCAA GUGGCACCGAGUCGGUGC | 165 |

TABLE 4

Target sites in PCSK9 genes

| Name | Sequence | SEQ ID NO: |
|---|---|---|
| hsgCAG2 | GAGGTTGCCTGGCACCTACGTGG | 166 |
| hsgCAG3 | GAGACCCACCTCTCGCAGTCAGA | 167 |
| hsgCAG4 | GCCCCATGTCGACTACATCGAGG | 168 |
| hsgCAG7 | ATGGTCACCGACTTCGAGAATGT | 169 |
| hsgCAG8 | ACCTTGGCTTTGTTCCTCCCAGG | 170 |
| hsgCAG9 | GGCTTTGTTCCTCCCAGGCCTGG | 171 |
| hsgCAG10 | GTGGTGCTGCTGCCCCTGGCGGG | 172 |
| hsgCAG11 | TGCTGCTGCCCCTGGCGGGTGGG | 173 |
| hsgCAG12 | ACCCACCTCCTCACCTTTCCAGG | 174 |
| hsgCAG14 | AGCGACTGCAGCACCTGCTTTGT | 175 |
| hsgCAG15 | AACGCTTTTGGGGGTGAGGGTGT | 176 |
| hsgCAG16 | CCACACAGCTCCACCAGCTGAGG | 177 |
| hsgCAG17 | CACTGGGAGGTGGAGGACCTTGG | 178 |
| hsgCAG18 | CCCACAAGCCGCCTGTGCTGAGG | 179 |
| hsgCAG19 | AGGTCTGGAATGCAAAGTCAAGG | 180 |
| sgCAG2 | CTCTCGCAGTCAGAGCGCACTGC | 181 |
| sgCAG3 | CAGGCCCAGGCTGCCCGCCGGGG | 182 |
| sgCAG4 | TCTTTGCCCAGAGCATCCCGTGG | 183 |
| sgCAG7 | CACAGACAGGTAAGCACGGCCGT | 184 |
| sgCAG8 | AAGCCAGCTGGTCCAGCCTGTGG | 185 |
| sgCAG9 | GGTCCAGCCTGTGGGGCACTGG | 186 |
| sgCAG10 | CGCCTGCCAGCGCCTGGCGAGGG | 187 |
| sgCAG11 | TGCCAGCGCCTGGCGAGGGCTGG | 188 |
| sgCAG12 | AAGACCAGCCGGTGACCCTGGGG | 189 |
| sgCAG14 | ATCACAGGCTGCTGCCCACGTGG | 190 |
| sgCAG15 | CTACCCCAGGCCAACTGCAGCGT | 191 |
| sgCAG16 | CAACAGGGCCACGTCCTCACAGG | 192 |
| sgCAG17 | AGGTCAGCCCAACCAGTGCGTGG | 193 |
| sgCAG18 | CCAACCAGTGCGTGGGCCACAGG | 194 |
| sgCAG19 | CCCCTCAGGAGCAGGTGAAGAGG | 195 |

Example 7. Applicability of the isplitBE Design in Adenine Base Editors

This example confirms the applicability of the induced and split base editor (isplitBE) design in other types of base editors. The inhibitor used was mA3CDA2 and the editor was adenine base editor (ABE).

A schematic diagram illustrating the co-transfection of sgRNA and ABE fused with mA3CDA2 (or not as control) is shown in FIG. 35A. The editing efficiencies induced by indicated ABEs at RNF2 and FANCF sites are shown in FIG. 35B. With mA3CDA2 attached to the ABE, the editing efficiency was reduced as compared to ABE alone. When the mA3CDA2 was cleaved by 2A, the editing efficiency of ABE was restored, validating the isplitBE approach for ABE.

Example 8. Enhanced Prime Editing

The conventional base editors are limited to base transitions, not base transversions, insertions or deletions. Recently, a primer editing system was proposed, which employs a primer editor (PE) by conjugating a Cas9 nickase with a reverse transcriptase (RTase). The PE system can write genomes with almost any intended changes, including all types of base substitutions, small indels, and their combinations. The overall efficiency and specificity of the PE systems, however, are still limited.

In a first assay, this example tested a new design for the primer editing guide RNA (pegRNA). Conventionally, each guide RNA includes a scaffold. A commonly used scaffold sequence is GUUUUAGAGCUA-GAAAUAGCAAGUUAAAAUAAGGCUAGU-CCGUUAUCAACUU GAAAAAGUGGCACCGAGUCG-GUGC (SEQ ID NO:29). Another example is GUUUUAGAGCUA-GAAAUAGCAAGUUAAAAUAAGGCAUGU-CCGUUAUCAACUU GAAAAAGUGGCACCGAUUCG-GUGC (SEQ ID NO:30). A more generic consensus sequence is GUUUNAGAGCUAX$_1$UAGCAAGUUN-AAAUAAGGCNNGUCCGUUAUCAACUUX$_2$A AGUGGCACCGANUCGGUGC (SEQ ID NO:31), where N represents any base, and X1 and X2 denotes any nucleotide sequence of a length of 2-50 bases.

The scaffold is expected to form a secondary structure (illustrated in FIG. 36A, SEQ ID NO:30) due to its internal complementary sequences. A typical sgRNA used in base editors is about 96 nt in length which includes a spacer that is about 20 nt in length and binds to the target site. In a pegRNA, a reverse-transcription template and a primer-binding site are further added to the 3' end of the scaffold. Surprisingly, it is discovered herein that the original scaffold is not stable enough in the context of the pegRNA.

A new scaffold was therefore prepared, which forms a new pairing between positions 48 (e.g., A in SEQ ID NO:30) and 61 (e.g., G in SEQ ID NO:30). In the examples shown in FIGS. 36A and 36E, the new scaffold has G and C or C and G instead (SEQ ID NO:36, 37). This and additional example mutant scaffolds are shown in Table 5 below.

TABLE 5

Sequences of Guide RNA Scaffolds

| Description | Guide RNA Scaffold | SEQ ID NO: |
|---|---|---|
| Original | GUUUNAGAGCUA-X1-UAGCAAGUUNAAAUAAGGCNNGUCCGUUAUCAAC UU-X2-AAGUGGCACCGANUCGGUGC | 31 |
| New 1 | GUUUNAGAGCUA-X1-UAGCAAGUUNAAAUAAGGCNNGUCCGUUAUCGAC UU-X2-AAGUCGCACCGANUCGGUGC | 32 |
| New 2 | GUUUNAGAGCUA-X1-UAGCAAGUUNAAAUAAGGCNNGUCCGUUAUCCAC UU-X2-AAGUGGCACCGANUCGGUGC | 33 |
| New 3 | GUUUNAGAGCUA-X1-UAGCAAGUUNAAAUAAGGCNNGUCCGUUAUCAAC UU-X2-AAGUUGCACCGANUCGGUGC | 34 |
| New 4 | GUUUNAGAGCUA-X1-UAGCAAGUUNAAAUAAGGCNNGUCCGUUAUCUAC UU-X2-AAGUAGCACCGANUCGGUGC | 35 |
| Original 2 | GUUUUAGAGCUAGAAAUAGCAAGUUAAAAUAAGGCAUGUCCGUUAUCAAC UUGAAAAAGUGGCACCGAUUCGGUGC | 30 |
| New 5 | GUUUUAGAGCUAGAAAUAGCAAGUUAAAAUAAGGCAUGUCCGUUAUCGAC UUGAAAAAGUCGCACCGAUUCGGUGC | 36 |
| New 6 | GUUUUAGAGCUAGAAAUAGCAAGUUAAAAUAAGGCAUGUCCGUUAUCCAC UUGAAAAAGUGGCACCGAUUCGGUGC | 37 |
| New 7 | GUUUUAGAGCUAGAAAUAGCAAGUUAAAAUAAGGCAUGUCCGUUAUCAAC UUGAAAAAGUUGCACCGAUUCGGUGC | 38 |
| New 8 | GUUUUAGAGCUAGAAAUAGCAAGUUAAAAUAAGGCAUGUCCGUUAUCUAC UUGAAAAAGUAGCACCGAUUCGGUGC | 39 |
| Original 3 | GUUUUAGAGCUAGAAAUAGCAAGUUAAAAUAAGGCUAGUCCGUUAUCAAC UUGAAAAAGUGGCACCGAGUCGGUGC | 29 |
| New 9 | GUUUUAGAGCUAGAAAUAGCAAGUUAAAAUAAGGCUAGUCCGUUAUCGAC UUGAAAAAGUCGCACCGAGUCGGUGC | 40 |
| New 10 | GUUUUAGAGCUAGAAAUAGCAAGUUAAAAUAAGGCUAGUCCGUUAUCCAC UUGAAAAAGUGGCACCGAGUCGGUGC | 41 |
| New 11 | GUUUUAGAGCUAGAAAUAGCAAGUUAAAAUAAGGCUAGUCCGUUAUCAAC UUGAAAAAGUUGCACCGAGUCGGUGC | 42 |

TABLE 5-continued

Sequences of Guide RNA Scaffolds

| Description | Guide RNA Scaffold | SEQ ID NO: |
|---|---|---|
| New 12 | GUUUUAGAGCUAGAAAUAGCAAGUUAAAAUAAGGCUAGUCCGUUAUCUAC UUGAAAAAGUAGCACCGAGUCGGUGC | 43 |

Figure 36D:
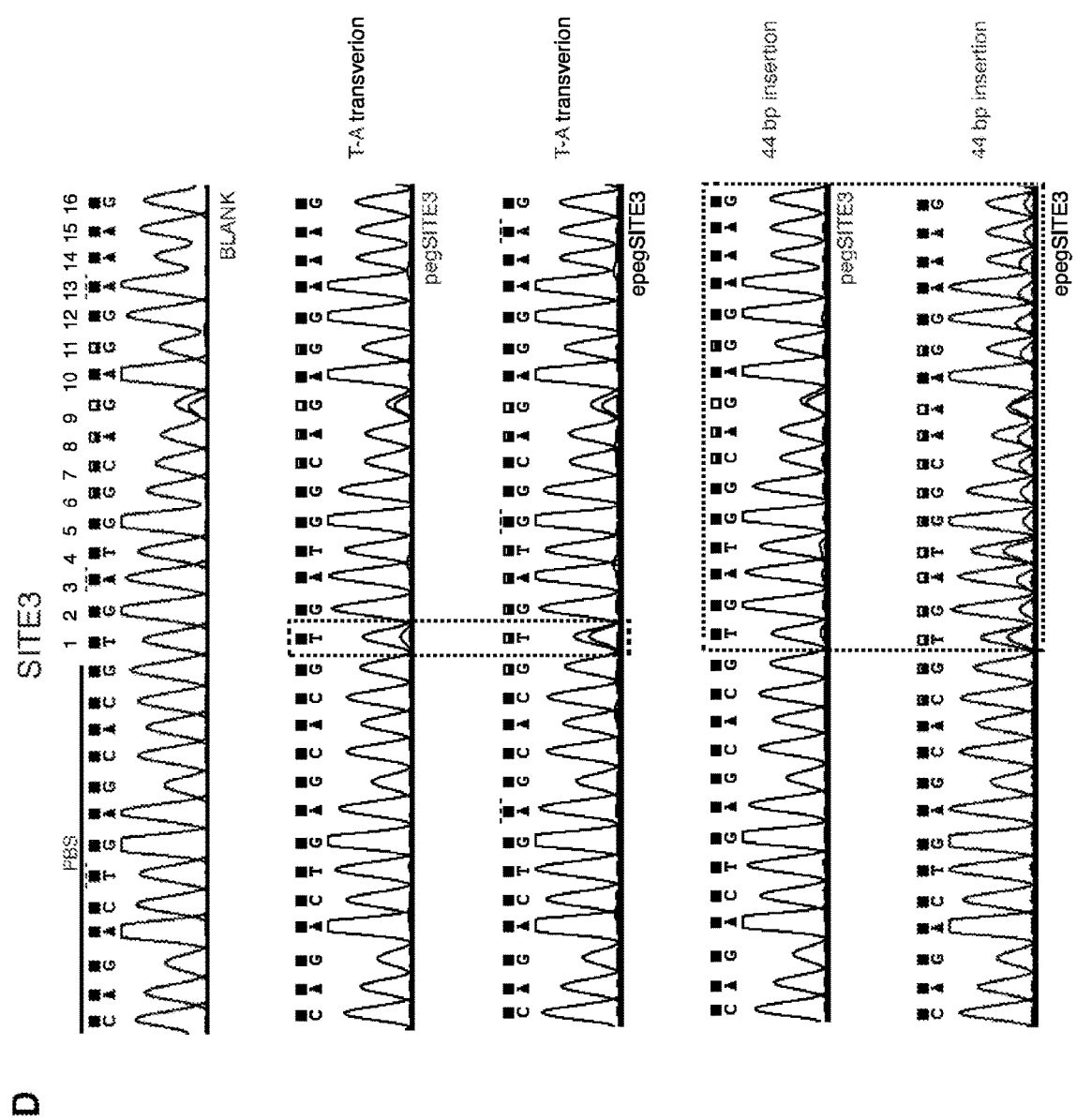

Constructs for testing the conventional pegRNA and the newly designed, enhanced pegRNA (epegRNA) were prepare as shown in FIGS. 36B and 36F for PE2, and the testing results are shown in FIGS. 36C-36D and 36G. Comparison of prime editing efficiencies induced with pegRNA and epegRNA. The epegRNA, with greatly improved stem stability, exhibited much higher editing efficiency than pegRNA across the board.

Likewise, according to the schematic diagram in FIG. 37A, co-transfection of pegRNA, nicking sgRNA with PE2-NG (SEQ ID NO:132) or xPE2 (SEQ ID NO:133) was made to test the editing efficiency for TGATG deletion. The results are shown in FIG. 37B. PE2-NG has an engineered Cas9 that can recognize relaxed NG PAMs (see, e.g., Nishimasu et al., Science 361, 1259-62 (2018)). xPE2 has an engineered Cas9 that can recognize relaxed NG, GAA and GAT PAMs (see, e.g., Hu et al., Nature 556, 57-63 (2018)). The sequences of PE2-NG (SEQ ID NO:44), xPE2 (SEQ ID NO:45), SpCas9-NG (SEQ ID NO:46), and xSpCas9 (SEQ ID NO:47) are shown in Table 6 below.

TABLE 6

Cas and PE sequences

| Name | Sequence | SEQ ID NO: |
|---|---|---|
| PE2-NG | MDKKYSIGLDIGTNSVGWAVITDEYKVPSKKFKVLGNTDRHSIKKNLIGALLFDSGETAEAT RLKRTARRRYTRRKNRICYLQEIFSNEMAKVDDSFFHRLEESFLVEEDKKHERHPIFGNIVD EVAYHEKYPTIYHLRKKLVDSTDKADLRLIYLALAHMIKFRGHFLIEGDLNPDNSDVDKLFI QLVQTYNQLFEENPINASGVDAKAILSARLSKSRRLENLIAQLPGEKKNGLFGNLIALSLGL TPNFKSNFDLAEDAKLQLSKDTYDDDLDNLLAQIGDQYADLFLAAKNLSDAILLSDILRVNT EITKAPLSASMIKRYDEHHQDLTLLKALVRQQLPEKYKEIFFDQSKNGYAGYIDGGASQEEF YKFIKPILEKMDGTEELLVKLNREDLLRKQRTFDNGSIPHQIHLGELHAILRRQEDFYPFLK DNREKIEKILTFRIPYYVGPLARGNSRFAWMTRKSEETITPWNFEEVVDKGASAQSFIERMT NFDKNLPNEKVLPKHSLLYEYFTVYNELTKVKYVTEGMRKPAFLSGEQKKAIVDLLFKTNRK VTVKQLKEDYFKKIECFDSVEISGVEDRFNASLGTYHDLLKIIKDKDFLDNEENEDILEDIV LTLTLFEDREMIEERLKTYAHLFDDKVMKQLKRRRYTGWGRLSRKLINGIRDKQSGKTILDF LKSDGFANRNFMQLIHDDSLTFKEDIQKAQVSGQGDSLHEHIANLAGSPAIKKGILQTVKVV DELVKVMGRHKPENIVIEMARENQTTQKGQKNSRERMKRIEEGIKELGSQILKEHPVENTQL QNEKLYLYYLQNGRDMYVDQELDINRLSDYDVDAIVPQSFLKDDSIDNKVLTRSDKNRGKSD NVPSEEVVKKMKNYWRQLLNAKLITQRKFDNLTKAERGGLSELDKAGFIKRQLVETRQITKH VAQILDSRMNTKYDENDKLIREVKVITLKSKLVSDFRKDFQFYKVREINNYHHAHDAYLNAV VGTALIKKYPKLESEFVYGDYKVYDVRKMIAKSEQEIGKATAKYFFYSNIMNFFKTEITLAN GEIRKRPLIETNGETGEIVWDKGRDFATVRKVLSMPQVNIVKKTEVQTGGFSKESIRPKRNS DKLIARKKDWDPKKYGGFVSPTVAYSVLVVAKVEKGKSKKLKSVKELLGITIMERSSFEKNP IDFLEAKGYKEVKKDLIIKLPKYSLFELENGRKRMLASARFLQKGNELALPSKYVNFLYLAS HYEKLKGSPEDNEQKQLFVEQHKHYLDEIIEQISEFSKRVILADANLDKVLSAYNKHRDKPI REQAENIIHLFTLTNLGAPRAFKYFDTTIDRKVYRSTKEVLDATLIHQSITGLYETRIDLSQ LGGDGTSGGSSGGSSGSETPGTSESATPESSGGSSGGSSTLNIEDEYRLHETSKEPDVSLGS TWLSDFPQAWAETGGMGLAVRQAPLIIPLKATSTPVSIKQYPMSQEARLGIKPHIQRLLDQG ILVPCQSPWNTPLLPVKKPGTNDYRPVQDLREVNKRVEDIHPTVPNPYNLLSGLPPSHQWYT VLDLKDAFFCLRLHPTSQPLFAFEWRDPEMGISGQLTWTRLPQGFKNSPTLFNEALHRDLAD FRIQHPDLILLQYVDDLLLAATSELDCQQGTRALLQTLGNLGYRASAKKAQICQKQVKYLGY LLKEGQRWLTEARKETVMGQPTPKTPRQLREFLGKAGFCRLFIPGFAEMAAPLYPLTKPGTL FNWGPDQQKAYQEIKQALLTAPALGLPDLTKPFELFVDEKQGYAKGVLTQKLGPWRRPVAYL SKKLDPVAAGWPPCLRMVAAIAVLTKDAGKLTMGQPLVILAPHAVEALVKQPPDRWLSNARM THYQALLLDTDRVQFGPVVALNPATLLPLPEEGLQHNCLDILAEAHGTRPDLTDQPLPDADH TWYTDGSSLLQEGQRKAGAAVTTETEVIWAKALPAGTSAQRAELIALTQALKMAEGKKLNVY TDSRYAFATAHIHGEIYRRRGWLTSEGKEIKNKDEILALLKALFLPKRLSIIHCPGHQKGHS AEARGNRMADQAARKAAITETPDTSTLLIENSSP | 44 |
| xPE2 | MDKKYSIGLDIGTNSVGWAVITDEYKVPSKKFKVLGNTDRHSIKKNLIGALLFDSGETAEAT RLKRTARRRYTRRKNRICYLQEIFSNEMAKVDDSFFHRLEESFLVEEDKKHERHPIFGNIVD EVAYHEKYPTIYHLRKKLVDSTDKADLRLIYLALAHMIKFRGHFLIEGDLNPDNSDVDKLFI QLVQTYNQLFEENPINASGVDAKAILSARLSKSRRLENLIAQLPGEKKNGLFGNLIALSLGL TPNFKSNFDLAEDTKLQLSKDTYDDDLDNLLAQIGDQYADLFLAAKNLSDAILLSDILRVNT EITKAPLSASMIKLYDEHHQDLTLLKALVRQQLPEKYKEIFFDQSKNGYAGYIDGGASQEEF YKFIKPILEKMDGTEELLVKLNREDLLRKQRTFDNGIIPHQIHLGELHAILRRQEDFYPFLK DNREKIEKILTFRIPYYVGPLARGNSRFAWMTRKSEETITPWNFEKVVDKGASAQSFIERMT NFDKNLPNEKVLPKHSLLYEYFTVYNELTKVKYVTEGMRKPAFLSGDQKKAIVDLLFKTNRK VTVKQLKEDYFKKIECFDSVEISGVEDRFNASLGTYHDLLKIIKDKDFLDNEENEDILEDIV LTLTLFEDREMIEERLKTYAHLFDDKVMKQLKRRRYTGWGRLSRKLINGIRDKQSGKTILDF LKSDGFANRNFIQLIHDDSLTFKEDIQKAQVSGQGDSLHEHIANLAGSPAIKKGILQTVKVV DELVKVMGRHKPENIVIEMARENQTTQKGQKNSRERMKRIEEGIKELGSQILKEHPVENTQL QNEKLYLYYLQNGRDMYVDQELDINRLSDYDVDAIVPQSFLKDDSIDNKVLTRSDKNRGKSD | 45 |

TABLE 6-continued

Cas and PE sequences

| Name | Sequence | SEQ ID NO: |
|---|---|---|
| | NVPSEEVVKKMKNYWRQLLNAKLITQRKFDNLTKAERGGLSELDKAGFIKRQLVETRQITKH<br>VAQILDSRMNTKYDENDKLIREVKVITLKSKLVSDFRKDFQFYKVREINNYHHAHDAYLNAV<br>VGTALIKKYPKLESEFVYGDYKVYDVRKMIAKSEQEIGKATAKYFFYSNIMNFFKTEITLAN<br>GEIRKRPLIETNGETGEIVWDKGRDFATVRKVLSMPQVNIVKKTEVQTGGFSKESILPKRNS<br>DKLIARKKDWDPKKYGGFDSPTVAYSVLVVAKVEKGKSKKLKSVKELLGITIMERSSFEKNP<br>IDFLEAKGYKEVKKDLIIKLPKYSLFELENGRKRMLASAGVLQKGNELALPSKYVNFLYLAS<br>HYEKLKGSPEDNEQKQLFVEQHKHYLDEIIEQISEFSKRVILADANLDKVLSAYNKHRDKPI<br>REQAENIIHLFTLTNLGAPAAFKYFDTTIDRKRYTSTKEVLDATLIHQSITGLYETRIDLSQ<br>LGGDGTSGGSSGGSSGSETPGTSESATPESSGGSSGGSSTLNIEDEYRLHETSKEPDVSLGS<br>TWLSDFPQAWAETGGMGLAVRQAPLIIPLKATSTPVSIKQYPMSQEARLGIKPHIQRLLDQG<br>ILVPCQSPWNTPLLPVKKPGTNDYRPVQDLREVNKRVEDIHPTVPNPYNLLSGLPPSHQWYT<br>VLDLKDAFFCLRLHPTSQPLFAFEWRDPEMGISGQLTWTRLPQGFKNSPTLFNEALHRDLAD<br>FRIQHPDLILLQYVDDLLLAATSELDCQQGTRALLQTLGNLGYRASAKKAQICQKQVKYLGY<br>LLKEGQRWLTEARKETVMGQPTPKTPRQLREFLGKAGFCRLFIPGFAEMAAPLYPLTKPGTL<br>FNWGPDQQKAYQEIKQALLTAPALGLPDLTKPFELFVDEKQGYAKGVLTQKLGPWRRPVAYL<br>SKKLDPVAAGWPPCLRMVAAIAVLTKDAGKLTMGQPLVILAPHAVEALVKQPPDRWLSNARM<br>THYQALLLDTDRVQFGPVVALNPATLLPLPEEGLQHNCLDILAEAHGTRPDLTDQPLPDADH<br>TWYTDGSSLLQEGQRKAGAAVTTETEVIWAKALPAGTSAQRAELIALTQALKMAEGKKLNVY<br>TDSRYAFATAHIHGEIYRRRGWLTSEGKEIKNKDEILALLKALFLPKRLSIIHCPGHQKGHS<br>AEARGNRMADQAARKAAITETPDTSTLLIENSSP | |
| SpCas9-NG | MDKKYSIGLDIGTNSVGWAVITDEYKVPSKKFKVLGNTDRHSIKKNLIGALLFDSGETAEAT<br>RLKRTARRRYTRRKNRICYLQEIFSNEMAKVDDSFFHRLEESFLVEEDKKHERHPIFGNIVD<br>EVAYHEKYPTIYHLRKKLVDSTDKADLRLIYLALAHMIKFRGHFLIEGDLNPDNSDVDKLFI<br>QLVQTYNQLFEENPINASGVDAKAILSARLSKSRRLENLIAQLPGEKKNGLFGNLIALSLGL<br>TPNFKSNFDLAEDAKLQLSKDTYDDDLDNLLAQIGDQYADLFLAAKNLSDAILLSDILRVNT<br>EITKAPLSASMIKRYDEHHQDLTLLKALVRQQLPEKYKEIFFDQSKNGYAGYIDGGASQEEF<br>YKFIKPILEKMDGTEELLVKLNREDLLRKQRTFDNGSIPHQIHLGELHAILRRQEDFYPFLK<br>DNREKIEKILTFRIPYYVGPLARGNSRFAWMTRKSEETITPWNFEEVVDKGASAQSFIERMT<br>NFDKNLPNEKVLPKHSLLYEYFTVYNELTKVKYVTEGMRKPAFLSGEQKKAIVDLLFKTNRK<br>VTVKQLKEDYFKKIECFDSVEISGVEDRFNASLGTYHDLLKIIKDKDFLDNEENEDILEDIV<br>LTLTLFEDREMIEERLKTYAHLFDDKVMKQLKRRRYTGWGRLSRKLINGIRDKQSGKTILDF<br>LKSDGFANRNFMQLIHDDSLTFKEDIQKAQVSGQGDSLHEHIANLAGSPAIKKGILQTVKVV<br>DELVKVMGRHKPENIVIEMARENQTTQKGQKNSRERMKRIEEGIKELGSQILKEHPVENTQL<br>QNEKLYLYYLQNGRDMYVDQELDINRLSDYDVDHIVPQSFLKDDSIDNKVLTRSDKNRGKSD<br>NVPSEEVVKKMKNYWRQLLNAKLITQRKFDNLTKAERGGLSELDKAGFIKRQLVETRQITKH<br>VAQILDSRMNTKYDENDKLIREVKVITLKSKLVSDFRKDFQFYKVREINNYHHAHDAYLNAV<br>VGTALIKKYPKLESEFVYGDYKVYDVRKMIAKSEQEIGKATAKYFFYSNIMNFFKTEITLAN<br>GEIRKRPLIETNGETGEIVWDKGRDFATVRKVLSMPQVNIVKKTEVQTGGFSKESIRPKRNS<br>DKLIARKKDWDPKKYGGFVSPTVAYSVLVVAKVEKGKSKKLKSVKELLGITIMERSSFEKNP<br>IDFLEAKGYKEVKKDLIIKLPKYSLFELENGRKRMLASARFLQKGNELALPSKYVNFLYLAS<br>HYEKLKGSPEDNEQKQLFVEQHKHYLDEIIEQISEFSKRVILADANLDKVLSAYNKHRDKPI<br>REQAENIIHLFTLTNLGAPRAFKYFDTTIDRKVYRSTKEVLDATLIHQSITGLYETRIDLSQ<br>LGGD | 46 |
| xSpCas9 | MDKKYSIGLDIGTNSVGWAVITDEYKVPSKKFKVLGNTDRHSIKKNLIGALLFDSGETAEAT<br>RLKRTARRRYTRRKNRICYLQEIFSNEMAKVDDSFFHRLEESFLVEEDKKHERHPIFGNIVD<br>EVAYHEKYPTIYHLRKKLVDSTDKADLRLIYLALAHMIKFRGHFLIEGDLNPDNSDVDKLFI<br>QLVQTYNQLFEENPINASGVDAKAILSARLSKSRRLENLIAQLPGEKKNGLFGNLIALSLGL<br>TPNFKSNFDLAEDTKLQLSKDTYDDDLDNLLAQIGDQYADLFLAAKNLSDAILLSDILRVNT<br>EITKAPLSASMIKLYDEHHQDLTLLKALVRQQLPEKYKEIFFDQSKNGYAGYIDGGASQEEF<br>YKFIKPILEKMDGTEELLVKLNREDLLRKQRTFDNGIIPHQIHLGELHAILRRQEDFYPFLK<br>DNREKIEKILTFRIPYYVGPLARGNSRFAWMTRKSEETITPWNFEKVVDKGASAQSFIERMT<br>NFDKNLPNEKVLPKHSLLYEYFTVYNELTKVKYVTEGMRKPAFLSGDQKKAIVDLLFKTNRK<br>VTVKQLKEDYFKKIECFDSVEISGVEDRFNASLGTYHDLLKIIKDKDFLDNEENEDILEDIV<br>LTLTLFEDREMIEERLKTYAHLFDDKVMKQLKRRRYTGWGRLSRKLINGIRDKQSGKTILDF<br>LKSDGFANRNFIQLHDDSLTFKEDIQKAQVSGQGDSLHEHIANLAGSPAIKKGILQTVKVV<br>DELVKVMGRHKPENIVIEMARENQTTQKGQKNSRERMKRIEEGIKELGSQILKEHPVENTQL<br>QNEKLYLYYLQNGRDMYVDQELDINRLSDYDVDHIVPQSFLKDDSIDNKVLTRSDKNRGKSD<br>NVPSEEVVKKMKNYWRQLLNAKLITQRKFDNLTKAERGGLSELDKAGFIKRQLVETRQITKH<br>VAQILDSRMNTKYDENDKLIREVKVITLKSKLVSDFRKDFQFYKVREINNYHHAHDAYLNAV<br>VGTALIKKYPKLESEFVYGDYKVYDVRKMIAKSEQEIGKATAKYFFYSNIMNFFKTEITLAN<br>GEIRKRPLIETNGETGEIVWDKGRDFATVRKVLSMPQVNIVKKTEVQTGGFSKESILPKRNS<br>DKLIARKKDWDPKKYGGFDSPTVAYSVLVVAKVEKGKSKKLKSVKELLGITIMERSSFEKNP<br>IDFLEAKGYKEVKKDLIIKLPKYSLFELENGRKRMLASAGVLQKGNELALPSKYVNFLYLAS<br>HYEKLKGSPEDNEQKQLFVEQHKHYLDEIIEQISEFSKRVILADANLDKVLSAYNKHRDKPI<br>REQAENIIHLFTLTNLGAPAAFKYFDTTIDRKRYTSTKEVLDATLIHQSITGLYETRIDLSQ<br>LGGD | 47 |

A complete prime editor requires a construct (about 11 kb) that is much larger than what an AAV vehicle can accommodate. Accordingly, a Split PE system was designed and tested. The original PE system is illustrated on the left panel of FIG. 38A, and the newly designed Split PE system is illustrated on the right panel, in which the nickase and the RTase are packaged into different AAV particles. The RTase is fused to an RNA binding protein MCP, and the pegRNA includes a binding site MS2. When taken up into a cell, the RTase can be recruited by the pegRNA, through the MS2-MCP binding, and come in contact with the nickase.

An example co-transfection system is illustrated in FIG. 38B, and the testing results are shown in FIG. 38C, at the EMX1 site.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A dual guide RNA system, comprising:
a target single guide RNA comprising a first spacer having sequence complementarity to a target nucleic acid sequence proximate to a first protospacer adjacent motif (PAM) site,
a helper single guide RNA comprising a second spacer having sequence complementarity to a second nucleic acid sequence proximate to a second PAM site, wherein said second spacer is 8-15 bases in length,
a clustered regularly interspaced short palindromic repeats (CRISPR)-associated (Cas) protein, and
a nucleobase deaminase,
wherein the second PAM site is from 10 to 150 bases from the first PAM site.

2. The dual guide RNA system of claim 1, wherein the second PAM site is from 34 to 91 bases from the first PAM site.

3. The dual guide RNA system of claim 2, wherein the second PAM site is upstream to the first PAM site.

4. The dual guide RNA system of claim 1, wherein the second spacer is 9-12 bases in length.

5. A method for conducting genetic editing in a cell at a target nucleic acid sequence, comprising introducing to the cell:
   a target single guide RNA comprising a first spacer having sequence complementarity to the target nucleic acid sequence proximate to a first protospacer adjacent motif (PAM) site,
   a helper single guide RNA comprising a second spacer having sequence complementarity to a second nucleic acid sequence proximate to a second PAM site, wherein said second spacer is 8-15 bases in length,
   a clustered regularly interspaced short palindromic repeats (CRISPR)-associated (Cas) protein, and
   a nucleobase deaminase,
wherein the second PAM site is from 10 to 150 bases from the first PAM site on the target nucleic acid sequence.

6. The method of claim 5, wherein the second PAM site is from 34 to 91 bases from the first PAM site.

7. The method of claim 6, wherein the second PAM site is upstream to the first PAM site.

8. The method of claim 5, wherein the second spacer is 9-12 bases in length.

9. The method of claim 5, wherein the Cas protein and the nucleobase deaminase are introduced to the cell with one or more encoding polynucleotides.

10. The method of claim 5, wherein the target single guide RNA and the helper single guide RNA each is introduced to the cell as an RNA molecule or with encoding DNA.

11. The method of claim 5, wherein the nucleobase deaminase is fused to an inhibitory domain of the nucleobase deaminase or a second nucleobase deaminase through a protease cleavage site, and the method further comprises introducing to the cell a protease capable of cleaving the cleavage site.

12. The method of claim 5, wherein the cell is in vivo.

13. The method of claim 12, wherein the cell is in a human subject.

* * * * *

```
                              SEQUENCE LISTING

Sequence total quantity: 283
SEQ ID NO: 1              moltype = AA  length = 223
FEATURE                   Location/Qualifiers
REGION                    1..223
                          note = Synthetic
source                    1..223
                          mol_type = protein
                          organism = synthetic construct
SEQUENCE: 1
MSSSTLSNIC LTKGLPETRF WVEGRRMDPL SEEEFYSQFY NQRVKHLCYY HRMKPYLCYQ   60
LEQFNGQAPL KGCLLSEKGK QHAEILFLDK IRSMELSQVT ITCYLTWSPC PNCAWQLAAF  120
KRDRPDLILH IYTSRLYFHW KRPFQKGLCS LWQSGILVDV MDLPQFTDCW TNFVNPKRPF  180
WPWKGLEIIS RRTQRRLRRI KESWGLQDLV NDFGNLQLGP PMS                   223

SEQ ID NO: 2              moltype = AA  length = 166
FEATURE                   Location/Qualifiers
REGION                    1..166
                          note = Synthetic
source                    1..166
                          mol_type = protein
                          organism = synthetic construct
SEQUENCE: 2
MNPQIRNPME RMYRDTFYDN FENEPILYGR SYTWLCYEVK IKRGRSNLLW DTGVFRGQVY   60
FKPQYHAEMC FLSWFCGNQL PAYKCFQITW FVSWTPCPDC VAKLAEFLSE HPNVTLTISA  120
ARLYYYWERD YRRALCRLSQ AGARVKIMDY EEFAYCWENF VYNEGQ                 166

SEQ ID NO: 3              moltype = AA  length = 119
FEATURE                   Location/Qualifiers
REGION                    1..119
                          note = Synthetic
source                    1..119
                          mol_type = protein
                          organism = synthetic construct
SEQUENCE: 3
MGESLFKGPR DYNPISSTIC HLTNESDGHT TSLYGIGFGP FIITNKHLFR RNNGTLLVQS   60
LHGVFKVKNT TTLQQHLIDG RDMIIIRMPK DFPPFPQKLK FREPQREERI CLVTTNFQT   119

SEQ ID NO: 4              moltype = AA  length = 116
FEATURE                   Location/Qualifiers
REGION                    1..116
                          note = Synthetic
source                    1..116
                          mol_type = protein
                          organism = synthetic construct
SEQUENCE: 4
MKSMSSMVSD TSCTFPSSDG IFWKHWIQTK DGQCGSPLVS TRDGFIVGIH SASNFTNTNN   60
YFTSVPKNFM ELLTNQEAQQ WVSGWRLNAD SVLWGGHKVF MVKPEEPFQP VKEATQ      116

SEQ ID NO: 5              moltype = AA  length = 7
FEATURE                   Location/Qualifiers
REGION                    1..7
                          note = Synthetic
source                    1..7
                          mol_type = protein
                          organism = synthetic construct
SEQUENCE: 5
ENLYFQS                                                              7
```

```
SEQ ID NO: 6              moltype = AA   length = 246
FEATURE                   Location/Qualifiers
REGION                    1..246
                          note = Synthetic
source                    1..246
                          mol_type = protein
                          organism = synthetic construct
SEQUENCE: 6
MASSNSMFRG LRDYNPISNN ICHLTNVSDG ASNSLYGVGF GPLILTNRHL FERNNGELVI    60
KSRHGEFVIK NTTQLHLLPI PDRDLLLIRL PKDVPPFPQK LGFRQPEKGE RICMVGSNFQ   120
TKSITSIVSE TSTIMPVENS QFWKHWISTK DGQCGSPMVS TKDGKILGLH SLANFQNSIN   180
YFAAFPDDFA EKYLHTIEAH EWVKHWKYNT SAISWGSLNI QASQPSGLFK VSKLISDLDS   240
TAVYAQ                                                              246

SEQ ID NO: 7              moltype = AA   length = 7
FEATURE                   Location/Qualifiers
REGION                    1..7
                          note = Synthetic
source                    1..7
                          mol_type = protein
                          organism = synthetic construct
SEQUENCE: 7
GGCSHQS                                                               7

SEQ ID NO: 8              moltype = AA   length = 246
FEATURE                   Location/Qualifiers
REGION                    1..246
                          note = Synthetic
source                    1..246
                          mol_type = protein
                          organism = synthetic construct
SEQUENCE: 8
MASSKSLFRG LRDYNPIASS ICQLNNSSGA RQSEMFGLGF GGLIVTNQHL FKRNDGELTI    60
RSHHGEFVVK DTKTLKLLPC KGRDIVIIRL PKDFPPFPRR LQFRTPTTED RVCLIGSNFQ   120
TKSISSTMSE TSATYPVDNS HFWKHWISTK DGHCGLPIVS TRDGSILGLH SLANSNTNTQN  180
FYAAFPDNFE TTYLSNQDND NWIKQWRYNP DEVCWGSLQL KRDIPQSPFT ICKLLTDLDG   240
EFVYTQ                                                              246

SEQ ID NO: 9              moltype = AA   length = 8
FEATURE                   Location/Qualifiers
REGION                    1..8
                          note = Synthetic
source                    1..8
                          mol_type = protein
                          organism = synthetic construct
SEQUENCE: 9
QVVVHQSK                                                              8

SEQ ID NO: 10             moltype = AA   length = 247
FEATURE                   Location/Qualifiers
REGION                    1..247
                          note = Synthetic
source                    1..247
                          mol_type = protein
                          organism = synthetic construct
SEQUENCE: 10
MASAKSLMRG LRDFNPIAQT VCRLKVSVEY GASEMYGFGF GAYIVANHHL FRSYNGSMEV    60
QSMHGTFRVK NLHSLSVLPI KGRDIILIKM PKDFPVFPQK LHFRAPTQNE RICLVGTNFQ   120
EKYASSIITE TSTTYNIPGS TFWKHWIETD NGHCGLPVVS TADGCIVGIH SLANNAHTTN   180
YYSAFPDEDFE SKYLRTNEHN EWVKSWVYNP DTVLWGPLKL KDSTPKGLFK TTKLVQDLID  240
HDVVEQ                                                              247

SEQ ID NO: 11             moltype = AA   length = 8
FEATURE                   Location/Qualifiers
REGION                    1..8
                          note = Synthetic
source                    1..8
                          mol_type = protein
                          organism = synthetic construct
SEQUENCE: 11
YDVRHQSR                                                              8

SEQ ID NO: 12             moltype = AA   length = 239
FEATURE                   Location/Qualifiers
REGION                    1..239
                          note = Synthetic
```

```
source                  1..239
                        mol_type = protein
                        organism = synthetic construct
SEQUENCE: 12
MASDMYIERA GDITWEKDAE VTGNSPRLDV ALDESGDFSL VEEDGPPMRE GGGGSGGGGS    60
GALWDVPAPK EVKKGETTDG VYRVMTRRLL GSTQVGVGVM QEGVFHTMWH VTKGAALRSG   120
EGRLDPYWGD VKQDLVSYCG PWKLDAAWDG LSEVQLLAVP PGERARNIQT LPGIFKTKDG   180
DIGAVALDYP AGTSGSPILD KCGRVIGLYG NGVVIKNGSY VSAITQGKRE EETPVECFE    239

SEQ ID NO: 13           moltype = AA   length = 8
FEATURE                 Location/Qualifiers
REGION                  1..8
                        note = Synthetic
source                  1..8
                        mol_type = protein
                        organism = synthetic construct
SEQUENCE: 13
KERKRRGA                                                              8

SEQ ID NO: 14           moltype = AA   length = 243
FEATURE                 Location/Qualifiers
REGION                  1..243
                        note = Synthetic
source                  1..243
                        mol_type = protein
                        organism = synthetic construct
SEQUENCE: 14
MASSTDMWIE RTADISWESD AEITGSSERV DVRLDDDGNF QLMNDPGAPW KGGGGSGGGG    60
GVLWDTPSPK EYKKGDTTTG VYRIMTRGLL GSYQAGAGVM VEGVFHTLWH TTKGAALMSG   120
EGRLDPYWGS VKEDRLCYGG PWKLQHKWNG QDEVQMIVVE PGKNVKNVQT KPGVFKTPEG   180
EIGAVTLDFP TGTSGSPIVD KNGDVIGLYG NGVIMPNGSY ISAIVQGERM DEPIPAGFEP   240
EML                                                                 243

SEQ ID NO: 15           moltype = AA   length = 8
FEATURE                 Location/Qualifiers
REGION                  1..8
                        note = Synthetic
source                  1..8
                        mol_type = protein
                        organism = synthetic construct
SEQUENCE: 15
KQKKRGGK                                                              8

SEQ ID NO: 16           moltype = RNA  length = 19
FEATURE                 Location/Qualifiers
misc_feature            1..19
                        note = Synthetic
source                  1..19
                        mol_type = other RNA
                        organism = synthetic construct
SEQUENCE: 16
acatgaggat cacccatgt                                                 19

SEQ ID NO: 17           moltype = RNA  length = 136
FEATURE                 Location/Qualifiers
misc_feature            1..136
                        note = Synthetic
source                  1..136
                        mol_type = other RNA
                        organism = synthetic construct
SEQUENCE: 17
gtttgagagc taggccaaca tgaggatcac ccatgtctgc agggcctagc aagttcaaat    60
aaggctagtc cgttatcaac ttggccaaca tgaggatcac ccatgtctgc agggccaagt   120
ggcaccgagt cggtgc                                                   136

SEQ ID NO: 18           moltype = RNA  length = 25
FEATURE                 Location/Qualifiers
misc_feature            1..25
                        note = Synthetic
source                  1..25
                        mol_type = other RNA
                        organism = synthetic construct
SEQUENCE: 18
ggagcagacg atatggcgtc gctcc                                          25

SEQ ID NO: 19           moltype = RNA  length = 122
FEATURE                 Location/Qualifiers
misc_feature            1..122
                        note = Synthetic
```

```
source                     1..122
                           mol_type = other RNA
                           organism = synthetic construct
SEQUENCE: 19
gtttgagagc taccggagca gacgatatgg cgtcgctccg gtagcaagtt caaataaggc  60
tagtccgtta tcaacttgga gcagacgata tggcgtcgct ccaagtggca ccgagtcggt 120
gc                                                                122

SEQ ID NO: 20              moltype = RNA  length = 15
FEATURE                    Location/Qualifiers
misc_feature               1..15
                           note = Synthetic
source                     1..15
                           mol_type = other RNA
                           organism = synthetic construct
SEQUENCE: 20
gccctgaaga agggc                                                   15

SEQ ID NO: 21              moltype = RNA  length = 106
FEATURE                    Location/Qualifiers
misc_feature               1..106
                           note = Synthetic
source                     1..106
                           mol_type = other RNA
                           organism = synthetic construct
SEQUENCE: 21
gtttgagagc tagggccctg aagaagggcc ctagcaagtt caaataaggc tagtccgtta  60
tcaacttggg ccctgaagaa gggcccaagt ggcaccgagt cggtgc                106

SEQ ID NO: 22              moltype = AA  length = 117
FEATURE                    Location/Qualifiers
REGION                     1..117
                           note = Synthetic
source                     1..117
                           mol_type = protein
                           organism = synthetic construct
SEQUENCE: 22
MASNFTQFVL VDNGGTGDVT VAPSNFANGI AEWISSNSRS QAYKVTCSVR QSSAQNRKYT   60
IKVEVPKGAW RSYLNMELTI PIFATNSDCE LIVKAMQGLL KDGNPIPSAI AANSGIY     117

SEQ ID NO: 23              moltype = AA  length = 123
FEATURE                    Location/Qualifiers
REGION                     1..123
                           note = Synthetic
source                     1..123
                           mol_type = protein
                           organism = synthetic construct
SEQUENCE: 23
MGSKTIVLSV GEATRTLTEI QSTADRQIFE EKVGPLVGRL RLTASLRQNG AKTAYRVNLK   60
LDQADVVDSG LPKVRYTQVW SHDVTIVANS TEASRKSLYD LTKSLVATSQ VEDLVVNLVP  120
LGR                                                                123

SEQ ID NO: 24              moltype = AA  length = 23
FEATURE                    Location/Qualifiers
REGION                     1..23
                           note = Synthetic
source                     1..23
                           mol_type = protein
                           organism = synthetic construct
SEQUENCE: 24
MGNARTRRRE RRAEKQAQWK AAN                                          23

SEQ ID NO: 25              moltype = AA  length = 83
FEATURE                    Location/Qualifiers
REGION                     1..83
                           note = Synthetic
source                     1..83
                           mol_type = protein
                           organism = synthetic construct
SEQUENCE: 25
TNLSDIIEKE TGKQLVIQES ILMLPEEVEE VIGNKPESDI LVHTAYDEST DENVMLLTSD   60
APEYKPWALV IQDSNGENKI KML                                          83

SEQ ID NO: 26              moltype = AA  length = 22
FEATURE                    Location/Qualifiers
REGION                     1..22
                           note = Synthetic
```

```
                            -continued source                  1..22
                        mol_type = protein
                        organism = synthetic construct
SEQUENCE: 26
GSGATNFSLL KQAGDVEENP GP                                      22

SEQ ID NO: 27           moltype = AA  length = 21
FEATURE                 Location/Qualifiers
REGION                  1..21
                        note = Synthetic
source                  1..21
                        mol_type = protein
                        organism = synthetic construct
SEQUENCE: 27
GSGEGRGSLL TCGDVEENPG P                                       21

SEQ ID NO: 28           moltype = AA  length = 23
FEATURE                 Location/Qualifiers
REGION                  1..23
                        note = Synthetic
source                  1..23
                        mol_type = protein
                        organism = synthetic construct
SEQUENCE: 28
GSGQCTNYAL LKLAGDVESN PGP                                     23

SEQ ID NO: 29           moltype = RNA  length = 76
FEATURE                 Location/Qualifiers
misc_feature            1..76
                        note = Synthetic
source                  1..76
                        mol_type = other RNA
                        organism = synthetic construct
SEQUENCE: 29
gttttagagc tagaaatagc aagttaaaat aaggctagtc cgttatcaac ttgaaaaagt   60
ggcaccgagt cggtgc                                                  76

SEQ ID NO: 30           moltype = RNA  length = 76
FEATURE                 Location/Qualifiers
misc_feature            1..76
                        note = Synthetic
source                  1..76
                        mol_type = other RNA
                        organism = synthetic construct
SEQUENCE: 30
gttttagagc tagaaatagc aagttaaaat aaggcatgtc cgttatcaac ttgaaaaagt   60
ggcaccgatt cggtgc                                                  76

SEQ ID NO: 31           moltype = RNA  length = 70
FEATURE                 Location/Qualifiers
misc_feature            1..70
                        note = Synthetic
misc_feature            5
                        note = n is a, c, g, or u
misc_feature            13
                        note = n is a, c, g, or u
misc_feature            23
                        note = n is a, c, g, or u
misc_feature            33..34
                        note = n is a, c, g, or u
misc_feature            50
                        note = n is a, c, g, or u
misc_feature            63
                        note = n is a, c, g, or u
source                  1..70
                        mol_type = other RNA
                        organism = synthetic construct
SEQUENCE: 31
gtttnagagc tantagcaag ttnaaataag gcnngtccgt tatcaacttn aagtggcacc   60
gantcggtgc                                                         70

SEQ ID NO: 32           moltype = RNA  length = 70
FEATURE                 Location/Qualifiers
misc_feature            1..70
                        note = Synthetic
misc_feature            5
                        note = n is a, c, g, or u
misc_feature            13
                        note = n is a, c, g, or u
```

```
misc_feature          23
                      note = n is a, c, g, or u
misc_feature          33..34
                      note = n is a, c, g, or u
misc_feature          50
                      note = n is a, c, g, or u
misc_feature          63
                      note = n is a, c, g, or u
source                1..70
                      mol_type = other RNA
                      organism = synthetic construct
SEQUENCE: 32
gtttnagagc tantagcaag ttnaaataag gcnngtccgt tatcgacttn aagtcgcacc    60
gantcggtgc                                                          70

SEQ ID NO: 33         moltype = RNA   length = 70
FEATURE               Location/Qualifiers
misc_feature          1..70
                      note = Synthetic
misc_feature          5
                      note = n is a, c, g, or u
misc_feature          13
                      note = n is a, c, g, or u
misc_feature          23
                      note = n is a, c, g, or u
misc_feature          33..34
                      note = n is a, c, g, or u
misc_feature          50
                      note = n is a, c, g, or u
misc_feature          63
                      note = n is a, c, g, or u
source                1..70
                      mol_type = other RNA
                      organism = synthetic construct
SEQUENCE: 33
gtttnagagc tantagcaag ttnaaataag gcnngtccgt tatccacttn aagtggcacc    60
gantcggtgc                                                          70

SEQ ID NO: 34         moltype = RNA   length = 70
FEATURE               Location/Qualifiers
misc_feature          1..70
                      note = Synthetic
misc_feature          5
                      note = n is a, c, g, or u
misc_feature          13
                      note = n is a, c, g, or u
misc_feature          23
                      note = n is a, c, g, or u
misc_feature          33..34
                      note = n is a, c, g, or u
misc_feature          50
                      note = n is a, c, g, or u
misc_feature          63
                      note = n is a, c, g, or u
source                1..70
                      mol_type = other RNA
                      organism = synthetic construct
SEQUENCE: 34
gtttnagagc tantagcaag ttnaaataag gcnngtccgt tatcaacttn aagttgcacc    60
gantcggtgc                                                          70

SEQ ID NO: 35         moltype = RNA   length = 70
FEATURE               Location/Qualifiers
misc_feature          1..70
                      note = Synthetic
misc_feature          5
                      note = n is a, c, g, or u
misc_feature          13
                      note = n is a, c, g, or u
misc_feature          23
                      note = n is a, c, g, or u
misc_feature          33..34
                      note = n is a, c, g, or u
misc_feature          50
                      note = n is a, c, g, or u
misc_feature          63
                      note = n is a, c, g, or u
```

```
source                     1..70
                           mol_type = other RNA
                           organism = synthetic construct
SEQUENCE: 35
gtttnagagc tantagcaag ttnaaataag gcnngtccgt tatctacttn aagtagcacc    60
gantcggtgc                                                          70

SEQ ID NO: 36              moltype = RNA   length = 76
FEATURE                    Location/Qualifiers
misc_feature               1..76
                           note = Synthetic
source                     1..76
                           mol_type = other RNA
                           organism = synthetic construct
SEQUENCE: 36
gtttagagc tagaaatagc aagttaaaat aaggcatgtc cgttatcgac ttgaaaaagt     60
cgcaccgatt cggtgc                                                   76

SEQ ID NO: 37              moltype = RNA   length = 76
FEATURE                    Location/Qualifiers
misc_feature               1..76
                           note = Synthetic
source                     1..76
                           mol_type = other RNA
                           organism = synthetic construct
SEQUENCE: 37
gttttagagc tagaaatagc aagttaaaat aaggcatgtc cgttatccac ttgaaaaagt    60
ggcaccgatt cggtgc                                                   76

SEQ ID NO: 38              moltype = RNA   length = 76
FEATURE                    Location/Qualifiers
misc_feature               1..76
                           note = Synthetic
source                     1..76
                           mol_type = other RNA
                           organism = synthetic construct
SEQUENCE: 38
gtttagagc tagaaatagc aagttaaaat aaggcatgtc cgttatcaac ttgaaaaagt     60
tgcaccgatt cggtgc                                                   76

SEQ ID NO: 39              moltype = RNA   length = 76
FEATURE                    Location/Qualifiers
misc_feature               1..76
                           note = Synthetic
source                     1..76
                           mol_type = other RNA
                           organism = synthetic construct
SEQUENCE: 39
gtttagagc tagaaatagc aagttaaaat aaggcatgtc cgttatctac ttgaaaaagt     60
agcaccgatt cggtgc                                                   76

SEQ ID NO: 40              moltype = RNA   length = 76
FEATURE                    Location/Qualifiers
misc_feature               1..76
                           note = Synthetic
source                     1..76
                           mol_type = other RNA
                           organism = synthetic construct
SEQUENCE: 40
gtttagagc tagaaatagc aagttaaaat aaggctagtc cgttatcgac ttgaaaaagt     60
cgcaccgagt cggtgc                                                   76

SEQ ID NO: 41              moltype = RNA   length = 76
FEATURE                    Location/Qualifiers
misc_feature               1..76
                           note = Synthetic
source                     1..76
                           mol_type = other RNA
                           organism = synthetic construct
SEQUENCE: 41
gtttagagc tagaaatagc aagttaaaat aaggctagtc cgttatccac ttgaaaaagt     60
ggcaccgagt cggtgc                                                   76

SEQ ID NO: 42              moltype = RNA   length = 76
FEATURE                    Location/Qualifiers
misc_feature               1..76
                           note = Synthetic
```

```
source                   1..76
                         mol_type = other RNA
                         organism = synthetic construct
SEQUENCE: 42
gttttagagc tagaaatagc aagttaaaat aaggctagtc cgttatcaac ttgaaaaagt    60
tgcaccgagt cggtgc                                                    76

SEQ ID NO: 43            moltype = RNA   length = 76
FEATURE                  Location/Qualifiers
misc_feature             1..76
                         note = Synthetic
source                   1..76
                         mol_type = other RNA
                         organism = synthetic construct
SEQUENCE: 43
gttttagagc tagaaatagc aagttaaaat aaggctagtc cgttatctac ttgaaaaagt    60
agcaccgagt cggtgc                                                    76

SEQ ID NO: 44            moltype = AA   length = 2080
FEATURE                  Location/Qualifiers
REGION                   1..2080
                         note = Synthetic
source                   1..2080
                         mol_type = protein
                         organism = synthetic construct
SEQUENCE: 44
MDKKYSIGLD IGTNSVGWAV ITDEYKVPSK KFKVLGNTDR HSIKKNLIGA LLFDSGETAE     60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDA    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI RPKRNSDKLI ARKKDWDPKK YGGFVSPTVA   1140
YSVLVVAKVE KGKSKKLKSV KELLGITIME RSSFEKNPID FLEAKGYKEV KKDLIIKLPK   1200
YSLFELENGR KRMLASARFL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PRAFKYFDTT IDRKVYRSTK EVLDATLIHQ SITGLYETRI DLSQLGGDGT SGGSSGGSSG   1380
SETPGTSESA TPESSGGSSG GSSTLNIEDE YRLHETSKEP DVSLGSTWLS DFPQAWAETG   1440
GMGLAVRQAP LIIPLKATST PVSIKQYPMS QEARLGIKPH IQRLLDQGIL VPCQSPWNTP   1500
LLPVKKPGTN DYRPVQDLRE VNKRVEDIHP TVPNPYNLLS GLPPSHQWYT VLDLKDAFFC   1560
LRLHPTSQPL FAFEWRDPEM GISGQLTWTR LPQGFKNSPT LFNEALHRDL ADFRIQHPDL   1620
ILLQYVDDLL LAATSELDCQ QGTRALLQTL GNLGYRASAK KAQICQKQVK YLGYLLKEGQ   1680
RWLTEARKET VMGQPTPKTP RQLREFLGKA GFCRLFIPGF AEMAAPLYPL TKPGTLFNWG   1740
PDQQKAYQEI KQALLTAPAL GLPDLTKPFE LFVDEKQGYA KGVLTQKLGP WRRPVAYLSK   1800
KLDPVAAGWP PCLRMVAAIA VLTKDAGKLT MGQPLVILAP HAVEALVKQP PDRWLSNARM   1860
THYQALLLDT DRVQFGPVVA LNPATLLPLP EEGLQHNCLD ILAEAHGTRP DLTDQPLPDA   1920
DHTWYTDGSS LLQEGQRKAG AAVTTETEVI WAKALPAGTS AQRAELIALT QALKMAEGKK   1980
LNVYTDSRYA FATAHIHGEI YRRRGWLTSE GKEIKNKDEI LALLKALFLP KRLSIIHCPG   2040
HQKGHSAEAR GNRMADQAAR KAAITETPDT STLLIENSSP                        2080

SEQ ID NO: 45            moltype = AA   length = 2080
FEATURE                  Location/Qualifiers
REGION                   1..2080
                         note = Synthetic
source                   1..2080
                         mol_type = protein
                         organism = synthetic construct
SEQUENCE: 45
MDKKYSIGLD IGTNSVGWAV ITDEYKVPSK KFKVLGNTDR HSIKKNLIGA LLFDSGETAE     60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DTKLQLSKDT YDDDLDNLLA QIGDQYADLF LAAKNLSDAI    300
LLSDILRVNT EITKAPLSAS MIKLYDEHHQ DLTLLKALVR QQLPEKYKEI FFDQSKNGYA    360
GYIDGGASQE EFYKFIKPIL EKMDGTEELL VKLNREDLLR KQRTFDNGII PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
```

```
SGDQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFIQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDA    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGVL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDGT SGGSSGGSSG   1380
SETPGTSESA TPESSGGSSG GSSTLNIEDE YRLHETSKEP DVSLGSTWLS DFPQAWAETG   1440
GMGLAVRQAP LIIPLKATST PVSIKQYPMS QEARLGIKPH IQRLLDQGIL VPCQSPWNTP   1500
LLPVKKPGTN DYRPVQDLRE VNKRVEDIHP TVPNPYNLLS GLPPSHQWYT VLDLKDAFFC   1560
LRLHPTSQPL FAFEWRDPEM GISGQLTWTR LPQGFKNSPT LFNEALHRDL ADFRIQHPDL   1620
ILLQYVDDLL LAATSELDCQ QGTRALLQTL GNLGYRASAK KAQICQKQVK YLGYLLKEGQ   1680
RWLTEARKET VMGQPTPKTP RQLREFLGKA GFCRLFIPGF AEMAAPLYPL TKPGTLFNWG   1740
PDQQKAYQEI KQALLTAPAL GLPDLTKPFE LFVDEKQGYA KGVLTQKLGP WRRPVAYLSK   1800
KLDPVAAGWP PCLRMVAAIA VLTKDAGKLT MGQPLVILAP HAVEALVKQP PDRWLSNARM   1860
THYQALLLDT DRVQFGPVVA LNPATLLPLP EEGLQHNCLD ILAEAHGTRP DLTDQPLPDA   1920
DHTWYTDGSS LLQEGQRKAG AAVTTETEVI WAKALPAGTS AQRAELIALT QALKMAEGKK   1980
LNVYTDSRYA FATAHIHGEI YRRRGWLTSE GKEIKNKDEI LALLKALFLP KRLSIIHCPG   2040
HQKGHSAEAR GNRMADQAAR KAAITETPDT STLLIENSSP                         2080

SEQ ID NO: 46           moltype = AA   length = 1368
FEATURE                 Location/Qualifiers
REGION                  1..1368
                        note = Synthetic
source                  1..1368
                        mol_type = protein
                        organism = synthetic construct
SEQUENCE: 46
MDKKYSIGLD IGTNSVGWAV ITDEYKVPSK KFKVLGNTDR HSIKKNLIGA LLFDSGETAE     60
ATRLKRTARR RYTARRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI RPKRNSDKLI ARKKDWDPKK YGGFVSPTVA  1140
YSVLVVAKVE KGKSKKLKSV KELLGITIME RSSFEKNPID FLEAKGYKEV KKDLIIKLPK  1200
YSLFELENGR KRMLASARFL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PRAFKYFDTT IDRKVYRSTK EVLDATLIHQ SITGLYETRI DLSQLGGD                1368

SEQ ID NO: 47           moltype = AA   length = 1368
FEATURE                 Location/Qualifiers
REGION                  1..1368
                        note = Synthetic
source                  1..1368
                        mol_type = protein
                        organism = synthetic construct
SEQUENCE: 47
MDKKYSIGLD IGTNSVGWAV ITDEYKVPSK KFKVLGNTDR HSIKKNLIGA LLFDSGETAE     60
ATRLKRTARR RYTARRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DTKLQLSKDT YDDDLDNLLA QIGDQYADLF LAAKNLSDAI   300
LLSDILRVNT EITKAPLSAS MIKLYDEHHQ DLTLLKALVR QQLPEKYKEI FFDQSKNGYA   360
GYIDGGASQE EFYKFIKPIL EKMDGTEELL VKLNREDLLR KQRTFDNGII PHQIHLGELH   420
AILRRQEDFY PFLKDNREKI EKILTFRIPY YVGPLARGNS RFAWMTRKSE ETITPWNFEK   480
VVDKGASAQS FIERMTNFDK NLPNEKVLPK HSLLYEYFTV YNELTKVKYV TEGMRKPAFL   540
SGDQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFIQLIHDD SLTFKEDIQK AQVSGQGDSL   720
```

```
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGVL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGD               1368

SEQ ID NO: 48          moltype = AA   length = 74
FEATURE                Location/Qualifiers
REGION                 1..74
                       note = Synthetic
source                 1..74
                       mol_type = protein
                       organism = synthetic construct
SEQUENCE: 48
SEKGKQHAEI LFLDKIRSME LSQVTITCYL TWSPCPNCAW QLAAFKRDRP DLILHIYTSR    60
LYFHWKRPFQ KGLC                                                     74

SEQ ID NO: 49          moltype = AA   length = 74
FEATURE                Location/Qualifiers
REGION                 1..74
                       note = Synthetic
source                 1..74
                       mol_type = protein
                       organism = synthetic construct
SEQUENCE: 49
SEKGKQHAEI LFLDKIRSME LSQVTITCYL TWSPCPNCAW QLAAFKRDRP DLIPHIYTSR    60
LYFHWKRPFQ KGLC                                                     74

SEQ ID NO: 50          moltype = AA   length = 74
FEATURE                Location/Qualifiers
REGION                 1..74
                       note = Synthetic
source                 1..74
                       mol_type = protein
                       organism = synthetic construct
SEQUENCE: 50
SEKGKQHAEI LFLDKIRSME LSQVTITCYL TWSPCPNCAW RLAAFKRDRP DLILHIYTSR    60
LYFHWKRPFQ KGLC                                                     74

SEQ ID NO: 51          moltype = AA   length = 74
FEATURE                Location/Qualifiers
REGION                 1..74
                       note = Synthetic
source                 1..74
                       mol_type = protein
                       organism = synthetic construct
SEQUENCE: 51
SEKGKQHAEI LFLNKIRSME LSQVTITCYL TWSPCPNCAW QLAAFKKDRP DLILHIYTSR    60
LYFHWKRPFQ KGLC                                                     74

SEQ ID NO: 52          moltype = AA   length = 74
FEATURE                Location/Qualifiers
REGION                 1..74
                       note = Synthetic
source                 1..74
                       mol_type = protein
                       organism = synthetic construct
SEQUENCE: 52
SKKGKQHAEI LFLDKIRSME LSQVTITCYL TWSPCPNCAW QLAAFKRDHP DLILHIYTSR    60
LYFHWKRPFQ KGLC                                                     74

SEQ ID NO: 53          moltype = AA   length = 74
FEATURE                Location/Qualifiers
REGION                 1..74
                       note = Synthetic
source                 1..74
                       mol_type = protein
                       organism = synthetic construct
SEQUENCE: 53
SKKGKQHAEI LFLEKIRSME LSQMRITCYL TWSPCPNCAW QLAAFQKDRP DLILHIYTSR    60
LYFHWRRIFQ KGLC                                                     74
```

-continued

```
SEQ ID NO: 54          moltype = AA   length = 74
FEATURE                Location/Qualifiers
REGION                 1..74
                       note = Synthetic
source                 1..74
                       mol_type = protein
                       organism = synthetic construct
SEQUENCE: 54
SKKGKQHAEI LFLEKIRSME LSQMRITCYL TWSPCPNCAW QLAAFQKDRP DLILHIYTSR   60
LYFHWRRIFQ KGLC                                                    74

SEQ ID NO: 55          moltype = AA   length = 74
FEATURE                Location/Qualifiers
REGION                 1..74
                       note = Synthetic
source                 1..74
                       mol_type = protein
                       organism = synthetic construct
SEQUENCE: 55
SKKGKQHAEI LFLDKIRSME LSQVRITCYL TWSPCPNCAW QLETFKKDRP DLILHIYTSR   60
LYFHWKRAFQ EGLC                                                    74

SEQ ID NO: 56          moltype = AA   length = 75
FEATURE                Location/Qualifiers
REGION                 1..75
                       note = Synthetic
source                 1..75
                       mol_type = protein
                       organism = synthetic construct
SEQUENCE: 56
SKKGKPHAEI LFLDKMWSME ELSQVRITCY LTWSPCPNCA RQLAAFKKDH PGLILRIYTS   60
RLYFYWRRKF QKGLC                                                   75

SEQ ID NO: 57          moltype = AA   length = 73
FEATURE                Location/Qualifiers
REGION                 1..73
                       note = Synthetic
source                 1..73
                       mol_type = protein
                       organism = synthetic construct
SEQUENCE: 57
KKGEQHVEIL FLEKMRSMEL SQVRITCYLT WSPCPNCARQ LAAFKKDHPD LILRIYTSRL   60
YFYWRKKFQK GLC                                                     73

SEQ ID NO: 58          moltype = AA   length = 74
FEATURE                Location/Qualifiers
REGION                 1..74
                       note = Synthetic
source                 1..74
                       mol_type = protein
                       organism = synthetic construct
SEQUENCE: 58
SKKGRQHAEI LFLEKVRSMQ LSQVRITCYL TWSPCPNCAW QLAAFKMDHP DLILRIYASR   60
LYFHWRRAFQ KGLC                                                    74

SEQ ID NO: 59          moltype = AA   length = 73
FEATURE                Location/Qualifiers
REGION                 1..73
                       note = Synthetic
source                 1..73
                       mol_type = protein
                       organism = synthetic construct
SEQUENCE: 59
NKKGKHAEIL FIDEMRSLEL GQVQITCYLT WSPCPNCAQE LAAFKSDHPD LVLRIYTSRL   60
YFHWRRKYQE GLC                                                     73

SEQ ID NO: 60          moltype = AA   length = 73
FEATURE                Location/Qualifiers
REGION                 1..73
                       note = Synthetic
source                 1..73
                       mol_type = protein
                       organism = synthetic construct
SEQUENCE: 60
NKKGKHAEIL FIDEMRSLEL GQARITCYLT WSPCPNCAQK LAAFKKDHPD LVLRVYTSRL   60
YFHWRRKYQE GLC                                                     73
```

```
SEQ ID NO: 61              moltype = AA   length = 73
FEATURE                    Location/Qualifiers
REGION                     1..73
                           note = Synthetic
source                     1..73
                           mol_type = protein
                           organism = synthetic construct
SEQUENCE: 61
NKKDKHAEIL FIDKMRSLEL CQVRITCYLT WSPCPNCAQE LAAFKKDHPD LVLRIYTSRL   60
YFHWRRKYQE GLC                                                     73

SEQ ID NO: 62              moltype = AA   length = 73
FEATURE                    Location/Qualifiers
REGION                     1..73
                           note = Synthetic
source                     1..73
                           mol_type = protein
                           organism = synthetic construct
SEQUENCE: 62
NKKGKHAEIL FIDEMRSLKL SQERITCYLT WSPCPNCAQE LAAFKRDHPG LVLRIYASRL   60
YFHWRRKYQE GLC                                                     73

SEQ ID NO: 63              moltype = AA   length = 72
FEATURE                    Location/Qualifiers
REGION                     1..72
                           note = Synthetic
source                     1..72
                           mol_type = protein
                           organism = synthetic construct
SEQUENCE: 63
NKRAKHAEIL LIDMMRSMEL GQVQITCYIT WSPCPTCAQE LAAFKQDHPD LVLRIYASRL   60
YFHWKRKFQK GL                                                      72

SEQ ID NO: 64              moltype = AA   length = 73
FEATURE                    Location/Qualifiers
REGION                     1..73
                           note = Synthetic
source                     1..73
                           mol_type = protein
                           organism = synthetic construct
SEQUENCE: 64
NKKGRHAEIC LIDEMRSLGL GKAQITCYLT WSPCRKCAQE LATFKKDHPD LVLRVYASRL   60
YFHWSRKYQQ GLC                                                     73

SEQ ID NO: 65              moltype = AA   length = 75
FEATURE                    Location/Qualifiers
REGION                     1..75
                           note = Synthetic
source                     1..75
                           mol_type = protein
                           organism = synthetic construct
SEQUENCE: 65
NKKGHHAEIR FIERIRSMGL DPSQDYQITC YLTWSPCLDC AFKLAKLKKD FPRLTLRIFT   60
SRLYFHWIRK FQKGL                                                   75

SEQ ID NO: 66              moltype = AA   length = 72
FEATURE                    Location/Qualifiers
REGION                     1..72
                           note = Synthetic
source                     1..72
                           mol_type = protein
                           organism = synthetic construct
SEQUENCE: 66
NKKGKHAEAR FVDKMRSMQL DHALITCYLT WSPCLDCSQK LAALKRDHPG LTLRIFTSRL   60
YFHWVKKFQE GL                                                      72

SEQ ID NO: 67              moltype = AA   length = 76
FEATURE                    Location/Qualifiers
REGION                     1..76
                           note = Synthetic
source                     1..76
                           mol_type = protein
                           organism = synthetic construct
SEQUENCE: 67
SPQKGHHAES RFIKRISSMD LDRSRSYQIT CFLTWSPCPS CAQELASFKR AHPHLRFQIF   60
VSRLYFHWKR SYQAGL                                                  76
```

```
SEQ ID NO: 68            moltype = AA  length = 74
FEATURE                  Location/Qualifiers
REGION                   1..74
                         note = Synthetic
source                   1..74
                         mol_type = protein
                         organism = synthetic construct
SEQUENCE: 68
KKGYHAESRF IKRICSMDLG QDQSYQVTCF LTWSPCPHCA QELVSFKRAH PHLRLQIFTA   60
RLFFHWKRSY QEGL                                                    74

SEQ ID NO: 69            moltype = AA  length = 74
FEATURE                  Location/Qualifiers
REGION                   1..74
                         note = Synthetic
source                   1..74
                         mol_type = protein
                         organism = synthetic construct
SEQUENCE: 69
KKGQHAEIRF IERIHSMALD QARSYQITCF LTWSPCPFCA QELASFKSTH PRVHLQIFVS   60
RLYFHWKRSY QEGL                                                    74

SEQ ID NO: 70            moltype = AA  length = 75
FEATURE                  Location/Qualifiers
REGION                   1..75
                         note = Synthetic
source                   1..75
                         mol_type = protein
                         organism = synthetic construct
SEQUENCE: 70
NKKGHHAEIR FIKKIRSLDL DQSQNYEVTC YLTWSPCPDC AQELVALTRS HPHVRLRLFT   60
SRLYFHWFWS FQEGL                                                   75

SEQ ID NO: 71            moltype = AA  length = 72
FEATURE                  Location/Qualifiers
REGION                   1..72
                         note = Synthetic
source                   1..72
                         mol_type = protein
                         organism = synthetic construct
SEQUENCE: 71
NRHAEICFID EIESMGLDKT QCYEVTCYLT WSPCPSCAQK LAAFTKAQVH LNLRIFASRL   60
YYHWRSSYQK GL                                                      72

SEQ ID NO: 72            moltype = AA  length = 72
FEATURE                  Location/Qualifiers
REGION                   1..72
                         note = Synthetic
source                   1..72
                         mol_type = protein
                         organism = synthetic construct
SEQUENCE: 72
NRHAEICFID EIESMGLDKT QCYEVTCYLT WSPCPSCAQK LVAFAKAQDH LNLRIFASRL   60
YYHWRRRYKE GL                                                      72

SEQ ID NO: 73            moltype = AA  length = 70
FEATURE                  Location/Qualifiers
REGION                   1..70
                         note = Synthetic
source                   1..70
                         mol_type = protein
                         organism = synthetic construct
SEQUENCE: 73
HVEICFIDKI ASMELDKTQC YDVTCYLTWS PCPSCAQKLA AFAKAQDHLN LRIFASRLYY   60
HWRRSYQKGL                                                         70

SEQ ID NO: 74            moltype = AA  length = 75
FEATURE                  Location/Qualifiers
REGION                   1..75
                         note = Synthetic
source                   1..75
                         mol_type = protein
                         organism = synthetic construct
SEQUENCE: 74
NKKKCHAEIC FINEIKSMGL DETQCYQVTC YLTWSPCSSC AWELVDFIKA HDHLNLGIFA   60
SRLYYHWCKP QQKGL                                                   75
```

```
SEQ ID NO: 75          moltype = AA   length = 76
FEATURE                Location/Qualifiers
REGION                 1..76
                       note = Synthetic
source                 1..76
                       mol_type = protein
                       organism = synthetic construct
SEQUENCE: 75
ENKKKCHAEI CFINEIKSMG LDETQCYQVT CYLTWSPCSS CAWELVDFIK AHDHLNLGIF     60
ASRLYYHWCK PQQKGL                                                    76

SEQ ID NO: 76          moltype = AA   length = 75
FEATURE                Location/Qualifiers
REGION                 1..75
                       note = Synthetic
source                 1..75
                       mol_type = protein
                       organism = synthetic construct
SEQUENCE: 76
NKKKCHAEIC FINEIKSMGL DETQCYQVTC YLTWSPCSSC AWKLVDFIQA HDHLNLRIFA     60
SRLYYHWCKP QQEGL                                                     75

SEQ ID NO: 77          moltype = AA   length = 75
FEATURE                Location/Qualifiers
REGION                 1..75
                       note = Synthetic
source                 1..75
                       mol_type = protein
                       organism = synthetic construct
SEQUENCE: 77
NKKKRHAEIR FINKIKSMGL DETQCYQVTC YLTWSPCPSC AWELVDFIKA HDHLNLGIFA     60
SRLYYHWCRH QQEGL                                                     75

SEQ ID NO: 78          moltype = AA   length = 75
FEATURE                Location/Qualifiers
REGION                 1..75
                       note = Synthetic
source                 1..75
                       mol_type = protein
                       organism = synthetic construct
SEQUENCE: 78
NKKKDHAEIR FINKIKSMGL DETQCYQVTC YLTWSPCPSC AGELVDFIKA HRHLNLRIFA     60
SRLYYHWRPN YQEGL                                                     75

SEQ ID NO: 79          moltype = AA   length = 75
FEATURE                Location/Qualifiers
REGION                 1..75
                       note = Synthetic
source                 1..75
                       mol_type = protein
                       organism = synthetic construct
SEQUENCE: 79
NKKKEHAEIR FINKIKSMGL DETQCYQVTC YLTWSPCPSC AGKLVDFIKA HHHLNLRIFA     60
SRLYYHWRPN YQEGL                                                     75

SEQ ID NO: 80          moltype = AA   length = 75
FEATURE                Location/Qualifiers
REGION                 1..75
                       note = Synthetic
source                 1..75
                       mol_type = protein
                       organism = synthetic construct
SEQUENCE: 80
NKKKHHAEIH FINKIKSMGL DETQCYQVTC YLTWSPCPSC ARELVDFIKA HRHLNLRIFA     60
SRLYYHWRPH YQEGL                                                     75

SEQ ID NO: 81          moltype = AA   length = 75
FEATURE                Location/Qualifiers
REGION                 1..75
                       note = Synthetic
source                 1..75
                       mol_type = protein
                       organism = synthetic construct
SEQUENCE: 81
NKKQRHAEIR FIDKINSLDL NPSQSYKIIC YITWSPCPNC ANELVNFITR NNHLKLEIFA     60
SRLYFHWIKP FKMGL                                                     75
```

```
SEQ ID NO: 82           moltype = AA  length = 75
FEATURE                 Location/Qualifiers
REGION                  1..75
                        note = Synthetic
source                  1..75
                        mol_type = protein
                        organism = synthetic construct
SEQUENCE: 82
NKKQRHAEIR FIDKINSLDL NPSQSYKIIC YITWSPCPNC ASELVDFITR NDHLDLQIFA   60
SRLYFHWIKP FKRGL                                                   75

SEQ ID NO: 83           moltype = AA  length = 75
FEATURE                 Location/Qualifiers
REGION                  1..75
                        note = Synthetic
source                  1..75
                        mol_type = protein
                        organism = synthetic construct
SEQUENCE: 83
NKKQRHAEIR FIDKINSLNL DRRQSYKIIC YITWSPCPRC ASELVDFITG NDHLNLQIFA   60
SRLYFHWKKP FQRGL                                                   75

SEQ ID NO: 84           moltype = AA  length = 75
FEATURE                 Location/Qualifiers
REGION                  1..75
                        note = Synthetic
source                  1..75
                        mol_type = protein
                        organism = synthetic construct
SEQUENCE: 84
NKKKRHAEIR FIDKINSLNL DQNQCYRIIC YVTWSPCHNC AKELVDFISN RHHLSLQLFA   60
SRLYFHWVRC YQRGL                                                   75

SEQ ID NO: 85           moltype = AA  length = 75
FEATURE                 Location/Qualifiers
REGION                  1..75
                        note = Synthetic
source                  1..75
                        mol_type = protein
                        organism = synthetic construct
SEQUENCE: 85
NKKKRHAEIR FIDKIKSLGL DRVQSYEITC YITWSPCPTC ALELVAFTRD YPRLSLQIFA   60
SRLYFHWRRR SIQGL                                                   75

SEQ ID NO: 86           moltype = AA  length = 75
FEATURE                 Location/Qualifiers
REGION                  1..75
                        note = Synthetic
source                  1..75
                        mol_type = protein
                        organism = synthetic construct
SEQUENCE: 86
NKKKRHAEIR FIDKINSLGL DQDQSYEITC YVTWSPCATC ACKLIKFTRK FPNLSRIFV    60
SRLYYHWFRQ NQQGL                                                   75

SEQ ID NO: 87           moltype = AA  length = 74
FEATURE                 Location/Qualifiers
REGION                  1..74
                        note = Synthetic
source                  1..74
                        mol_type = protein
                        organism = synthetic construct
SEQUENCE: 87
KKKRHAEIRF IDSIRALQLD QSQRFEITCY LTWSPCPTCA KELAMFVQDH PHISLRLFAS   60
RLYFHWRWKY QEGL                                                    74

SEQ ID NO: 88           moltype = AA  length = 74
FEATURE                 Location/Qualifiers
REGION                  1..74
                        note = Synthetic
source                  1..74
                        mol_type = protein
                        organism = synthetic construct
SEQUENCE: 88
KKKRHAEIRF IDNIKALRLD TSQRFEITCY VTWSPCPTCA KELVAFVRDH RHISLRLFAS   60
RLYFHWLREN KKGL                                                    74
```

```
SEQ ID NO: 89            moltype = AA   length = 75
FEATURE                  Location/Qualifiers
REGION                   1..75
                         note = Synthetic
source                   1..75
                         mol_type = protein
                         organism = synthetic construct
SEQUENCE: 89
NKKKRHAEIR FIDKIRSLQR DSSQTFEITC YVTWSPCFTC AEELVAFVRD HPHVRLRLFA   60
SRLYFHWLRK YQEGL                                                    75

SEQ ID NO: 90            moltype = AA   length = 75
FEATURE                  Location/Qualifiers
REGION                   1..75
                         note = Synthetic
source                   1..75
                         mol_type = protein
                         organism = synthetic construct
SEQUENCE: 90
NKKKRHAEIC FIDKIKSLTR DTSQRFEIIC YITWSPCPFC AEELVAFVKD NPHLSLRIFA   60
SRLYVHWRWK YQQGL                                                    75

SEQ ID NO: 91            moltype = AA   length = 75
FEATURE                  Location/Qualifiers
REGION                   1..75
                         note = Synthetic
source                   1..75
                         mol_type = protein
                         organism = synthetic construct
SEQUENCE: 91
NKKKRHAEIC FIDKIKSLTR DTSQRFEIIC YITWSPCPFC AEELVAFVKD NPHLSLRIFA   60
SRLYVHWRWK YQQGL                                                    75

SEQ ID NO: 92            moltype = AA   length = 75
FEATURE                  Location/Qualifiers
REGION                   1..75
                         note = Synthetic
source                   1..75
                         mol_type = protein
                         organism = synthetic construct
SEQUENCE: 92
NKKHRHAEVR FIAKIRSMSL DLDQKHQLTC YLTWSPCPSC AQELVTFMAE SRHLNLQVFV   60
SRLYFHWQRD FQQGL                                                    75

SEQ ID NO: 93            moltype = AA   length = 110
FEATURE                  Location/Qualifiers
REGION                   1..110
                         note = Synthetic
source                   1..110
                         mol_type = protein
                         organism = synthetic construct
SEQUENCE: 93
GRSYNWLCYE VKIKRGRSNL LWNTGVFRGQ MYSQPEHHAE MCFLSWFCGN QLPAYKCFQI   60
TWFVSWTPCP DCVAKLAEFL AEYPNVTLTI STARLYYYWE RDYRRALCRL              110

SEQ ID NO: 94            moltype = AA   length = 110
FEATURE                  Location/Qualifiers
REGION                   1..110
                         note = Synthetic
source                   1..110
                         mol_type = protein
                         organism = synthetic construct
SEQUENCE: 94
GRSYTWLCYE VKIRRGHSNL LWDTGVFRGQ MYSQPEHHAE MYFLSWFCGN QLPAYKCFQI   60
TWFVSWTPCP DCVAKLAEFL AEHPNVTLTI SAARLYYYWE RDYRRALCRL              110

SEQ ID NO: 95            moltype = AA   length = 110
FEATURE                  Location/Qualifiers
REGION                   1..110
                         note = Synthetic
source                   1..110
                         mol_type = protein
                         organism = synthetic construct
SEQUENCE: 95
GRSYTWLCYE VKIRRGHSNL LWDTGVFRGQ MYSQPEHHAE MCFLSWFCGN QLSAYKCFQI   60
TWFVSWTPCP DCVAKLAKFL AEHPNVTLTI SAARLYYYWE RDYRRALCRL              110
```

```
SEQ ID NO: 96              moltype = AA   length = 98
FEATURE                    Location/Qualifiers
REGION                     1..98
                           note = Synthetic
source                     1..98
                           mol_type = protein
                           organism = synthetic construct
SEQUENCE: 96
RNTVWLCYEV KTKGPSRPPL DAKIFRGQVY FEPQYHAEMC FLSWFCGNQL PAYKCFQITW      60
FVSWTPCPDC VAKLAEFLAE HPNVTLTISA ARLYYYWE                              98

SEQ ID NO: 97              moltype = AA   length = 108
FEATURE                    Location/Qualifiers
REGION                     1..108
                           note = Synthetic
source                     1..108
                           mol_type = protein
                           organism = synthetic construct
SEQUENCE: 97
RNTVWLCYEV KTKGPSRPRL DTKIFRGQVY FEPQYHAEMC FLSWFCGNQL PAYKCFQITW      60
FVSWTPCPDC VAKLAEFLAE HPNVTLTISA ARLYYYWERD YRRALCRL                   108

SEQ ID NO: 98              moltype = AA   length = 108
FEATURE                    Location/Qualifiers
REGION                     1..108
                           note = Synthetic
source                     1..108
                           mol_type = protein
                           organism = synthetic construct
SEQUENCE: 98
RNTVWLCYEV KTKGPSRPRL DAKIFRGQVY SQPEHHAEMC FLSWFCGNQL PAYKCFQITW      60
FVSWTPCPDC VAKLAEFLAE HPNVTLTISA ARLYYYWERD YRRALCRL                   108

SEQ ID NO: 99              moltype = AA   length = 108
FEATURE                    Location/Qualifiers
REGION                     1..108
                           note = Synthetic
source                     1..108
                           mol_type = protein
                           organism = synthetic construct
SEQUENCE: 99
RNTVWLCYEV KTRGPSMPTW GTKIFRGQVC FEPQYHAEMC FLSRFCGNQL PAYKRFQITW      60
FVSWTPCPDC VAKVAEFLAE HPNVTLTISA ARLYYYWETD YRRALCRL                   108

SEQ ID NO: 100             moltype = AA   length = 108
FEATURE                    Location/Qualifiers
REGION                     1..108
                           note = Synthetic
source                     1..108
                           mol_type = protein
                           organism = synthetic construct
SEQUENCE: 100
RNTVWLCYEV KTRGPSMPTW GTKIFRGQVC FEPQYHAEMC FLSRFCGNQL PAYKRFQITW      60
FVSWTPCPDC VAKVAEFLAE HPNVTLTISA ARLYYYWETD YRRALCRL                   108

SEQ ID NO: 101             moltype = AA   length = 108
FEATURE                    Location/Qualifiers
REGION                     1..108
                           note = Synthetic
source                     1..108
                           mol_type = protein
                           organism = synthetic construct
SEQUENCE: 101
RNTVWLCYEV KTRGPSMPTW GAKIFRGQVY FEPQYHAEMC FLSWFCGNQL PAYKRFQITW      60
FVSWTPCPDC VAKVAEFLAE HPNVTLTISA ARLYYYWETD YRRALCRL                   108

SEQ ID NO: 102             moltype = AA   length = 101
FEATURE                    Location/Qualifiers
REGION                     1..101
                           note = Synthetic
source                     1..101
                           mol_type = protein
                           organism = synthetic construct
SEQUENCE: 102
RNTVWLCYKV KTRGPSMPTW GTKIFRGQVY FQPQYHAEMC FLSWFCGNQL PAYKRFQITW      60
FVSWTPCPDC VVKVAEFLAE HPNVTLTISA ARLYYYWETD Y                          101
```

```
SEQ ID NO: 103          moltype = AA  length = 108
FEATURE                 Location/Qualifiers
REGION                  1..108
                        note = Synthetic
source                  1..108
                        mol_type = protein
                        organism = synthetic construct
SEQUENCE: 103
RNTVWLCYEV KTRGPSMPTW DTKIFRGQVY SKPEHHAEMC FLSRFCGNQL PAYKRFQITW    60
FVSWTPCPDC VAKVAEFLAE HPNVTLTISA ARLYYYWETD YRRALCRL                108

SEQ ID NO: 104          moltype = AA  length = 108
FEATURE                 Location/Qualifiers
REGION                  1..108
                        note = Synthetic
source                  1..108
                        mol_type = protein
                        organism = synthetic construct
SEQUENCE: 104
RNTVWLCYEV KTRGPSMPTW GTKIFRGQVY FQPQYHAEMC FLSRFCGNQL PAYKRFQITW    60
FVSWNPCPDC VAKVIEFLAE HPNVTLTISA ARLYYYWGRD WRRALRRL                108

SEQ ID NO: 105          moltype = AA  length = 110
FEATURE                 Location/Qualifiers
REGION                  1..110
                        note = Synthetic
source                  1..110
                        mol_type = protein
                        organism = synthetic construct
SEQUENCE: 105
GRSYTWLCYE VKIRKDPSKL PWYTGVFRGQ VYSKPEHHAE MCFLSRFCGN QLPAYKRFQI    60
TWFVSWNPCP DCVAKVIEFL AEHPNVTLTI SAARLYYYWS RDWQRALCRL              110

SEQ ID NO: 106          moltype = AA  length = 110
FEATURE                 Location/Qualifiers
REGION                  1..110
                        note = Synthetic
source                  1..110
                        mol_type = protein
                        organism = synthetic construct
SEQUENCE: 106
GRSYTWLCYE VKIRKDPSKL PWDTGVFRGQ VYSKPEHHAE MCFLSRFCGN QLPAYKRFQI    60
TWFVSWNPCP DCVAKVIEFL AEHPNVTLTI STARLYYYWG RDWQRALCRL              110

SEQ ID NO: 107          moltype = AA  length = 110
FEATURE                 Location/Qualifiers
REGION                  1..110
                        note = Synthetic
source                  1..110
                        mol_type = protein
                        organism = synthetic construct
SEQUENCE: 107
GRSYTWLCYE VKIRKDPSKL PWDTGVFRGQ VYSKPEHHAE MCFLSRFCGN QLPAYKRFQI    60
TWFVSWNPCP DCVAKVIEFL AEHPNVTLTI STARLYYYWG RDWQRALCRL              110

SEQ ID NO: 108          moltype = AA  length = 110
FEATURE                 Location/Qualifiers
REGION                  1..110
                        note = Synthetic
source                  1..110
                        mol_type = protein
                        organism = synthetic construct
SEQUENCE: 108
GRSYTWLCYE VKIRKDPSKL PWDTGVFRGQ VYSKPEHHAE MCFLSRFCGN QLPAYKRFQI    60
TWFVSWNPCP DCVVKVIEFL AEHPNVTLTI STARLYYYWG RDWQRALCRL              110

SEQ ID NO: 109          moltype = AA  length = 110
FEATURE                 Location/Qualifiers
REGION                  1..110
                        note = Synthetic
source                  1..110
                        mol_type = protein
                        organism = synthetic construct
SEQUENCE: 109
GRSYTWLCYE VKIRKDPSKL PWYTGVFRGQ VYSKPEHHAE MCFLSRFCGN QLPAYKRFQI    60
TWFVSWNPCP DCVAKVIEFL AEHPNVTLTI FTARLYYYWG RDWQRALCRL              110
```

```
SEQ ID NO: 110             moltype = AA  length = 110
FEATURE                    Location/Qualifiers
REGION                     1..110
                           note = Synthetic
source                     1..110
                           mol_type = protein
                           organism = synthetic construct
SEQUENCE: 110
GRSYTWLCYE VKIRKDPSKL PWDTGVFRGQ VYSKPEHHAE MCFLSRFCGN QLPAYKRFQI       60
TWFVSWNPCP DCVAKVTEFL AEHPNVTLTI STARLYYYWG RDWQRALCRL                 110

SEQ ID NO: 111             moltype = AA  length = 110
FEATURE                    Location/Qualifiers
REGION                     1..110
                           note = Synthetic
source                     1..110
                           mol_type = protein
                           organism = synthetic construct
SEQUENCE: 111
GRSYTWLCYE VKIRKDPSKL PWDTGVFRGQ VYSEPEHHAE MYFLSWFCGN QLPAYKRFQI       60
TWFVSWTPCP DCVAKVAEFL TEHPNVTLTI SAARLYYYRG RDWRRALCRL                 110

SEQ ID NO: 112             moltype = AA  length = 110
FEATURE                    Location/Qualifiers
REGION                     1..110
                           note = Synthetic
source                     1..110
                           mol_type = protein
                           organism = synthetic construct
SEQUENCE: 112
GRSYTWLCYE VKIRKDPSKL PWDTGVFRGQ VYSEPEHHAE MYFLSWFCGN QLPAYKRFQI       60
TWFVSWTPCP DCVAKVAEFL TEHPNVTLTI SAARLYYYRG RDWRRALCRL                 110

SEQ ID NO: 113             moltype = AA  length = 110
FEATURE                    Location/Qualifiers
REGION                     1..110
                           note = Synthetic
source                     1..110
                           mol_type = protein
                           organism = synthetic construct
SEQUENCE: 113
GRSYTWLCYE VKIRKDPSKL PWDTGVFRGQ MYSKPEHHAE MCFLSWFCGN QLPAHKRFQI       60
TWFVSWTPCP DCVAKVAEFL AEYPNVTLTI SAARLYYYWE TDYRRALCRL                 110

SEQ ID NO: 114             moltype = AA  length = 109
FEATURE                    Location/Qualifiers
REGION                     1..109
                           note = Synthetic
source                     1..109
                           mol_type = protein
                           organism = synthetic construct
SEQUENCE: 114
RSYTWLCYEV KIRKDPSKLP WDTGVFRGQM YFQPEYHAEM CFLSWFCGNQ LPAYKRFQIT       60
WFVSWTPCPD CVAKVAVFLA EHPNVTLTIS AARLYYYWEK DWQRALCRL                  109

SEQ ID NO: 115             moltype = AA  length = 110
FEATURE                    Location/Qualifiers
REGION                     1..110
                           note = Synthetic
SITE                       103
                           note = misc_feature - Xaa can be any naturally occurring
                            amino acid
source                     1..110
                           mol_type = protein
                           organism = synthetic construct
SEQUENCE: 115
GRSYTWLCYE VKIKKYPSKL LWDTGVFQGQ VYFQPQYHAE MCFLSRFCGN QLPAYKRFQI       60
TWFVSWNPCP DCVAKVTEFL AEHPNVTLTI SAARLYYYWE KDXRRALRRL                 110

SEQ ID NO: 116             moltype = AA  length = 110
FEATURE                    Location/Qualifiers
REGION                     1..110
                           note = Synthetic
source                     1..110
                           mol_type = protein
                           organism = synthetic construct
```

```
SEQUENCE: 116
GRSYTWLCYE VKIKEDPSKL LWDTGVFQGQ VYFQPQYHAE MCFLSRFCGN QLPAYKRFQI    60
TWFVSWNPCP DCVAKVTEFL AEHPNVTLTI SAARLYYYWG RDWRRALRRL              110

SEQ ID NO: 117           moltype = AA  length = 122
FEATURE                  Location/Qualifiers
REGION                   1..122
                         note = Synthetic
source                   1..122
                         mol_type = protein
                         organism = synthetic construct
SEQUENCE: 117
GRRYTWLCYE VKIKKDPSKL PWDTGVFPGQ VRPKFQSNRR YEVYFQPQYH AEMYFLSWFC    60
GNQLPAYKHF QITWFVSWNP CPDCVAKVTE FLAEHRNVTL TISAARLYYY WGKDWRRALC   120
RL                                                                  122

SEQ ID NO: 118           moltype = AA  length = 106
FEATURE                  Location/Qualifiers
REGION                   1..106
                         note = Synthetic
source                   1..106
                         mol_type = protein
                         organism = synthetic construct
SEQUENCE: 118
GRRYTWLCYE VKIKKDPSKL PWDTGVFPGQ PQYHAEMYFL SWFCGNQLPA YKHFQITWFV    60
SWNPCPDCVA KVTEFLAEHR NVTLTISAAR LYYYWGKDWR RALCRL                  106

SEQ ID NO: 119           moltype = AA  length = 122
FEATURE                  Location/Qualifiers
REGION                   1..122
                         note = Synthetic
source                   1..122
                         mol_type = protein
                         organism = synthetic construct
SEQUENCE: 119
GRRYTWLCYE VKIKKDPSKL PWDTGVFPGQ VRPKFQSNRR QKVYFQPQYH AEMYFLSWFC    60
GNQLPAYKHF QITWFVSWNP CPDCVAKVTE FLAEHRNVTL TISAARLYYY WGKDWRRALC   120
RL                                                                  122

SEQ ID NO: 120           moltype = AA  length = 122
FEATURE                  Location/Qualifiers
REGION                   1..122
                         note = Synthetic
source                   1..122
                         mol_type = protein
                         organism = synthetic construct
SEQUENCE: 120
GRRYTWLCYE VKIKKDPSKL PWDTGVFQGQ VRPKFQSNRR YEVYFQPQYH AEMCFLSWFC    60
GNQLPAYKHF QITWFVSWNP CPDCVAKVTE FLAEHPNVTL TISAARLYYY WGKDWRRALC   120
RL                                                                  122

SEQ ID NO: 121           moltype = AA  length = 131
FEATURE                  Location/Qualifiers
REGION                   1..131
                         note = Synthetic
source                   1..131
                         mol_type = protein
                         organism = synthetic construct
SEQUENCE: 121
GRSYTWLCYE VKIRKDPSKL PWDTGVFRGQ VRPKLQSNRR YELSNWECRK RVYFQPQYHA    60
EMYFLSWFCG NQLPANKRFQ ITWFASWNPC PDCVAKVTEF LAEHPNVTLT ISVARLYYYR   120
GKDWRRALRR L                                                        131

SEQ ID NO: 122           moltype = AA  length = 110
FEATURE                  Location/Qualifiers
REGION                   1..110
                         note = Synthetic
source                   1..110
                         mol_type = protein
                         organism = synthetic construct
SEQUENCE: 122
GRSYTWLCYE VKIRKDPSKL PWDTGVFRGQ VYFQPQYHAE MYFLSWFCGN QLPANKRFQI    60
TWFASWNPCP DCVAKVTEFL AEHPNVTLTI SVARLYYYRG KDWRRALRRL              110

SEQ ID NO: 123           moltype = AA  length = 110
FEATURE                  Location/Qualifiers
REGION                   1..110
                         note = Synthetic
```

```
                       source                 1..110
                                              mol_type = protein
                                              organism = synthetic construct
SEQUENCE: 123
GRSYTWLCYE VKIRKDPSKL PWDTGVFRDQ VYFQPQYHAE MCFLSWFCGN QLPANKRFQI    60
TWFVSWNPCP DCVTKVTEFL AEHPNVTLTI SVARLYYYRG KDWRRALRRL              110

SEQ ID NO: 124         moltype = AA  length = 110
FEATURE                Location/Qualifiers
REGION                 1..110
                       note = Synthetic
source                 1..110
                       mol_type = protein
                       organism = synthetic construct
SEQUENCE: 124
GRSYTWLCYE VKIRKDPSKL PWYTGVFRGQ VYFQPQYHAE MCFLSWFCGN QLPANKRFQI    60
TWFVSWNPCP DCVAKVTEFL AEHPNVTLTI SVARLYYYRG KDWRRALRRL              110

SEQ ID NO: 125         moltype = AA  length = 110
FEATURE                Location/Qualifiers
REGION                 1..110
                       note = Synthetic
source                 1..110
                       mol_type = protein
                       organism = synthetic construct
SEQUENCE: 125
GRSYTWLCYE VKIRKDPSKL PWDTGVFRGQ VYFQPQYHAE MCFLSWFCGN QLPAYKRFQI    60
TWFVSWNPCP DCVAKVTEFL AEHPNVTLTI SVARLYYYRG KDWRRALCRL              110

SEQ ID NO: 126         moltype = AA  length = 122
FEATURE                Location/Qualifiers
REGION                 1..122
                       note = Synthetic
source                 1..122
                       mol_type = protein
                       organism = synthetic construct
SEQUENCE: 126
GRSYTWLCYE VKIRRGSSNL LWNTGVFRGP VPPKLQSNHR QEVYFQFENH AEMCFLSWFC    60
GNRLPANRRF QITWFVSWNP CLPCVVKVTK FLAEHPNVTL TISAARLYYY RDREWRRVLR   120
RL                                                                  122

SEQ ID NO: 127         moltype = AA  length = 122
FEATURE                Location/Qualifiers
REGION                 1..122
                       note = Synthetic
source                 1..122
                       mol_type = protein
                       organism = synthetic construct
SEQUENCE: 127
GRSYTWLCYE VKIKRGCSNL IWDTGVFRGP VLPKLQSNHR QEVYFQFENH AEMCFFSWFC    60
GNRLPANRRF QITWFVSWNP CLPCVVKVTK FLAEHPNVTL TISAARLYYY QDREWRRVLR   120
RL                                                                  122

SEQ ID NO: 128         moltype = AA  length = 122
FEATURE                Location/Qualifiers
REGION                 1..122
                       note = Synthetic
source                 1..122
                       mol_type = protein
                       organism = synthetic construct
SEQUENCE: 128
GRSYTWLCYE VKIKRGCSNL IWDTGVFRGP VLPKLQSNHR QEVYFQFENH AEMCFFSWFC    60
GNRLPANRRF QITWFVSWNP CLPCVVKVTK FLAEHPNVTL TISAARLYYY QDREWRRVLR   120
RL                                                                  122

SEQ ID NO: 129         moltype = AA  length = 122
FEATURE                Location/Qualifiers
REGION                 1..122
                       note = Synthetic
source                 1..122
                       mol_type = protein
                       organism = synthetic construct
SEQUENCE: 129
GRSYTWLCYE VKIKRGRSNL LWDTGVFRGP VLPKRQSNHR QEVYFRFENH AEMCFLSWFC    60
GNRLPANRRF QITWFVSWNP CLPCVVKVTK FLAEHPNVTL TISAARLYYY RDRDWRWVLL   120
RL                                                                  122

SEQ ID NO: 130         moltype = AA  length = 122
FEATURE                Location/Qualifiers
```

```
REGION                  1..122
                        note = Synthetic
source                  1..122
                        mol_type = protein
                        organism = synthetic construct
SEQUENCE: 130
GRSYTWLCYE VKIRKDPSKL PWDKGVFRGQ VLPKFQSNHR QEVYFQLENH AEMCFLSWFC   60
GNQLPANRRF QITWFVSWNP CLPCVAKVTE FLAEHPNVTL TISAARLYYY RGRDWRRALR  120
RL                                                                 122

SEQ ID NO: 131          moltype = AA  length = 110
FEATURE                 Location/Qualifiers
REGION                  1..110
                        note = Synthetic
source                  1..110
                        mol_type = protein
                        organism = synthetic construct
SEQUENCE: 131
GKKYTWLCYE VKIKKDTSKL PWNTGVFRGQ VNFNPEHHAE MYFLSWFRGK LLPACKRSQI   60
TWFVSWNPCL YCVAKVAEFL AEHPNVTLTV STARLYCYWK KDWRRALRKL             110

SEQ ID NO: 132          moltype = AA  length = 110
FEATURE                 Location/Qualifiers
REGION                  1..110
                        note = Synthetic
source                  1..110
                        mol_type = protein
                        organism = synthetic construct
SEQUENCE: 132
GKKYTWLCYE VKIKKDTSKL PWNTGVFRGQ VNFNPEHHAE MYFLSWFRGK LLPACKRSQI   60
TWFVSWNPCL YCVAKVAEFL AEHPNVTLTV STARLYCYWK KDWRRALRKL             110

SEQ ID NO: 133          moltype = AA  length = 110
FEATURE                 Location/Qualifiers
REGION                  1..110
                        note = Synthetic
source                  1..110
                        mol_type = protein
                        organism = synthetic construct
SEQUENCE: 133
GRRYTWLCYE VKIMKDHSKL PWYTGVFRGQ VYFEPQNHAE MCFLSWFCGN QLPAYECCQI   60
TWFVSWTPCP DCVAKVTEFL AEHPNVTLTI SAARLYYYRG RDWRRALRRL             110

SEQ ID NO: 134          moltype = AA  length = 110
FEATURE                 Location/Qualifiers
REGION                  1..110
                        note = Synthetic
source                  1..110
                        mol_type = protein
                        organism = synthetic construct
SEQUENCE: 134
GRRYTWLCYE VKISKDPSKL PWDTGIFRGQ VYFEPQYHAE MCFLSWYCGN QLPAYKCFQI   60
TWFVSWTPCP DCVGKVAEFL AEHPNVTLTI SAARLYYYWE TDYRRALCRL             110

SEQ ID NO: 135          moltype = AA  length = 121
FEATURE                 Location/Qualifiers
REGION                  1..121
                        note = Synthetic
source                  1..121
                        mol_type = protein
                        organism = synthetic construct
SEQUENCE: 135
RNYTWLCYEV KIRKDPSKLA WDTGVFRGQV LPKLQSNHRR EVYFEPQYHA EMCFLSWFCG   60
NQLSAYERFQ ITWFVSWTPC PDCVAMLAEF LAEHPNVTLT VSAARLYYYW ERDYRGALRR  120
L                                                                  121

SEQ ID NO: 136          moltype = RNA  length = 126
FEATURE                 Location/Qualifiers
misc_feature            1..126
                        note = Synthetic
source                  1..126
                        mol_type = other RNA
                        organism = synthetic construct
SEQUENCE: 136
gaggttgcct ggcacctacg gtttgagagc taggccaaca tgaggatcac ccatgtctgc   60
agggcctagc aagttcaaat aaggctagtc cgttatcaac ttgaaaaagt ggcaccgagt  120
cggtgc                                                             126

SEQ ID NO: 137          moltype = RNA  length = 126
```

```
FEATURE                 Location/Qualifiers
misc_feature            1..126
                        note = Synthetic
source                  1..126
                        mol_type = other RNA
                        organism = synthetic construct
SEQUENCE: 137
gagacccacc tctcgcagtc gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 138          moltype = RNA  length = 126
FEATURE                 Location/Qualifiers
misc_feature            1..126
                        note = Synthetic
source                  1..126
                        mol_type = other RNA
                        organism = synthetic construct
SEQUENCE: 138
gccccatgtc gactacatcg gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 139          moltype = RNA  length = 126
FEATURE                 Location/Qualifiers
misc_feature            1..126
                        note = Synthetic
source                  1..126
                        mol_type = other RNA
                        organism = synthetic construct
SEQUENCE: 139
atggtcaccg acttcgagaa gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 140          moltype = RNA  length = 126
FEATURE                 Location/Qualifiers
misc_feature            1..126
                        note = Synthetic
source                  1..126
                        mol_type = other RNA
                        organism = synthetic construct
SEQUENCE: 140
accttggctt tgttcctccc gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 141          moltype = RNA  length = 126
FEATURE                 Location/Qualifiers
misc_feature            1..126
                        note = Synthetic
source                  1..126
                        mol_type = other RNA
                        organism = synthetic construct
SEQUENCE: 141
ggctttgttc ctcccaggcc gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 142          moltype = RNA  length = 126
FEATURE                 Location/Qualifiers
misc_feature            1..126
                        note = Synthetic
source                  1..126
                        mol_type = other RNA
                        organism = synthetic construct
SEQUENCE: 142
gtggtgctgc tgcccctggc gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 143          moltype = RNA  length = 126
FEATURE                 Location/Qualifiers
misc_feature            1..126
                        note = Synthetic
source                  1..126
                        mol_type = other RNA
                        organism = synthetic construct
```

-continued

```
SEQUENCE: 143
tgctgctgcc cctggcgggt gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 144           moltype = RNA  length = 126
FEATURE                  Location/Qualifiers
misc_feature             1..126
                         note = Synthetic
source                   1..126
                         mol_type = other RNA
                         organism = synthetic construct
SEQUENCE: 144
acccacctcc tcacctttcc gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 145           moltype = RNA  length = 126
FEATURE                  Location/Qualifiers
misc_feature             1..126
                         note = Synthetic
source                   1..126
                         mol_type = other RNA
                         organism = synthetic construct
SEQUENCE: 145
agcgactgca gcacctgctt gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 146           moltype = RNA  length = 126
FEATURE                  Location/Qualifiers
misc_feature             1..126
                         note = Synthetic
source                   1..126
                         mol_type = other RNA
                         organism = synthetic construct
SEQUENCE: 146
aacgcttttg ggggtgaggg gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 147           moltype = RNA  length = 126
FEATURE                  Location/Qualifiers
misc_feature             1..126
                         note = Synthetic
source                   1..126
                         mol_type = other RNA
                         organism = synthetic construct
SEQUENCE: 147
ccacacagct ccaccagctg gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 148           moltype = RNA  length = 126
FEATURE                  Location/Qualifiers
misc_feature             1..126
                         note = Synthetic
source                   1..126
                         mol_type = other RNA
                         organism = synthetic construct
SEQUENCE: 148
cactgggagg tggaggacct gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 149           moltype = RNA  length = 126
FEATURE                  Location/Qualifiers
misc_feature             1..126
                         note = Synthetic
source                   1..126
                         mol_type = other RNA
                         organism = synthetic construct
SEQUENCE: 149
cccacaagcc gcctgtgctg gtttgagagc taggccaaca tgaggatcac ccatgtctgc    60
agggcctagc aagttcaaat aaggctagtc cgttatcaac ttgaaaaagt ggcaccgagt   120
cggtgc                                                              126

SEQ ID NO: 150           moltype = RNA  length = 126
FEATURE                  Location/Qualifiers
```

| | | |
|---|---|---|
| misc_feature | 1..126 | |
| | note = Synthetic | |
| source | 1..126 | |
| | mol_type = other RNA | |
| | organism = synthetic construct | |

SEQUENCE: 150
```
aggtctggaa tgcaaagtca gtttgagagc taggccaaca tgaggatcac ccatgtctgc    60
agggcctagc aagttcaaat aaggctagtc cgttatcaac ttgaaaaagt ggcaccgagt   120
cggtgc                                                              126
```

| | | |
|---|---|---|
| SEQ ID NO: 151 | moltype = RNA  length = 126 | |
| FEATURE | Location/Qualifiers | |
| misc_feature | 1..126 | |
| | note = Synthetic | |
| source | 1..126 | |
| | mol_type = other RNA | |
| | organism = synthetic construct | |

SEQUENCE: 151
```
ctctcgcagt cagagcgcac gtttgagagc tagggccctg aagaagggcc ctagcaagtt    60
caaataaggc tagtccgtta tcaacttggg ccctgaagaa gggcccaagt ggcaccgagt   120
cggtgc                                                              126
```

| | | |
|---|---|---|
| SEQ ID NO: 152 | moltype = RNA  length = 126 | |
| FEATURE | Location/Qualifiers | |
| misc_feature | 1..126 | |
| | note = Synthetic | |
| source | 1..126 | |
| | mol_type = other RNA | |
| | organism = synthetic construct | |

SEQUENCE: 152
```
caggcccagg ctgcccgccg gtttgagagc tagggccctg aagaagggcc ctagcaagtt    60
caaataaggc tagtccgtta tcaacttggg ccctgaagaa gggcccaagt ggcaccgagt   120
cggtgc                                                              126
```

| | | |
|---|---|---|
| SEQ ID NO: 153 | moltype = RNA  length = 126 | |
| FEATURE | Location/Qualifiers | |
| misc_feature | 1..126 | |
| | note = Synthetic | |
| source | 1..126 | |
| | mol_type = other RNA | |
| | organism = synthetic construct | |

SEQUENCE: 153
```
tctttgccca gagcatcccg gtttgagagc tagggccctg aagaagggcc ctagcaagtt    60
caaataaggc tagtccgtta tcaacttggg ccctgaagaa gggcccaagt ggcaccgagt   120
cggtgc                                                              126
```

| | | |
|---|---|---|
| SEQ ID NO: 154 | moltype = RNA  length = 126 | |
| FEATURE | Location/Qualifiers | |
| misc_feature | 1..126 | |
| | note = Synthetic | |
| source | 1..126 | |
| | mol_type = other RNA | |
| | organism = synthetic construct | |

SEQUENCE: 154
```
cacagacagg taagcacggc gtttgagagc tagggccctg aagaagggcc ctagcaagtt    60
caaataaggc tagtccgtta tcaacttggg ccctgaagaa gggcccaagt ggcaccgagt   120
cggtgc                                                              126
```

| | | |
|---|---|---|
| SEQ ID NO: 155 | moltype = RNA  length = 126 | |
| FEATURE | Location/Qualifiers | |
| misc_feature | 1..126 | |
| | note = Synthetic | |
| source | 1..126 | |
| | mol_type = other RNA | |
| | organism = synthetic construct | |

SEQUENCE: 155
```
aagccagctg gtccagcctg gtttgagagc tagggccctg aagaagggcc ctagcaagtt    60
caaataaggc tagtccgtta tcaacttggg ccctgaagaa gggcccaagt ggcaccgagt   120
cggtgc                                                              126
```

| | | |
|---|---|---|
| SEQ ID NO: 156 | moltype = RNA  length = 126 | |
| FEATURE | Location/Qualifiers | |
| misc_feature | 1..126 | |
| | note = Synthetic | |
| source | 1..126 | |
| | mol_type = other RNA | |
| | organism = synthetic construct | |

-continued

```
SEQUENCE: 156
ggtccagcct gtggggccac gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 157            moltype = RNA   length = 126
FEATURE                   Location/Qualifiers
misc_feature              1..126
                          note = Synthetic
source                    1..126
                          mol_type = other RNA
                          organism = synthetic construct
SEQUENCE: 157
cgcctgccag cgcctggcga gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 158            moltype = RNA   length = 126
FEATURE                   Location/Qualifiers
misc_feature              1..126
                          note = Synthetic
source                    1..126
                          mol_type = other RNA
                          organism = synthetic construct
SEQUENCE: 158
tgccagcgcc tggcgagggc gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 159            moltype = RNA   length = 126
FEATURE                   Location/Qualifiers
misc_feature              1..126
                          note = Synthetic
source                    1..126
                          mol_type = other RNA
                          organism = synthetic construct
SEQUENCE: 159
aagaccagcc ggtgaccctg gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 160            moltype = RNA   length = 126
FEATURE                   Location/Qualifiers
misc_feature              1..126
                          note = Synthetic
source                    1..126
                          mol_type = other RNA
                          organism = synthetic construct
SEQUENCE: 160
atcacaggct gctgcccacg gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 161            moltype = RNA   length = 126
FEATURE                   Location/Qualifiers
misc_feature              1..126
                          note = Synthetic
source                    1..126
                          mol_type = other RNA
                          organism = synthetic construct
SEQUENCE: 161
ctacccagg ccaactgcag gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 162            moltype = RNA   length = 126
FEATURE                   Location/Qualifiers
misc_feature              1..126
                          note = Synthetic
source                    1..126
                          mol_type = other RNA
                          organism = synthetic construct
SEQUENCE: 162
caacagggcc acgtcctcac gtttgagagc tagggccctg aagaagggcc ctagcaagtt    60
caaataaggc tagtccgtta tcaacttggg ccctgaagaa gggcccaagt ggcaccgagt   120
cggtgc                                                              126
```

```
SEQ ID NO: 163         moltype = RNA   length = 126
FEATURE                Location/Qualifiers
misc_feature           1..126
                       note = Synthetic
source                 1..126
                       mol_type = other RNA
                       organism = synthetic construct
SEQUENCE: 163
aggtcagccc aaccagtgcg gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 164         moltype = RNA   length = 126
FEATURE                Location/Qualifiers
misc_feature           1..126
                       note = Synthetic
source                 1..126
                       mol_type = other RNA
                       organism = synthetic construct
SEQUENCE: 164
ccaaccagtg cgtgggccac gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 165         moltype = RNA   length = 126
FEATURE                Location/Qualifiers
misc_feature           1..126
                       note = Synthetic
source                 1..126
                       mol_type = other RNA
                       organism = synthetic construct
SEQUENCE: 165
cccctcagga gcaggtgaag gtttgagagc tagggccctg aagaagggcc ctagcaagtt    60
caaataaggc tagtccgtta tcaacttggg ccctgaagaa gggcccaagt ggcaccgagt   120
cggtgc                                                              126

SEQ ID NO: 166         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 166
gaggttgcct ggcacctacg tgg                                            23

SEQ ID NO: 167         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 167
gagacccacc tctcgcagtc aga                                            23

SEQ ID NO: 168         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 168
gccccatgtc gactacatcg agg                                            23

SEQ ID NO: 169         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 169
atggtcaccg acttcgagaa tgt                                            23

SEQ ID NO: 170         moltype = DNA   length = 23
FEATURE                Location/Qualifiers
```

```
                       -continued misc_feature           1..23
                       note = Synthetic
source                 1..23
                       mol_type = other DNA
                       organism = synthetic construct
SEQUENCE: 170
accttggctt tgttcctccc agg                                              23

SEQ ID NO: 171         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 171
ggctttgttc ctcccaggcc tgg                                              23

SEQ ID NO: 172         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 172
gtggtgctgc tgcccctggc ggg                                              23

SEQ ID NO: 173         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 173
tgctgctgcc cctggcgggt ggg                                              23

SEQ ID NO: 174         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 174
acccacctcc tcacctttcc agg                                              23

SEQ ID NO: 175         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 175
agcgactgca gcacctgctt tgt                                              23

SEQ ID NO: 176         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 176
aacgcttttg ggggtgaggg tgt                                              23

SEQ ID NO: 177         moltype = DNA   length = 23
FEATURE                Location/Qualifiers
misc_feature           1..23
                       note = Synthetic
source                 1..23
                       mol_type = other DNA
                       organism = synthetic construct
SEQUENCE: 177
ccacacagct ccaccagctg agg                                              23
```

```
SEQ ID NO: 178           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 178
cactgggagg tggaggacct tgg                                              23

SEQ ID NO: 179           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 179
cccacaagcc gcctgtgctg agg                                              23

SEQ ID NO: 180           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 180
aggtctggaa tgcaaagtca agg                                              23

SEQ ID NO: 181           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 181
ctctcgcagt cagagcgcac tgc                                              23

SEQ ID NO: 182           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 182
caggcccagg ctgcccgccg ggg                                              23

SEQ ID NO: 183           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 183
tctttgccca gagcatcccg tgg                                              23

SEQ ID NO: 184           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 184
cacagacagg taagcacggc cgt                                              23

SEQ ID NO: 185           moltype = DNA   length = 23
FEATURE                  Location/Qualifiers
misc_feature             1..23
                         note = Synthetic
source                   1..23
                         mol_type = other DNA
                         organism = synthetic construct
```

-continued

```
SEQUENCE: 185
aagccagctg gtccagcctg tgg                                              23

SEQ ID NO: 186          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 186
ggtccagcct gtggggccac tgg                                              23

SEQ ID NO: 187          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 187
cgcctgccag cgcctggcga ggg                                              23

SEQ ID NO: 188          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 188
tgccagcgcc tggcgagggc tgg                                              23

SEQ ID NO: 189          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 189
aagaccagcc ggtgaccctg ggg                                              23

SEQ ID NO: 190          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 190
atcacaggct gctgcccacg tgg                                              23

SEQ ID NO: 191          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 191
ctaccccagg ccaactgcag cgt                                              23

SEQ ID NO: 192          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 192
caacagggcc acgtcctcac agg                                              23

SEQ ID NO: 193          moltype = DNA   length = 23
FEATURE                 Location/Qualifiers
misc_feature            1..23
                        note = Synthetic
```

```
                        -continued source                  1..23
                        mol_type = other DNA
                        organism = synthetic construct
SEQUENCE: 193
aggtcagccc aaccagtgcg tgg                                           23

SEQ ID NO: 194          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 194
ccaaccagtg cgtgggccac agg                                           23

SEQ ID NO: 195          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 195
cccctcagga gcaggtgaag agg                                           23

SEQ ID NO: 196          moltype = RNA  length = 76
FEATURE                 Location/Qualifiers
misc_feature            1..76
                        note = Synthetic
source                  1..76
                        mol_type = other RNA
                        organism = synthetic construct
SEQUENCE: 196
gtttgagagc tagaaatagc aagttcaaat aaggctagtc cgttatcaac ttgaaaaagt   60
ggcaccgagt cggtgc                                                   76

SEQ ID NO: 197          moltype = RNA  length = 12
FEATURE                 Location/Qualifiers
misc_feature            1..12
                        note = Synthetic
source                  1..12
                        mol_type = other RNA
                        organism = synthetic construct
SEQUENCE: 197
gttttagagc ta                                                       12

SEQ ID NO: 198          moltype = RNA  length = 12
FEATURE                 Location/Qualifiers
misc_feature            1..12
                        note = Synthetic
source                  1..12
                        mol_type = other RNA
                        organism = synthetic construct
SEQUENCE: 198
gtttgagagc ta                                                       12

SEQ ID NO: 199          moltype = RNA  length = 14
FEATURE                 Location/Qualifiers
misc_feature            1..14
                        note = Synthetic
source                  1..14
                        mol_type = other RNA
                        organism = synthetic construct
SEQUENCE: 199
tagcaagtta aaat                                                     14

SEQ ID NO: 200          moltype =   length =
SEQUENCE: 200
000

SEQ ID NO: 201          moltype = RNA  length = 14
FEATURE                 Location/Qualifiers
misc_feature            1..14
                        note = Synthetic
source                  1..14
                        mol_type = other RNA
                        organism = synthetic construct
```

```
SEQUENCE: 201
aacttgaaaa agtg                                                         14

SEQ ID NO: 202          moltype = RNA   length = 15
FEATURE                 Location/Qualifiers
misc_feature            1..15
                        note = Synthetic
source                  1..15
                        mol_type = other RNA
                        organism = synthetic construct
SEQUENCE: 202
gcaccgagtc ggtgc                                                        15

SEQ ID NO: 203          moltype = RNA   length = 15
FEATURE                 Location/Qualifiers
misc_feature            1..15
                        note = Synthetic
source                  1..15
                        mol_type = other RNA
                        organism = synthetic construct
SEQUENCE: 203
gcaccgattc ggtgc                                                        15

SEQ ID NO: 204          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 204
tctgcttctc cagccctggc ctgggt                                            26

SEQ ID NO: 205          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 205
tctgcttctt cagccctggc ctgggt                                            26

SEQ ID NO: 206          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 206
ccactgtagt cacacagcac cagagt                                            26

SEQ ID NO: 207          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 207
ccactgtagt tacacagcac cagagt                                            26

SEQ ID NO: 208          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 208
gatgttccaa tcagtacgca gagagt                                            26

SEQ ID NO: 209          moltype = DNA   length = 23
FEATURE                 Location/Qualifiers
misc_feature            1..23
                        note = Synthetic
```

-continued

```
source                  1..23
                        mol_type = other DNA
                        organism = synthetic construct
SEQUENCE: 209
aggaccagcc tgagagagtt ggg                                              23

SEQ ID NO: 210          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 210
aggattagcc tgagagagtt ggg                                              23

SEQ ID NO: 211          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 211
gtcatcttag tcattacctg agg                                              23

SEQ ID NO: 212          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 212
gtcattttag tcattacctg agg                                              23

SEQ ID NO: 213          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 213
ggcccagact gagcacgtga tgg                                              23

SEQ ID NO: 214          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 214
ggcttagact gagcacgtga tgg                                              23

SEQ ID NO: 215          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 215
aggaccagcc tgagagagtt ggg                                              23

SEQ ID NO: 216          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 216
gtcatcttag tcattacctg agg                                              23
```

```
SEQ ID NO: 217          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 217
gtcattttag tcattacctg agg                                              23

SEQ ID NO: 218          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 218
ggctcagact gagcacgtga tgg                                              23

SEQ ID NO: 219          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 219
ggcttagact gagcacgtga tgg                                              23

SEQ ID NO: 220          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 220
ggaatccctt ctgcagcacc tgg                                              23

SEQ ID NO: 221          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 221
ggaatttctt ctgcagcacc tgg                                              23

SEQ ID NO: 222          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 222
ggaattcctt ctgcagcacc tgg                                              23

SEQ ID NO: 223          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 223
gaacacaaag catagactgc ggg                                              23

SEQ ID NO: 224          moltype = DNA  length = 23
FEATURE                 Location/Qualifiers
misc_feature            1..23
                        note = Synthetic
source                  1..23
                        mol_type = other DNA
                        organism = synthetic construct
```

```
SEQUENCE: 224
gaacataaag catagactgc ggg                                            23

SEQ ID NO: 225          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 225
gaatataaag catagactgc ggg                                            23

SEQ ID NO: 226          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 226
ggcactgcgg ctggaggtgg ggg                                            23

SEQ ID NO: 227          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 227
ggcattgcgg ctggaggtgg ggg                                            23

SEQ ID NO: 228          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 228
ggaatccctt ctgcagcacc tgg                                            23

SEQ ID NO: 229          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 229
gaacacaaag catagactgc ggg                                            23

SEQ ID NO: 230          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 230
ggcactgcgg ctggaggtgg ggg                                            23

SEQ ID NO: 231          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 231
tctgcttctc cagccctggc ctgggt                                         26

SEQ ID NO: 232          moltype = DNA   length = 23
FEATURE                 Location/Qualifiers
misc_feature            1..23
                        note = Synthetic
```

```
source                  1..23
                        mol_type = other DNA
                        organism = synthetic construct
SEQUENCE: 232
aggaccagcc tgagagagtt ggg                                              23

SEQ ID NO: 233          moltype = DNA  length = 26
FEATURE                 Location/Qualifiers
misc_feature            1..26
                        note = Synthetic
source                  1..26
                        mol_type = other DNA
                        organism = synthetic construct
SEQUENCE: 233
acgtgctcag tctgggcccc aaggat                                           26

SEQ ID NO: 234          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 234
gtcattttag tcattacctg agg                                              23

SEQ ID NO: 235          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 235
gtcatcttag tcattacctg agg                                              23

SEQ ID NO: 236          moltype = DNA  length = 26
FEATURE                 Location/Qualifiers
misc_feature            1..26
                        note = Synthetic
source                  1..26
                        mol_type = other DNA
                        organism = synthetic construct
SEQUENCE: 236
gatgttccaa tcagtacgca gagagt                                           26

SEQ ID NO: 237          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 237
ggcccagact gagcacgtga tgg                                              23

SEQ ID NO: 238          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 238
gagtccgagc agaagaagaa ggg                                              23

SEQ ID NO: 239          moltype = DNA  length = 26
FEATURE                 Location/Qualifiers
misc_feature            1..26
                        note = Synthetic
source                  1..26
                        mol_type = other DNA
                        organism = synthetic construct
SEQUENCE: 239
tctgcttctc cagccctggc ctgggt                                           26
```

```
SEQ ID NO: 240           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 240
gagtctaagc agaagaagaa gag                                              23

SEQ ID NO: 241           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 241
gaggccgagc agaagaaaga cgg                                              23

SEQ ID NO: 242           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 242
ggaatcccct ctgcagcacc tgg                                              23

SEQ ID NO: 243           moltype = DNA   length = 26
FEATURE                  Location/Qualifiers
misc_feature             1..26
                         note = Synthetic
source                   1..26
                         mol_type = other DNA
                         organism = synthetic construct
SEQUENCE: 243
ggacgtgtgt gtctgtgtgg gtgagt                                           26

SEQ ID NO: 244           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 244
ggaaccccgt ctgcagcacc agg                                              23

SEQ ID NO: 245           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 245
accatccctc ctgcagcacc agg                                              23

SEQ ID NO: 246           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 246
ttcctccaga ggttctgttt ggg                                              23

SEQ ID NO: 247           moltype = DNA   length = 26
FEATURE                  Location/Qualifiers
misc_feature             1..26
                         note = Synthetic
source                   1..26
                         mol_type = other DNA
                         organism = synthetic construct
```

```
SEQUENCE: 247
ccactgtagt cacacagcac cagagt                                              26

SEQ ID NO: 248          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 248
agcctccagg ggttctgttt tgg                                                 23

SEQ ID NO: 249          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 249
ttcctcctga gattctgttt agg                                                 23

SEQ ID NO: 250          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 250
gagtccgagc agaagaagaa ggg                                                 23

SEQ ID NO: 251          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 251
attgccacga agcaggccaa tgg                                                 23

SEQ ID NO: 252          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 252
cgccgtctcc aaggtgaaag cgg                                                 23

SEQ ID NO: 253          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 253
ggaatccctt ctgcagcacc tgg                                                 23

SEQ ID NO: 254          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 254
ctccaccgct ttcccaagag tgg                                                 23

SEQ ID NO: 255          moltype = DNA  length = 23
FEATURE                 Location/Qualifiers
misc_feature            1..23
                        note = Synthetic
```

```
source                  1..23
                        mol_type = other DNA
                        organism = synthetic construct
SEQUENCE: 255
atcccgtgac tcagaacccc tgg                                               23

SEQ ID NO: 256          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 256
ctctcgcagt cagagcgcac tgc                                               23

SEQ ID NO: 257          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 257
caggcccagg ctgcccgccg ggg                                               23

SEQ ID NO: 258          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 258
tctttgccca gagcatcccg tgg                                               23

SEQ ID NO: 259          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 259
cacagacagg taagcacggc cgt                                               23

SEQ ID NO: 260          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 260
aagccagctg gtccagcctg tgg                                               23

SEQ ID NO: 261          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 261
ggtccagcct gtggggccac tgg                                               23

SEQ ID NO: 262          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 262
cgcctgccag cgcctggcga ggg                                               23
```

```
SEQ ID NO: 263            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 263
tgccagcgcc tggcgagggc tgg                                               23

SEQ ID NO: 264            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 264
aagaccagcc ggtgaccctg ggg                                               23

SEQ ID NO: 265            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 265
atcacaggct gctgcccacg tgg                                               23

SEQ ID NO: 266            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 266
ctacccagg ccaactgcag cgt                                                23

SEQ ID NO: 267            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 267
caacagggcc acgtcctcac agg                                               23

SEQ ID NO: 268            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 268
aggtcagccc aaccagtgcg tgg                                               23

SEQ ID NO: 269            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 269
ccaaccagtg cgtgggccac agg                                               23

SEQ ID NO: 270            moltype = DNA   length = 23
FEATURE                   Location/Qualifiers
misc_feature              1..23
                          note = Synthetic
source                    1..23
                          mol_type = other DNA
                          organism = synthetic construct
```

-continued

```
SEQUENCE: 270
cccctcagga gcaggtgaag agg                                                      23

SEQ ID NO: 271            moltype = DNA  length = 23
FEATURE                   Location/Qualifiers
misc_feature              1..23
                          note = Synthetic
source                    1..23
                          mol_type = other DNA
                          organism = synthetic construct
SEQUENCE: 271
gtcatcttag tcattacctg agg                                                      23

SEQ ID NO: 272            moltype = DNA  length = 23
FEATURE                   Location/Qualifiers
misc_feature              1..23
                          note = Synthetic
source                    1..23
                          mol_type = other DNA
                          organism = synthetic construct
SEQUENCE: 272
gtcgtcttag tcattacctg agg                                                      23

SEQ ID NO: 273            moltype = DNA  length = 23
FEATURE                   Location/Qualifiers
misc_feature              1..23
                          note = Synthetic
source                    1..23
                          mol_type = other DNA
                          organism = synthetic construct
SEQUENCE: 273
ggaatcccett ctgcagcacc tgg                                                     23

SEQ ID NO: 274            moltype = RNA  length = 119
FEATURE                   Location/Qualifiers
misc_feature              1..119
                          note = Synthetic
misc_feature              1..119
                          note = N can be any base
source                    1..119
                          mol_type = other RNA
                          organism = synthetic construct
SEQUENCE: 274
nnnnnnnnnn nnnnnnnnnn gttttagagc tagaaatagc aagttaaaat aaggctagtc              60
cgttatcaac ttgaaaaagt gggaccgagt cggtccnnnn nnnnnnnnnn nnnnnnnn                119

SEQ ID NO: 275            moltype = RNA  length = 119
FEATURE                   Location/Qualifiers
misc_feature              1..119
                          note = Synthetic
misc_feature              1..119
                          note = N is any base
source                    1..119
                          mol_type = other RNA
                          organism = synthetic construct
SEQUENCE: 275
nnnnnnnnnn nnnnnnnnnn gttttagagc tagaaatagc aagttaaaat aaggctagtc              60
cgttatcgac ttgaaaaagt cggaccgagt cggtccnnnn nnnnnnnnnn nnnnnnnn                119

SEQ ID NO: 276            moltype = DNA  length = 29
FEATURE                   Location/Qualifiers
misc_feature              1..29
                          note = Synthetic
source                    1..29
                          mol_type = other DNA
                          organism = synthetic construct
SEQUENCE: 276
cagactgagc acgtgatggc agaggaaag                                                29

SEQ ID NO: 277            moltype = DNA  length = 29
FEATURE                   Location/Qualifiers
misc_feature              1..29
                          note = Synthetic
source                    1..29
                          mol_type = other DNA
                          organism = synthetic construct
SEQUENCE: 277
cagactgagc acgctatggc agaggaaga                                                29
```

-continued

```
SEQ ID NO: 278            moltype = DNA  length = 29
FEATURE                   Location/Qualifiers
misc_feature              1..29
                          note = Synthetic
source                    1..29
                          mol_type = other DNA
                          organism = synthetic construct
SEQUENCE: 278
cagactgagc acgtgatggc aaaggaaag                                    29

SEQ ID NO: 279            moltype = RNA  length = 119
FEATURE                   Location/Qualifiers
misc_feature              1..119
                          note = Synthetic
misc_feature              1..119
                          note = N is any base
source                    1..119
                          mol_type = other RNA
                          organism = synthetic construct
SEQUENCE: 279
nnnnnnnnnn nnnnnnnnnn gttttagagc tagaaatagc aagttaaaat aaggctagtc   60
cgttatcaac ttgaaaaagt gggaccgagt cggtccnnnn nnnnnnnnnn nnnnnnnnn   119

SEQ ID NO: 280            moltype = RNA  length = 119
FEATURE                   Location/Qualifiers
misc_feature              1..119
                          note = Synthetic
misc_feature              1..119
                          note = N is any base
source                    1..119
                          mol_type = other RNA
                          organism = synthetic construct
SEQUENCE: 280
nnnnnnnnnn nnnnnnnnnn gttttagagc tagaaatagc aagttaaaat aaggctagtc   60
cgttatcgac ttgaaaaagt cggaccgagt cggtccnnnn nnnnnnnnnn nnnnnnnnn   119

SEQ ID NO: 281            moltype = DNA  length = 29
FEATURE                   Location/Qualifiers
misc_feature              1..29
                          note = Synthetic
source                    1..29
                          mol_type = other DNA
                          organism = synthetic construct
SEQUENCE: 281
cagactgagc acgggatagg aaaggaaac                                    29

SEQ ID NO: 282            moltype = DNA  length = 29
FEATURE                   Location/Qualifiers
misc_feature              1..29
                          note = Synthetic
source                    1..29
                          mol_type = other DNA
                          organism = synthetic construct
SEQUENCE: 282
cagactgagc acgggatagg aaaggaagc                                    29

SEQ ID NO: 283            moltype = DNA  length = 29
FEATURE                   Location/Qualifiers
misc_feature              1..29
                          note = Synthetic
source                    1..29
                          mol_type = other DNA
                          organism = synthetic construct
SEQUENCE: 283
ccgagcagaa gaagaagggc tcccatcac                                    29
```